(12) United States Patent
Trainer

(10) Patent No.: US 10,386,283 B2
(45) Date of Patent: Aug. 20, 2019

(54) METHODS AND APPARATUS FOR DETERMINING PARTICLE CHARACTERISTICS BY UTILIZING FORCE ON PARTICLES

(71) Applicant: Michael Trainer, Coopersburg, PA (US)

(72) Inventor: Michael Trainer, Coopersburg, PA (US)

(*) Notice: Subject to any disclaimer, the term of this patent is extended or adjusted under 35 U.S.C. 154(b) by 0 days.

(21) Appl. No.: 15/660,409

(22) Filed: Jul. 26, 2017

(65) Prior Publication Data

US 2017/0322133 A1    Nov. 9, 2017

Related U.S. Application Data

(63) Continuation-in-part of application No. 14/254,958, filed on Apr. 17, 2014, now abandoned, which is a
(Continued)

(51) Int. Cl.
*G01N 21/53*      (2006.01)
*G01N 15/02*      (2006.01)
(Continued)

(52) U.S. Cl.
CPC ........ *G01N 15/0205* (2013.01); *G01J 3/0218* (2013.01); *G01J 3/4412* (2013.01); *G01J 3/453* (2013.01); *G01N 15/0211* (2013.01); *G01N 15/042* (2013.01); *G01N 15/1459* (2013.01); *G01N 15/1463* (2013.01); *G01N 21/474* (2013.01); *G01N 21/53* (2013.01); *G02B 6/32* (2013.01); *G01N 2015/0053* (2013.01); *G01N 2015/025* (2013.01); *G01N 2015/0222* (2013.01); *G01N 2015/1486* (2013.01); *G01N 2015/1493* (2013.01); *G01N 2015/1497* (2013.01); *G01N 2021/4707* (2013.01)

(58) Field of Classification Search
CPC ........ G01N 2333/916; G01N 2500/10; G01N 25/4866; G01N 27/3276; G01N 27/409; G01N 2800/387; G01N 2800/52; G01N 33/2835; G01N 33/49; G01N 33/5041; G01N 33/5308; G01N 33/543; G01N 33/54366; G01N 33/54386; G01N 33/557; G01N 33/56966; G01N 33/56972; G01N 33/57488; G01N 33/57492; G01N 33/66; G01N 33/6854; G01N 33/6857; G01N 33/6863; G01N 33/6893; G01N 33/86; G01N 33/88; G01N 33/92; G01N 35/0092; G01N 35/026; G01N 35/1002; G01N 35/1016; G01N 35/1065
See application file for complete search history.

(56) References Cited

U.S. PATENT DOCUMENTS 7,294,513 B2 * 11/2007 Wyatt ................ G01N 356/338

* cited by examiner

*Primary Examiner* — Michael P Stafira
(74) *Attorney, Agent, or Firm* — William H. Eilberg

(57) ABSTRACT

An instrument for measuring characteristics of particles. A particle sample is introduced into a sample cell. The sample particles are subjected to gravitational or centrifugal forces wherein particle motion is dependent upon particle characteristics. The particles are illuminated by an illumination device to produce light scattered by the particles. The light is detected by at least one detector. Characteristics of the particles are determined from the detector signals.

36 Claims, 80 Drawing Sheets

Related U.S. Application Data continuation-in-part of application No. 12/749,714, filed on Mar. 30, 2010, now Pat. No. 8,705,040, which is a continuation-in-part of application No. 11/928,095, filed on Oct. 30, 2007, now abandoned, and a continuation-in-part of application No. 11/930,588, filed on Oct. 31, 2007, now abandoned, said application No. 11/928,095 is a continuation-in-part of application No. 10/599,737, filed on Oct. 6, 2006, now abandoned, said application No. 11/930,588 is a continuation-in-part of application No. 10/599,737, filed as application No. PCT/US2005/012173 on Apr. 9, 2005, now abandoned, said application No. 12/749,714 is a continuation-in-part of application No. 11/924,327, filed on Oct. 25, 2007, now abandoned, which is a continuation-in-part of application No. 11/538,669, filed on Oct. 4, 2006, now abandoned, which is a continuation-in-part of application No. 10/598,443, filed as application No. PCT/US2005/007308 on Mar. 7, 2005, now Pat. No. 7,471,393.

(60) Provisional application No. 60/561,164, filed on Apr. 10, 2004, provisional application No. 60/561,165, filed on Apr. 10, 2004, provisional application No. 60/550,591, filed on Mar. 6, 2004, provisional application No. 60/723,639, filed on Oct. 5, 2005.

(51) Int. Cl.
| | |
|---|---|
| *G01N 15/14* | (2006.01) |
| *G01J 3/44* | (2006.01) |
| *G01J 3/453* | (2006.01) |
| *G02B 6/32* | (2006.01) |
| *G01N 15/04* | (2006.01) |
| *G01N 21/47* | (2006.01) |
| *G01J 3/02* | (2006.01) |
| *G01N 15/00* | (2006.01) |

METHODS AND APPARATUS FOR DETERMINING PARTICLE CHARACTERISTICS BY UTILIZING FORCE ON PARTICLES

RELATED APPLICATIONS

This is a continuation-in-part of U.S. patent application Ser. No. 14/254,958, filed Apr. 17, 2014, which is a continuation-in-part of U.S. patent application Ser. No. 12/749,714, filed Mar. 30, 2010. The latter application is a continuation-in-part of U.S. patent application Ser. No. 11/928,095, filed Oct. 30, 2007 and U.S. patent application Ser. No. 11/930,588, filed Oct. 31, 2007, which are both a continuation-in-part of U.S. patent application Ser. No. 10/599,737, filed Oct. 6, 2006, now abandoned, which is the national phase of PCT/US05/12173, filed Apr. 9, 2005, which claims priority of U.S. Provisional Patent Application No. 60/561,164, filed Apr. 10, 2004 and U.S. Provisional Patent Application No. 60/561,165, filed Apr. 10, 2004.

Also, application Ser. No. 12/749,714 is a continuation-in-part of U.S. patent application Ser. No. 11/924,327, filed Oct. 25, 2007, which is a continuation of U.S. patent application Ser. No. 11/538,669, filed Oct. 4, 2006, now abandoned, which is a continuation-in-part of U.S. patent application Ser. No. 10/598,443, filed Aug. 30, 2006, now U.S. Pat. No. 7,471,393, which is a U.S. national phase of PCT/US05/07308, which claims the priority of U.S. provisional application Ser. No. 60/550,591, filed Mar. 6, 2004. Priority is also claimed from U.S. provisional application Ser. No. 60/723,639, filed Oct. 5, 2005.

TECHNICAL FIELD OF THE INVENTION

In general, the present invention relates to apparatus and methods which analyze particles. More particularly, the present invention relates to systems and methods which analyze light to determine the size and characteristics of particles.

SUMMARY OF THE INVENTION

The present invention comprises an apparatus and method for determining particle characteristics comprising an illumination means which illuminates particles, a sample cell which contains a particle dispersion and which provides optical access for said light source to illuminate at least one particle in said sample cell, wherein a portion of said light is scattered by particles, at least one detection means which measures at least one parameter derived from light scattered from particles, wherein said detection means comprises at least one light detector, a force means which produces forces on said particles to cause particle motion, and a calculation means which determines at least one characteristic of said particles by utilizing said measurements of said detection means wherein said measurements are affected by at least one motion characteristic of said particle motion. The force means comprises means to produce gravitational or centrifugal force on said particles.

DETAILED DESCRIPTION OF THE INVENTION

Dynamic light scattering has been used to measure particle size by sensing the Brownian motion of particles. Since the Brownian motion velocities are higher for smaller particles, the Doppler spectral broadening of the scattered light is size dependent. Both heterodyne and homodyne methods have been employed to create interference between light scattered from each particle, and either the incident light beam (heterodyne) or light scattered from the other particles (homodyne) of the particle ensemble. Heterodyne detection provides much higher signal to noise due to the mixing of the scattered light with the high intensity light, from the source which illuminates the particles, onto a detector. Usually either the power spectrum or the autocorrelation function of the detector current is measured to determine the particle size. These functions are inverted using algorithms such as iterative deconvolution to determine the particle size distribution. This document describes concepts which use a beamsplitter, and a mirror or partial reflector, to mix the light from the source with light scattered by the particles. This document also describes concepts which use a fiber optic coupler to mix the light from the source with light scattered by the particles.

Figure 1:
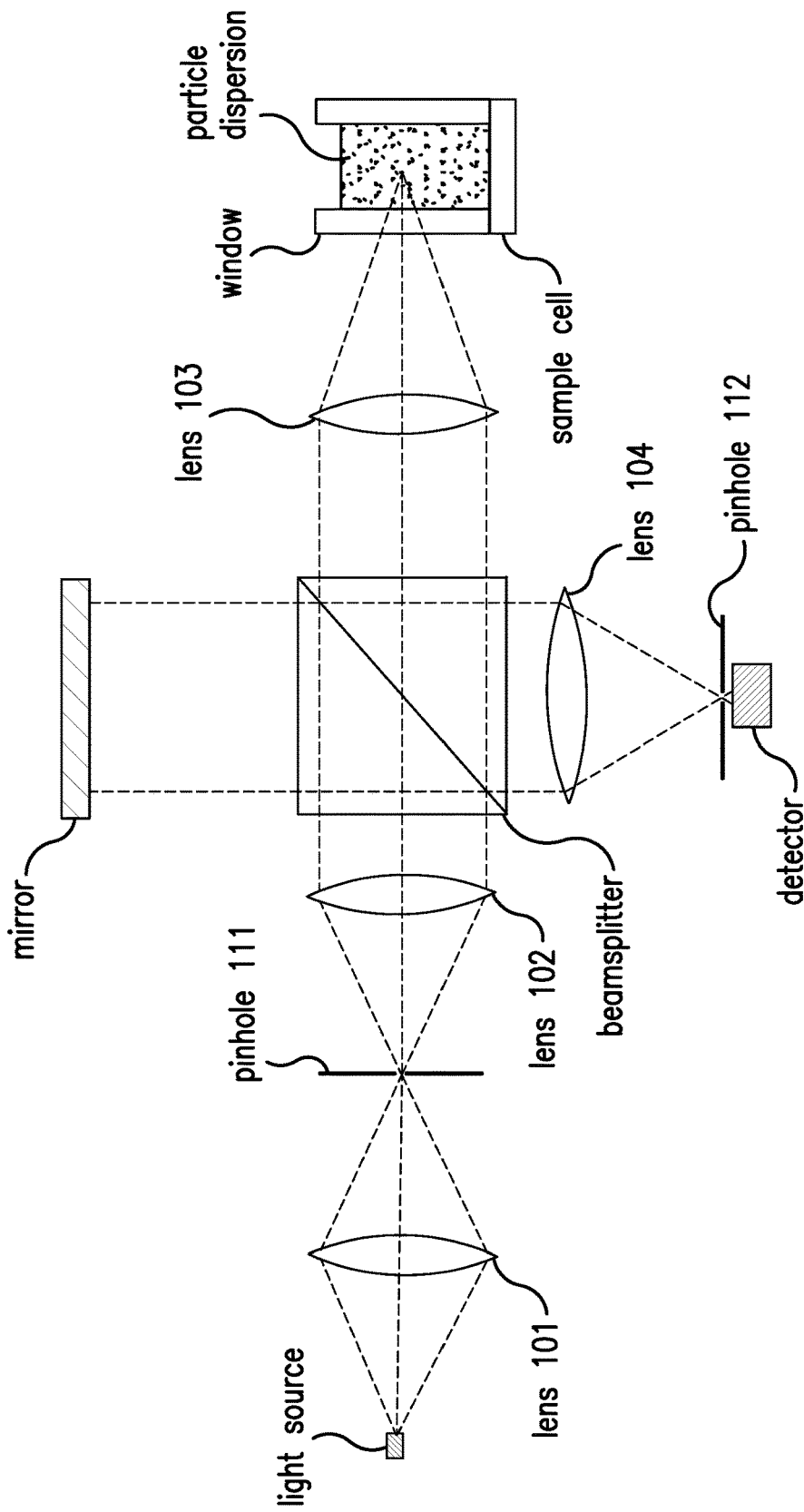
FIG. 1 provides a schematic diagram of an optical system, according to the present invention, mixing source and scattered light to measure the motion and size distribution of particles.

In FIG. 1 a light source is focused through a pinhole by lens 101 to remove spatial defects in the source beam. If few spatial source defects exist, the source could replace pinhole 111, eliminating lens 1 in FIGS. 1, 2, 3, and 4, as shown in FIG. 5. The focused beam is recollimated by lens 102 which projects the beam through an appropriate beamsplitter (plate, cube, etc.). The diverging light source, lens 101, pinhole 111, and lens 102 could all be replaced by an approximately collimated beam, as produced by certain lasers. This generally collimated beam is focused by lens 103 into the particle dispersion which is contained in a sample cell or container with a window to pass the beam. The focused beam illuminates particles in the dispersion and light scattered by the particles passes back through the window and lens 103 to be reflected by the beamsplitter though lens 104 and pinhole 112 to a detector. A portion of the incident collimated source beam is reflected from the beamsplitter towards a mirror, which reflects the source light back though the beamsplitter and through the same lens 104 and pinhole 112 to be mixed with the scattered light on the detector. This source light provides the local oscillator for heterodyne detection of the scattered light from the particles. The local oscillator is light from the light source which is mixed with the scattered light on the detector to produce optical interference between the source light and scattered light. This optical interference produces the heterodyne signal in the detector current. The heterodyne signal has high signal to noise, allowing the use of silicon photodiodes for detection. Also, the dependence of the heterodyne signal amplitude on particle diameter in the Rayleigh scattering region is diameter to the third power for heterodyne, instead of diameter to the sixth power for homodyne. Hence, heterodyne detection has an advantage that small particles are more easily detected when mixed with larger particles. The mirror position must be adjusted to match (to within the coherence length of the source) the optical pathlengths traveled by the source light and the scattered light.

This is accomplished by approximately matching the optical path length from the beam splitter to the scattering particles and from the beam splitter to the mirror. The interference between scattered and source light indicates the velocity and size of the particles. The visibility of this interference is maintained by pinhole 112 which improves the spatial coherence on the detector. Pinhole 112 and the aperture of lens 103 restrict the range of scattering angle (the angle between the incident beam and the scattered light direction) to an angular range which is approximately centered around 180 degrees. However other scattering angles can also be used.

Multiple scattering produces errors in the power spectrum or autocorrelation function of the detector current. Multiple scattering can be reduced by adjusting the focus of lens 103 to be close to the inner surface (the interface of the dispersion and the window) of the sample cell window. Then each scattered ray will encounter very few other particles before reaching the inner window surface. Particles far from the window will show multiple scattering, but they will contribute less to the scattered light because pinhole 112 restricts the acceptance aperture, which will capture a smaller solid angle of scattered light from particles which are far from the inner window surface. If the sample cell is a removable cuvette, multiple scattering will be reduced as long as the short distance of inner window surface to the focal point (in the dispersion) of lens 103 is maintained by appropriate position registration of the cuvette.

This design can provide very high numerical aperture at the sample cell, which improves signal to noise, reduces multiple scattering, and reduces Mie resonances in the scattering function. Light polarization is also preserved, maximizing the interference visibility.

Figure 2:
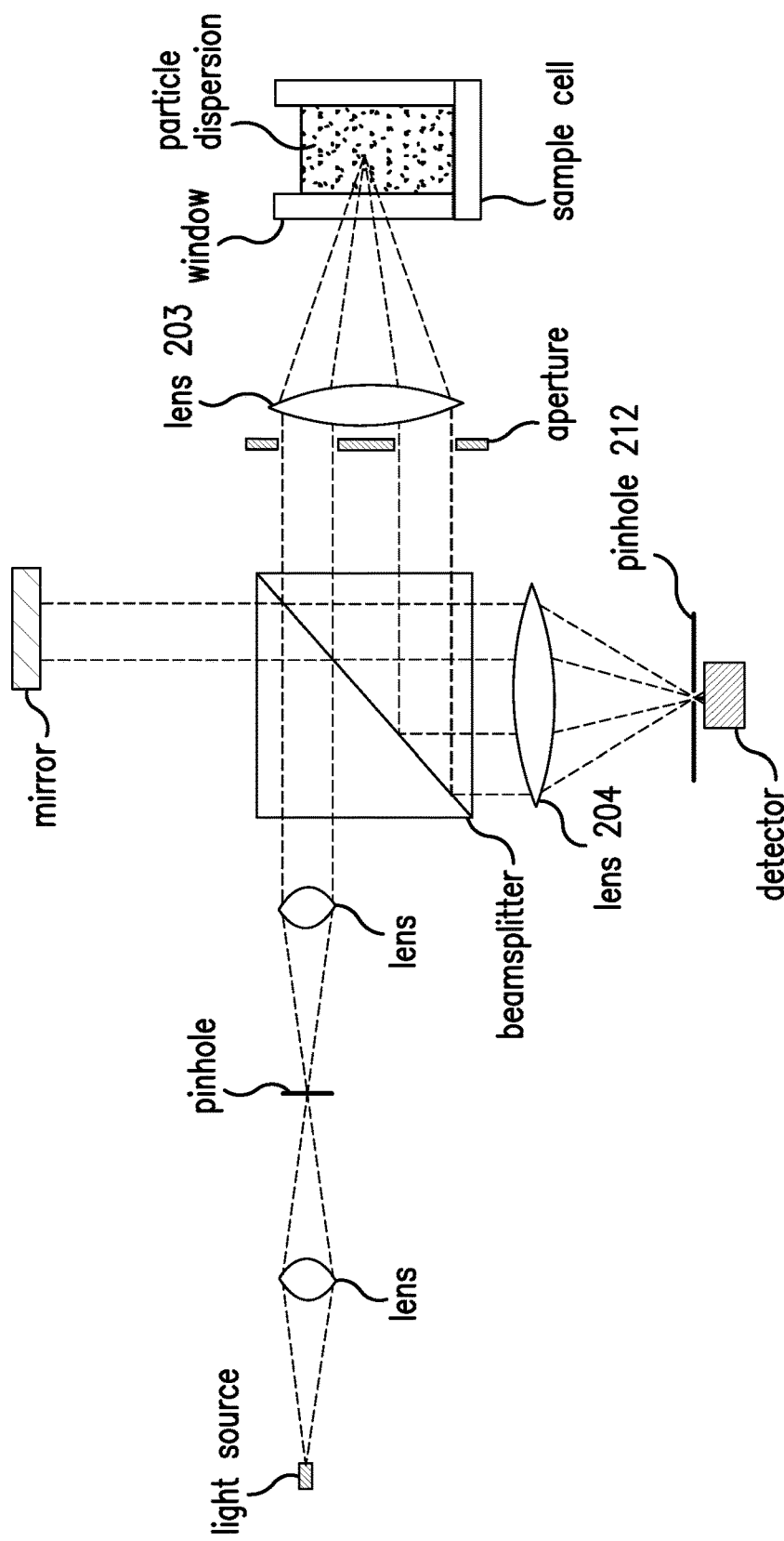
FIG. 2 shows a variation of the system of FIG. 1, providing measurement at lower scattering angles.

FIG. 2 shows another version of this concept where lower scattering angles are measured by separating the incident and scattered beams. Mie resonances are reduced at lower scattering angles. Also multiple scattering is reduced by eliminating the scattering contribution of particles far from the lens 203 focus in the particle dispersion. Only particles in the volume of the intersection of the incident light cone and scattered light cone, defined by the image of the pinhole 212 in the sample cell, contribute to scattering passing through pinhole 212. If this volume is close to the inner wall of the sample cell window, all scattered rays will have a very short transit through the particle dispersion, with minimal multiple scattering. The sample cell window should be tilted slightly so that the Fresnel reflection of the incident beam from the window surface does not enter pinhole 212 though the aperture on lens 204. However if this reflection were large enough, the window surface reflected light could provide the local oscillator for heterodyne detection, without the need for the mirror by providing the proper window tilt to pass the window reflection through the lens 203 aperture and pinhole 212.

Figure 3:
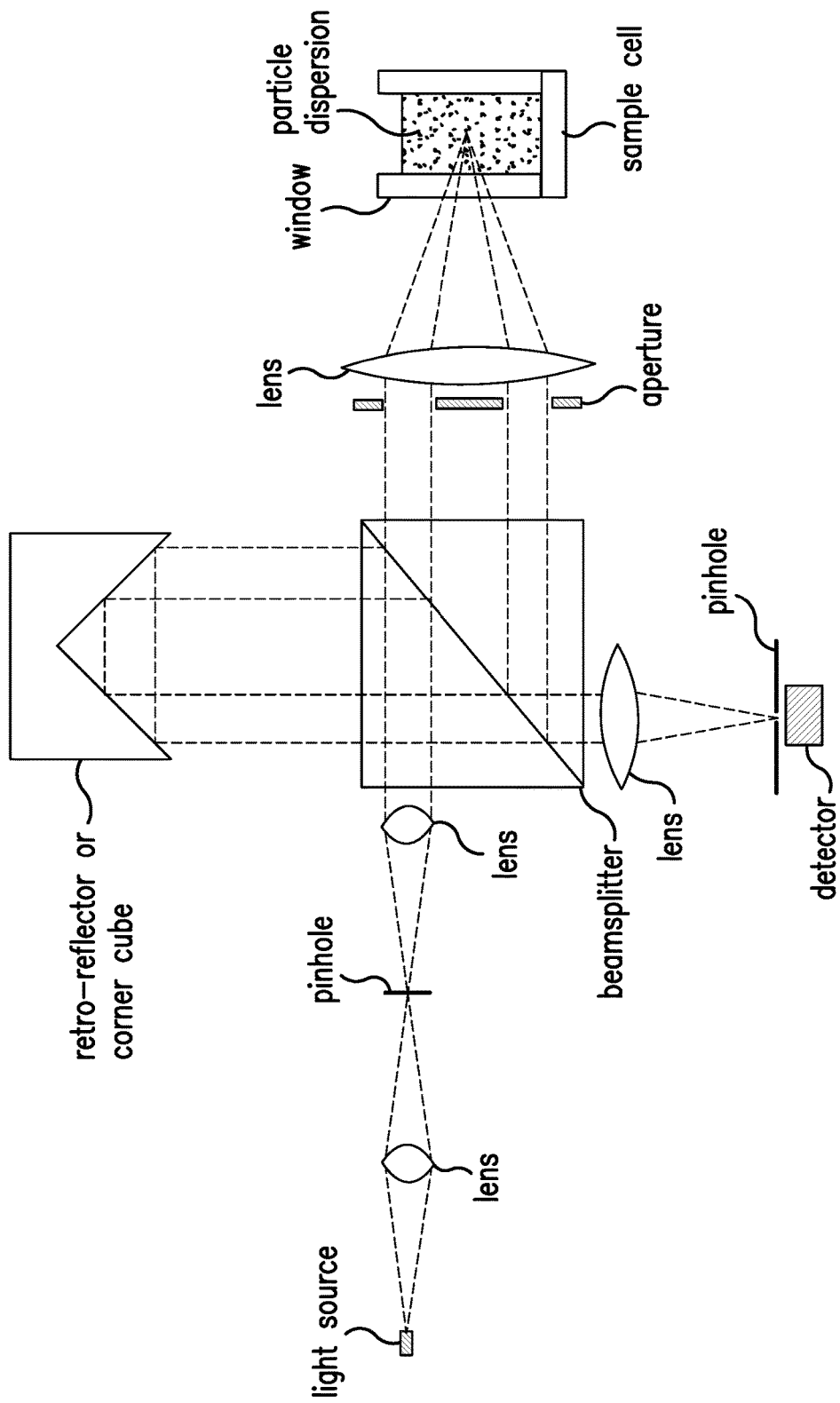
FIG. 3 provides a variation of FIG. 1, utilizing a retro-reflector, to maintain optical alignment, with separated source and scatter beams.

FIG. 3 shows a similar configuration to FIGS. 1 and 2, except that the mirror has been replaced by a retro-reflector or corner cube. The alignment of this configuration will be more stable because the retro-reflector reflects light at 180 degrees to the incident beam over a wide range of incident angles. The corner cube could also be replaced by 2 flat mirrors, which reflect the light through the detector lens. This design has many advantages. The scattered light is collected at a scattering angle less than 180 degrees, which has a more stable scatter resonance structure. Also, since no source light is reflected back in to the source by the beamsplitter, feedback induced laser noise is reduced. If particle settling effects need to be removed from the power spectrum or autocorrelation function of the detector current, the scattering plane shown in the plane of FIG. 3 should be oriented perpendicular to the direction of gravity. This concept is described in more detail in FIG. 73.

Figure 4:
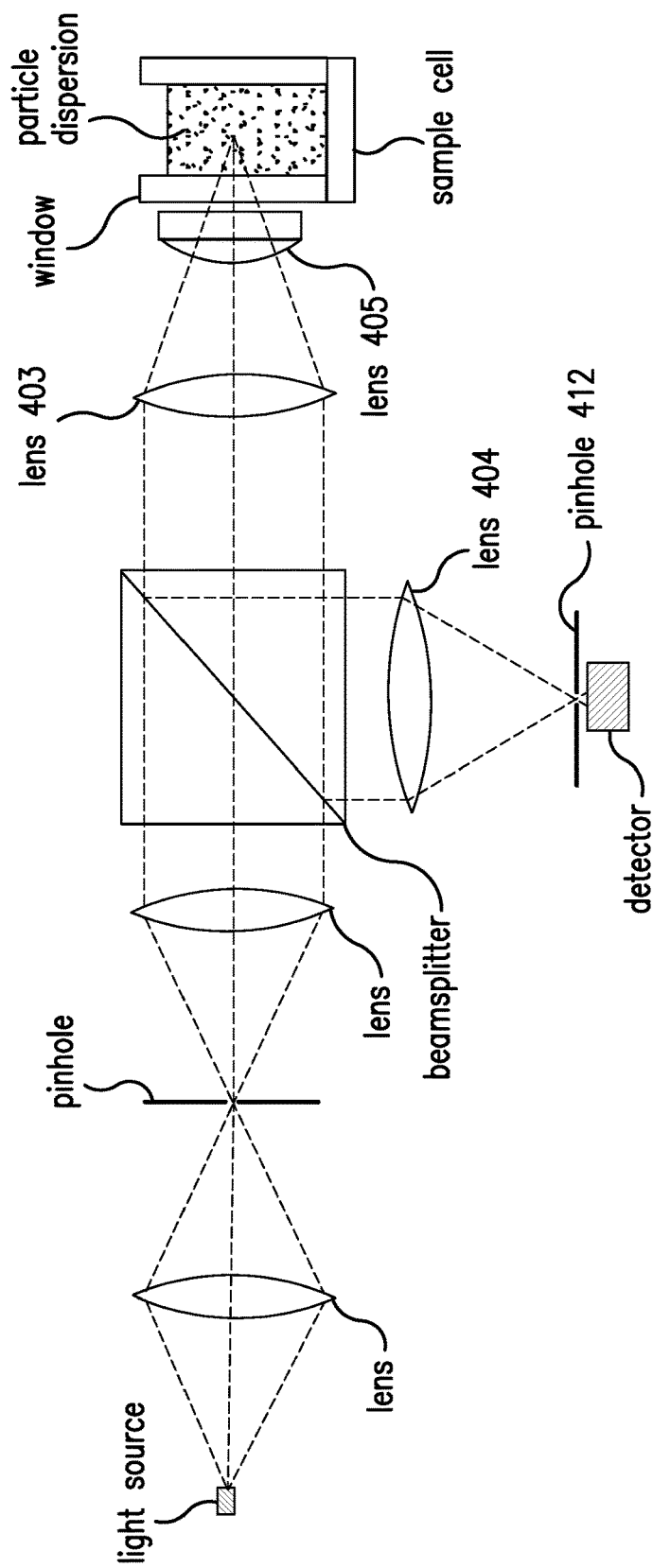
FIG. 4 provides a variation of FIG. 1, utilizing a partially reflecting surface in the light beam.
Figure 5:
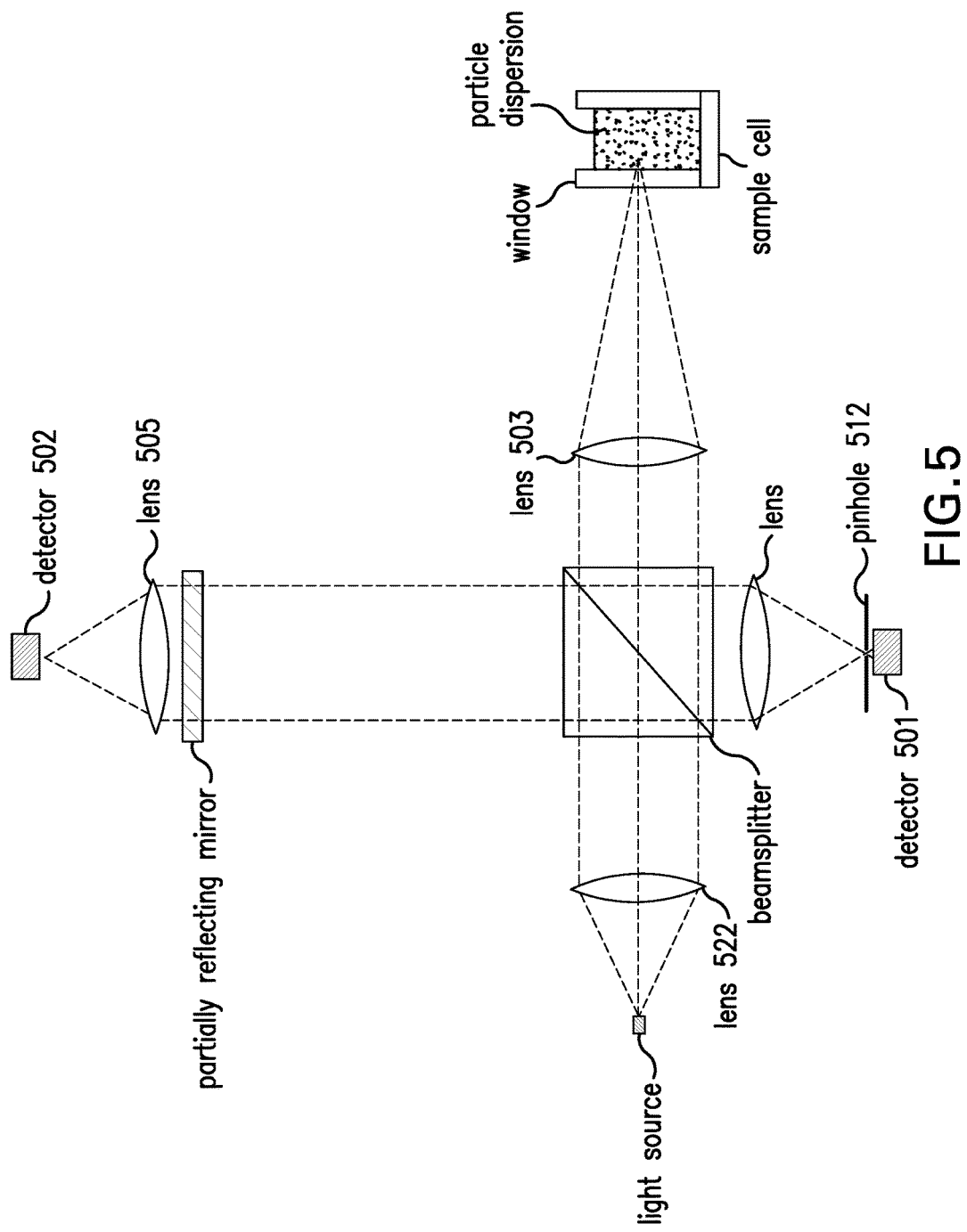
FIG. 5 provides a variation of FIG. 1, utilizing a light source monitor detector.

FIG. 4 shows a configuration where the local oscillator is created by a reflection from the coated convex surface of a plano-convex lens (lens 405) or some other partially reflecting convex surface. The center of curvature of this convex surface coincides with the focus of the incident laser beam, from lens 403, in air. This convex surface provides a partially reflecting surface which is normal to the incident rays. Therefore, the reflected light will focus through pinhole 412, along with the scattered light, even though the reflecting surface is not coincident with the focus. If the beam focus were focused at the inner surface of the sample cell window, then this planar sample cell window surface could provide the reflection for the local oscillator, without the need for the convex surface. However, then the signal would be sensitive to the motion of the sample cell, requiring stable mechanical registration of the cuvette. Lens 405 can be attached firmly to the structure of the optical system, maintaining the high mechanical stability required by an interferometer. Also the reflectivity of the convex surface is more easily increased by reflective coatings, than the inner surface of the sample cell window. Lens 405 could also be replaced by a plano partially reflecting mirror between the beamsplitter and lens 403. The tilt of this partially reflecting mirror must be adjusted to reflect a portion of source light back through lens 404 and pinhole 412. These configurations could also be used with a fiber optic coupler instead of a beam splitter, with appropriate coupling optics at each port of the coupler.

Figure 69:
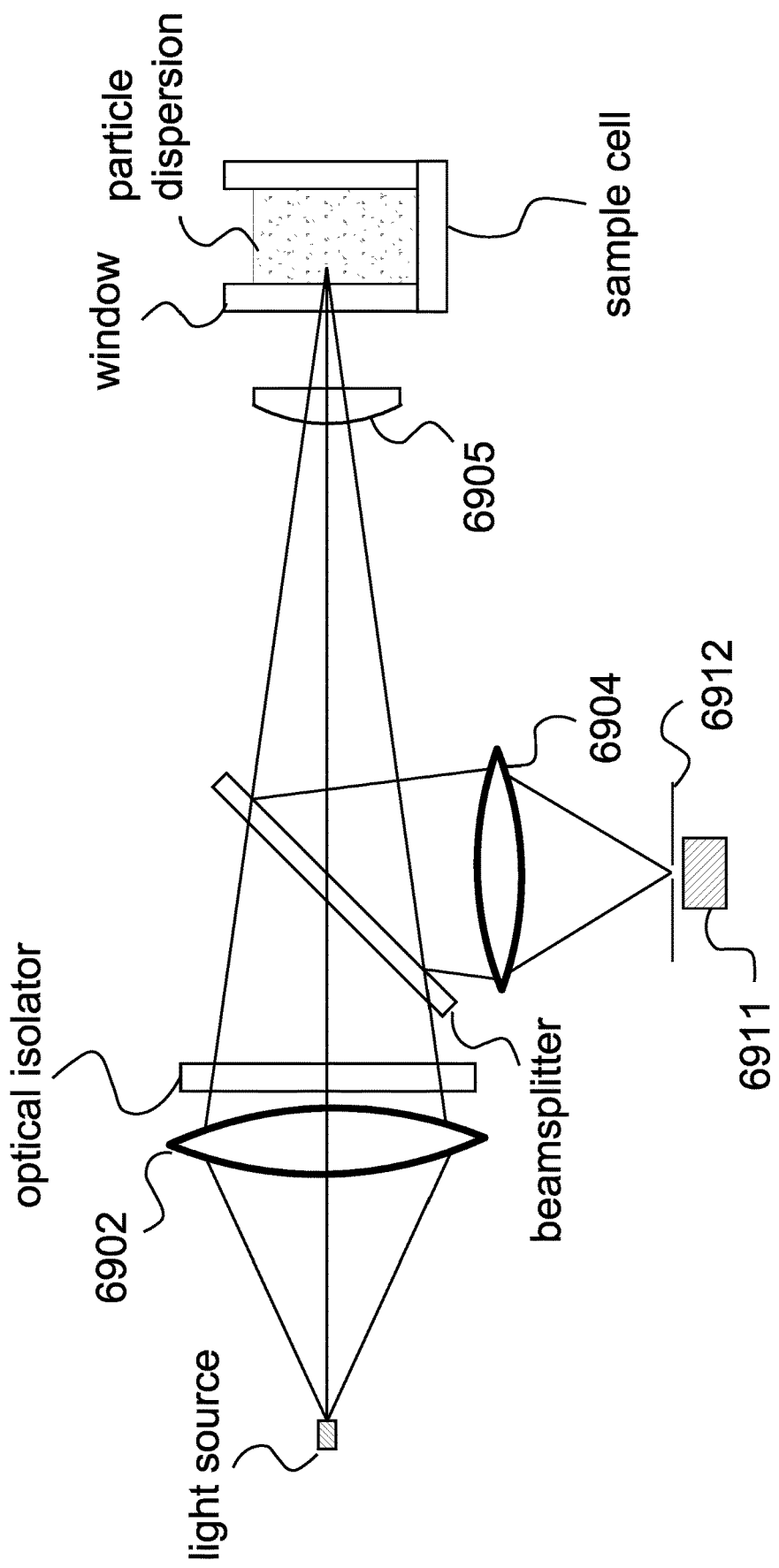
FIG. 69 provides a schematic diagram of an optical system, according to the present invention, mixing source and scattered light to measure the motion and size distribution of particles, using one lens to collect scattered light. The source light is reflected by a convex surface.
Figure 70:
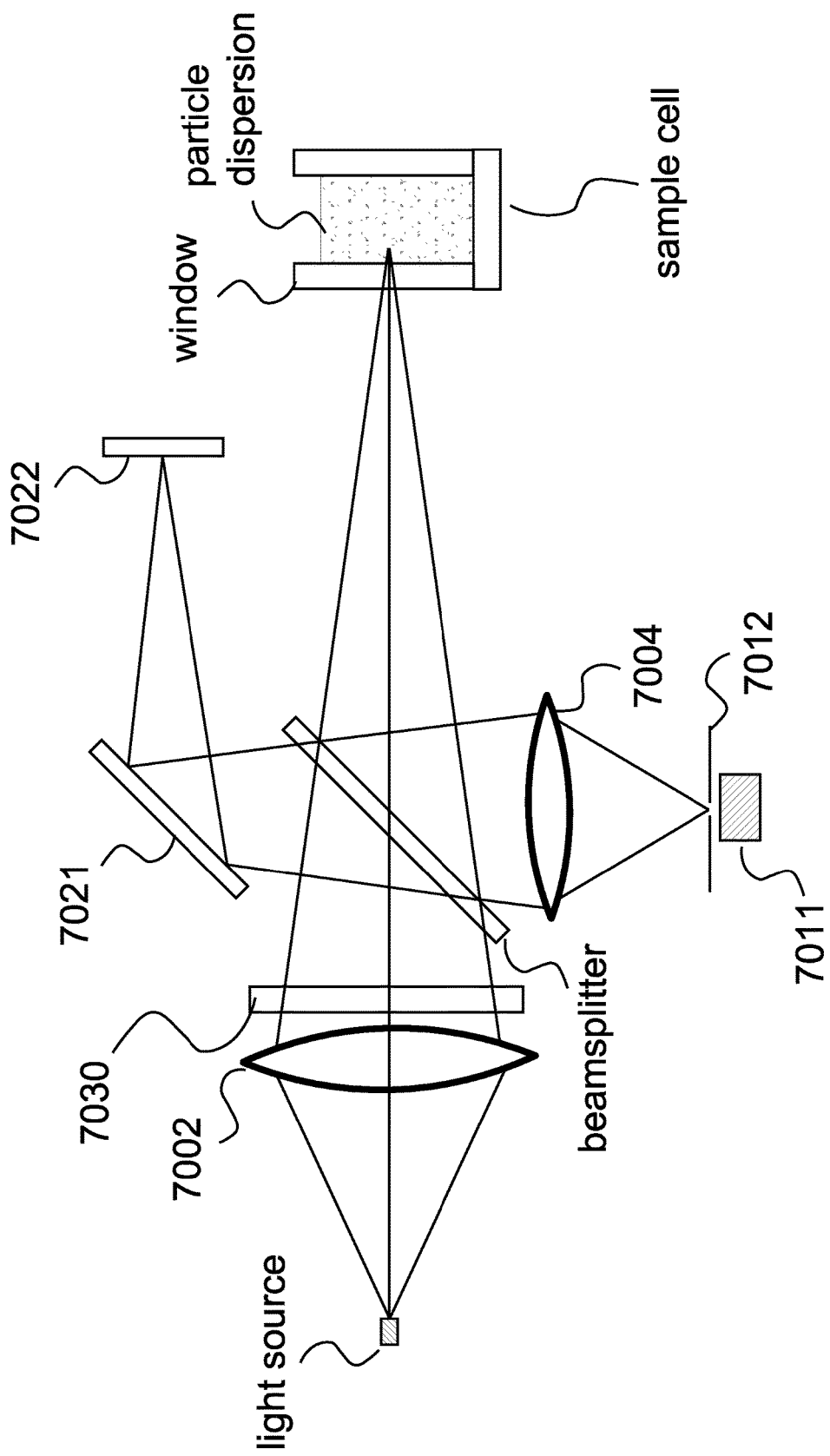
FIG. 70 provides a schematic diagram of an optical system, according to the present invention, mixing source and scattered light to measure the motion and size distribution of particles, using one lens to collect scattered light. The source light is reflected by a mirror.

FIG. 69 and FIG. 70 show other variations of FIG. 4 and FIG. 1, respectively. Lens 403 (or 103) is eliminated and lens 6902 (or lens 7002) directly focuses the laser light into the particle dispersion. Lens 6904 (or lens 7004) images the source focus spot in the dispersion to pinhole 6912 (or 7012), which passes light to detector 6911 (or detector 7011). The local oscillator is provided by source light reflected by either the partially reflecting convex surface, 6905 in FIG. 69, or by the optional folding mirror 7021 and mirror 7022, which is placed at the focus of the source beam in FIG. 70. An optional optical isolator, 7030, may be used to reduce reflected light, which could enter the laser and cause laser noise.

Figure 6:
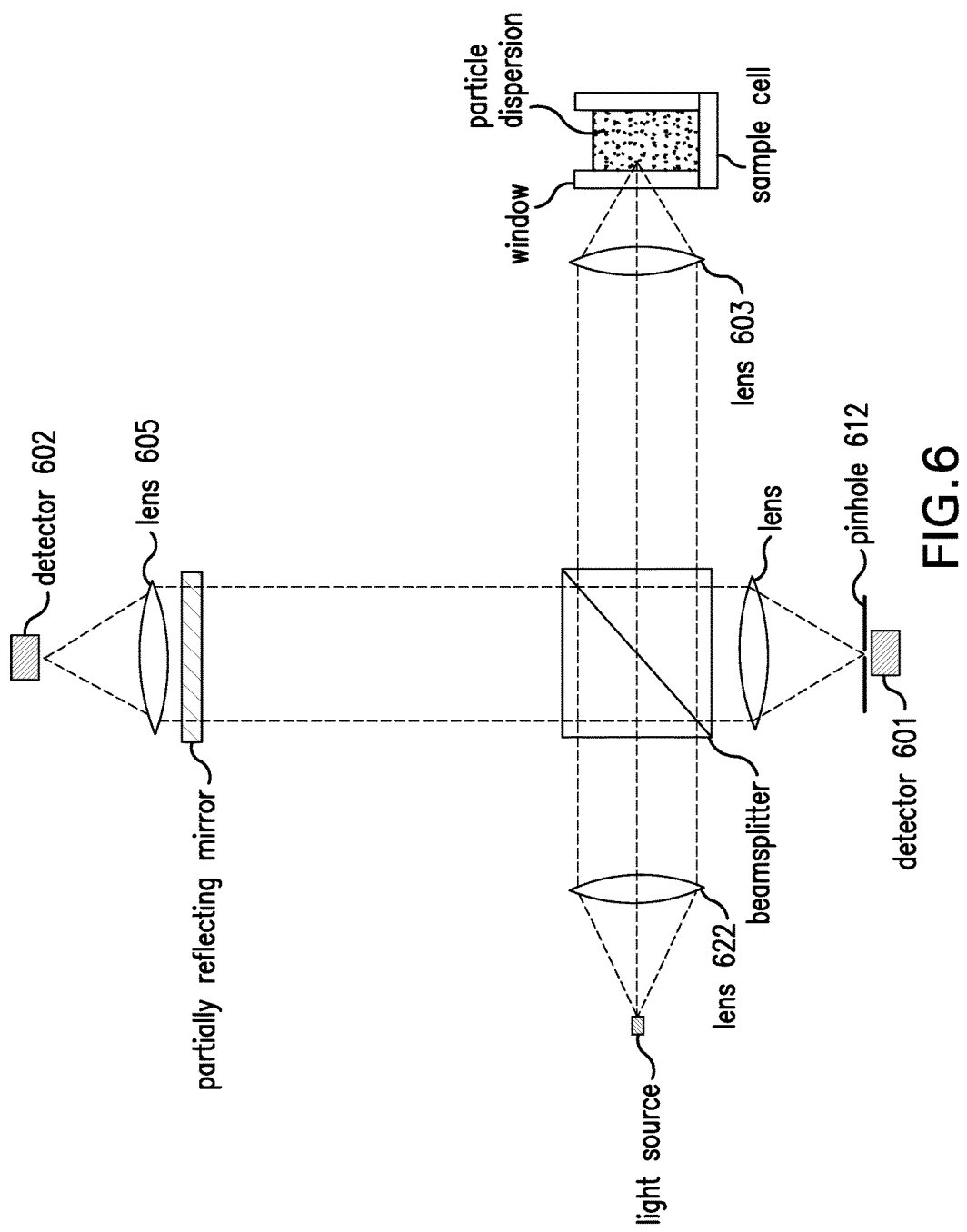
FIG. 6 provides a variation of FIG. 5, utilizing a short focal length lens.

In some cases, the beam focus will define an interaction volume, in the dispersion, which is too small to contain a statistically significant number of particles. The interaction volume is the volume of the particle dispersion which contributes to the scattered light, collected by the optics, which is received by the detector. In particular, a sample of larger particles at low concentration may not be representative of the total sample if the exchange of particles in and out of interaction volume is slow. In this case a larger interaction volume is required to maintain sufficient particles in the beam. So changing the beam focus size and divergence may be appropriate in some applications. FIGS. 5 and 6 show the interchange of two lenses, lens 503 and lens 603, to change the size of the interaction volume in the dispersion. In each case the focus of lens 503 or 603 is placed in the dispersion, with a position which can be adjusted by moving this lens in any direction. For any position of the lens, the scattered light will pass back through pinhole 512 or 612 with the local oscillator reflection from the mirror. The partial reflecting mirror in FIGS. 5 and 6 could also be replaced by the plano partial reflecting mirror between the beamsplitter and lens 503 or lens 603, as described previously for FIG. 4.

Another aspect of FIGS. 5 and 6 is the use of a partially reflecting mirror to produce the local oscillator for heterodyne detection and to monitor the laser intensity fluctuations. The source light which passes through the partially reflecting mirror is focused by lens 505 or 605 onto detector 502 or 602. The signal from detector 502 or 602 is used to correct the signal on detector 501 or 601 for intensity variations and noise in the light source as described by the inventor in this document. The mirror could also be removed to measure the homodyne (self beating) spectrum of the scattered light from the particles.

Also notice that a lens and a pinhole have been removed in FIGS. 5 and 6 to show the configuration without removal of spatial defects in the beam. For example, the source could be a laser diode in these figures. If a low divergence beam from a collimated laser, such as a gas laser, were used, the collimating lens 522 or 622 could also be eliminated.

Figure 7:
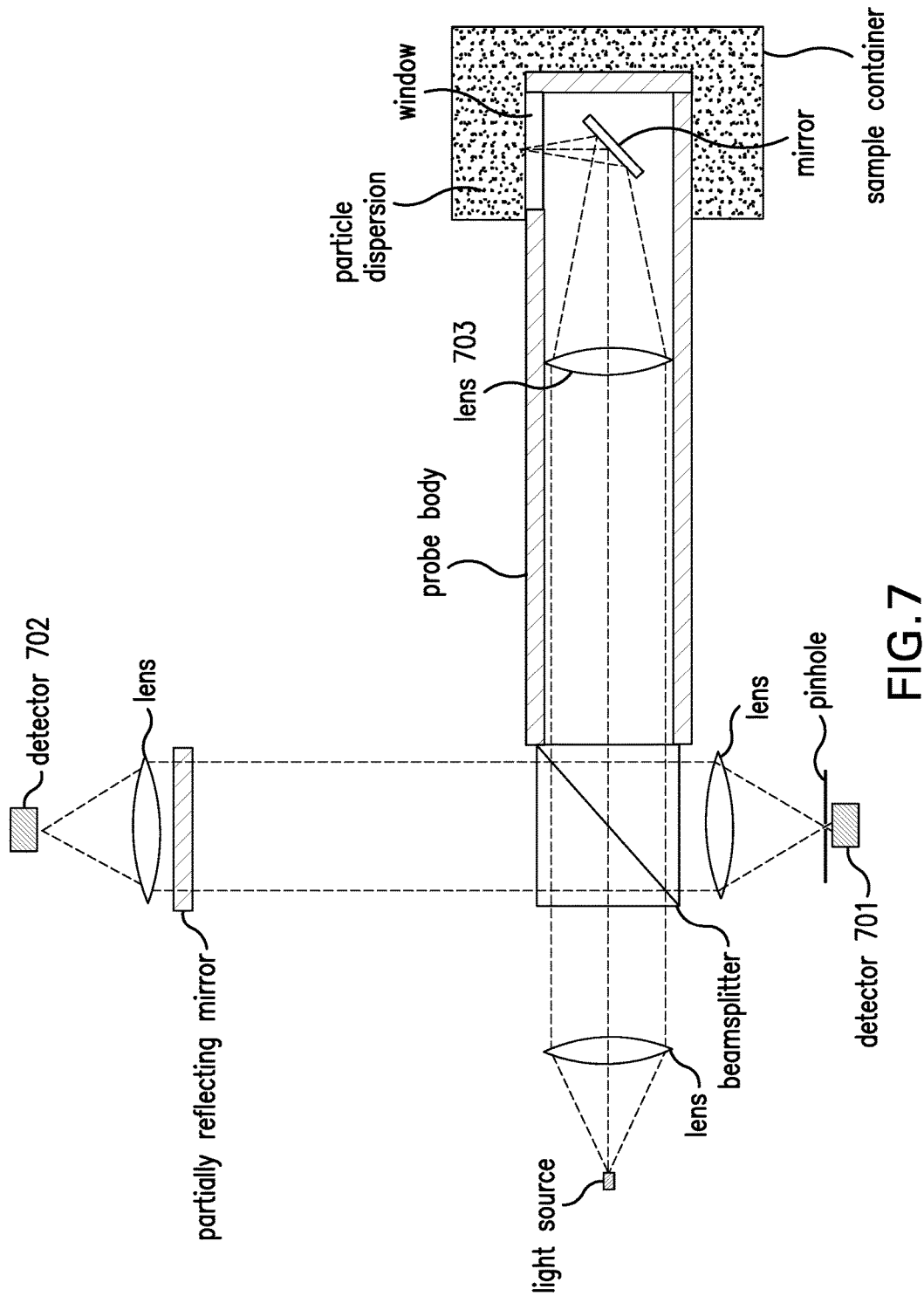
FIG. 7 provides a schematic diagram of an optical system, according to the present invention, mixing source and scattered light to measure the motion and size distribution of particles and utilizing a probe configuration.

FIG. 7 shows a probe version of this invention which can be dipped into the dispersion in a container such as a beaker. Since the particles may settle, the beam is folded by a mirror just before passing through the window. Then the beam is projected into the sample in a direction generally perpendicular to the direction of gravitational settling so that as particles settle out of the interaction volume, they are replaced by other particles which settle into the volume from above. This perpendicular orientation also reduces Doppler shifts in the scattered light due to the settling velocity of the particles. As shown before, the partially reflecting mirror could be fully reflecting. This mirror could also be eliminated for homodyne detection or replaced by a partially reflecting convex surface placed between lens 703 and the window, for heterodyne detection, as shown previously in FIG. 4.

Figure 8:
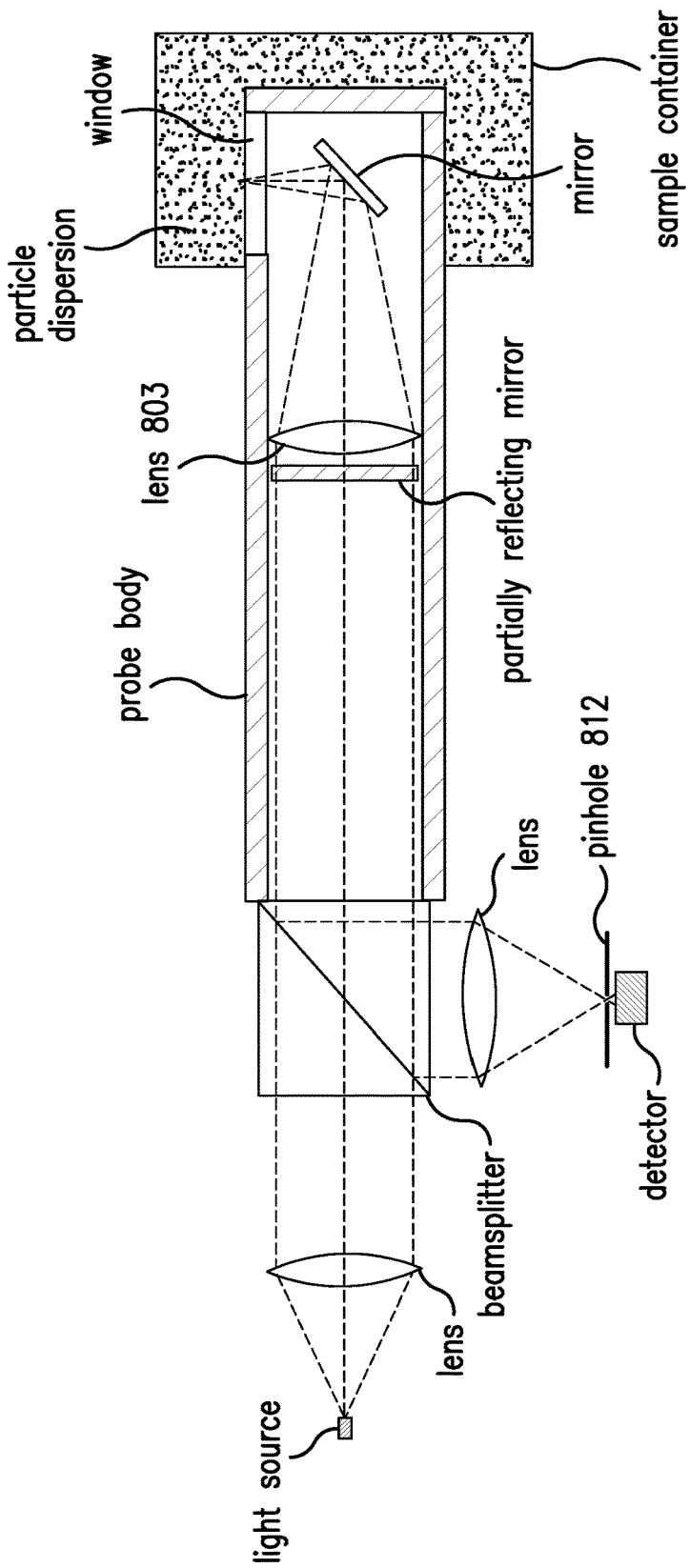
FIG. 8 provides a schematic diagram of an optical system, according to the present invention, mixing source and scattered light to measure the motion and size distribution of particles and utilizing a probe configuration with a partially reflecting surface.

FIG. 8 shows another variation where a partially reflecting flat mirror, which produces the local oscillator, is placed in the collimated portion of the beam between the beamsplitter and lens 803. The tilt of this mirror would be adjusted to send the reflection back through pinhole 812. The partially reflecting local oscillator mirror can be placed in this position (between the beamsplitter and the next optic towards the particle sample) in all configurations in this application, where the light is generally collimated through the beamsplitter.

Another issue is the shift in the heterodyne spectrum due to convection currents in the sample. This is usually small when the divergence of the beam focus is low and the focus is close to the interface between the dispersion and the window. However, this problem may be reduced by surrounding the interaction volume with a chamber as shown in crossection drawing in FIG. 9. This chamber may be made out of material with high thermal capacity and conductivity to bring the interaction volume to thermal equilibrium. Also the height of the inner chamber wall must be sufficient distance from the interaction volume to prevent the larger particles from settling out of the interaction volume during data collection. The shape of the chamber should accommodate the shape of the light beam to avoid scattering from chamber surfaces.

All of these configurations can generate a local oscillator for heterodyne detection using the following methods. In all cases the reflector, which generates the local oscillator, must be held in a stable location relative to the rest of the interferometer:

1) partially or totally reflecting mirror at the beam splitter, as shown in FIG. 1 and FIG. 5
2) flat partially reflecting surface close to the focus of the beam in the sample. If this is the inner surface of a removable cuvette, it must have stable mechanical registration to avoid interferometric noise due to motion of the partially reflective surface. This would replace the mirror in item 1.
3) A flat partially reflecting flat surface between the beamsplitter and lens 103 or 503 could replace the mirror in item 1
4) A partially reflective convex surface with center of curvature at the beam focus in air could replace the mirror in item 1.

One of the key advantages of this invention is that the beam focus in the dispersion does not need to be coincident or near to a partially reflecting surface, such as the inner surface of a cuvette. If the inner surface of cuvette is not close to the beam focus in the dispersion, very little of the reflection from that surface will be returned through pinhole 112 to contribute interferometric noise from small motion of that surface. This allows the use of inexpensive cuvettes whose poor tolerances may not accommodate the requirements of the optical interferometry in the systems shown above.

Figure 71:
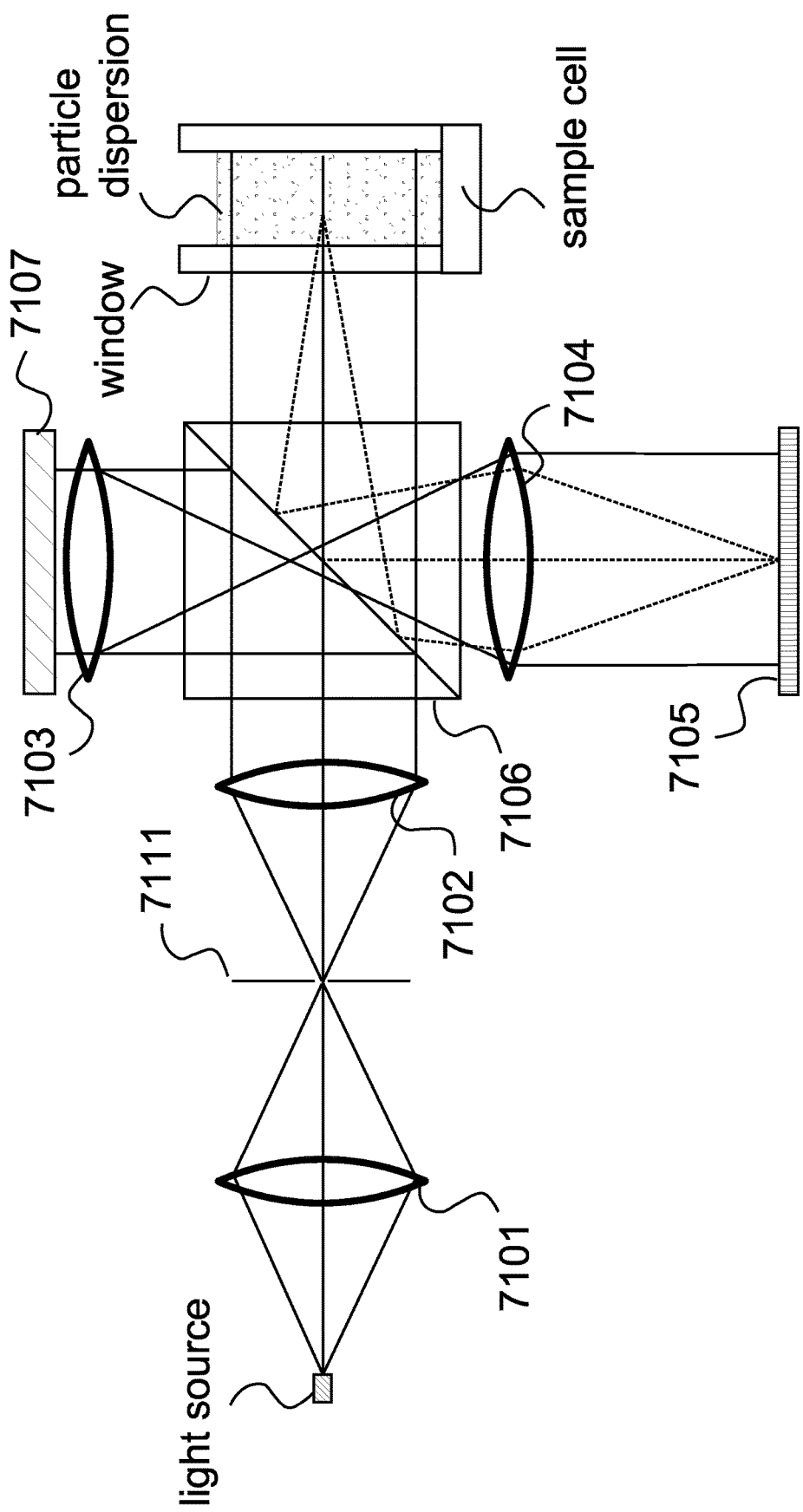
FIG. 71 provides a schematic diagram of an optical system, according to the present invention, mixing source and scattered light to measure the motion and size distribution of particles, using multiple detectors to view multiple regions in the particle dispersion.
Figure 72:
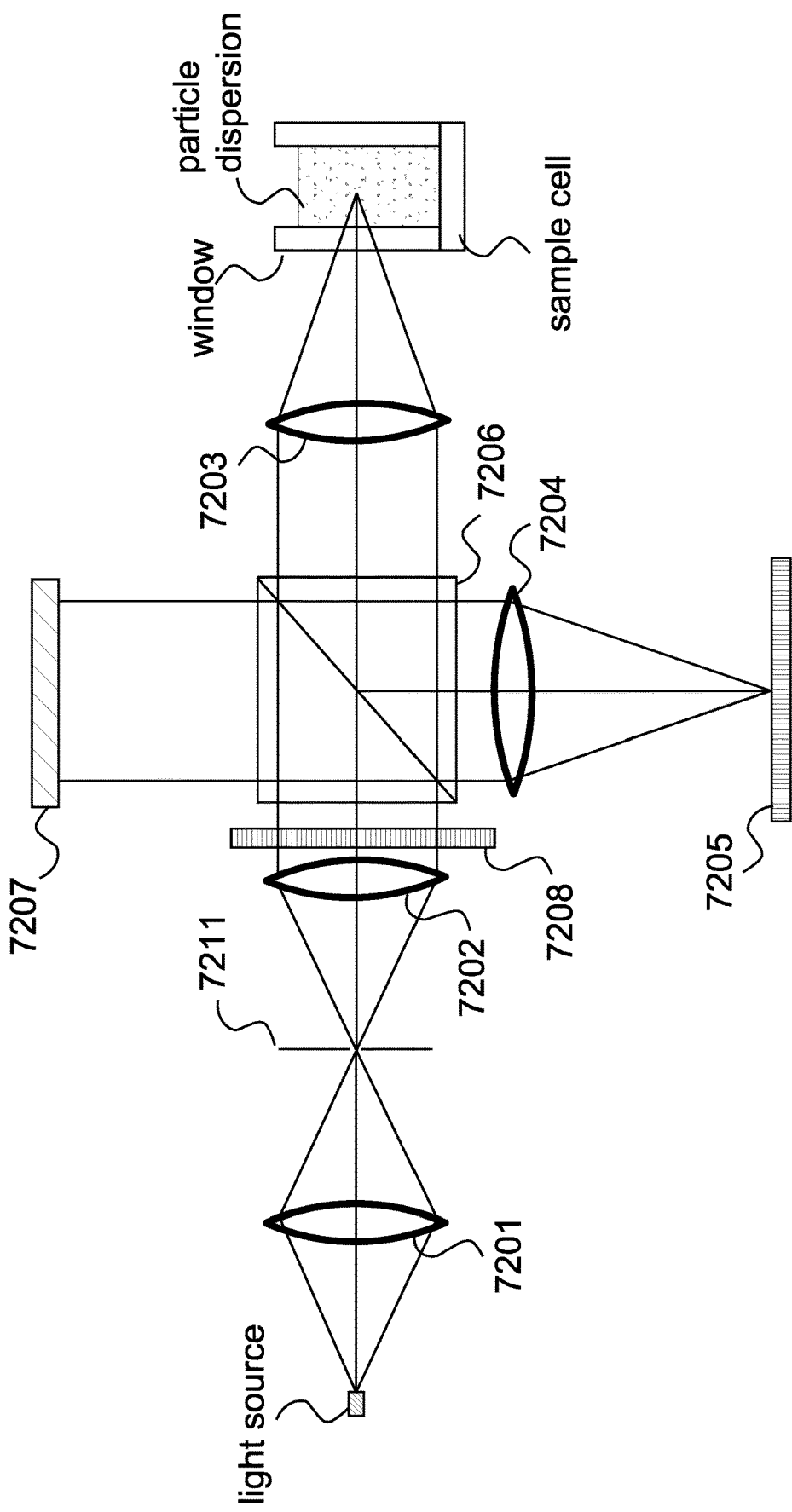
FIG. 72 provides a schematic diagram of an optical system, according to the present invention, mixing source and scattered light to measure the motion and size distribution of particles, using multiple detectors to view multiple regions in the particle dispersion. A diffractive and/or refractive optic provides multiple source spots in the particle dispersion; each spot is viewed by a separate detector.

Another advantage of these designs is the ease of alignment. All of the components in each design can be positioned to within standard machining tolerances. Only two components need alignment during manufacture: the pinhole and/or the local oscillator reflector. These systems have the following advantages over fiber optic systems:
better interferometric efficiency in both polarization and coherence
more flexibility for choice of scattering angle
better photometric efficiency
better control over the local oscillator level
higher numerical aperture in the scattering volume to reduce multiple scattering and increase
scatter signal level
simple adjustment of scattering volume numerical aperture and position in the sample
adjustable scattering volume
lower multiple scattering
lower cost The accuracy of dynamic light scattering systems is limited by the total time required to collect the data needed to accurately determine the stochastic properties, such as the power spectrum, of the stochastic process of particle Brownian motion. FIG. 71 shows a detector array (7105), which is in the image plane of the particle sample, via lens 7104. The same array is also illuminated by unscattered source light via the beamsplitter (7106), mirror (7107) and lens (7103). The combination of lens 7103 and mirror 7107 are designed to create a light beam which covers the detector array 7105, after passing through lens 7104. This combination of lens 7103 and mirror 7107 could also be replaced by a convex or concave mirror, depending upon the positions of the optics and the focal length of lens 7104. Lens 7103 could also have either negative or positive optical power depending upon the positions of the optics and the focal length of lens 7104. FIG. 71 shows a case where the combination of lens 7103 and mirror 7107 creates a focused spot generally in the focal plane of lens 7104, producing a generally collimated beam of source light which covers the detector array. The detector array can also include a group of detectors, without an array structure. This creates an array of heterodyne detectors, each of which views scatter from a different portion of the particle dispersion. Hence the heterodyne signal on each detector element is not correlated with signals from other elements. This means that the average of the power spectra of the detector element currents from this array will have better reproducibility than a single detector. An individual power spectrum is calculated from the digitized signal of each detector element; then these individual power spectra are summed at each frequency, in the spectra, to create an average spectrum for the entire set of detectors. This average spectrum will have better reproducibility than a single detector spectrum. The standard deviation of the averaged power spectrum will decrease as one divided by the square root of the number of power spectra in the average. For example, the averaged power spectrum from 9 detector elements would reduce the standard deviation by a factor of 3. FIG. 72 shows a similar concept where a 2-dimensional diffracting structure (7208) (such as an array of holes, an optical phase array, or a binary optic) creates a set of illumination spots (only one of the illumination focal spots is shown) in the sample cell and also creates a matching set of local oscillator spots (only one of the local oscillator focal spots is shown) through the beamsplitter 7206 and mirror 7207, one for each element in the 2-dimensional detector array(7205). Lenses 7203 and 7204 image the scattered light from these illumination spots onto the array of detectors, such that scattered light from each spot is individually detected by one of the detectors (one to one correspondence between illumination spots and detectors). The system in FIG. 72 could be more efficient, than the system in FIG. 71, because each detector receives light from an individual focused laser spot. This technique will also work for any set of detectors such as a linear 1-Dimensional array, using a 1-dimensional diffracting/refracting structure (such as a diffraction grating of parallel lines) for 7208. Custom binary optics or other custom diffracting/refracting optics can produce the array of laser spots, directly, eliminating lens 7203 and requiring lens 7204 to directly image the illumination spots onto the detectors. The size of each detector should be minimized to only include one (or at most a few) speckles of the spatial interference pattern to maximize interferometric visibility and heterodyne signal amplitude. In FIGS. 71 and 72 the pinhole (7111 and 7211) and the first lens (7101 and 7201), remove spatial defects in the light source, if required. If the source is sufficiently free of spatial defects, the pinhole and first lens can be eliminated by replacing the pinhole with the light source. This concept, of making multiple concurrent measurements from different portions of the particle dispersion and averaging the resulting power spectra, can be applied to measurements from multiple optical systems. This idea of using concurrent power spectral measurements from multiple scatter signals, each originating from a different portion of the particle dispersion, and averaging the resulting power spectra is also claimed for cases where multiple optical systems are used to measure the multiple scattering signals. The concepts described in FIG. 71 and FIG. 72 are the most economical designs for implementing this concept.

Figure 22:
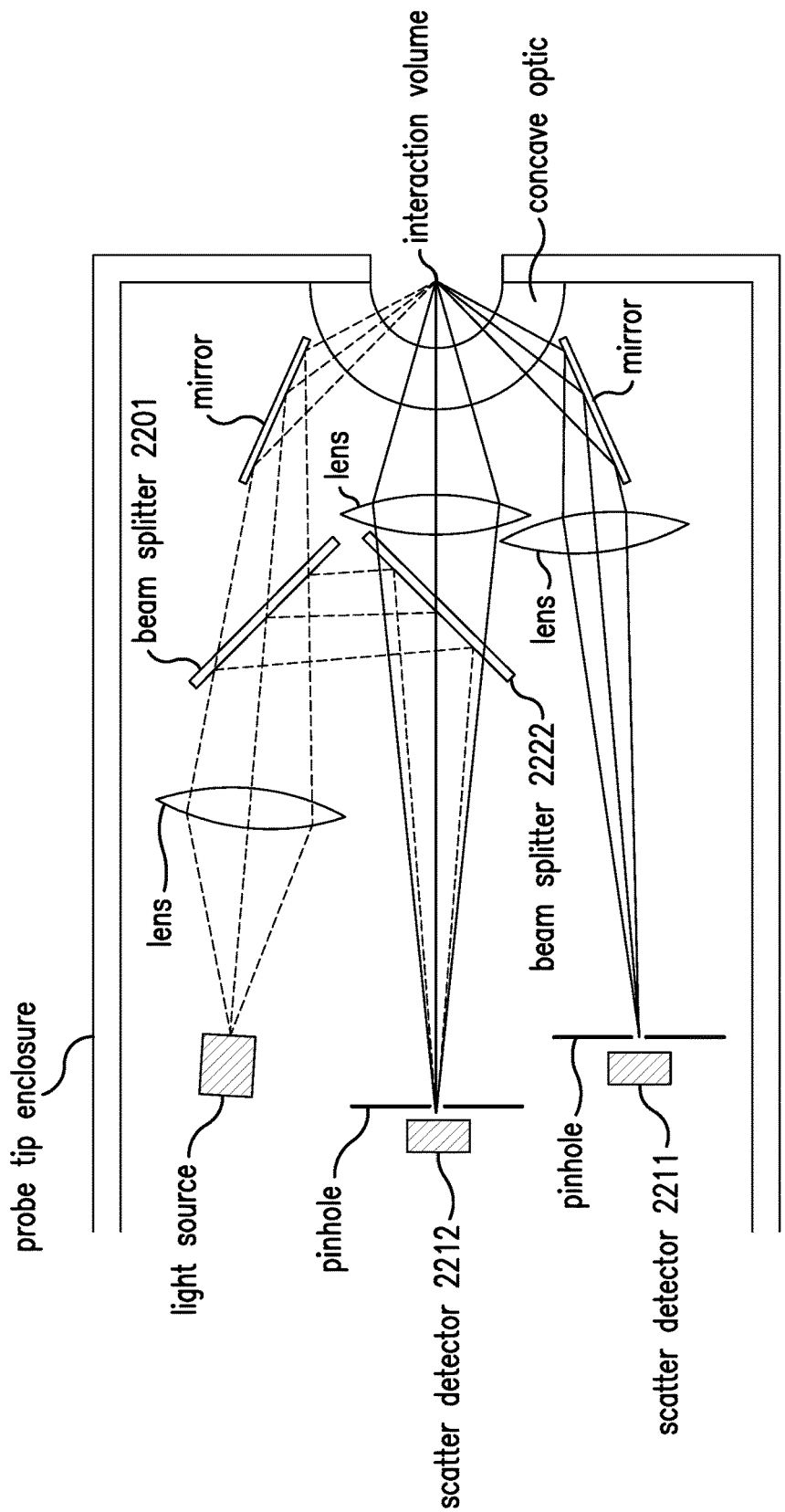
FIG. 22 shows a variation of FIG. 20, mixing source and scattered light to measure the motion and size distribution of particles.

The diffracting/refracting structure, optic 7208, can be added to many designs, including those in FIG. 3 and FIG. 22, to measure scattered light from multiple portions of the particle dispersion, concurrently. In FIG. 3, a 7208 optic could be placed in this sequence: light source, lens, pinhole, lens, 7208 optic, beamsplitter. In FIG. 22, a 7208 optic could be placed in this sequence: light source, lens, 7208 optic, beamsplitter 2201. In both cases, the 7208 optic would produce multiple illumination spots in the particle dispersion and a matching set of local oscillator spots on the detector. In both cases, the scatter detector and pinhole would be replaced by an array of detectors, whose positions match the image of the multiple illumination spots and local oscillator spots on the detector array.

Figure 73:
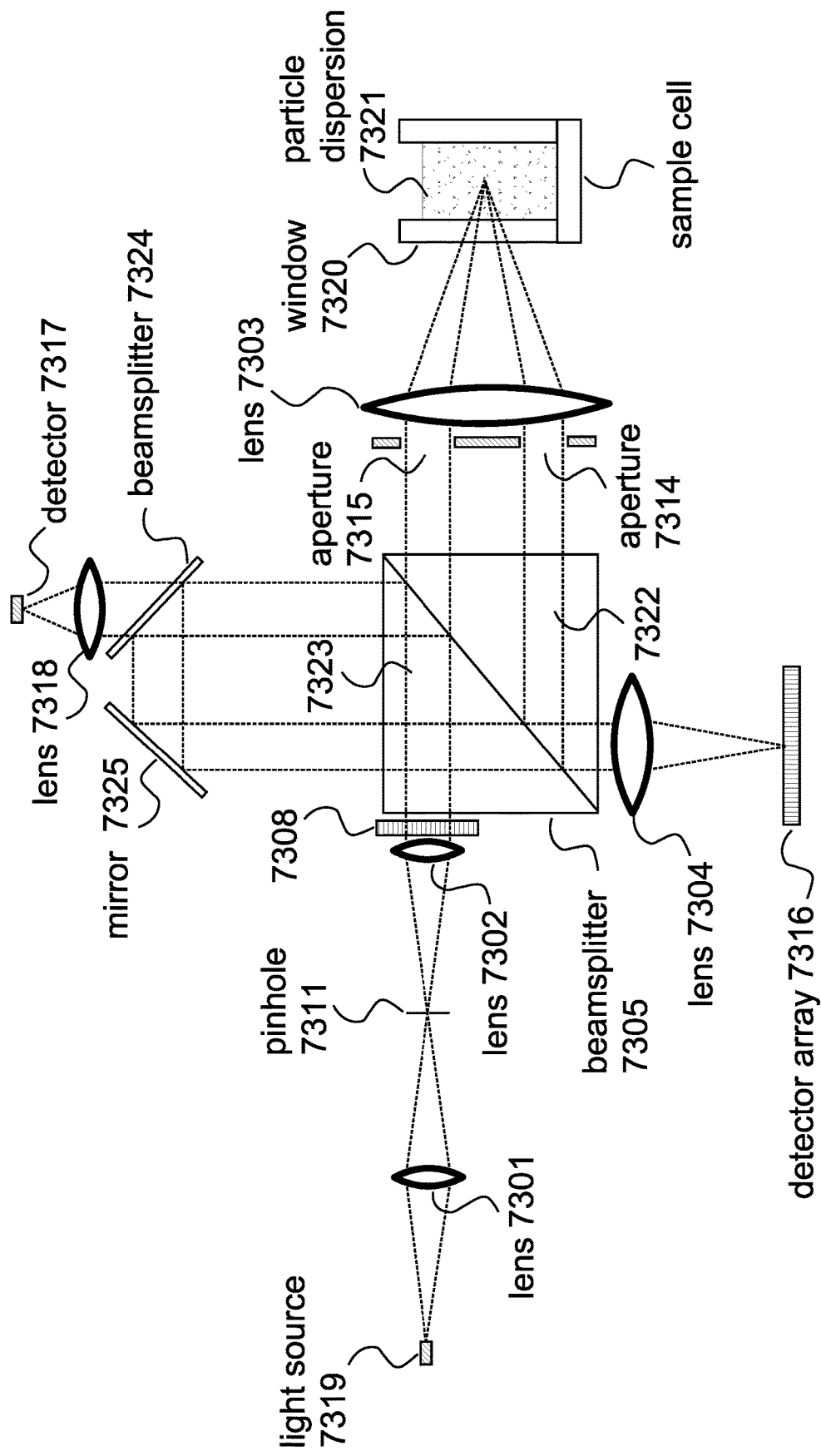
FIG. 73 provides a variation of FIG. 1, utilizing mirrors, to maintain optical alignment, with separated source and scatter beams. Multiple detectors view multiple regions within the particle dispersion.

FIG. 73 shows the combination of the concepts in FIG. 3 and FIG. 72. Scattered light is detected individually from each of at least one region in the particle dispersion. The scattered light from each region produces a current in a separate detector, in one-to-one correspondence. Each detector current can be digitized to produce a separate power spectrum or autocorrelation function of each detector current. These functions are then averaged over the group of detectors to produce a final averaged function of higher accuracy and repeatability. The averaging process comprises averaging the values at each point (frequency in the power spectrum or delay time in the autocorrelation function) in the function, over all of the detector signals. This process produces an averaged function of higher accuracy because the scattered light from each region in the particle dispersion is uncorrelated with scattered light from other regions when those regions do not overlap. A light source 7319 is focused through a pinhole 7311 by lens 7301. This pinhole 7311 removes long tails and artifacts in the intensity distribution of the light source. Lens 7302 produces a light beam which is generally collimated. This beam passes through a diffractive/refractive optic, 7308, which produces multiple illumination beams 7323 from the light beam exiting lens 7302. The optic 7308 can be constructed from optical structures, including diffractive arrays, refractive arrays (groups of prisms), and binary optics, which serve the same function as 7208 in FIG. 72. These multiple beams, which each have a different angular direction, are focused through optical window 7320 into the particle dispersion 7321 by lens 7303, after passing through optional aperture 7315. Each of these beams creates a separate focused illumination spot in the particle dispersion. Only one of these focused beams is shown in FIG. 73. Scattered light from each focused spot passes back through lens 7303, which produces a scattered beam which is generally collimated for each illumination spot. These scattered beams 7322 pass through optional aperture 7314 and are partially reflected by beamsplitter 7305 to detector array 7316, through lens 7304, which produces a focused spot on the detector array for each of the 7322 beams. Apertures 7314 and 7315 act as light baffles to control stray light, if required. Aperture 7314 also defines the scattering angle range for detection. Beamsplitter 7305 also partially reflects the illumination beams 7323 to partially reflecting mirror beamsplitter 7324 and mirror 7325, which directs the illumination beams to detector array 7316 through beamsplitter 7305 and lens 7304, which produces a focused spot on the detector array for each of the 7323 illumination beams. This partially reflected source light provides the local oscillator for heterodyne detection. The detector array 7316 is aligned with the focused spots from lens 7304, such that each focused spot of scattered light falls on a separate detector. The tilt of mirror 7325 is adjusted, such that each focused spot of illumination light also falls on a separate detector. Each detector receives an individual illumination light spot and scattered light spot, which interfere to create the heterodyne signal. Each detector size must be limited to only allow one, or at most a few, interference speckles, or coherence areas, to maximize the interferometric visibility and heterodyne signal. If detectors are large, each detector should have an aperture to limit the effective size of the detector. This concept holds for any number of detectors, including one detector, as shown in FIG. 3 without optic 7308. The partially reflecting mirror beamsplitter 7324 passes illumination light onto detector 7317, which, as detector 502, measures noise in the light source to accommodate light source noise correction techniques described in this application. Beams 7322 and 7323 can be separated so that local oscillator light does not pass back though lens 7302 to the light source.

Beamsplitter 7305 could also be split into two beamsplitters: one beamsplitter for beam 7323 and the other beamsplitter for beam 7322. Lens 7303 could also be split into two lenses, one lens for beam 7323 and the other lens for beam 7322. Then the angle between beams 7323 and 7322 could be increased so that beams could pass generally through the centers of each lens and still intersect in the particle dispersion. This configuration could produce lower optical aberrations than the single lens 7303. This concept, shown in FIG. 73, can be applied for any number of detector arrays with any number of individual detectors, including the case of one illumination spot and one single detector, without optic 7308.

Figure 74:
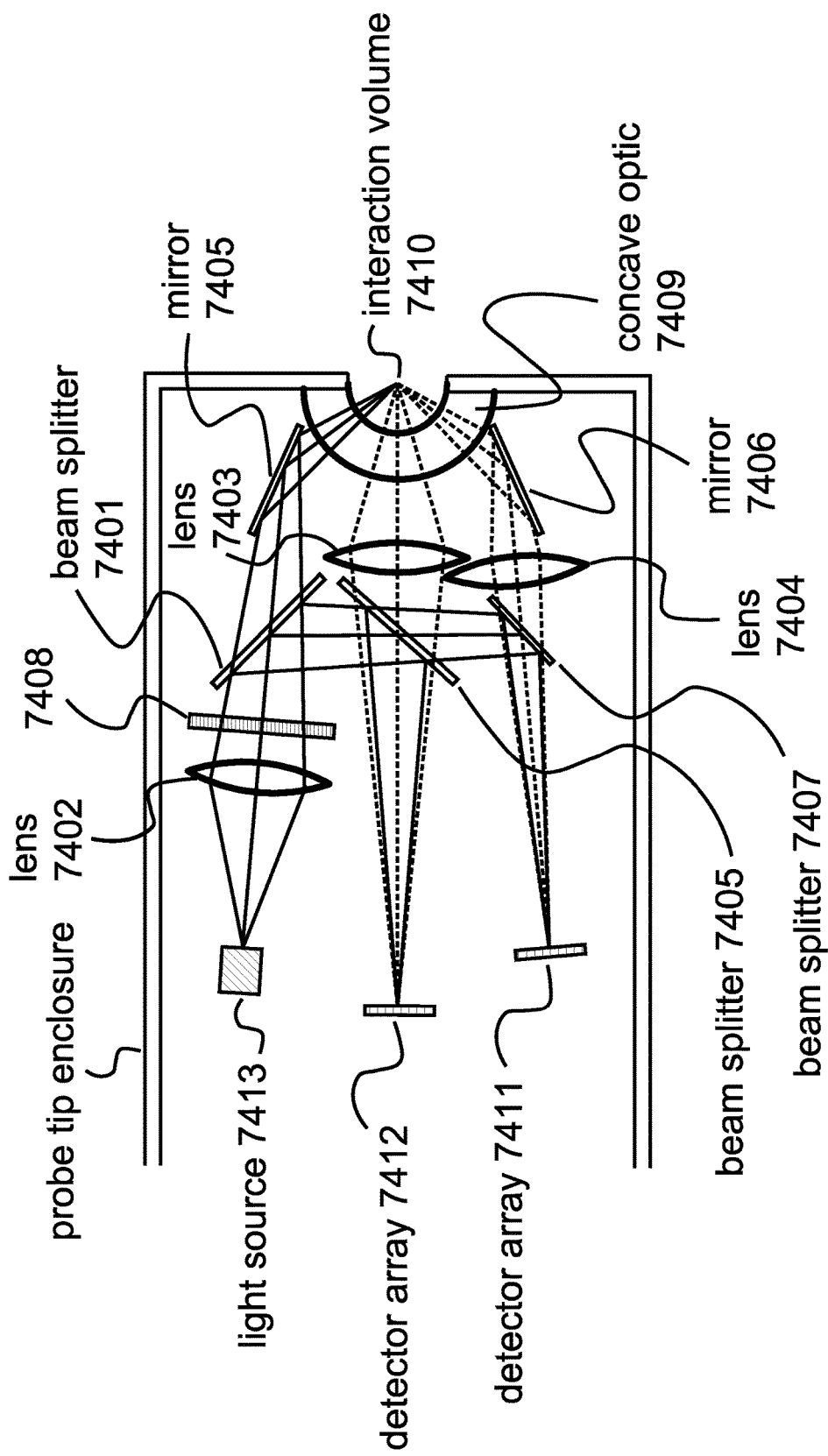
FIG. 74 provides a variation of FIG. 22, utilizing groups of detectors to detect scattered light from multiple regions within the particle dispersion and over various ranges of scattering angle.
Figure 76:
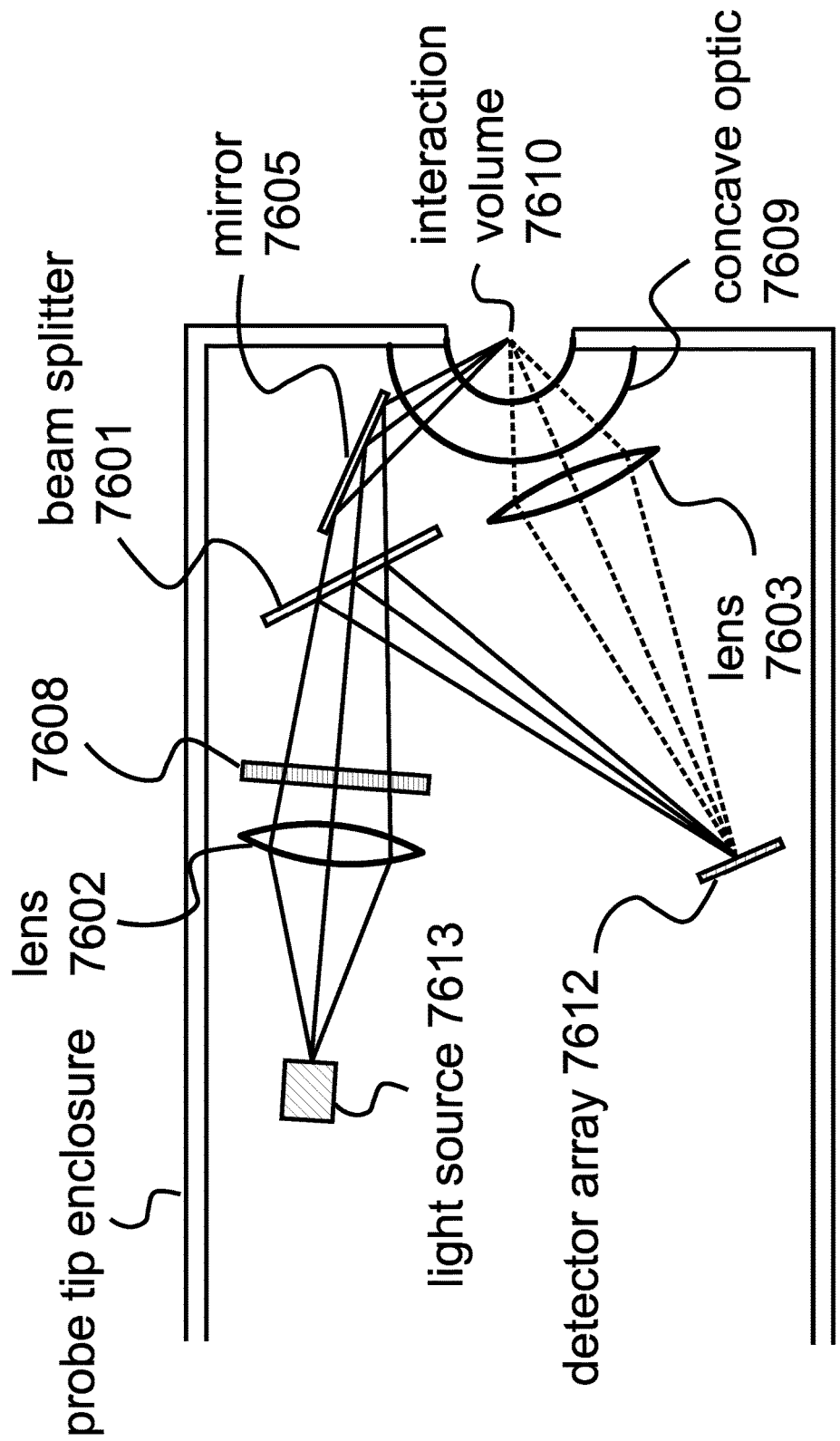
FIG. 76 provides a variation of FIG. 74, utilizing groups of detectors to detect scattered light from multiple regions within the particle dispersion and over various ranges of scattering angle, with direct reflection of source light to the scatter detector array.

FIG. 74 shows the combination of the concepts in FIG. 22 and FIG. 72. Scattered light is detected individually from each of at least one region in the particle dispersion. The scattered light from each region produces a current in a separate detector, in one-to-one correspondence. Each detector current can be digitized to produce a separate power spectrum or autocorrelation function of each detector current. These functions are then averaged over the group of detectors to produce a final averaged function of higher accuracy and repeatability. The averaging process comprises averaging the values at each point (frequency in the power spectrum or delay time in the autocorrelation function) in the function, over all of the detector signals. This process produces an averaged function of higher accuracy because the scattered light from each region in the particle dispersion is uncorrelated with scattered light from other regions when those regions do not overlap. The detector spacing is chosen to separate adjacent regions. A light source 7413 is focused into the particle dispersion, through the diffractive/refractive optic 7408, beamsplitter 7401, and mirror 7405, by lens 7402. Diffractive/refractive optic 7408 produces multiple illumination beams from the light beam exiting lens 7402. The optic 7408 can be constructed from optical structures, including diffractive arrays, refractive arrays (groups of prisms), and binary optics, which serve the same function as 7208 in FIG. 72. These multiple beams, which each have a different angular direction, are focused through concave optic 7409 into the particle dispersion, creating multiple illumination spots and interaction volumes in the particle dispersion. The concave optic has a least one concave surface, with a center of curvature coincident with the interaction volume to avoid focal shifts due to changes in dispersant refractive index. If only one dispersant is used, this concave optic could also be replaced by a flat window on the probe or the flat window of a sample cell. Each of these beams creates a separate focused illumination spot in the particle dispersion. Only one of these focused spots and interaction volumes (7410) is shown in FIG. 74. Scattered light from each focused spot passes through lenses 7403 and 7404, which focus the scattered light onto detector arrays 7412 and 7411, respectively. Each detector array, 7412 and 7411, is generally in the image plane of the illumination spots in the dispersion, through lenses 7403 and 7404, respectively. Each detector array, 7412 and 7411, is also generally in the image plane of the illumination spots from the light source 7413, through beamsplitters 7405 and 7407, respectively. Lenses 7403 and 7404 define a different range of scattering angle for each of the two detector arrays, so that each detector array measures scattered light over a different range of scattering angle. Beamsplitter 7401 also partially reflects the illumination beams from optic 7408 to partially reflecting mirrors (beamsplitters) 7405 and 7407, which direct the illumination beams to detector array 7412 and detector array 7411, respectively to provide the local oscillator for heterodyne detection. For a single detector array system, the tilt of beamsplitter 7401 could be changed to direct source light directly to the detector array 7412, allowing removal of beamsplitter 7405, as shown in FIG. 76. This may require that detector array 7412 be moved towards the position of detector array 7411, so that the source beam, reflected by beamsplitter 7401, will not contact the 7408 optic. This would also require change in position of lens 7403 to reposition the scattered light onto detector 7412. This beamsplitter tilt and beamsplitter removal modification is also applicable to single detector systems, including the system shown in FIG. 22. Each detector array is aligned with the focused spots from lens 7402, such that each focused spot of scattered light falls on a separate detector. The tilts of beamsplitters 7405 and 7407 are adjusted, such that each focused spot of illumination light also falls on a separate detector, in each detector array. Each detector receives an individual illumination light spot and scattered light spot, which interfere to create the heterodyne signal. Each detector size must be limited to only allow one, or at most a few, interference speckles, or coherence areas, to maximize the interferometric visibility and heterodyne signal. If detectors are large, each detector should have an aperture to limit the effective size of the detector. This concept holds for any number of detectors per detector array, including one detector, as shown in FIG. 22. The designs in FIGS. 73 and 74 are converted to single detector systems by removing the diffractive/refractive optic and replacing each detector array by a single detector and pinhole, as shown in FIG. 22, for example. Also, the characteristics of the interaction volume may be chosen to simplify alignment by choosing the magnification of lens 7402 and the magnifications of lenses 7403 and 7404, such that each illumination spot is either larger or smaller than the volume viewed by each detector. Then the alignment tolerance between the illumination spot and detector view, for each detector, is relaxed. This design choice is also applicable to single detector systems, as shown in FIG. 22, for example. This concept can be applied for any number of detector arrays with any number of individual detectors, including the case of one illumination spot and one single detector, without optic 7408.

Scatter measurements at multiple scattering angles can improve the accuracy of particle size measurement. The design in FIG. 74 is expanded to more than 2 detector arrays by adding more lenses with the function of 7403 and 7404 and by adding more beamsplitters with the function of 7405 and 7407.

FIG. 76 shows a modification of FIG. 74, where the source light is reflected directly onto the detector array by beamsplitter 7601, without the need for beamsplitter 7405. All of the components of similar function with those in FIG. 74 are given the same number, by replacing the 74 prefix with 76. So the description for FIG. 74 can be applied to FIG. 76, except for the function of beamsplitter 7601, which now directs source light directly onto detector array 7612. This concept can also be applied to FIG. 22, for a single detector. Multiple detector arrays and multiple scattering angles could also be employed by adding more lenses with similar function to 7603 and a beamsplitter, for each detector array, between beamsplitter 7601 and mirror 7605. Each beamsplitter would reflect source light to a different detector array. And as before, this concept can be applied for any number of detector arrays with any number of individual detectors, including the case of one illumination spot and one single detector, without optic 7608.

The equivalent of diffractive/refractive optic 7408, can be removed from any multiple detector system, including systems shown in FIGS. 72, 73, 74, and 76. Then a portion of the particle dispersion will be illuminated by a beam of generally uniform intensity. Each detector will still receive scattered light from a separate portion of the particle dispersion. And the reflected source light beam, of generally uniform intensity, will irradiate the detectors for heterodyne detection. Heterodyne detection will occur at each detector element, as shown in FIG. 71, for example.

The multiple detector ideas can be applied to many systems described previously, including FIGS. 1, 2, 3, 4, 5, 6, 7, 8, 20, and 22. The configuration of FIG. 71 can be used in these systems, without the diffractive/refractive optic, 7208. And the configuration of FIG. 72 can be used in these systems, with the diffractive/refractive optic, 7208. In each Figure, the diffractive/refractive optic, 7208, is placed between the optics of equivalent function to lens 7202 and beamsplitter 7206. Also these multiple detector systems can be used in homodyne (self-beating) mode by removal of the local oscillator reflection.

In the cases where fiber optic systems may have other advantages (such as electromagnetic immunity when using remote sensing) these designs can be changed to gain some of the advantages which are listed above. The following describes some concepts for fiber optic systems.

Fiber Optic Methods and Apparatus

Figure 10:
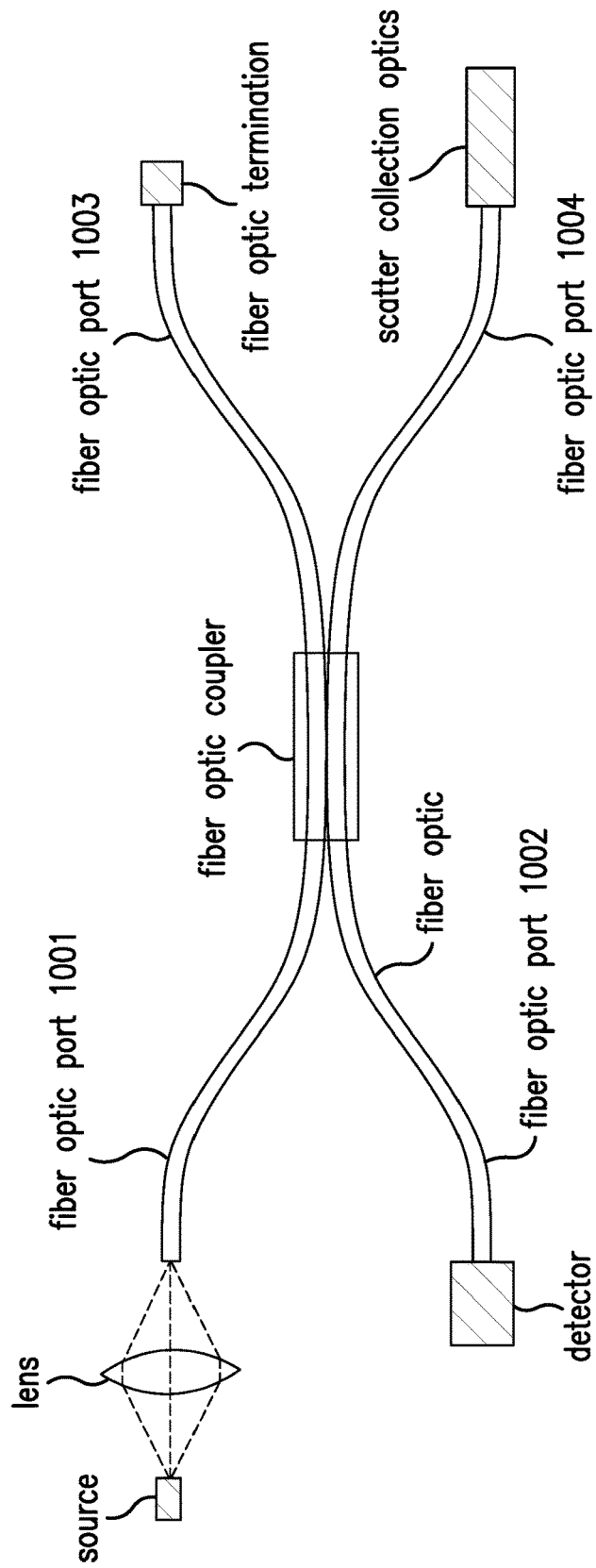
FIG. 10 provides a schematic diagram of a fiber optic system, according to the present invention, which system mixes source and scattered light to measure the motion and size distribution of particles.
Figure 36:
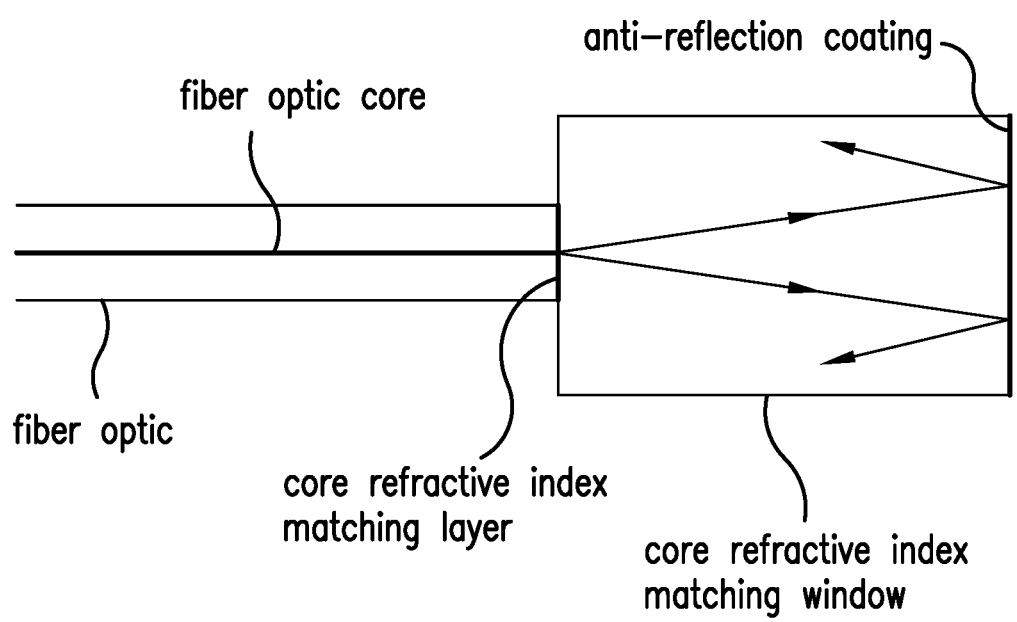
FIG. 36 shows an optical fiber termination with low back reflection, as used in the present invention.

The basic fiber optic interferometer is illustrated in FIG. 10. A light source is focused into port 1001 of a fiber optic coupler. This source light is transferred to port 1004 and light scattering optics, which focus the light into the particle dispersion and collect light scattered from the particles. This scattered light is transferred back through the fiber optic and coupler to the detector on port 1002. If the coupler has a third port, a portion of the source light also continues on to port 1003 which may provide a local oscillator with a reflective layer. If the local oscillator is not provided at port 1003, a beam dump or anti-reflective layer may be placed onto port 1003 to eliminate the reflection which may produce interferometric noise in the fiber optic interferometer. The beam dump could consist of a thick window which is attached to the tip of the fiber with transparent adhesive whose refractive index generally matches that of the fiber and the window, as shown in FIG. 36. This will reduce the amount of light which is Fresnel reflected back into the fiber at the fiber tip. The other surface of the window can be anti-reflection coated, and/or be sufficiently far (thick window) from the fiber tip, so that no light, which is reflected from that surface, can enter the fiber.

Figure 11A:
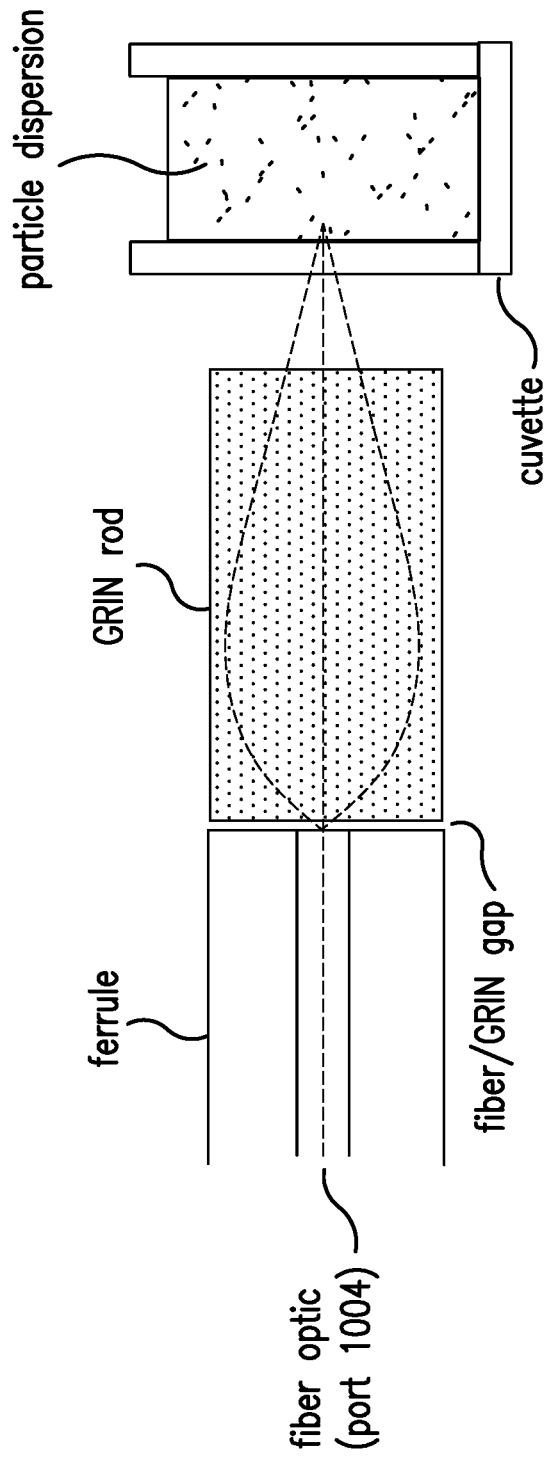
FIG. 11A shows a configuration, for port 1004 of FIG. 10, providing access to particle dispersion in a cuvette.
Figure 13:
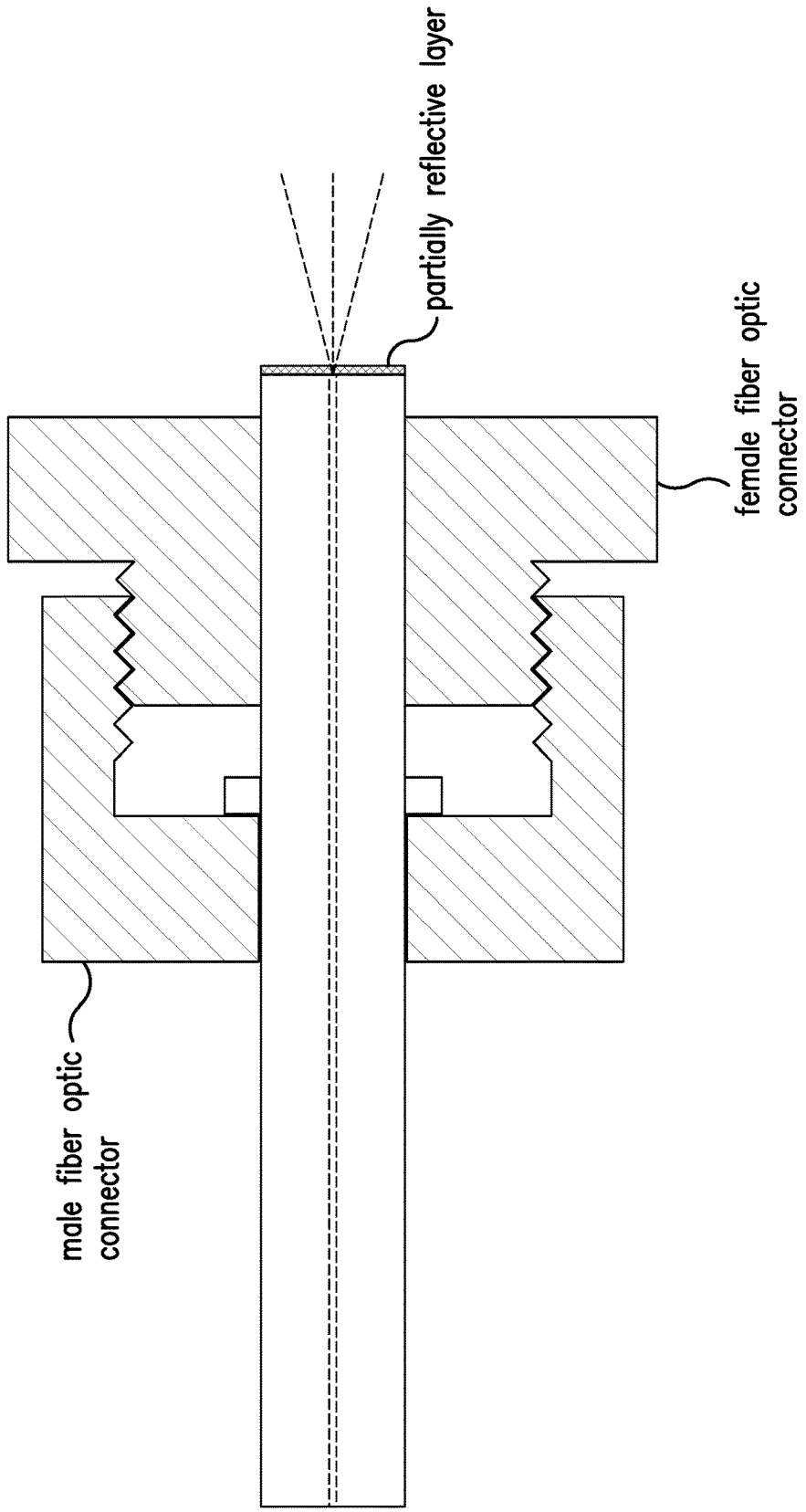
FIG. 13 shows a variation of the fiber tip design in FIG. 12, using a partially reflective layer on the fiber optic tip.
Figure 14:
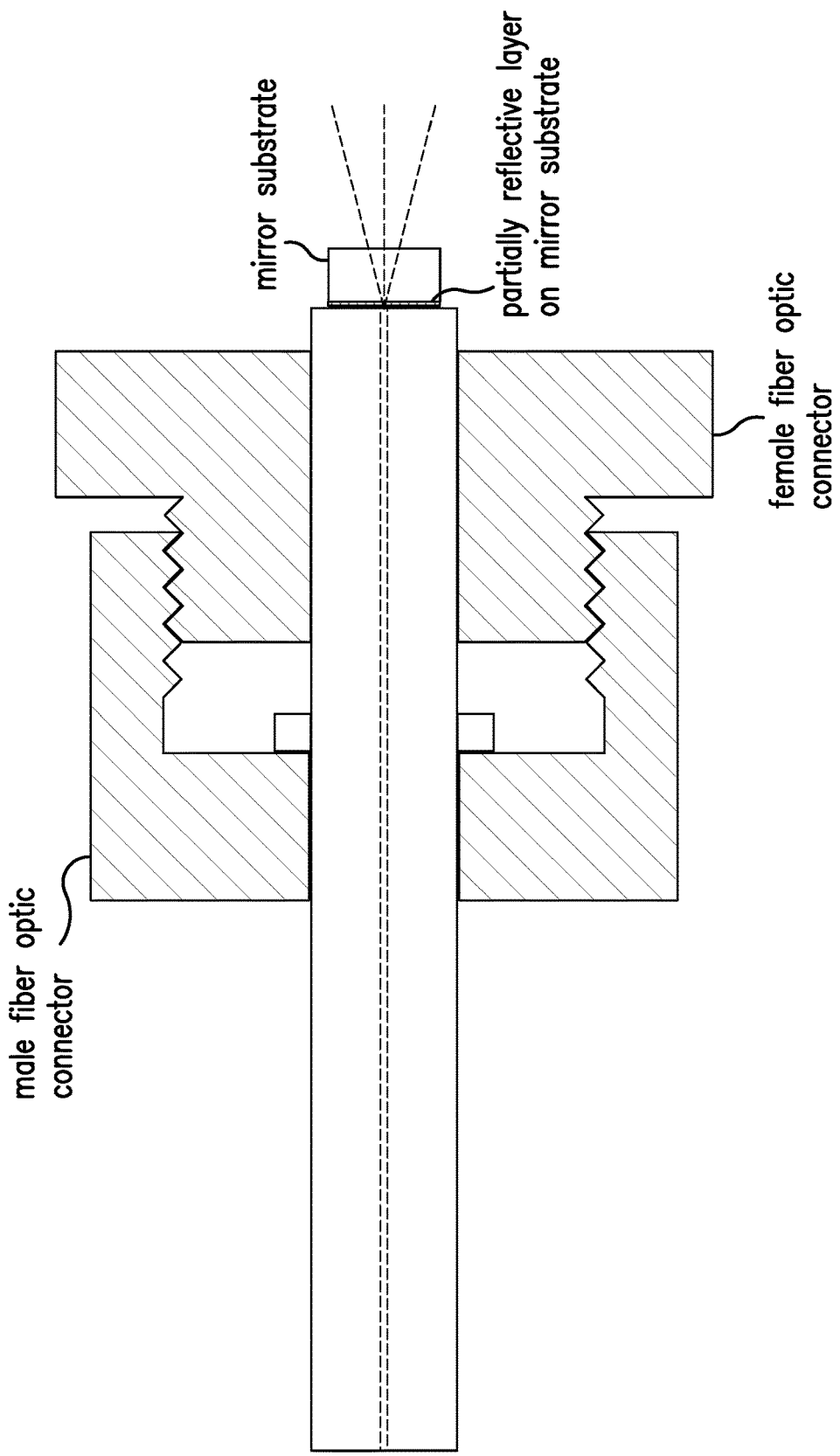
FIG. 14 shows a variation of the fiber tip design of FIG. 12, using a partially reflective layer on a transparent mirror substrate.

FIG. 11A shows one version of the scatter optics on port 1004. A lens or gradient index optic (GRIN) focuses the source light into the particle dispersion in a cuvette through a transparent wall of the cuvette. A partially-reflective layer on the tip of the fiber or on the surface of the GRIN rod, at the fiber/GRIN gap, provides the reflection for the local oscillator light to travel back through port 1004 with light scattered by the particles. If the fiber surface is partially reflecting, the GRIN surface could be anti-reflection coated or it could be placed sufficiently far from the fiber to avoid reflections from the GRIN surface back into the fiber. Reflections from both surfaces could produce an optical interferometric signal which may contaminate the heterodyning signal from the scattering particles. The GRIN rod surface, which is closest to the cuvette, could also be anti-reflection coated. The reflected source light and the scattered light, from particles in the cuvette, travel back through the coupler and are combined on the detector at port 1002. The interference between these two light components is indicative of the Brownian motion of the particles and the particle size. Since the local oscillator is generated at the exit surface of port 1003 or port 1004, as opposed to the cuvette surface, the interference signal is not degraded by small errors in the position of the cuvette surfaces, allowing use of inexpensive disposable cuvettes. The local oscillator is provided by light reflected from either port 1003 or port 1004 fiber optic (or GRIN rod surface). The reflection is provided by a partially reflective surface close to exit surface of the fiber or a layer on the fiber itself as shown in FIGS. 14 and 13, respectively. Both of these methods can be used on either port 1003 or port 1004 to create a reflection for the local oscillator. Since the partially reflecting surface is at the exit of the fiber optic, no optical alignment is required for the scattered light or the local oscillator light. This partially reflecting surface can be placed on any surface, which is conjugate to the tip of the port 1004 fiber optic.

The fiber optic port 1004 could also be immersed directly into the particle dispersion, without projection through the cuvette window. Also the GRIN rod could be designed to image the fiber optic tip at the GRIN surface, farthest from the fiber, which is then immersed directly into the particle dispersion. In either case, the local oscillator source light is provided by the Fresnel reflection at the interface between the final optical surface (either the fiber tip or GRIN surface) and the particle dispersion.

Figure 11B:
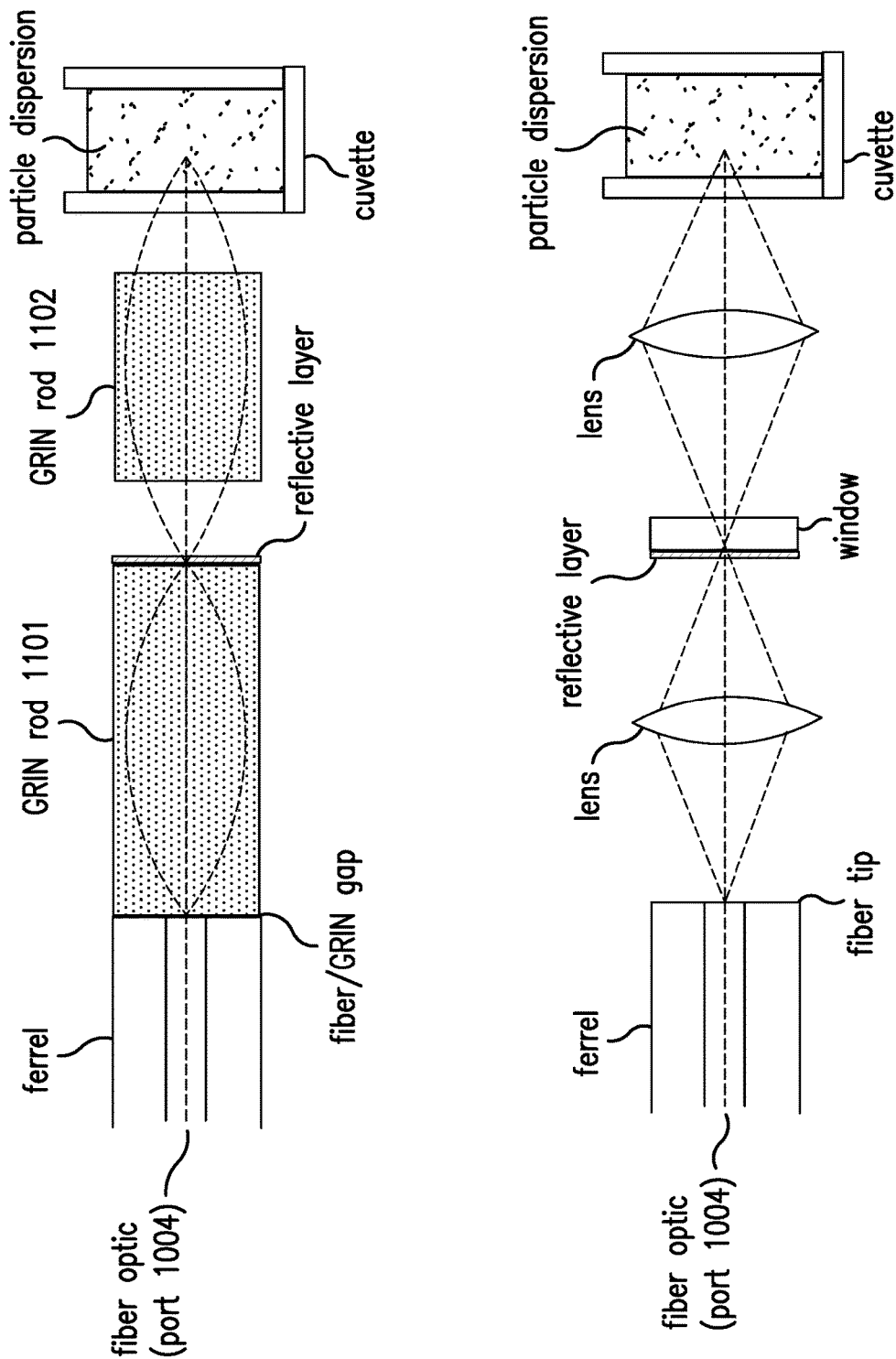
FIG. 11B shows variations of FIG. 11A, with a partially reflecting layer in an intermediate plane.

FIG. 11B shows another concept where the reflective layer is placed on the end of GRIN rod 1101, which is coated to provide the local oscillator reflection. The GRIN rod pitch is chosen so that this surface is conjugate to the fiber tip. Wide spacing, anti-reflection coating, or index matching can be used in the fiber/GRIN gap to reduce reflection at that surface. This configuration has the advantage that only GRIN rod 1101 needs to be coated. So hundreds of GRIN rods could be coated in one evaporation or sputtering operation. GRIN rod 1102 then transfers the beam into the cuvette. Conventional lenses could also be used to accomplish this design by replacing each GRIN rod with a lens and placing a planar reflecting surface at the intermediate plane which is optically conjugate to the fiber tip, as shown in FIG. 11B. Object and image planes of an optical system are conjugate to each other.

FIG. 11B also shows a conventional lens version of this idea which uses a coated window surface at the intermediate conjugate plane to create the local oscillator reflection.

Figure 12:
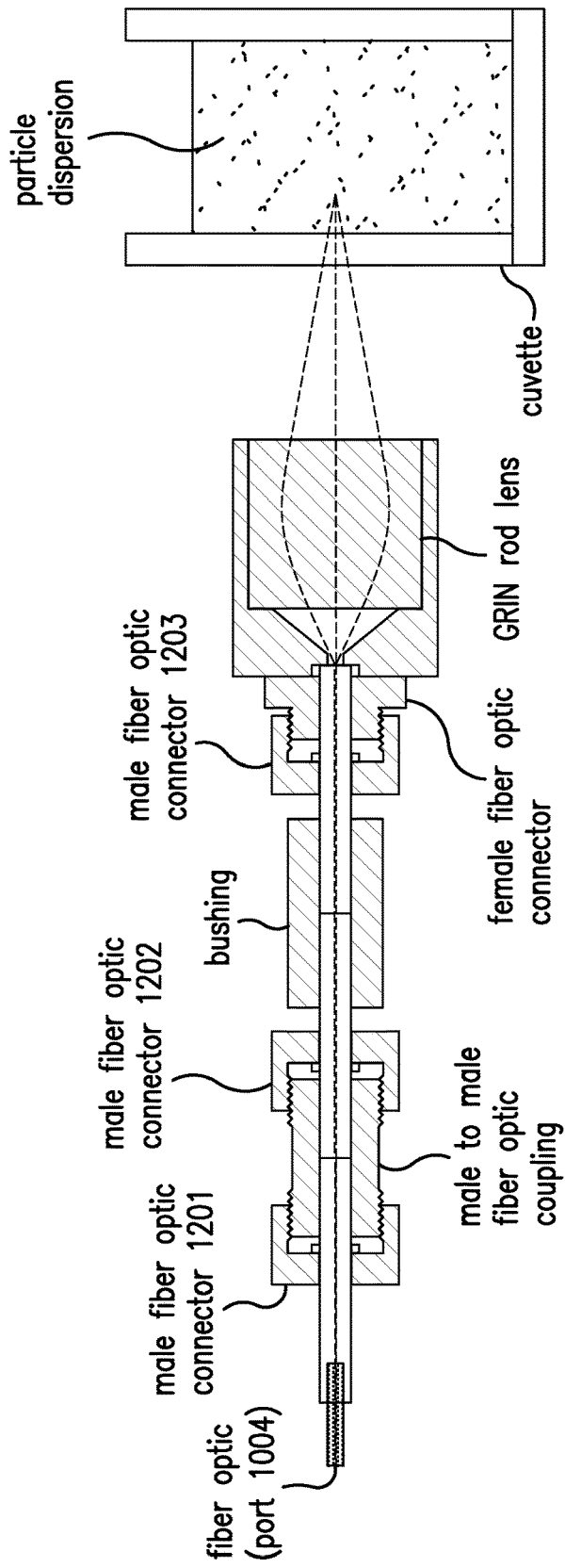
FIG. 12 shows a configuration, for port 1004 of FIG. 10, providing a partially reflecting layer on the tip of a fiber optic.

Placing a reflective layer on the tip of the fiber could require placing the entire fiber optic coupler into a vacuum chamber for evaporated or sputtered coatings. The design shown in FIG. 12 shows a fiber tip assembly which is removable from the coupler port. The fiber optic from port 1004 is connected to other fiber optics and connectors which transfer the light to a GRIN rod (or conventional optic). This GRIN rod focuses the light into the particle dispersion. This design allows many fiber tip assemblies to be placed into the sputtering chamber at one time to reduce coating costs. Only the assembly of male fiber optic connectors 1202 and 1203, or connector 1203 alone, needs to be placed into the vacuum chamber for sputtering a partially reflective layer on the tip of connector 1203. Index matching gel is placed in the gap between connectors 1201 and 1202 to reduce reflected light at these surfaces. The GRIN rod assembly with attached female connector can be removed and replaced with other assemblies containing different types of lenses to change the interaction volume (the volume of the particle dispersion which contributes to the scattered light collected by the optics and received by the detector) in the particle dispersion to control the number of particles viewed by the optics. This can be important when concentrations are low and only a few particles are in the interaction volume, producing poor signal statistics. The GRIN rod could also be replaced by a conventional lens. In either case, the lens focal length and position can be adjusted to change the interaction volume, scattering angle range, and numerical aperture (to control scattering sample depth and multiple scattering). For example, by changing the focal length of the GRIN rod and adjusting the position of the GRIN rod relative to the tip of the fiber optic, the magnification of GRIN rod is adjusted to control the size of the light beam focus in the particle dispersion. Larger beam focus size can be used at low particle concentrations to increase the number of particles in the beam and avoid signal fluctuations due to Poisson statistics of particles passing in and out of the beam. The male/male connector assembly is easily manufactured by butting two male connectors, back-to-back, through a sleeve and pushing a fiber through the entire assembly. This fiber is potted and end polished in both connectors using standard techniques.

Figure 15:
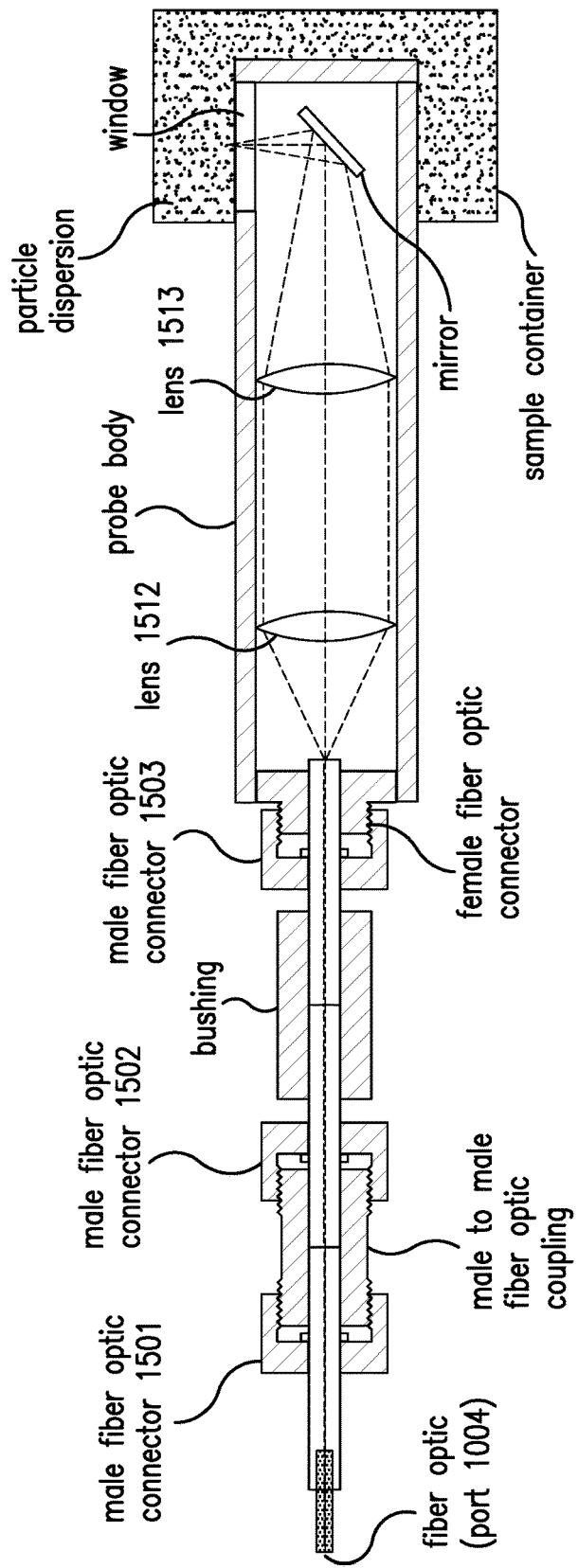
FIG. 15 shows a configuration for port 1004 of FIG. 10, utilizing a probe configuration.

Other types of optical systems could also be attached to this port. An example of a probe attachment (using a concept similar to that shown in FIG. 7), for insertion directly into the dispersion, is shown in FIG. 15. The female connector is part of the probe assembly (FIG. 15) or the standard GRIN assembly (FIG. 12); so that both of these assemblies can be interchanged onto the same coupler without any optical alignment. The source light exits the probe and enters the particle dispersion approximately perpendicular to gravity so that particles that settle out of the interaction volume are replaced by other particles which settle into the volume from above. In all of these cases, the coupling system which consists of male connectors 1502 and 1503 can be eliminated if the local oscillator is placed directly onto either the fiber tip at port 1003 or the fiber tip of male connector 1501. And in both of these assembly designs, the partially reflecting surface, for producing the local oscillator, can be placed on any surface which is conjugate to the exit tip of the port 1004 fiber optic and which is mechanically stable with respect to the port 1004 tip. One example of this surface is a flat partial reflector between lenses 1512 and 1513 in FIG. 15, or adding a second lens in FIG. 12, between the tip of the fiber optic (in fiber optic connector 1203) and the particle dispersion, to create an intermediate plane, which is conjugate to the fiber tip, where the partially reflecting surface is placed (similar to FIG. 11B). However, some optical alignment may be required in these designs.

Another attachment design could use all anti-reflection coated optics, without the partially reflecting surfaces, to completely eliminate any local oscillator source, for homodyne detection.

Also note that in all of the heterodyne designs with the local oscillator reflector in the scatter sensing arm, the optical path difference between the scatter light path and the local oscillator path (the difference between the optical path length from the local oscillator partial reflector to the detector and the scattering particle to the detector) must be less than the coherence length of the light source to provide sufficient interferometric visibility.

Figure 16:
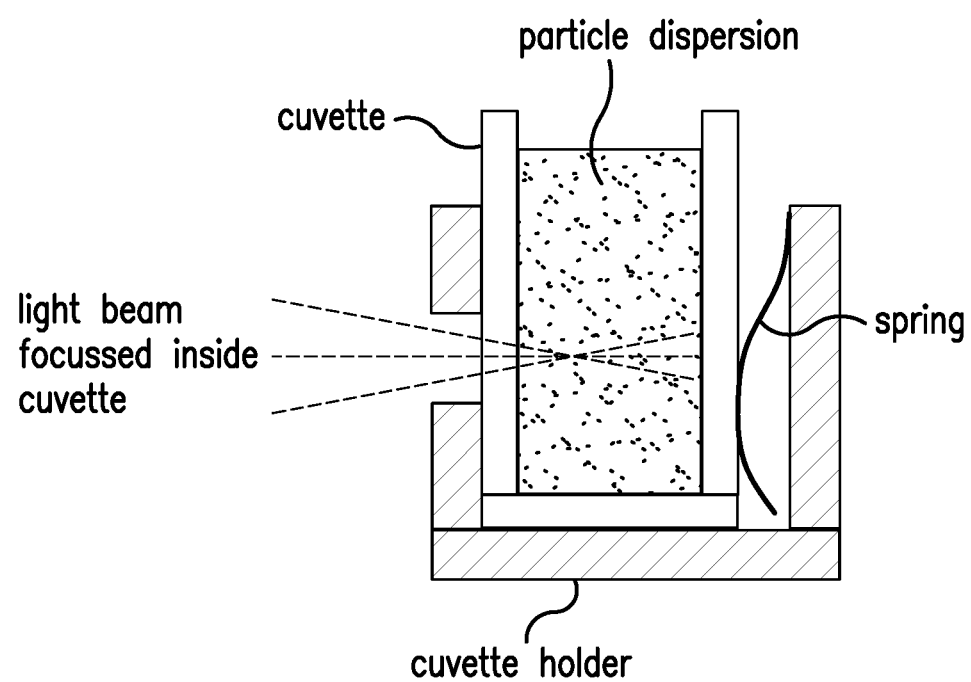
FIG. 16 shows a cuvette holder, with cuvette surface positioned inside of light beam focus, according to the present invention.

For both the fiber optic and non-fiber optic systems, the local oscillator reflection can be generated at appropriate surfaces, such as those described previously. All other surfaces may be tilted and/or anti-reflection coated so as to contribute minimal interferometric signal on the detector. In both the fiber and non-fiber systems, the source beam is focused within the cuvette (or sample cell). If the focused point is far into in the dispersion (see FIG. 16), the local oscillator reflection must be created at another surface (other than the cuvette/dispersion interface) as described above. In any case, a spring could be employed to press the cuvette against a registration surface, as shown in FIG. 16, to firmly register and position the cuvette. The spring could also be replaced by a clamping screw to avoid the low frequency mechanical resonances of the spring. The cuvette (and cuvette holder) must be mechanically registered to the optical system for two reasons. If the cuvette surface reflection generates the local oscillator, movement of the surface will create interferometric noise. If the local oscillator is produced by another partially reflective surface as described above, and the cuvette is far from the beam focus as shown in FIG. 16, then stability of the cuvette will reduce the interferometric noise caused by the small amount of reflected light, from the cuvette window surface, which passes though the optical fiber (or pinhole 112 in FIG. 1) and creates an optical interference signal with the local oscillator. Also if the cuvette and/or the particles move relative to the optics due to mechanical vibration, non-Brownian Doppler shifts of the scattered light will be detected and will confound the size determination.

Figure 17:
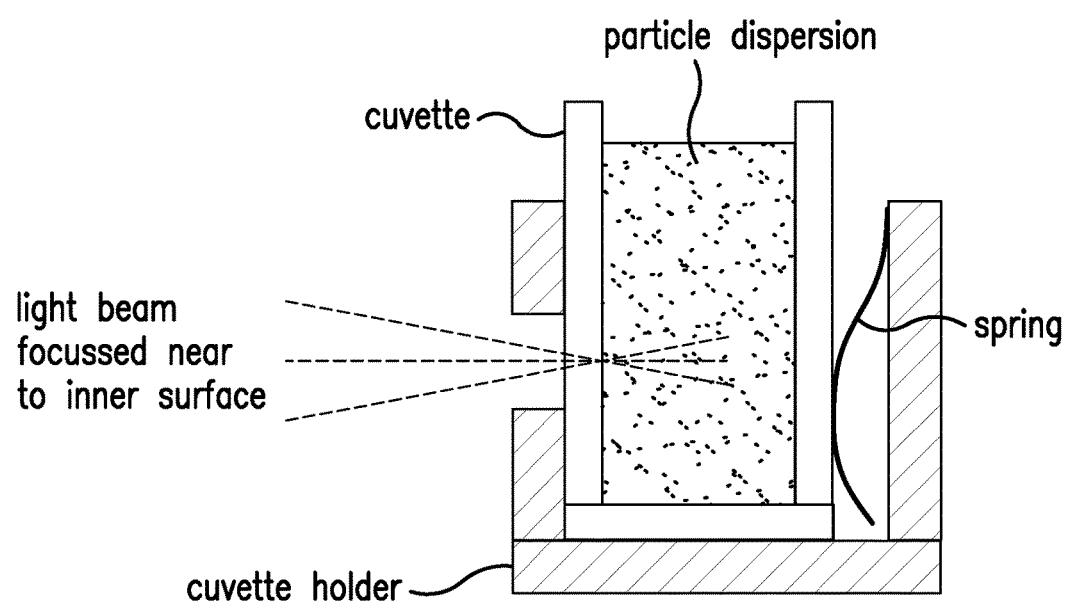
FIG. 17 shows a cuvette holder, with cuvette surface positioned near to a light beam focus, according to the present invention.
Figure 18:
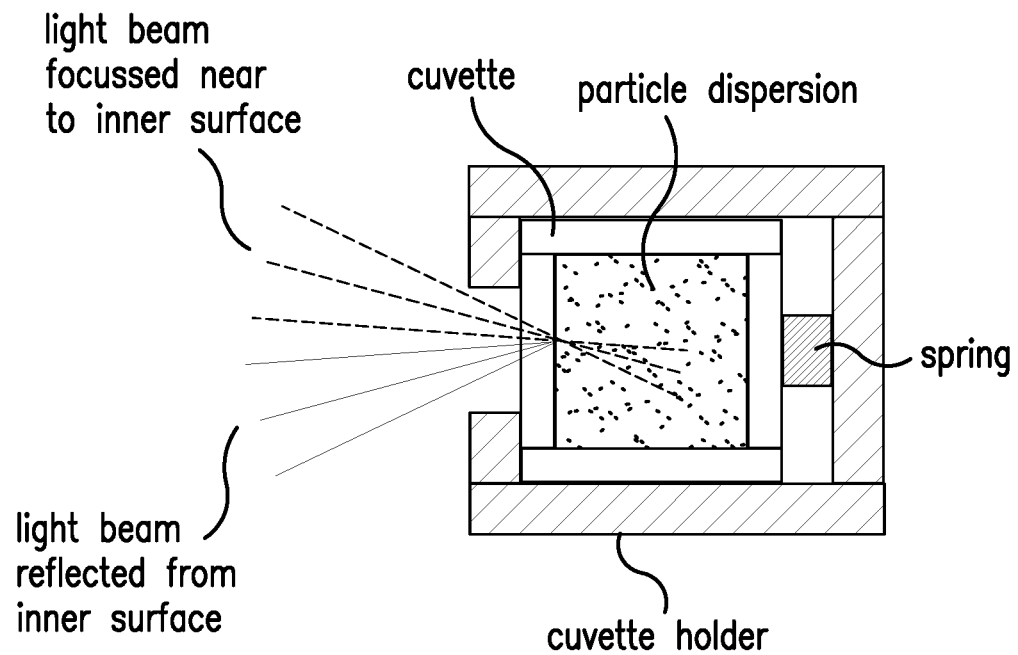
FIG. 18 shows another view of FIG. 17, utilizing beam tilt to reduce light reflected back into the optical system.

This positional registration is even more critical when the beam focus is at the inner surface of the cuvette (the surface contacting the dispersion) and the reflection from that surface is used to generate the local oscillator (see FIG. 17). Then any motion of the cuvette will create interferometric noise in the heterodyne signal. So the cuvette must be pinned against a reference surface as shown in FIG. 17, where a spring holds the cuvette against an inner surface of the cuvette holder. The beam focus might be placed close to this inner surface to either provide the local oscillator by reflection from that surface or to reduce multiple scattering into the pinhole 112 or fiber optic. If the only reason is to reduce multiple scattering and the local oscillator reflection is produced at another surface (other than the cuvette/dispersion interface), then the incident light beam might approach the cuvette at a non-normal incidence angle (see FIG. 18 which is the top view of FIG. 17) so that the reflected light from that inner surface cannot pass back through the optical system and through the pinhole or fiber to the detector. All reflected light, except for the local oscillator reflection, should be suppressed to reduce interferometric noise from mechanical vibrations and from laser phase noise, and to reduce reflections back into a laser source to reduce laser noise. In any case, where no cuvette surfaces are used to reflect source light for the local oscillator, the cuvette should be tilted to divert the cuvette window reflected light away from the detector. If the light beam is tilted relative to the perpendicular of the gravitational direction, the tilt should be in a plane perpendicular to the settling direction of the particles to avoid Doppler shifts in the detector current spectrum due to the settling velocity, when measuring Brownian motion.

Figure 19:
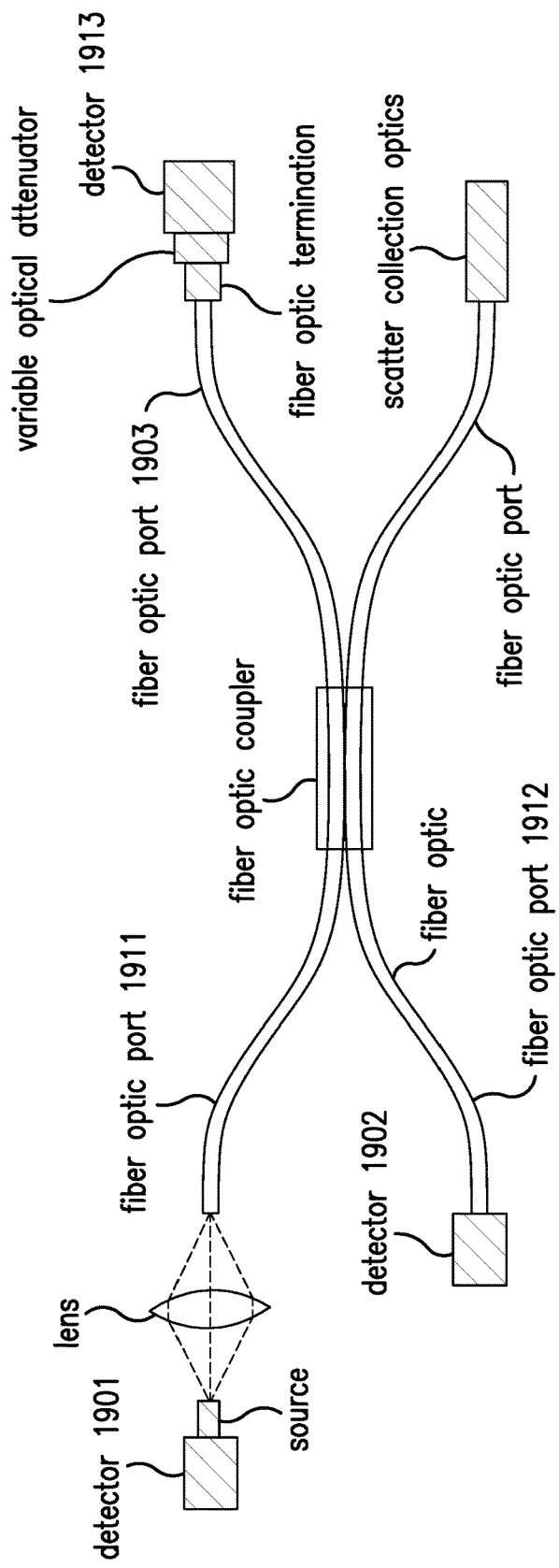
FIG. 19 shows a variation of FIG. 10, coupling a variable optical attenuator and detector to fiber optic port 1903.

For small particles, the heterodyne signals will be buried in laser source noise. FIG. 5, FIG. 6, and FIG. 7 show detectors 501, 601,701, which measure the heterodyne signal from the particles. In FIG. 19, detector 1902 is the heterodyne detector. FIG. 5, FIG. 6, and FIG. 7 show additional detectors 502, 602, 702, which measure the intensity of the local oscillator laser noise. FIG. 19 also shows additional detectors, detector 1901 (the detector on the light source) and detector 1913 (a laser power monitor on port 1903 of the fiber coupler). Any of these additional detectors, or any detector which monitors the laser power, can be used to monitor the laser noise. Another possibility is to monitor the light that has passed through the particle dispersion by placing a detector in the sample cell area. In any event, if we define a heterodyne detector current as I1 and the laser monitor detector current as I2 we obtain the following equations which hold for each of the heterodyne detectors.

$$I1 = sqrt(R*R*T*Rm*Io(t)*Is(t))*COS(F*t+A) + R*T*Rm*Io$$

$$I1 = sqrt(R*R*T*Rm*Io(t)*S*R*T*Io)*COS(F*t+A) + R*T*Rm*Io$$

$$I2 = K*R*Tm*Io(t)$$

where:
I1 and I2 are normalized (detector responsivity=1).
COS(x)=cosine of x
The symbol * indicates multiply
K is a constant which describes the ratio of other efficiencies (optical and electrical), between the I1 and I2 channels, which are not due to the beamsplitter and partial reflecting mirror.
R and T are the reflectivity and transmission of the beamsplitter, respectively.
Rm and Tm are the reflectivity and transmission of the partially reflecting mirror, respectively.
sqrt(x)=square root of x
Io(t) is the source beam intensity as function of time t
F is the heterodyne beat frequency at a heterodyne detector due to the motion of the scatterer which produces Is(t). And A is an arbitrary phase angle for the particular particle.
Is(t) is the scattered light intensity from the particle:
Is(t)=S*R*T*Io(t) where S is the scattering efficiency for the particle. S includes the product of the scattered intensity per incident intensity and optical scatter collection efficiency.
The light source intensity will consist of a constant portion Ioc and noise n(t):

$$Io(t) = Ioc + n(t)$$

We may then rewrite equations for I1 and I2:

$$I1 = R*T*sqrt(S*R*Rm*(Ioc+n(t))*COS(F*t+A) + R*T*Rm*(Ioc+n(t))$$

$$I2 = K*R*Tm*(Ioc+n(t))$$

If we use high pass filters to accept only the higher frequencies, which contain the size information, we obtain high pass signals for I1 and I2:

$$I1hp = R*T*sqrt(S*R*Rm)*Ioc*COS(F*t+A) + R*T*Rm*n(t)$$

$$I2hp = K*R*Tm*n(t)$$

Where we have assumed that n(t) is much smaller than Ioc. And also n(t) is the portion of the laser noise that is passed by the high pass filter bandwidth (see below). In certain situations, these high pass filters are replaced by band pass filters which only pass frequencies carrying particle information.

The laser noise can be removed to produce the pure heterodyne signal, Idiff, through the following relationship:

$$Idiff = I1hp - (T*Rm)/(K*Tm)*I2hp = R*T*Sqrt(S*R*Rm)*Ioc*COS(F*t+A)$$

This relationship is realized by high pass filtering each of the I1 and I2 detector currents. One or both of these filtered signals are amplified by programmable amplifiers, whose gains and phase shifts are adjustable. The difference of the two outputs of these amplifiers is generated by a difference circuit or differential amplifier. With no particles in the beam, the gain and phase shift of at least one of the programmable amplifiers is adjusted, under computer or manual control, to minimize the output of the difference circuit. At this minimum, the theoretical gain ratio, (gain of I2)/(gain of I1)=T*Rm/(K*Tm), should be obtained. At this gain, the source intensity noise component in the heterodyne detector beat signal, with particles present, is removed in the difference signal, which is fed to an analog to digital converter (A/D), for inversion to particle size.

This entire correction could be accomplished in the computer by using a separate A/D for each filtered signal and doing the difference by digital computation inside the computer. The phase and gain adjustments mentioned above, without particles in the beam, could be accomplished digitally. Then the coefficient ratio R/K can be calculated to be used in the equation for Idiff, using the following equation:

$$T*Rm/(K*Tm) = I1dc/I2dc$$

Where I1dc and I2dc are the DC offsets of the unfiltered signals I1 and I2, respectively.

If both signals were digitized separately, other correlation techniques could be used to reduce the effects of source intensity noise. In any case, the beamsplitter reflection is adjusted to obtain shot noise limited heterodyne detection, with excess laser noise removed by the difference circuit or difference calculation shown above.

These noise correction techniques can be applied to any heterodyning system by simply adjusting the filtering of currents I1 and I2 to pass the signal of interest, while blocking the generally zero frequency component (Ioc) of Io(t). Excess laser noise and other noise components, which are present in both the heterodyne signal and the light source, can be removed from the signal of interest through this procedure. One application is dynamic light scattering, where the heterodyne signal is contaminated by laser source noise in the optical mixing process. The filters on I1 and I2 would be designed to pass the important portion of the Doppler broadened spectrum and to remove the large signal offset due to the local oscillator. Then by using the subtraction equation for Idiff, described previously, the effects of laser noise can be removed from the Doppler spectrum, improving the particle size accuracy. In the case of fiber optic heterodyning systems, the laser monitor current, I2, could be obtained at the exit of the unused output port (port 1903 in FIG. 19) of the fiber optic coupler which is used to transport the light to and from the particle sample, because this port carries light only from the optical source, without any scattered light. I2 could also be obtained from the laser detector (for example the detector on a light source as shown by detector 1901 in FIG. 19). This subtraction for Idiff could be accomplished by the analog difference circuit or by digital subtraction after digitization of both the filtered contaminated heterodyne signal and the filtered source monitor as outlined previously. This procedure could also be accomplished using the unfiltered signals, but with much poorer accuracy due to the large signal offsets.

Using FIG. 19 we can describe another version of this correction which simply measures the power spectrum at port 1912 (detector 1902) and port 1903 (detector 1913) in FIG. 19. The signal at port 1911 (detector 1901) could also be used in place of the detector 1913 signal. Also the signals at port 1912 and port 1903 in FIG. 19 could be replaced by the signals at detectors 501, 601, 701 (1912) and detectors 502, 602, 702 (1903) respectively, in FIGS. 5, 6, and 7. Let us define the following power spectrum measurements, which are all functions of frequency:

P2bkg=power spectrum measured at port 1912 with clean dispersant (without particles) in the sample region P3bkg=power spectrum measured at port 1903, while P2bkg is being measured on port 1912

P2meas=power spectrum measured at port 1912 from the particle dispersion (with particles) in the sample region P3meas=power spectrum measured at port 1903, while P2meas is being measured on port 1912

I3dc=DC offset, constant portion, or mean of signal producing P3meas

I2dc=DC offset, constant portion, or mean of signal producing P2meas

Then the measured power spectrum, P2meas, can be corrected for the background power spectrum and the drift in the background power spectrum by using the following equations, where P(f~0) is the power spectral density at frequencies close and equal to zero:

$$Pcorrected = P2meas - P2bkg - ((I2dc/I3dc)^2)*(P3meas - P3bkg)$$

or $$Pcorrected = P2meas - P2bkg - (P2meas(f\sim 0)/P3meas(f\sim 0))*(P3meas - P3bkg)$$

All of the power spectra are functions of frequency, so these mathematical operations are done at each frequency. The background corrected power spectrum, Pcorrected, would then be inverted to obtain the particle size distribution.

The correction described previously for Idiff removes common mode noise between the scattered heterodyne signal and the laser monitor. This correction is made directly to the signal. While this technique is useful in the case of dynamic light scattering and many other heterodyne systems, another method may be more easily implemented to correct the power spectrum in dynamic light scattering, for the noise component due to laser noise. In most cases the local oscillator is adjusted to provide shot noise limited detection, However, usually some excess laser noise (included in laser noise in the following description), beyond the shot noise, is observed. We will start with some definitions for power spectral densities which are all functions of frequency f:

Psd=total power spectral density of the scattering detector (detectors 501, 601, 701 for FIGS. 5, 6, and 7 and detector 1902 for FIG. 19)

Psc=power spectral density component of the scattering detector current due to particle scattering Pssh=shot noise component of power spectral density of the scattering detector Psls=laser noise component of power spectral density of the scattering detector Pld=total power spectral density of the laser monitor detector (detectors 502, 602, 702 for FIGS. 5, 6, and 7 and detector 1901 or 1913 for FIG. 19)

Plsh=shot noise component of power spectral density of the laser monitor detector Plls=laser noise component of power spectral density of the laser monitor detector Ios=mean detector current of the scattering detector Iol=mean detector current of the laser monitor detector Pssh=2*e*(Ios) (scatter detector shot noise)

Plsh=2*e*(Iol) (laser monitor detector shot noise)

Where e is the electron charge

Psls=B*g(f,ic)*((Ios)^2) (scatter detector laser noise component)

Plls=B*g(f,ic)*((Iol)^2) (laser monitor detector laser noise component)

Since these noise sources and scattering signals are uncorrelated, the following equations hold:

$$Psd = Psc + Pssh + Psls$$

$$Pld = Plsh + Plls$$

$$Psd = (Psc + 2*e*(Ios) + B*g(f,ic)*((Ios)^2))*Gs(f)$$

$$Pld = (2*e*(Iol) + B*g(f,ic)*((Iol)^2))*Gl(f)$$

Where B is a constant, which describes the ratio of noise power to square of the average current, and g(f,ic) is the spectral function for laser noise, f is frequency and ic is laser current. Gs(f) and Gl(f) are the electronic spectral gain of the detector electronics for the scatter detector and laser monitor detector, respectively.

From these last two equations, we want to determine Psc, the power spectrum component due to the light scattered from the particles. Solving these two equations for Psc, we can obtain two versions of the solution:

$$Psc(f) = (Psd(f)/Gs(f)) - (2*e*(Ios)) - (((Pld(f)/Gl(f)) - (2*e*(Iol)))*((Ios)^2)/((Iol)^2))$$

$$Psc(f) = (Psd(f)/Gs(f)) - (Pld(f)/Gl(0) - (2*e*(Ios-Iol))) - B*g(f,ic)*((Ios^2) - (Iol^2))$$

The first version of solutions is more useful, because knowledge of B*g(f,ic) is not required. This equation assumes that the excess laser induced amplitude noise (noise in excess of the shot noise) is proportional to the mean detector current due to the laser. This assumption is described by the proportionality to the square of the mean detector currents of power spectral density in the following equations:

Psls=B*g(f,i)*((Ios)^2) (scatter detector laser noise component)

Plls=B*g(f,i)*((Iol)^2) (laser monitor detector laser noise component)

However, in general the excess noise components may have a more complicated and unknown dependence given by the function gn:

Psls=B*gn(f,i,Ios) (scatter detector laser noise component)

Plls=B*gn(f,i,Iol) (laser monitor detector laser noise component)

In this case, the functional dependence gn(f,i,I) could be determined by measuring Psls and Plls at various levels of Ios and Iol. Since the function gn(f,i,I) could possibly change between lasers, an easier method is to adjust the mean detector currents, Ios and Iol, to be equal with a variable optical attenuator, such as two polarizers with adjustable rotation angles. This attenuator could be placed on front of either the heterodyne detector or the laser monitor detector (as shown by detector 1913 in FIG. 19 for example). When Ios and Iol are made equal, we obtain:

$$Psc=(Psd/Gs(f))-((Pld/Gl(f))$$

Another method is to measure Psd and Pld without any particles in the beam and calculate the ratio RT as a function of frequency:

RT(f)=Psd(f)/Pld(f) measured without particles in the sample volume

Then Psc(f)=Psd(f)−(RT(f)*Pld(f)) measured with particles in the sample volume

This is only an estimate to the true correction, but it may work well in cases where the excess noise and mean detector currents do not vary significantly.

In heterodyne detection of scattered light, the measured power spectrum of the scatter detector current is corrected for the background noise by measuring the background signal spectrum without the presence of particles in the light beam. This background spectrum is then subtracted from the spectrum measured when particles are present. However this correction will not be precise when the laser power or system optical losses drift between the scatter and background measurements. In most cases the local oscillator is adjusted to provide shot noise limited detection, However, usually some excess laser noise (called laser noise in the following description), beyond the shot noise, is observed. From the equation derived previously:

$$Psd=Psc+Pssh+Psls$$

$$Psd=Psc+2*e*(Ios)+B*g(f,Ios)*((Ios)\hat{}2)$$

Where B is a constant and g(f,Ios) is the spectral function for laser noise, f is frequency.

In most cases, Ios is primarily due to the local oscillator, used for heterodyne detection, which is proportional to the laser intensity corrected for system losses. If the laser intensity or system losses drift between when the background and scatter signals are measured, then we have:

Psdbk is the background Psd measured (with no particles), with average <Ios>=Iosa during the measurement of Psdbk. (where <x> means time average of x)

$$Psdbk=2*e*(Iosa)+B*g(f,Iosa)*((Iosa)\hat{}2) \quad 1)$$

Psdp is Psd with particles present, with average <Ios>=Iosb during the measurement of Psdp $$Psdp=Psc+2*e*(Iosb)+B*g(f,Iosb)*((Iosb)\hat{}2) \quad 2)$$

If we assume that Iosb and Iosa are sufficiently close so that g(f,Iosa)=g(f,Iosb)=g(f), then, solving equations 1 and 2 for Psdp to eliminate B and g(f) we obtain:

$$Psdp=Psc+2*e*(Iosb)+((Psdbk-(2*e*Iosa))*(Iosb\hat{}2)/(Iosa\hat{}2))$$

And the power spectral density due to particle scatter is:

$$Psc=Psdp-(2*e*(Iosb)+((Psdbk-(2*e*Iosa))*(Iosb\hat{}2)/(Iosa\hat{}2)))$$

This method can be used on each measurement of Psdp from a set of Psdp's measured from the same particle sample, and using the initial Psdbk. Each Psdp measurement would be corrected for the value of Iosb for that particular Psdp measurement, using the above equation for Psc. Then all of these Psc's would be summed together to produce the final particle scatter spectrum. If the data collection period for each Psdp is short, Ios will not change significantly during the averaging process to obtain an accurate value for Iosb=<Ios>. Then for the ith Psdp (Psdpi) and corresponding Iosb (Iosbi), the corresponding Psc (Psci) becomes:

$$Psci=Psdpi-(2*e*(Iosbi)+((Psdbk-(2*e*Iosa))*(Iosbi\hat{}2)/(Iosa\hat{}2)))$$

And Psc=SUMi(Psci) where SUMi is sum over index i
When the laser noise is much larger than the shot noise:

$$Psci=Psdpi-(Psdbk*(Iosbi\hat{}2)/(Iosa\hat{}2))$$

If Ios is generally constant over each data collection period, Iosbi could be measured at the start and end of the each period, with averaging of the two measurements; or use only one of these two measurements. The same could be done for Iosa during the period of measurement for Iosa.

Notice: any products, divisions, additions, or subtractions in this document between functions (or vectors) are assumed to be inner operations (i.e. the function(x) values at each value of x are multiplied, divided, added, or subtracted).

The noise correction can also be determined from background measurements and assumptions for the form of the power spectral density for the particles and for the noise. The power spectrum of the scatter detector current from particles under Brownian motion takes the form:

$$P(f)=4*Io*Is*(K/pi)/(f\hat{}2+I(\hat{}2) \text{ for particles of a single size}$$

Where
x^2 is the square of quantity x
pi is constant pi
P(f) is the power spectral density of the detector current
f is the frequency of the detector current
Io is the detector current due to the local oscillator intensity
Is is the detector current due to the mean scattered light intensity
K is a constant which is particle size dependent
The total power spectral density measured from a group of particles is given by:

$$Pt(f)=SUMj(4*Io*Isj*(Kj/pi)/(f\hat{}2+Kj\hat{}2))+Pb(f)$$

Where the SUMj is over each jth particle with scattering Isj and constant Kj.

Pb(f) is the power spectral density of the detector current due to background such as excess laser noise and shot noise. Pb(f) is usually measured by scatter from clean dispersant without particles. Examination of these equations provides the following approximations:

$$Pt(\infty)=Pb(f\sim\infty)$$

Pb(∞)=B at high frequencies, if the background spectrum is white
The spectral density Pb=constant at very high frequencies
Pt(~∞)=A/(f^2+C)+B at moderately high frequencies f>>Kj
Where A, B, and C are constants to be determined.

Figure 24:
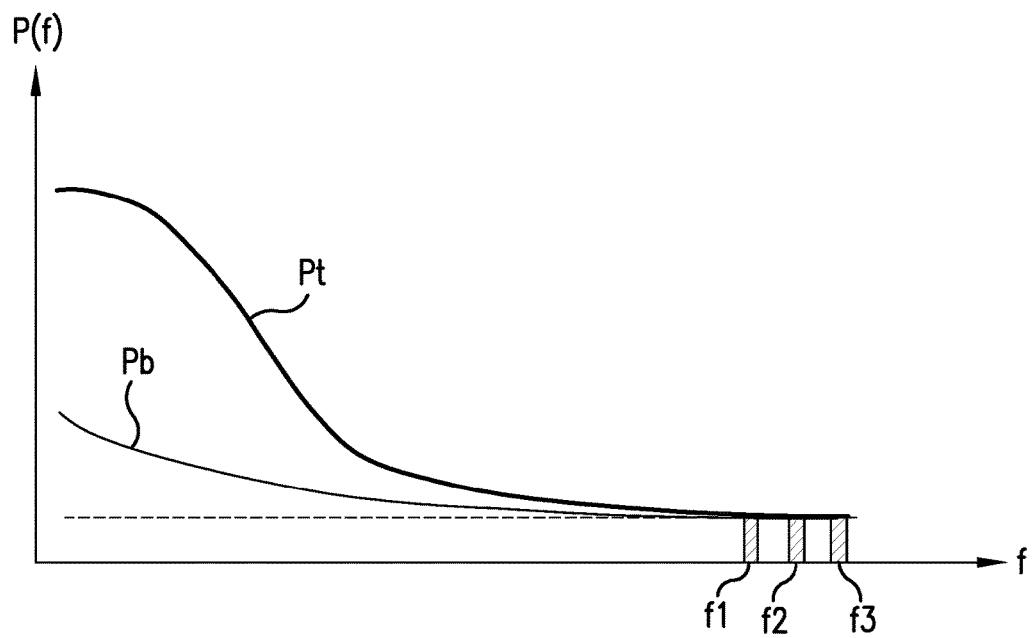
FIG. 24 shows plots of the power spectrum and background power spectrum measured from detecting the mixture of source and scattered light, according to the present invention.
Figure 24:
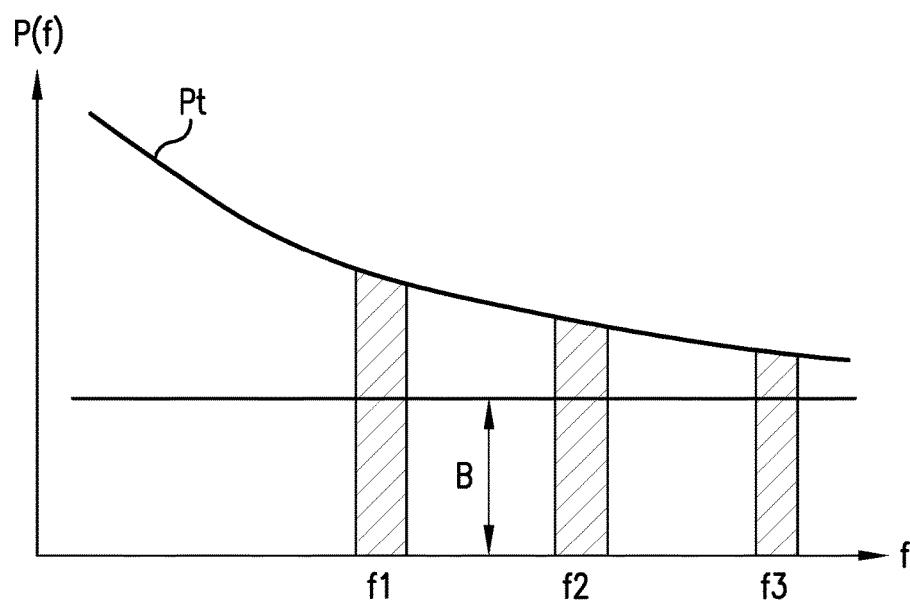

This dependence is illustrated in FIG. 24, which shows the measurement of Pt(f) in three different frequency bands. This can be accomplished by integration of the digitally generated power spectral density over these frequency bands or by using analog electronic filters and RMS modules to measure the power in the bands. These bands must be chosen at frequencies where the approximations, which are shown above, hold. The analog filters have an advantage, over digitally generated power spectrum measurements, that they can be placed at very high frequencies without affecting the design of the analog to digital converter and FFT algorithm used to measure the lower frequency power spectrum of the scatter signal from the particles. Then we can solve for B by using the following simultaneous equations to solve for A, B, and C:

$$Pt(f1)=A/(f1^2+C)+B$$

$$Pt(f2)=A/(f2^2+C)+B$$

$$Pt(f3)=A/(f3^2+C)+B$$

Where Pt(f1) is the mean power spectral density in the band about frequency f1, and likewise for f2 and f3.

If the frequency bands are at very high frequencies then f^2 is much greater than C and the following two simultaneous equations can be used to solve for B:

$$Pt(f1)=A/(f1^2)+B$$

$$Pt(f2)=A/(f2^2)+B$$

And B is then given by:

$$B=(Pt(f1)*f1^2-Pt(f2)*f2^2)/(f1^2-f2^2)$$

Usually B is not a stable value and can change between successive digitized data sets (digitization of the detector current over a certain measurement period) and their corresponding power spectral density calculations. Each digitized data set is the set of digitized values of the detector current, taken at various times during a certain measurement time period. However, the calculation, shown above, will determine the specific value of B for each data set and calculation of Pt(f) for that data set.

Pb(f) can be calculated from the value of B by using the following procedure. Measure Pb(f) and B from the background signal of clean dispersant without particles. In this case B is simply the value of Pb(f) at a very high frequency where Pb(f) has a white noise spectrum. Let Bo=B and Pbo(f)=Pb(f) from this clean dispersant measurement. Then when Pt(f) and B are measured from a particle dispersion by the method described previously, Pb(f) can be determined by:

$$Pb(f)=Pbo(f)-Bo+B$$

Pb(f) can also be calculated from a function of B or by using a lookup table, either which can be produced by many measurements of Pb(f) for various values of B, by simply monitoring the instrument for a few days under different starting and environmental conditions. For example Pb(f) could be fit to a polynomial, in f, whose coefficients are functions of B:

$$Pb(f)=B+G1(B)*f+G2(B)*f^2+G3(B)*f^3+\ldots$$

And then the power spectrum of the signal component due to particle scattering is given by subtracting the background power spectrum, Pb(f) (calculated from the polynomial and B), from the measured power spectrum Pt(f):

$$Pp(f)=Pt(f)-Pb(f)$$

This power spectral density Pp(f) can then be inverted to produce the particle size distribution or it can be integrated on a logarithmic scale for deconvolution. This process can also be used directly with the logarithmic scale power spectral data. On the logarithmic frequency scale the following variable transformations are made:

$$x=\ln(f) \text{ (ln is the natural logarithm)}$$

$$f=\exp(x)$$

Then creating the power spectrum on the logarithmic scale, R(x) we obtain:

$$R(x)=Pt(f)*\partial f/\partial x=f*Pt(f)=Pl(x)=A/(\exp(x)+C\exp(-x))+B*\exp(x)$$

We can now measure the power in three logarithmic frequency bands, analogous to f1, f2 and f3 in the previous description. For example the three simultaneous equations now become:

$$R(x1)=A/(\exp(x1)+C\exp(-x1))+B*\exp(x1)$$

$$R(x2)=A/(\exp(x2)+C\exp(-x1))+B*\exp(x2)$$

$$R(x3)=A/(\exp(x3)+C\exp(-x3))+B*\exp(x3)$$

Where R(x) is the spectral power in the logarithmic frequency band at logarithmic frequency x=ln(f). And A, B, and C are new constants to be determined from solution of the simultaneous equations and B*exp(x) is the white noise background to be subtracted from the power spectrum measured in analogy to the linear frequency case described above. Rb(x) can be calculated from the value of B by using the following procedure. Measure Rb(f) and B*exp(x) from the background signal of clean dispersant without particles. In this case B*exp(x) is simply Rb(x) at a very high frequency where Pb(f) has a white noise spectrum. Let Bo and Rbo(x) be the values of B and Rb(x), respectively, which are determined from this clean dispersant measurement. Then when Rt(x) and B are measured from a particle dispersion by the method described previously and the simultaneous equations are solved for B, Rb(x) can be determined by:

$$Rb(x)=Rbo(x)-Bo*\exp(x)+B*\exp(x)$$

$$Rp(x)=Rt(x)-Rb(x)$$

Rp(x) is the portion, of the power spectrum on the logarithmic frequency scale, which is due to particle scatter. Rp(x) is deconvolved by known methods to produce the particle size distribution.

In all of the power spectrum methods described above, all of the digitized signal samples collected from the particle dispersion consist of a group of data sets, which are collected sequentially. Each data set consists of a group of sequential digitized samples of the signal. In all of the cases described above, the power spectrum for each data set is corrected by calculations using measurements made during that set of digitized signal samples. The change of the power spectrum background should not be significant during any one data set, so that the power spectrum from each data set is corrected using the most accurate correction parameters present during the period of that data set. All of these corrected power spectra are then added or averaged together, at each frequency, to obtain the final corrected power spectrum. This could also be accomplished by adding up all of the uncorrected power spectra and all of the corrections (corrected background to subtract from the measured power spectrum), and then subtract the sum of corrected backgrounds from the sum of measured power spectra to obtain the final corrected power spectra. The only requirement is that the corrections must be calculated at sufficiently short intervals such that the background characteristics can be accurately described by one set of parameters during any single data set, even though the background may be changing significantly during the entire data collection period, which spans many data sets.

Another improvement to signal to noise can be gained by analog filtering of the scatter signal before signal digitization and calculation of the power spectrum. The following equation describes the power spectral density of the scatter detector current, as described before:

$$P(f)=4*Io*Is*(K/pi)/(f^2+K^2)$$

This function is maximum at f=0 and drops off at higher frequencies as shown in FIG. 24. Is is proportional to the square of the particle diameter for larger particles and to the sixth power of the diameter for smaller particles. K is inversely proportional to the particle diameter. So smaller particles produce more high frequency scatter signal, but with much lower amplitude. Since these low amplitude high frequency signals are mixed with high amplitude low frequency signals, the analog to digital conversion (ADC) bit error noise shows higher percentage errors for the smaller particles. One method to reduce these errors is to use an analog filter before the ADC to attenuate the lower frequency components more than the high frequency components and use either higher optical intensity or electronic gain to increase the signal to fill the range of the ADC. In this way the spectrum of the scatter signal is made more spectrally uniform before digitization to provide uniform percentage signal error due to ADC bit quantization. After the signal is digitized and the power spectrum is created, the power spectrum can be divided by the power spectral transmission vs. frequency values from the analog filter to restore the original spectrum of the signal before the filter.

Figure 20:
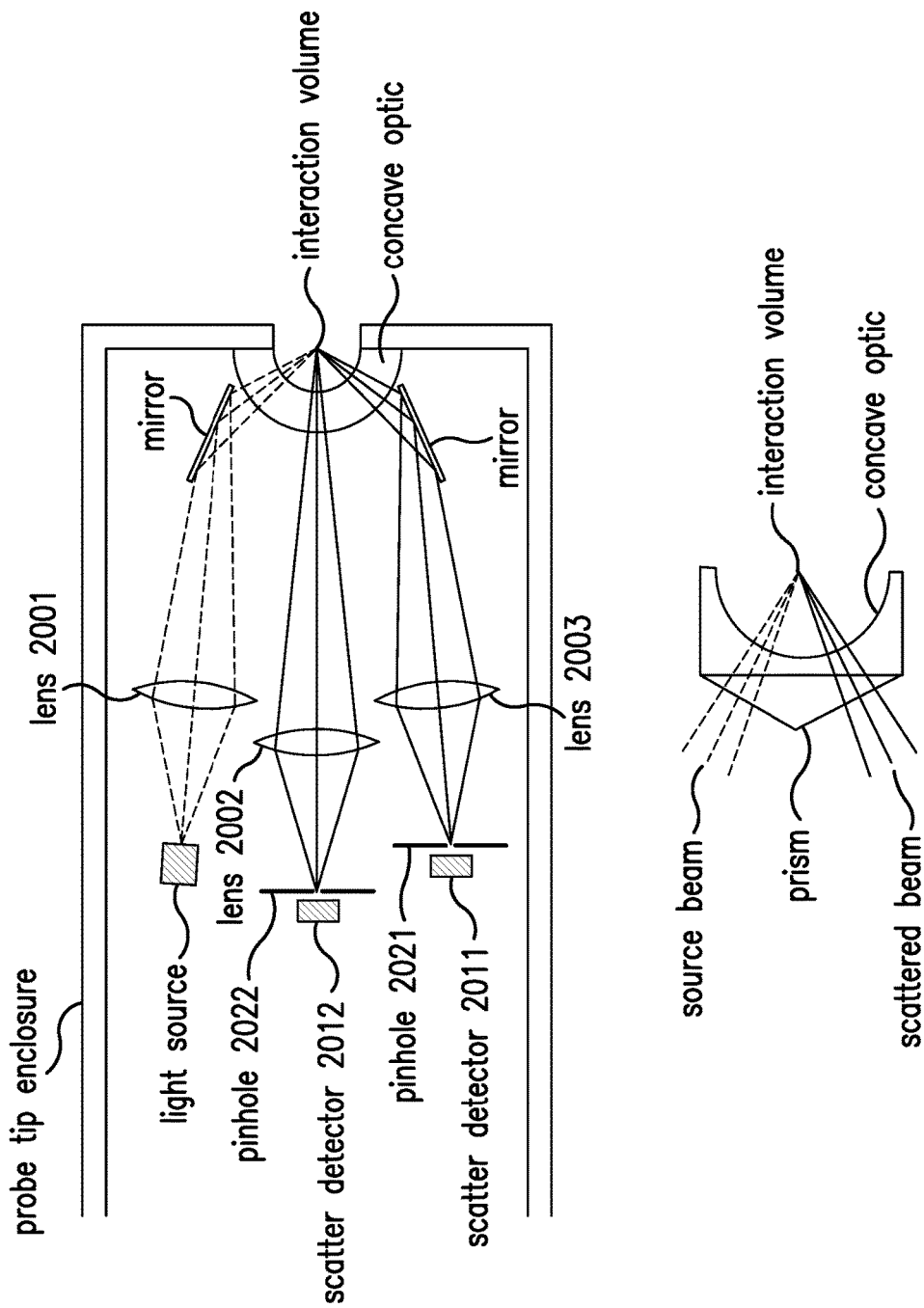
FIG. 20 provides a schematic diagram of an optical system and probe tip configuration, measuring scattered light at multiple scattering angles, according to the present invention.
Figure 21:
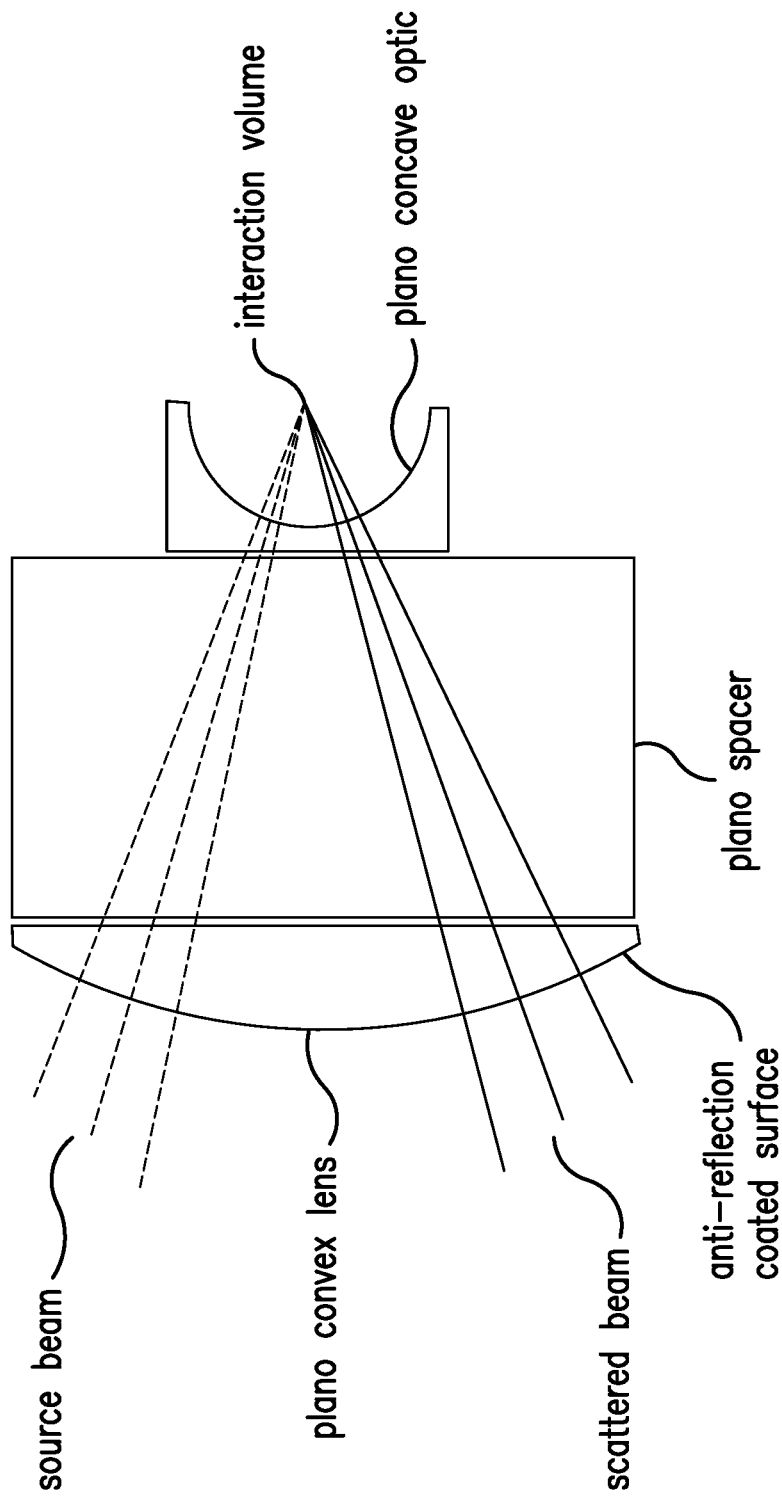
FIG. 21 provides a variation in the optical element design of FIG. 20.

Another method to reduce noise in the scatter signal is to measure self-beating (homodyning) instead of heterodyning. FIG. 20 shows a homodyning scatter probe which uses pinholes to define a scatter interaction volume with the source beam. The scatter interaction volume is the volume of particle dispersion which produces particle scattered light on the detector. Lens 2001 focuses the source beam through a mirror and an optical window with two concave surfaces which have a common center of curvature. The particle dispersion fills the concave surface which is closest to the focus spot or interaction volume. Two scatter detectors collect scattered light through pinholes which each view a volume common with the best focus volume of the source. This volume, which contains the source focus point and viewing volumes of the pinholes, is nominally at the center of curvature of the two concave surfaces. This common volume is called the interaction volume because only particles in this volume can interact with the source beam and produce scattered light at the detectors. Detectors 2011 and 2012 collect scattered light though pinholes 2021 and 2022 respectively and lenses 2003 and 2002 (collector lenses) respectively. These detectors provide dynamic scattering signals from two different scattering angles, which may provide better particle size information. The entire optical assembly could be placed into a probe enclosure which could be inserted directly into the particle dispersion. Also more scattering angles could be measured by adding more collector lens/pinhole/detector assemblies which all view the same volume though the concave surfaces. The possibly expensive double concave surface optic could also be replaced by a standard plano concave lens and a prism (optically cemented) as shown in the bottom portion of FIG. 20 or by a plano convex lens, spacer, and plano concave lens as shown in FIG. 21. Also, lenses 2001, 2002 and 2003 could be replaced by a single lens, which focuses the source light and collects the scattered light.

Figure 23:
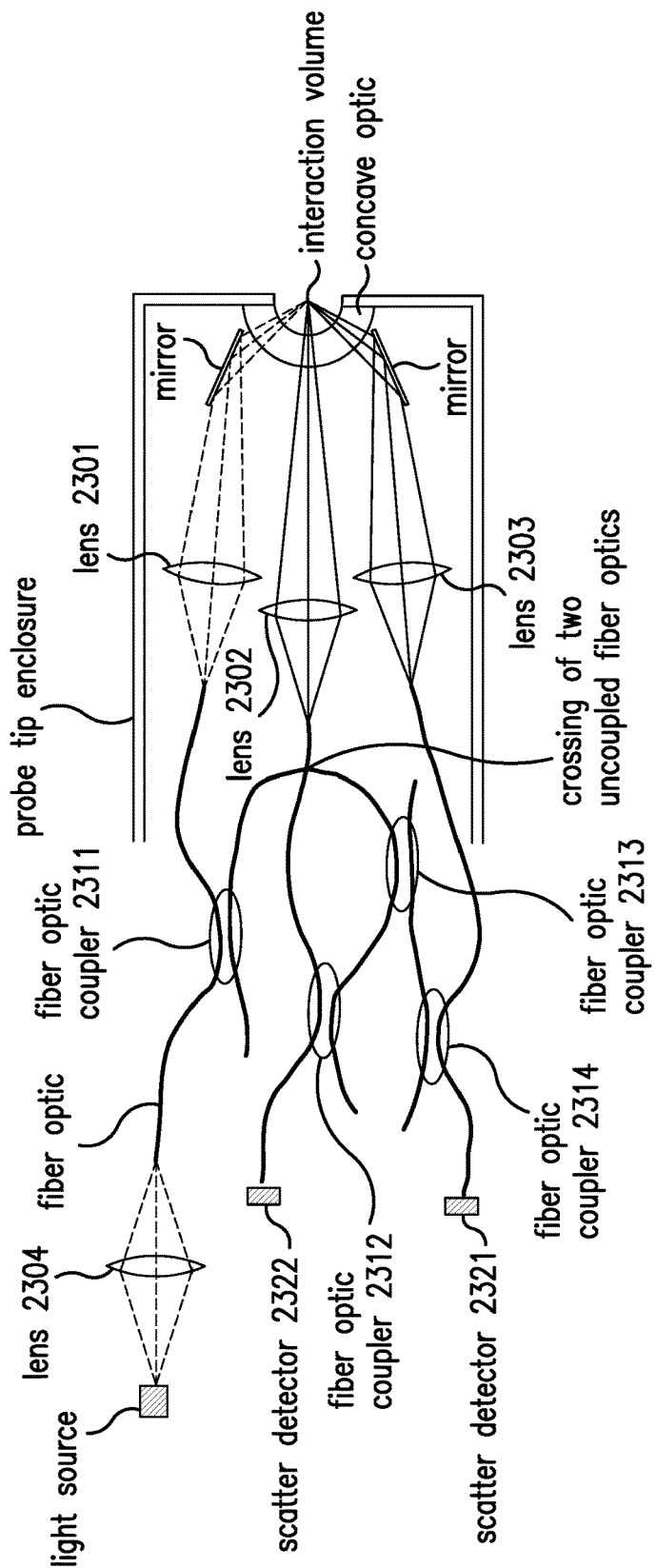
FIG. 23 shows a variation of FIG. 22, where light mixing is provided by a fiber optic system.

This system is designed to measure dynamic light scattering in the homodyne mode, without a local oscillator which usually causes scatter signal noise. Both detectors only see scattering from the interaction volume which could be very close to the inner concave surface, providing very short optical path for scattered rays and reduced multiple scattering at high particle concentrations. This configuration may have advantages when measuring very small particles whose scattering signal is lost in the fluctuations of the background signal caused by small fluctuations in the large local oscillator needed for heterodyne detection. However, in some cases (larger particles for example), heterodyne detection is still the optimal detection means. FIG. 23 shows how the ideas in FIG. 20 can be adapted for heterodyne detection by using fiber optics and fiber optic couplers to distribute and mix source light with the scattered light at each detector. Lens 2304 focuses the source light into the fiber optic which guides the light to lens 2301 as shown in FIG. 20. A portion of the light is split off by a fiber coupler 2311 and distributed, by coupler 2313, to other couplers, 2312 and 2314, which mix the source light with the scattered light which is collected by lenses 2302 and 2303, respectively. Scattered light which is collected by lens 2302 or lens 2303 is guided by each of two separate fiber optics to scatter detectors 2322 or 2321, respectively. The source light from fiber coupler 2311 is split by fiber coupler 2313 to be distributed to fiber couplers 2312 and 2314 for mixing with scattered light for detectors 2322 and 2321, respectively. This fiber optic system could also be replaced by the analogous waveguide structures in an integrated optic chip.

Another configuration for using the design, shown in FIG. 20, in heterodyne mode is shown in FIG. 22. This concept is very similar to that in FIG. 20, except that a portion of the source beam is split off by beam splitter 2201 to be combined with the scattered light on scatter detector 2212 through beam splitter 2222. This configuration provides two advantages: the high signal to noise of heterodyne detection and very low back reflection into the light source. Back reflection, from the scatter detector 2212 surface into the light source, can be reduced by placing the detector some distance from the pinhole and by tilting the detector such that the reflected light does not pass back through the pinhole or other optics. This detector tilting technique can be used with all of the scatter detectors, including the detectors in FIGS. 1, 2, 3, 4, 10 and detectors 501, 601, 701, 1902, 2212. Back reflection into laser sources can cause excess laser noise. The back reflections can be further reduced by anti-reflection coating of optical surfaces, in particular, the first air-glass surface of the concave optic. FIG. 22 shows the combination of a heterodyne channel (detector 2212) and a homodyne channel (detector 2211). However, the source light transmitted through beam splitter 2222 could also be combined with the detector 2211 scattered light using a third beam splitter to produce a second heterodyne channel. FIG. 21 shows a method for creating the concave optic from two or three mass produced optics. A plano-convex lens and plano-concave lens are positioned so that the centers of curvature for their curved surfaces are coincident at the interaction volume. If required, a plano spacer can be placed between these two optics. In any case, all plano surfaces can be bonded to the adjacent plano surface with index matching adhesive to reduce internal reflections.

In all cases, the data from the detectors is processed to produce the power spectrum or autocorrelation function of the detector current. These functions are then inverted (by known methods such as deconvolution) to produce the particle size distribution. In the cases where multiple scattering angles or detection means (heterodyne or homodyne) are combined, the analysis will be optimized for the size range and concentration of the particles. This analysis optimization may include choosing the best measured data, from the various available types of data, for the particular particle sample or analysis of all of the data together using optimization methods described in other applications by this inventor. If the particle size range is larger than the optimal size range of any single scattering angle and detection means (a configuration), then each configuration is chosen to calculate only the portion of the size distribution which is in the optimal size range for that configuration. The individual particle size distributions inverted individually from data of each of many chosen configurations are combined by concatenation of these size distributions and blending of the size distribution results in the regions where the size distributions overlap.

Figure 25:
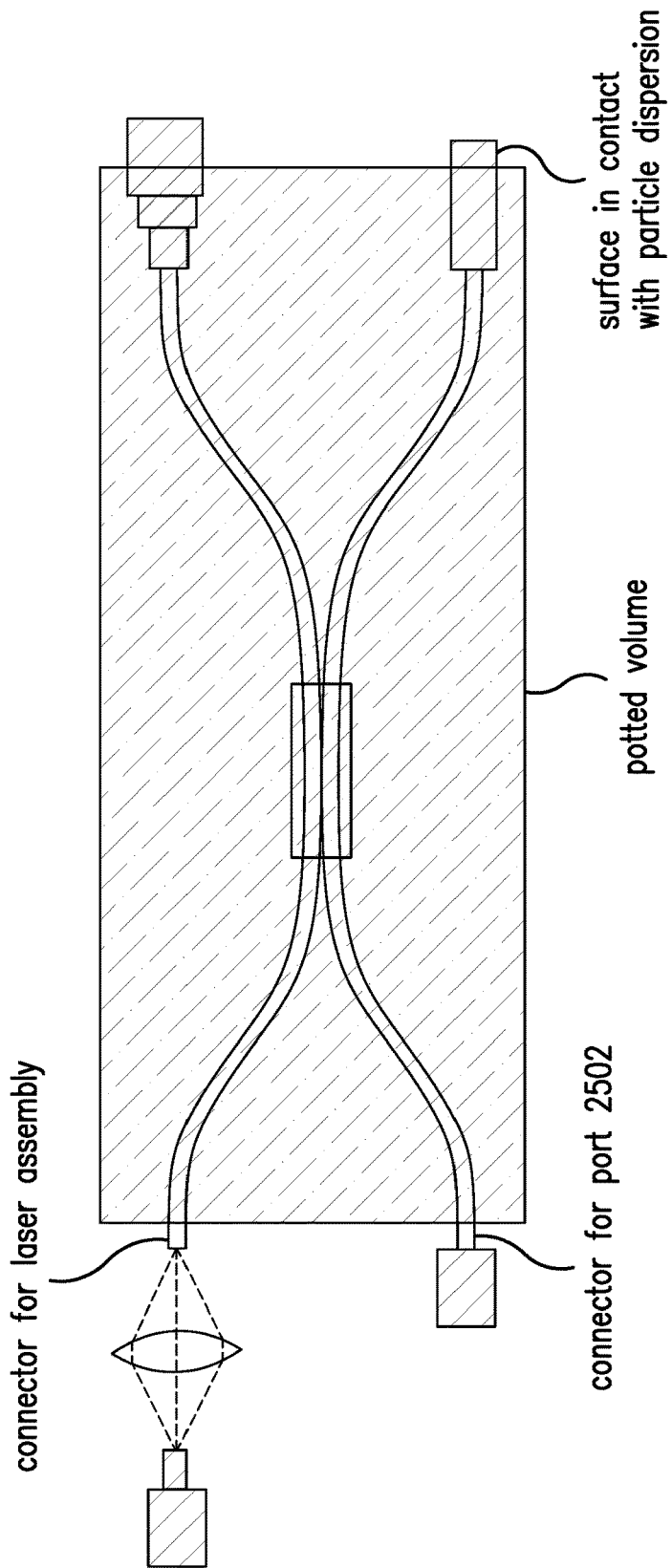
FIG. 25 shows a variation of FIG. 10 and FIG. 19, utilizing a potted volume to reduce motion of fiber optics.
Figure 26:
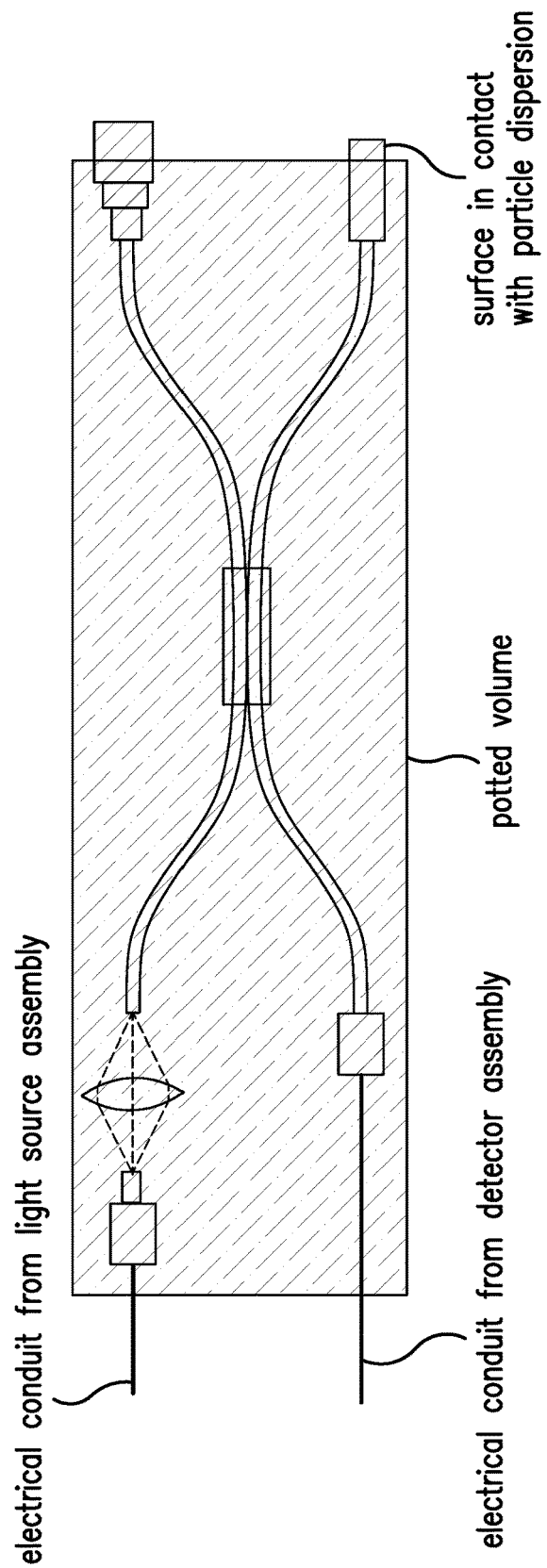
FIG. 26 shows a variation of FIG. 25, including the source and detector in a potted volume.

One source of signal noise in fiber optic dynamic light scattering systems is interferometric noise due to motion of the optical fibers. This noise can occur in both single and multimode fiber optics and couplers. FIGS. 25 and 26 show two concepts for reducing the fiber motion by potting the fiber optic assembly in a solid potting material, which can be cured from a liquid to a solid. Most potting materials will work well, but materials with high thermal conductivity and/or low thermal coefficient of expansion may be most appropriate. FIG. 25 shows the fiber optic system, from FIG. 19, potted with fiber optic connectors to the light source and detectors which remain outside of the potted volume (but one half of each connector is potted into the potted volume so that all flexible fiber sections are potted). This provides for replacement of the detector or light source. FIG. 26 shows the same fiber optic system which is entirely potted, with access to the detectors and light source through electrical connections needed for powering and monitoring the source and detector. See FIG. 19 for port designations. The detector at port 1903 can also be outside of the potted volume and connected by a fiber optic connector to port 1903 (as shown in FIG. 25 for port 1912) or it could be potted into the structure and accessed through an electrical conduit as shown in FIG. 26 for port 1912. In FIG. 26, the optical path must be kept free of potting material to avoid attenuation or distortion of the optical beam. These voids in the potting volume are not explicitly shown in FIG. 26. Depending upon the mechanism creating the interferometric noise, the fiber optic cable sheath and/or fiber optic buffer could be removed so that the potting material adheres directly to either the buffer or the cladding of the fiber. Or In cases where only the cable needs to be immobilized and the fiber can be allowed to move within the cable, the cable can be left on the fiber. Then the potting material will adhere to the cable surface. In any case, this potting method should reduce the frequency and amplitude of the fiber motion induced noise so that it can be removed from scatter signal as a small correction.

Figure 27:
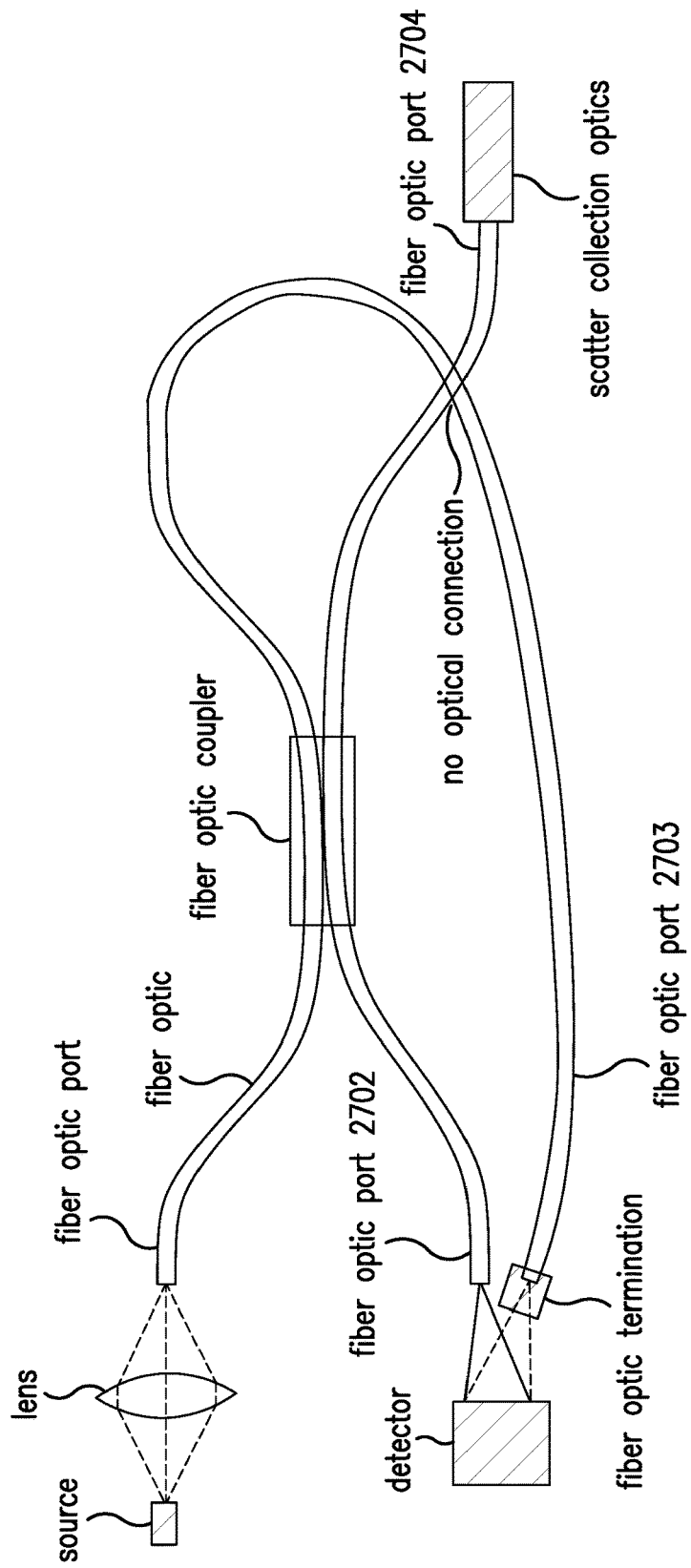
FIG. 27 shows a variation of FIG. 10, utilizing fiber optic port 2703 to provide the source light for mixing source and scattered light on a detector.

FIG. 27 shows another version of the fiber optic system, where the source light is mixed with the scattered light through fiber optic port 2703. The source light from port 2703 and the scattered light from the scatter optics, through port 2702, are mixed onto the detector to produce the heterodyne signal. In this case, the surfaces in the scatter collection optics, at port 2704, and in the optics at port 2703 are anti-reflection coated to avoid back reflections of source light into port 2702. Additionally, the port 2703 can be terminated by the structure in FIG. 36, which reduces backreflection into the fiber. This provides two advantages. Firstly, the amount of light out of port 2703 can be much larger than the light that was intentionally back reflected from port 1004, in FIG. 10, creating a larger local oscillator and larger heterodyne signal. Additionally, very little light is back reflected into the light source in this design. Back reflection into laser sources can cause excess laser noise. In all of the cases shown in this disclosure, back reflection into light source can be reduced by use of a polarizer and quarter wave plate to produce an optical isolator at the exit of the light source assembly. However, in the fiber optic systems, this requires the use of expensive single mode polarization preserving fiber optics and couplers; and it produces circular polarized light at the particles. And it will also not work with multimode fiber optics. However, this disclosure claims the use of an isolator to reduce back reflections into the laser to reduce laser amplitude and phase noise in this application, when it is appropriate.

Figure 28:
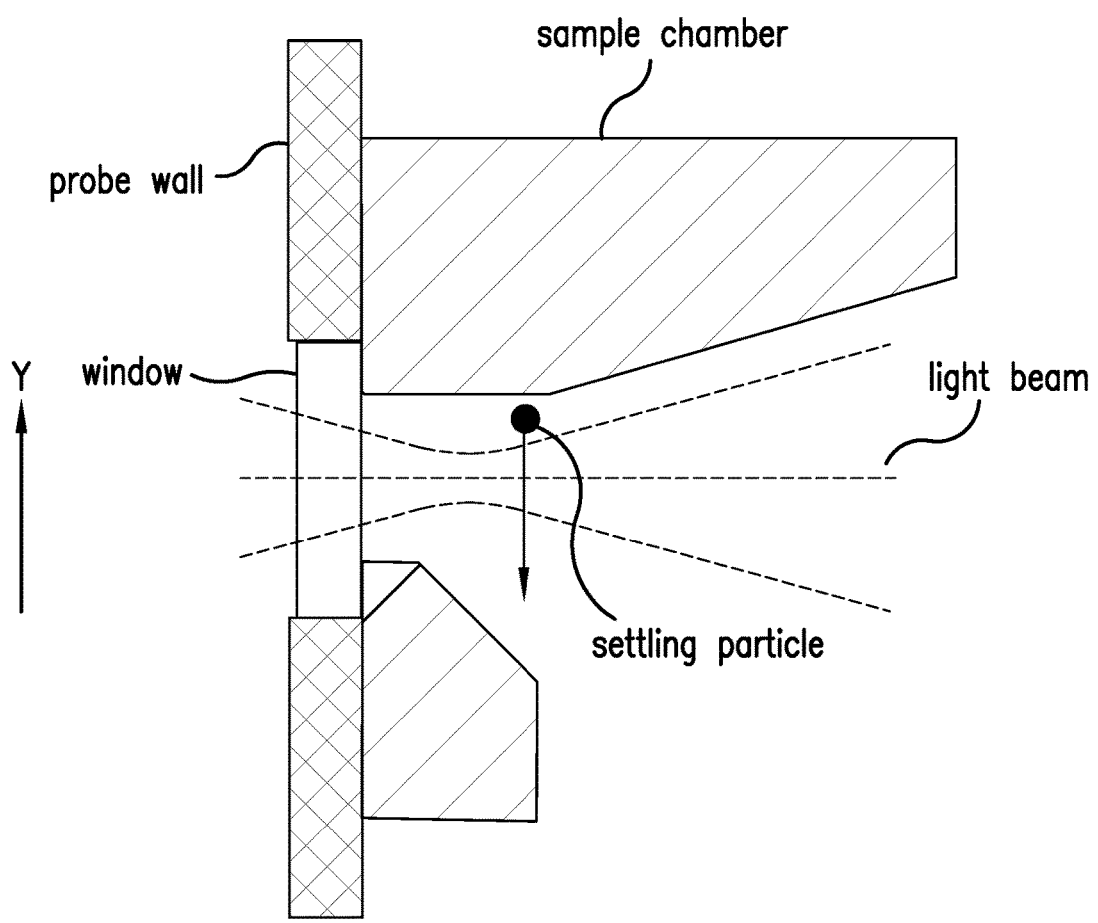
FIG. 28 shows a variation of FIG. 9, allowing particles to settle out of the scattering volume.

In some cases, very large particles can contribute scatter signals which will distort the signals from smaller particles. In this case, particle settling could be used to remove larger particles from the interaction volume, as shown in FIG. 28 which shows a variation on the concept in FIG. 9. The sample chamber has an extension above the interaction volume so that particles cannot settle into the interaction volume from above. Hence, the interaction volume will gradually be depleted of larger particles, which settle out of the volume. Scatter data can be collected at various times during this settling process to measure different size ranges of the distribution separately. The bottom portion of the sample cell enclosure is shortened or removed completely to allow the particle dispersion to flow down and out of the interaction volume when the sample cell is emptied and rinsed in preparation for the next sample.

Figure 29:
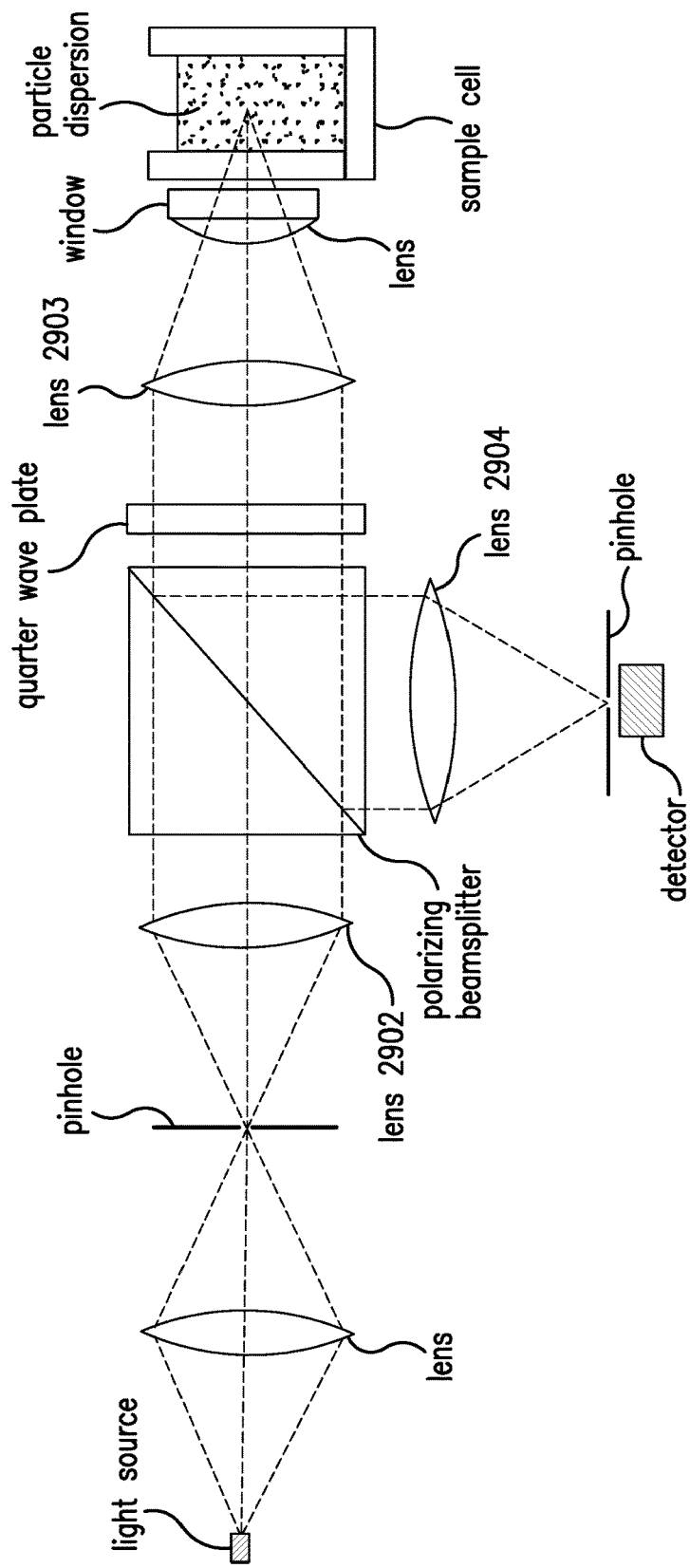
FIG. 29 provides a schematic diagram of an optical system, utilizing polarizing elements to reduce back-reflection of light into the light source and improve optical efficiency, according to the present invention.
Figure 30:
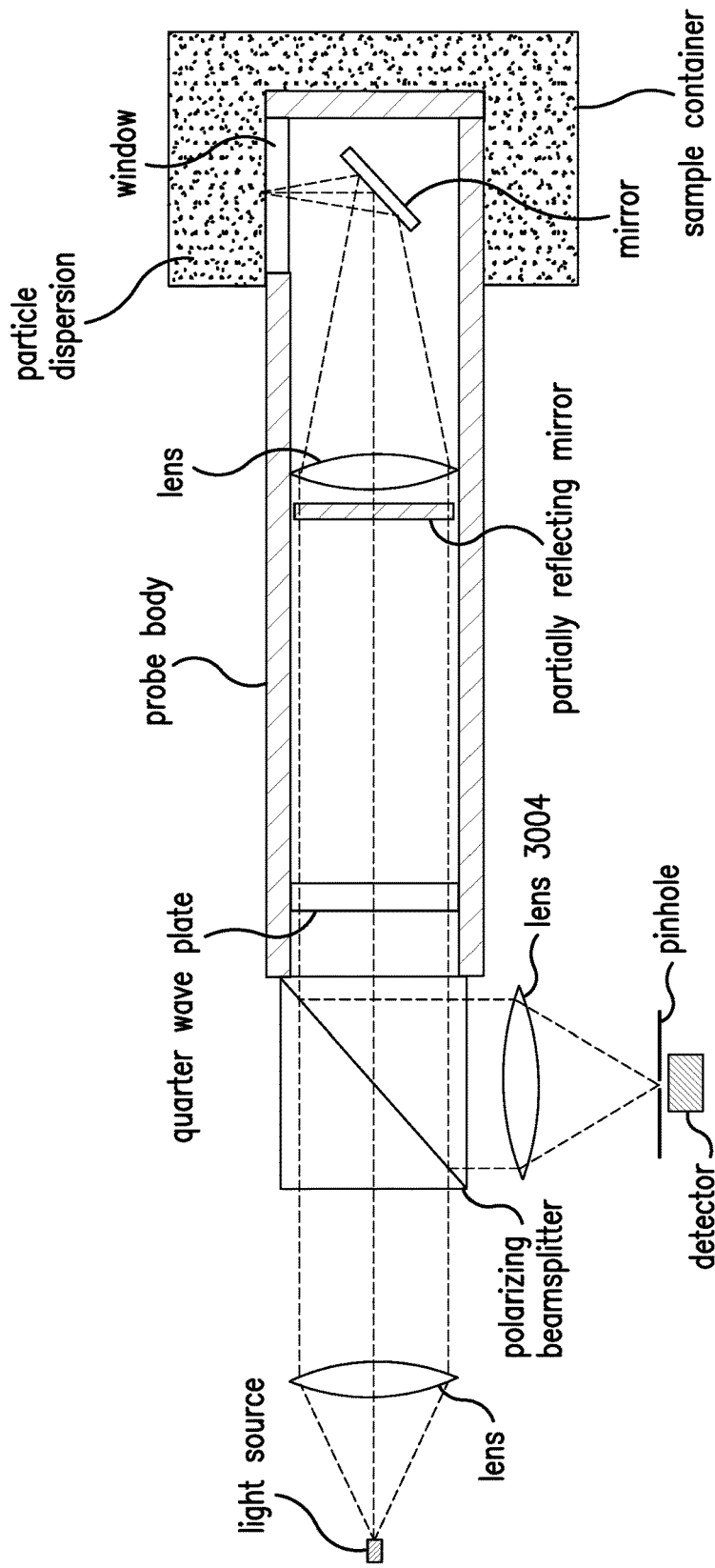
FIG. 30 provides a schematic diagram of a probe optical system, utilizing polarizing elements to reduce back-reflection of light into the light source and improve optical efficiency, according to the present invention.

As mentioned before, one cause of laser noise is laser light which is reflected back into the laser. FIGS. 29 and 30 show versions of FIGS. 4 and 8, respectively, where a polarizing beamsplitter and quarter wave plate are utilized to increase the optical efficiency of the detection path and reduce the light back-reflected into the laser. The polarizing beam splitter is oriented to provide maximum transmission for the polarization of the laser. The polarized light passes through a quarter wave plate with axes at 45 degrees to the polarization direction of the source. The local oscillator light, which is reflected back from the convex surface in FIG. 29 or from the partial reflecting mirror in FIG. 30, will pass back through the quarter wave plate on the return path towards the polarizing beamsplitter. In both cases, the light gains a second quarter wave of phase in one polarization, accumulating a total of one half wave which will rotate the polarization by 90 degrees. When passing back through the polarizing beamsplitter, the 90 degree polarization rotated light will be reflected by the beamsplitter and very little light will transmit through the beamsplitter to be focused back into the laser source. The scattered light will propagate through the same process, and also be reflected by the polarizing beamsplitter. So both the source light and scattered light will be reflected by the polarizing beamsplitter through the lens 2904 or 3004 to the detector, where mixing, of the local oscillator and scattered light, and heterodyne detection of the scattered light occurs. Any flat surfaces between lenses 2902 and 2903, except for a surface which reflects the local oscillator, shall be tilted slightly, and/or anti-reflection coated, so that the reflection from that surface will not pass into the laser source. For example, the beamsplitter and quarter wave plate should both be tilted slightly off of normal to the optical axis so that reflections from their surfaces cannot pass back to the laser. All of these surfaces, except for those reflecting the local oscillator reflection, should also be anti-reflection coated. One end of a fiber optic (preferably polarization preserving fiber optic) with an attached scattering optic assembly on the other end, as shown previously in this disclosure, could also be aligned with the final light source focal point (where the interaction volume would be) of either FIG. 29 or FIG. 30 to provide a flexible extension and scattering probe. Light would pass to and from the optical system into this fiber. The scatter optics on the other end of the fiber would interface with the particle sample by various methods including those shown in FIGS. 11A, 11B, 12, 13, and 14. In this case, the local oscillator could be created by a reflecting surface inside of the scattering optics assembly, which contacts the particle dispersion, so that the scattered light and local oscillator travel through the same optical paths to get to the detector. The local oscillator could also be generated by any of the methods described previously. The other end of the fiber optic could also be immersed directly into the particle dispersion without any scatter optics. This extension could also be used with the systems in FIGS. 1 through 8, with multimode or single mode fiber optics.

Other Noise Correction Techniques

The basic fiber optic interferometer is illustrated in FIG. 10. A light source is focused into port 1001 of a fiber optic coupler. This source light is transferred to port 1004 and light scattering optics which focus the light into the particle dispersion and collect light scattered from the particles. This scattered light is transferred back through the fiber optic and coupler to the detector on port 1002. If the coupler has a third port, a portion of the source light also continues on to port 1003 which may provide a local oscillator with a reflective layer. If the local oscillator is not provided at port 1003, a beam dump or anti-reflective layer may be placed onto port 1003 to eliminate the reflection which may produce interferometric noise in the fiber optic interferometer. The beam dump could consist of a thick window which is attached to the tip of the fiber with transparent adhesive whose refractive index generally matches that of the fiber and the window, as shown in FIG. 36. This will reduce the amount of light which is Fresnel reflected back into the fiber at the fiber tip. The other surface of the window can be anti-reflection coated, and/or be sufficiently far (thick window) from the fiber tip, to minimize the reflected light, from that surface, that can enter the fiber.

FIG. 11A shows one version of the scatter optics on port 1004. A lens or gradient index optic (GRIN) focuses the source light into the particle dispersion in a cuvette through a transparent wall of the cuvette. A partially-reflective layer on the tip of the fiber or on the surface of the GRIN rod, at the fiber/GRIN gap, provides the local oscillator light to travel back through port 1004 with light scattered by the particles. If the fiber surface is partially reflecting, the GRIN surface could be anti-reflection coated or it could be placed sufficiently far from the fiber to avoid reflections from the GRIN surface back into the fiber. Reflections from both surfaces could produce an optical interference signal which may contaminate the heterodyning signal from the scattering particles. The reflected source light and the scattered light, from particles in the cuvette, travel back through the coupler and are combined on the detector at port 1002. The interference between these two light components is indicative of the Brownian motion of the particles and the particle size. The local oscillator light could also be produced by reflection from the fiber tip of port 1003, by removing the fiber optic termination and coating the tip with a reflecting layer. If port 1003 is used for the local oscillator, the optics on port 1004 should be antireflection coated to prevent optical interference between light from port 1003 and port 1004. Since the local oscillator is generated at the exit surface of port 1003 or port 1004, as opposed to the cuvette surface, the interference signal is not degraded by small errors in the position of the cuvette surfaces, allowing use of inexpensive disposable cuvettes. The local oscillator is provided by light reflected from either port 1003 or port 1004 fiber optic.

Other designs for port 1004 could incorporate a window, on the surface of the GRIN rod, which contacts the particle dispersion directly.

The port 1002 detector current is digitized for analysis to determine the particle size in the dispersion. The following analysis can also be applied to electrical current from all of the scatter detectors, including the detectors in FIGS. 1, 2, 3, 4, 10 and detectors 501, 601, 701, 1902, 2212. The power spectrum of the optical detector current contains a constant local oscillator and a frequency dependent component due to light scattered from particles in Brownian motion. The frequency dependent component is described by the following equations:

$$P(f) = (S(d,a,nm,np)) * (E*(K^2))/(4pi^2*(f)^2 + (E*(K^2))^2) + n(f)$$

where $K = 2*nm*\sin(a/2)/wl$ $$E = kT/(3*pi*eta*d)$$

P(f)=power spectral density of the detector current (or voltage) at frequency f
S=scattering efficiency per unit particle volume
d=particle diameter
eta=dispersant viscosity
f=frequency
np=refractive index of particle
nm=refractive index of dispersant
a=scattering angle
c=constant which depends on dispersant viscosity and particle shape
^2=square of quantity
g=acceleration
k=Boltzman's constant
T=dispersant temperature
wl=wavelength of the source light
n(f)=baseline noise power spectral density This equation describes the power spectrum from a single particle of diameter d. For groups of particles of various sizes, the power spectrum is the sum of the spectra from the individual particles. Then the total spectrum must be deconvolved to find the particle size distribution. Usually the spectrum from clean dispersant is measured to determine n(f), which is the portion of the spectrum due to laser noise, detector noise, modal interference due to fiber optic vibrations, and other noise sources. This baseline noise is the power spectrum measured without any particles in the dispersant. This baseline noise spectrum is subtracted from the power spectrum measured from the particles to determine the spectrum which is only due to Brownian motion of the particles. However, n(f) is not usually stable during the long period required to gather sufficient digitized data to create an accurate estimation of the power spectrum.

One useful property of the fluctuating portion of the baseline noise is that the noise is usually generally white and shows strong correlation with values of n(f) at high frequencies. As shown by the equation for P(f), the power spectrum component due to light scattered from the particles drops off very rapidly at high frequencies and becomes negligible as compared to n(f) at high frequencies. At high frequencies, the particle scatter portion of the spectrum drops as approximately $1/f^2$. In any event the detector current could be sampled at sufficiently high frequencies to measure the power spectrum where the contribution from the particles is small.

One method for noise correction is to generate an empirical set of n(f) functions by measuring n(fp) in the frequency region where the particles contribute to P(f), while also measuring n(fh)) at high frequencies where the particle contribution would normally be small. The parameters fp and fh indicate frequency regions, not individual frequencies. So various P(f) samples are measured without particles to generate a function G:

$$n(fp)=G(n(fh))$$

The portion of the spectrum n(fh) could be measured from the calculated power spectrum of the digitized data. But then the detector current must be sampled at rates well beyond those required to measure the particles. The value for n(fh) could also be measured by band pass analog electronic filters and power measuring circuits, to measure the total power in a bandpass, in frequency regions where the scatter signal from particles will have very small contributions.

In either case, once the function G(n(fh)) is created, it can be used to correct the spectrum measured from particles by measuring n(fh) each time a data segment is recorded by digitizing the scatter detector current for a short period. An FFT is created to produce the contribution of this short period signal to the total power spectrum of the entire measurement period. This particular ni(fp)=G(ni(fh)) is then subtracted from the Pi(f) for the ith data segment to correct that data segment for the n(f) during that segment. In this way, as ni(f) fluctuates, the ith data segment is corrected precisely for the noise in that segment. This could also be accomplished by summing all of the Pi(f) functions over i to get Pt(f) and all of the ni(f) functions over i to get nt(f) and then using Pt(f)−nt(f) to calculated the spectrum contribution from the particles.

G(n(fh) could also be determined from many data points in both the upper fp, and fh regions to produce better conditioning of the simultaneous equations used to solve for the parameters in the function G. In any case, if the fluctuating component of n(t) is white noise and is flat out to fh, then the correction is simple because n(fp)=n(fh). But in general, a function G may be required to get precise correction over the entire range of fluctuations and frequencies. G can take the form of a polynomial function of f (over both regions fp and fh) or a group of n(fp) functions in a look-up table, where interpolation between the 2 table n(fp) functions, with the closest corresponding values for n(fh) to the measured value of ni(fh), would be used to determine the ni(fp) for the ith data segment. In some cases, G will be proportional to the inverse of the square-root of frequency f, but in general G can be described by a polynomial function of frequency f, with coefficients Ai which are functions of n(fh). The functional forms of these coefficients Ai are determined by measuring n(fp) for different cases of n(fp) and n(fh) and solving for Ai and Bj coefficients. Then a functional relationship is created between Ai and all Bj coefficients for each value of i.

$$n(f)=A0+A1*f+A2*f^2+A3*f^3+\ldots f \text{ in } fp \text{ region}$$

$$n(f)=B0+B1*f+B2*f^2+B3*f^3+f \text{ in } fh \text{ region}$$

Where Ai=Ai(B1, B2, B3, . . . )

In some cases regions fp and fh may have some overlap.

Other parameterized functions could be used instead of the polynomial form to represent the functionality of G or Ai. This correction procedure is only required in the frequency regions where the fluctuations in n(f) cause unacceptable errors in the calculated particle size distribution. Typically this will be in the higher frequency end of the fp region, where the smaller particle information is contained. At lower frequencies, a single measurement of n(f) before or after the particle measurement may be sufficient, without using G.

Another method which may be utilized is to solve entire the problem in a generalized fashion. This method would use all of the power spectrum data, P(fp) and P(fh), to solve for the particle contribution and baseline contribution using an iterative procedure (optimization or search algorithm) which assumes the existence of both. However, the G function method described above may be more effective because more apriori knowledge is provided to the algorithm.

These methods can be applied to the power spectrum on any frequency scale, including but not limited to a logarithmic progression in f. However, if the fluctuating portion of the baseline noise is generally white or uniform in density, then a linear scale in f may be optimal for calculation of G.

The background can be solved for as part of the total solution in this background drift problem and many other similar problems where a system model is inverted to solve for the particle size distribution. Consider the generalized model below:

$$F=H*V$$

Where F is the measured data (power spectrum of scattered light signal, angular distribution of scattered light, etc.), V is the size distribution to be solved for, and H is the matrix which describes the system model (Brownian motion/Doppler effect, angular light scattering, etc.). This model is usually inverted to produce the size distribution:

$$V=F/H \text{ (a matrix inversion, not a literal division)}$$

Where F/H represents the solution of the matrix equation by any means including iterative techniques with constraints on the values of V. The actual values for F are calculated by subtraction of the actual background from the measured FB, which includes the background.

$$FB\_measured=F\_actual+B\_actual$$

Where F and B are the actual scattering data (with particles) and the background (without particles), respectively.

However the computed values (called Fc) for F use the measured values of B which may differ from the actual values of B (due to drift of B) by the error vector E.

$$B\_actual=B\_measured+E$$

$$Fc=FB\_measured-B\_measured$$

$$Fc=F\_actual+E$$

Then the matrix equation above becomes:

$$Fc-E=H*V$$

Solving this matrix equation for V, we obtain $$V=(Fc-E)/H \text{ (/ is not a literal division, / represents solution of the matrix equation above for } V)$$

If V has m unknowns, F has n measured values, and E is described by k number of parameters, then V and E can be solved from this equation as long as m+k<n. This method works well when E is much smaller than B_measured so that the correction E is small and accurately described using only a few parameters. For example, in the previous case, E could be simply white noise times a constant which determines the amount of white noise which must be added to the noise background, which was measured without particles in the source beam. E is determined to obtain the best result for V, or in other words the result which minimizes the RMS error:

$$SQRT(SUM(((Fc-E)-(H*V))^2))$$

Where SUM is the summation over the vector elements. This function can be minimized by known iterative methods, such as simply changing E and inverting Fc−E=H*V multiple times and choosing the result for V and E which minimizes the RMS error above. Also optimization methods such as Marquardt Levenberg or Newton's method could be used to determine the E vector which minimizes the RMS error.

Figure 31:
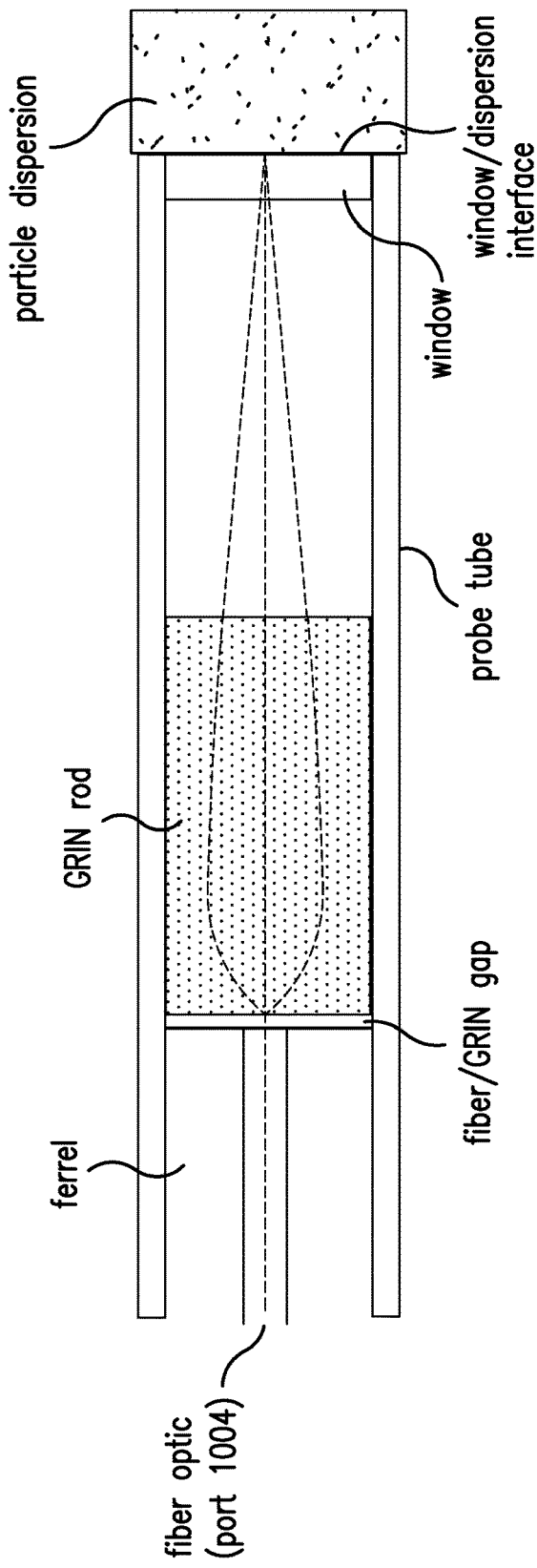
FIG. 31 provides a schematic diagram of a probe optical system for fiber optic port 1004, utilizing a long focal length lens to provide a larger scattering volume in the particle dispersion, according to the present invention.

FIG. 10 shows a fiber optic system for measuring the Brownian motion and size of particles. FIG. 31 shows an extension of this idea, where port 1004 is designed as a probe tip with integral window. The probe is immersed into the particle dispersion and the Fresnel reflection, from the interface between the window and the particle dispersion, provides the local oscillator light for heterodyne detection by providing a path for this reflected light to travel back through the fiber optic with the scattered light, creating the heterodyne interference signal on the detector. Single mode fiber optics have core diameters in the 5 to 8 micron range. Since this small core size will collect light from a very small volume of dispersion, larger particles may not be easily detected due to their low count per unit volume. The probability of larger particles entering this small interaction volume is small and so the signals from larger particles are sporadic and discontinuous. FIG. 31 shows a high magnification configuration for the probe tip, where the core of the single mode fiber is imaged to the window/dispersion interface at high magnification. This produces a large interaction volume and better detection of larger particles. All of the optical surfaces in the probe can be antireflection coated, except for the surface which interfaces with the dispersion and produces the local oscillator reflection. Also the GRIN rod could be designed to fill the entire space between the fiber optic tip and the window; or the window thickness could be increased to produce only a small gap separation between optical components. Then all gaps between optical components could be filled with refractive index matching gel or epoxy to reduce reflections. Also the GRIN rod could be replaced by antireflection-coated conventional spherical or aspherical optics which provide the required magnification. The fiber/GRIN gap could be widened, and filled with air to provide the local oscillator from the Fresnel reflection at the fiber optic tip of port 4. Then the GRIN rod would focus the beam farther into the dispersion, not at the window interface, to avoid the interfering reflection from the window. This design could also be used with homodyne systems by projecting the image of the core tip farther into the dispersion, reducing the amount of light, which is Fresnel reflected back into the fiber core, or by antireflection coating of the dispersion/window interface. This dispersion/window interface surface coating must account for the refractive index of the dispersion to minimize the reflection at the dispersion/window interface.

For example, a magnification of 5 will provide a 40 micron diameter illumination region (and scattered light collection region) at the dispersion/window interface from an 8 micron core single mode fiber optic. This larger region will provide both larger width and larger depth for the effective scattering volume in the dispersion, because particles can contribute scattered light farther from the window/dispersion interface due to the larger diameter illumination and larger diameter scattered light collection region, determined by the size of the image of the fiber core at the window/dispersion interface. The scattering volume should be large enough to provide significant probability (>50%) for containing one of the particles, of interest, at the lowest number concentration. The size of this scattering volume and the corresponding optical magnification will depend upon the number concentration of the particles with the lowest number concentration in the particle size distribution. These are usually the largest particles. Magnifications beyond 5 may be required for lower number concentrations or magnifications less than 5 for higher number concentrations.

Ensemble particle size measuring systems gather data from a large group of particles and then invert the scattering information from the large particle group to determine the particle size distribution. This scatter data usually consists of a scatter signal vs. time (dynamic scattering) or scatter signal vs. scattering angle (static scattering). The data is collected in data sets, which are then combined into a single larger data record for processing and inversion to produce the particle size distribution. Inversion techniques such as deconvolution and search routines have been used. The data set for dynamic light scattering consists of a digital record of the detector signal over a certain time, perhaps 1 second. The power spectra or autocorrelation functions of the data sets are usually combined to produce the combined input to the inversion algorithm for dynamic light scattering to invert the power spectrum or autocorrelation function into a particle size distribution. Also the data sets can be combined by concatenation, or by windowing and concatenation, to produce longer data sets prior to power spectrum estimation or autocorrelation. Then these power spectra or autocorrelation functions are averaged (the values at each frequency or delay are averaged over the data sets) to produce a single power spectrum function for inversion to particle size. Likewise for angular scattering, the angular scatter signals from multiple detectors are integrated over a short interval. These angular scattering data sets are combined by simply averaging data values at each scattering angle over multiple data sets.

Since the inverse problem for these systems is usually ill-conditioned, detecting small amounts of large particles mixed in a sample of smaller particles may be difficult because all of the particle signals from the particle sample are inverted as one signal set. If the signals, from only a few larger particles, are mixed with the signals from all of the other smaller particles, the total large particle scatter signal may be less than 0.01 percent of the total and be lost in the inversion process. However, in the single short data set which contained the larger particle's scattered light, the larger particle scatter may make up 50% to 90% of the total signal. The larger particle will easily be detected during inversion of these individual data sets.

Users of these systems usually want to detect small numbers of large particles in a much larger number of smaller particles, because these larger particles cause problems in the use of the particle sample. For example, in lens polishing slurries, only a few larger particles can damage the optical surface during the polishing process. In most cases these larger particles represent a very small fraction of the sample on a number basis. Therefore, if many signal sets (a signal set is a digitized signal vs. time for dynamic scattering or digitized signal vs. scattering angle for static scattering) are collected, only a few sets will include any scattered signals from larger particles. An algorithm could sort out all of the data sets which contain signals from larger particles and invert them separately, in groups, to produce multiple size distributions, which are then weighted by their total signal time and then combined to form the total particle size distribution. The data sets may also be sorted into groups of similar characteristics, and then each group is inverted separately to produce multiple size distributions, which are then weighted by their total signal time and then summed over each size channel to form the total particle size distribution. In this way, the larger particles are found easily and the smaller particle data sets are not distorted by scatter signals from the larger particles. Even if the total of all of the signals for large particles over the full data collection time is less than 1% of the total signal, including large and small particles, this small amount would be inverted separately and the resulting distribution would be added to the rest of the size distribution with the proper percentage.

This technique works better when many short pieces of data are analyzed separately, because then the best discrimination and detection of particles is obtained. However, this also requires much pre-inversion analysis of a large number of data sets. The key is that these data sets can be categorized with very little analysis, to save computation time. In the case of angular light scattering, comparison of signal values from a few scattering angles from each signal set is sufficient to determine which signal sets include signals from larger particles or have specific characteristics. In the case of dynamic light scattering, the spectral power in certain frequency bands, as measured by fast Fourier transform of the data set or by analog electronic bandpass filters could be used to categorize data sets. Consider a dynamic scattering system where the scattering signal from the detector (in heterodyne or homodyne mode) is digitized by an analog to digital converter for presentation to a computer inversion algorithm. In addition, the signal is connected to multiple analog filters and RMS circuits, which are sequentially sampled by the analog to digital converter to append each digitized data set with values of total power in certain appropriate frequency bands which provide optimal discrimination for larger particles. The use of analog filters may shorten the characterization process when compared to the computation of the Fourier transform. These frequency band power values are then used to sort the data sets into groups of similar characteristics. Since larger particles will usually produce a large signal pulse, both signal amplitude and/or frequency characteristics can be used to sort the data sets. The total data from each formed group is then processed and inverted separately from each of the other groups to produce an individual particle size distribution. These particle size distributions are summed together after each distribution is weighted by the total time of the data collected for the corresponding group.

The use of analog filters is only critical when the computer speed is not sufficient to calculate the power spectrum of each data set. Otherwise the power spectra could be calculated from each data set first, and then the power values in appropriate frequency bands, as determined from the computed power spectrum, could be used to sort the spectra into groups before the total data from each group is then processed and inverted separately to produce an individual particle size distribution. For example the ratio of the power in two different frequency bands can indicate the presence of large particles. The resulting particle size distributions are summed together after each distribution is weighted by the total time of the data collected for the corresponding group. This process could also be accomplished using the autocorrelation function instead of the power spectrum of the scatter signal. Then the frequency would be replaced by time delay of the autocorrelation function and different bands of time delay would be analyzed to sort the data sets before creating data groups.

In angular scattering, a group of detectors measure scattered light from the particles over a different angular range for each detector. These detector signals are integrated over a certain measurement interval and then the integrals are sampled by multiplexer and an analog to digital converter. In this case, the angular scattering values at appropriate angles, which show optimal discrimination for larger particles, could be used to sort the angular scattering data sets into groups before the total data from each group is then processed and inverted separately to produce an individual particle size distribution for that group. These resulting particle size distributions are summed together after each distribution is weighted by the total time of the data collected for the corresponding group.

These sorting techniques can also be used to eliminate certain data sets from any data set group which is inverted to produce the particle size distribution. For example, in dynamic scattering, very large particles may occasionally pass through the interaction volume of the optical system and produce a large signal with non-Brownian characteristics which would distort the results for the data set group to which this defective data set would be added. Large particles, which are outside of the instrument size range, may also cause errors in the inverted size distribution for smaller particles when their data sets are combined. Also vibration or external noise sources may be present only during small portions of the data collection. These contaminated data sets could be identified and discarded, before being combined with the rest of the data. Therefore, such defective data sets should be rejected and not added to any group. This method would also be useful in conventional dynamic light scattering systems, where multiple groups are not used, to remove bad data sets from the final grouped data which is inverted. By breaking the entire data record into small segments and sorting each segment, the bad data segments can be found and discarded prior to combination of the data into power spectra or autocorrelation functions and final data inversion. This method would also be useful in static angular scattering to eliminate data sets from particles which are outside of the instrument size range.

In some cases, a large number of categories for sorted groups are appropriate to obtain optimal separation and characterization of the particle sample. The number of categories is only limited by the cumulated inversion time for all of the sorted groups. The total inversion time may become too long for a large number of groups, because a separate inversion must be done for each group. However, after the information is sorted, abbreviated inversion techniques may be used because the high accuracy of size distribution tails would not be required to obtain high accuracy in the final combined particle size distribution. In many cases, only two groups are necessary to separate out the largest particles or to eliminate defective data sets.

This disclosure claims sorting of data sets for any characteristics of interest (not only large particles) and for any applications where large data sets can be broken up into smaller segments and sorted prior to individual analysis or inversion of each individual set. Then the resulting distributions are combined to create the final result. This includes applications outside of particle size measurement.

Another application is Zeta potential measurement. Low scattering angles are desirable in measurement of mobility of particles to reduce the Doppler spectral broadening due to Brownian motion. However, large particles scatter much more at small angles than small particles do; and so the scatter from any debris in the sample will swamp the Doppler signal from the motion of the smaller charged particles in the electric field. This inventor has disclosed methods of measuring Dynamic light scattering from small interaction volumes created by restricting the size of the illuminating beam and the effective viewing volume. When only scattered light from a very small sample volume is measured, the scatter from large dust particles will be very intermittent, due to their small count per unit volume. So the techniques outlined above can be used to eliminate the portions of the signal vs. time record which contain large signal bursts due to passage of a large particle. In this way, Zeta potential measurements can be made at low scattering angles without the scattering interference from dust contaminants.

Figure 9:
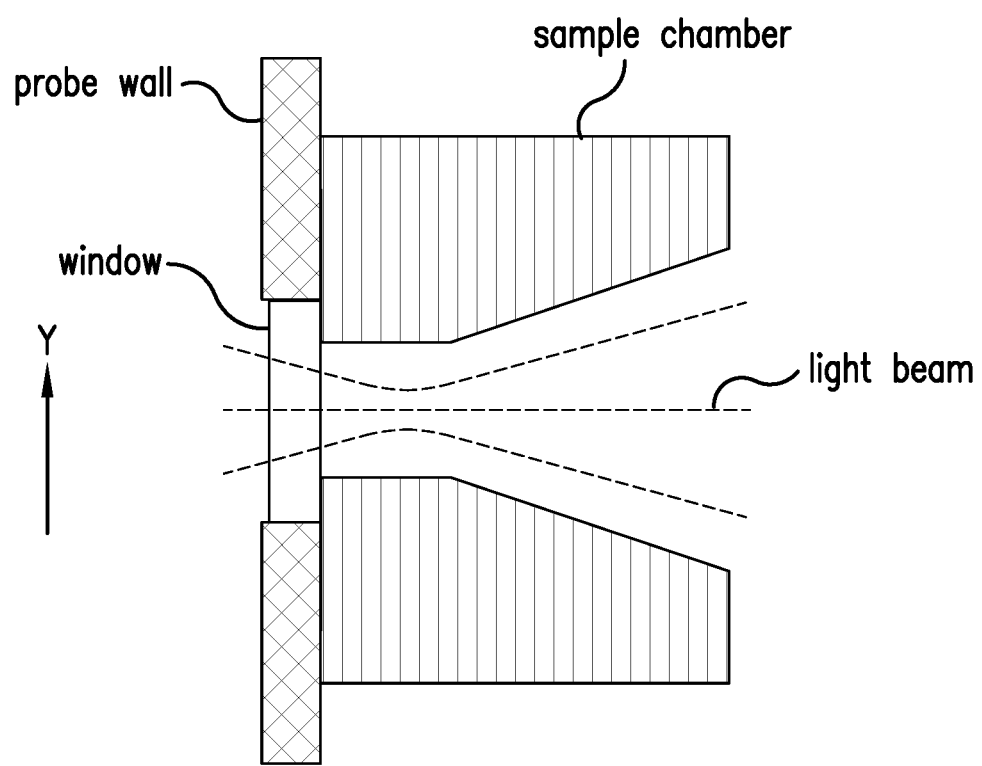
FIG. 9 shows a sample chamber, providing particle sample stability, as used in the present invention.

The half power point of the Lorentzian form of P(f), shown previously, occurs at approximately 10 Hz for a 3 micron particle in water. For larger particles, the spectral broadening due to Brownian motion is smaller and the signal to noise is degraded by the increasing 1/f noise below 10 Hz. Hence, dynamic light scattering is typically limited to measuring particles smaller than 3 microns, with optimal performance below 0.5 microns. Particle counters, which determine the size of individual particles by measuring scattered light, usually perform well above 1 micron, with drop in performance below 0.5 micron due to the strong drop of scattering crossection for small particles. Therefore these two methods complement each other in that each method is strong in the size range where the other is weak. For broad size distributions, ensemble dynamic light scattering techniques have problems detecting small particles in the presence of large particles due to the large difference in scattering signal. Therefore, the larger particles should be removed from detection in the dynamic light scattering system. This could be accomplished with a particulate filter, but with the inconvenience of filter changing and blockage. The configuration shown in FIG. 28 could also be used to remove larger particles from the interaction volume by settling. Also the data segments, which show characteristics of large particles, can be eliminated from the data sets which are combined to create the final power spectrum, as described above. The system would consist of a chamber, as shown in FIG. 28 or FIG. 9, which is connected as a flow though device with inlet and outlet valves. These valves divert the flow from the particle counting sample cell to pass though the sample chamber. The sample concentration is adjusted to provide optimal concentration for the dynamic scattering measurement and then the valves are turned to close off the chamber from the counter flow stream, creating a static sample in the chamber. More dispersant is then added to the counter system to reduce the particle concentration to appropriate levels for single particle counting. Signals are measured from the dynamic scattering and counting systems concurrently to produce two size distributions which are concatenated and blended (in a size overlap region) to produce one distribution over the entire size range. Since the larger particles will have higher settling velocities, they will settle out of the interaction volume first in the dynamic scattering chamber. Hence the particle size distribution in the interaction volume will change with time. After a long period of time, only the smaller particles will remain. The sample chamber could also have an inlet for direct insertion of sample dispersion for small samples which cannot fill the entire flow loop. In the case where the settling velocity of unwanted particles is low, the interaction volume must be reduced to shorten the time required for large particles to settle out of that volume. Any particle size sensor system (for example systems in FIGS. 1, 2, 3, 4, 5, 6, 7, 8, 10, 11A, 11B, 19, and 27) in this application could interact with the particle dispersion directly or through a window, with a vertical orientation (parallel to the gravitational acceleration) of the optical axis of the scattering optics. The beam would be focused with high numerical aperture close to the optical surface which interfaces with the dispersion. Then only particles close to the focus will contribute to the scattered light signal. The interaction volume can be reduced to less than 100 microns in length, so that slowly settling particles, moving parallel to the optical axis, will quickly settle out of the interaction volume.

The chamber in FIG. 28 is designed to block particles from settling into the interaction volume from above. This could also be accomplished by a generally horizontal plate which resides above the interaction volume, assuming that the direction of gravity is generally in a vertical direction or generally perpendicular to the horizontal direction. This plate could be turned out of position while the chamber is filled to avoid trapping air bubbles. Then the plate could be turned into position above the interaction volume when large particle removal, by settling, is required. The plate should be shaped appropriately to follow the shape of the interaction volume, so large particles settle out of all portions of the interaction volume in approximately the same time period. The analysis methods described in the section, "Starting with a generally homogeneous concentration distribution of particles over the entire cell" can be applied to this settling process, which is blocked from above. As the larger particles settle out of the interaction volume, scattering measurements, made at various times from that interaction volume, will be equivalent to scattering measurements made at various values of R in a sample cell after centrifugation or settling. In general, the plane of the plate is generally perpendicular to the direction of force on the particles. This force can originate from either centrifugal or gravitational acceleration. The plate may also be shaped to avoid source light illumination of the plate and resulting high scattering background.

Figure 75:
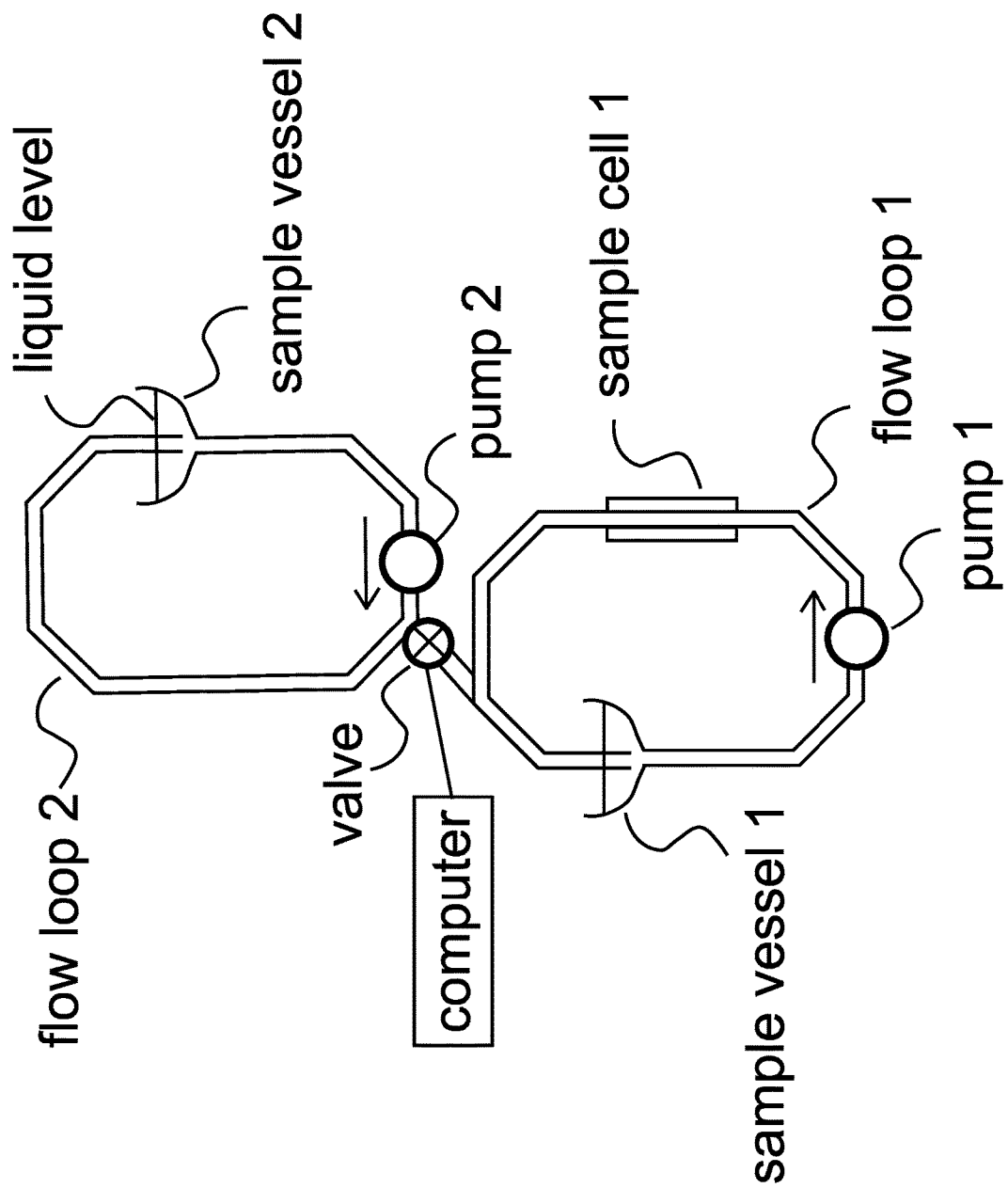
FIG. 75 provides a schematic diagram of a fluid flow system with two flow loops for adjusting the particle concentration to an optimum value.

The chamber in FIG. 28 or FIG. 9 could also be interfaced with a flow system as shown in FIG. 75. The system consists of two flow loops, each with an open sample vessel, which is optional on flow loop 1. In a particle counting system, the particle concentration must be optimized to provide the largest count levels while still insuring single particle counting. The concentration may be optimized by computer control of particle injection into the flow loop which contains the sample cell, as shown in FIG. 75. Concentrated sample is introduced into flow loop 2 through sample vessel 2. The sample vessel may also contain a stirring means for maintaining a homogenous dispersion in the vessel. Pump 2 pumps the dispersion around the loop to provide a homogenous dispersion in the loop and to prevent loss of larger particles through settling. A second flow system, flow loop 1, is attached to flow loop 2 through a computer controlled valve with minimal dead space. The computer opens the valve for a predetermined period to inject a small volume of concentrated dispersion into loop 1. The optical system counts the particles and determines the probability of coincidence counting based upon Poisson statistics of the counting process. The computer then calculates the amount of additional particles needed to optimize the concentration and meters out another injection of concentrated sample into loop 1, through the valve. Actually, both the concentration and pump speed for loop 1 may be controlled by computer to optimize counting statistics. When the particle concentration is low, higher pump speed will maintain a sufficient particle count rate for good count statistics. The optimum concentration may be different for different detectors and detection systems. Therefore the computer valve may adjust the concentration to various levels in succession. At each concentration level, data is taken with the appropriate detector(s) for that concentration level or detector array for a sufficient period and flow rate to accumulate enough counts to reduce the count uncertainty (due to Poisson statistics) to an acceptable level. The dynamic scattering chamber (FIG. 9 or FIG. 28) is inserted into flow loop 2 in sample region 2. In this way, the dynamic light scattering system can measure at the higher particle concentration of flow loop 2, while the counter, using sample cell 1, counts particles at the lower particle concentration of flow loop 1. If the particle concentration needs to be adjusted for the dynamic light scattering system, that system may be connected to flow loop 1, where the concentration is easily controlled.

The particle size distributions are calculated from each of the particle count and dynamic scattering systems. These distributions are converted to the same function (particle number vs. particle size or particle volume vs. particle size) and then the converted distributions are combined into one size distribution by concatenation of the converted distributions and blending of these distributions in the size regions where they overlap.

Small Particle Detector for Large Fluid Volumes

Semiconductor processes require very clean fluids with less than one 0.1 micron particle per cubic meter. The light scattered by a particle of this size can be detected as it passes through a focused laser beam. However at 10 meters per second flow rate, interrogation of a cubic meter of fluid would consume over 3 years through a laser volume of 1000 cubic microns (cubic volume of 10 microns on each side). This invention describes an apparatus for detecting the presence of one particle per cubic meter at a rate of generally 1 cubic meter per hour. The system is shown in FIG. 32.

Figure 32:
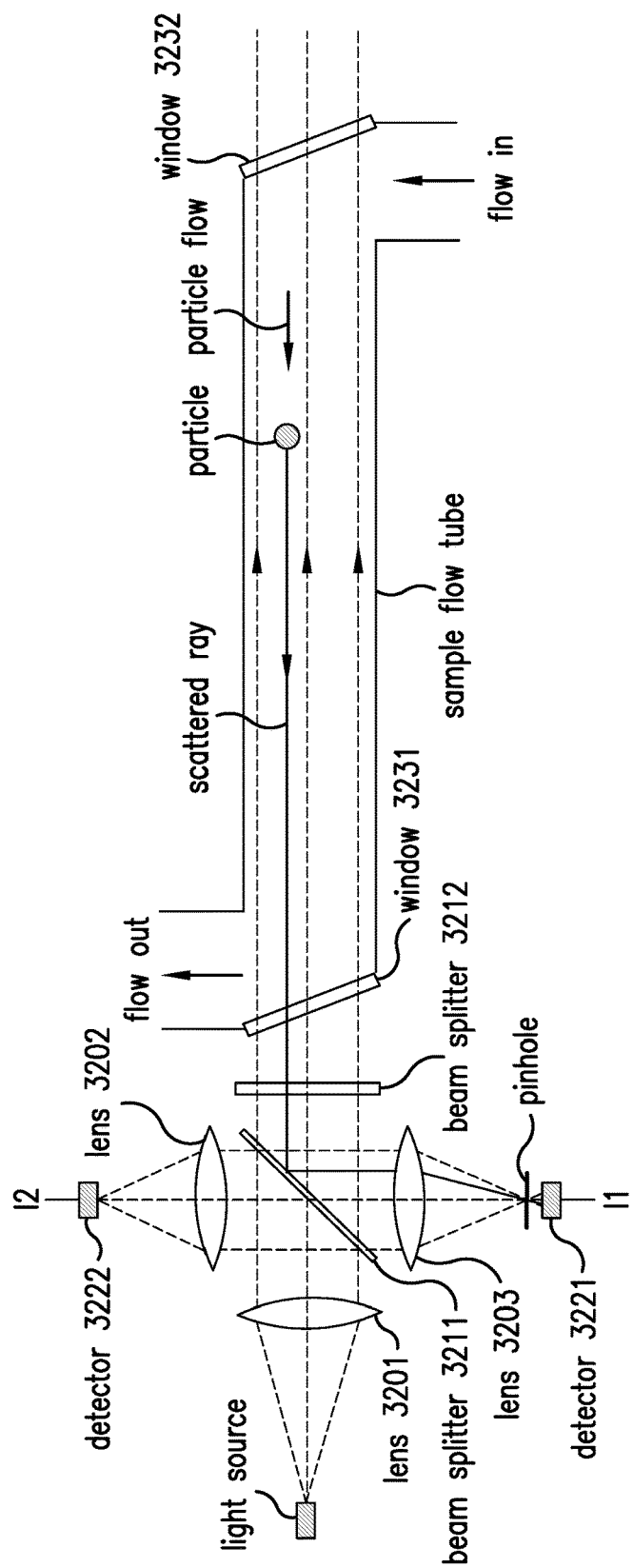
FIG. 32 provides a schematic diagram of an optical system for detecting particles at low particle concentration, according to the present invention.

A light source is projected into a sample flow tube by lens 3201, as shown in FIG. 32. The optics may be adjusted to collimate the beam within the tube or to produce a beam waist inside the tube. Beam splitter 3211 reflects a portion of the beam onto lens 3202 which focuses that light onto detector 3222. Detector 3222 measures the source intensity to correct for source fluctuations. The unreflected portion of the beam proceeds through beamsplitter 3212 which reflects a portion of the beam back through lens 3203, providing a local oscillator for heterodyne detection of scattered light from particles in the sample flow tube. The unreflected portion of the beam proceeds through optical window 3231 and travels down a long sample tube, through which the test fluid is pumped. Window 3232 allows the beam to exit the tube with minimal reflections back into the tube. Any particle passing down the tube will scatter light back to detector 3221 through beam splitter 3211, lens 3203 and a pinhole which maintains coherence requirements for heterodyne detection and eliminates background light from hitting detector 3221.

The major advantage of this system is the large crosssection of the interrogated volume in the sample flow tube and the long interaction distance within the tube, which could be meters in length. The two normalized (detector responsivity=1) detector currents, I1 from detector 3221 and I2 from detector 3222, can be described by the following equations:

$$I1 = \text{sqrt}(R1*T1*R*Io(t)*Is(t))*COS(F*t+A) + R1*T1*R*Io$$

$$I2 = K*R1*Io(t)$$

where:

COS(x)=cosine of x

K is a constant which describes the ratio of other efficiencies (optical and electrical), between the I1 and I2 channels, which are not due to the beamsplitters. R and T are the reflectivity and transmission of beamsplitter 3212, respectively. R1 and T1 are the reflectivity and transmission of beamsplitter 3211, respectively.

sqrt(x)=square root of x

Io(t) is the source beam intensity as function of time t

F is the heterodyne beat angular frequency at detector 3221 due to the motion of the scatterer in the flow tube. And A is an arbitrary phase angle for the particular particle. Is(t) is the scattered light intensity from the particle:

Is(t)=S*T1*R1*T*T*Io(t) where S is the scattering efficiency for the particle. S includes the product of the scattered intensity per incident intensity and optical scatter collection efficiency.

The light source intensity will consist of a constant portion Ioc and noise n(t):

$$Io(t) = Ioc + n(t)$$

We may then rewrite equations for I1 and I2:

$$I1 = R1*T1*T*\text{sqrt}(S*R)*(Ioc+n(t))*COS(F*t+A) + R1*T1*R*(Ioc+n(t))$$

$$I2 = K*R1*(Ioc+n(t))$$

The heterodyne beat from a particle traveling with generally constant velocity down the flow tube will cover a very narrow spectral range with high frequency F. For example, at 1 meter per second flow rate, the beat frequency (F/(2pi)) would be in the megahertz range. If we use narrow band filters to only accept the narrow range of beat frequencies we obtain the narrow band components for I1 and I2:

$$I1nb = R1*T1*T*\text{sqrt}(S*R)*Ioc*COS(F*t+A) + R1*T1*R*n(t)$$

$$I2nb = K*R1*n(t)$$

where we have assumed that n(t) is much smaller than Ioc.

The laser noise can be removed through the following relationship:

$$Idiff = I1nb - (T1*R/K)*I2nb = R1*T1*T*\text{Sqrt}(S*R)*Ioc*COS(F*t+A)$$

This relationship is realized by narrowband filtering of each of the I1 and I2 detector currents. One or both of these filtered signals are amplified by programmable amplifiers, with adjustable gains. The difference of the two outputs of these amplifiers is generated by a difference circuit or differential amplifier. With no particles in the beam, the gain of at least one of the programmable amplifiers is adjusted, under computer or manual control, to minimize the output of the difference circuit. At this gain (for example gain ratio (I1 signal gain)/(I2 signal gain)=K/(T1*R)), the source intensity noise component, in the detector 3221 beat signal, is removed from the difference signal Idiff which is fed to an analog to digital converter (A/D), through a third narrowband filter, for analysis to sense the beat signal buried in noise. This filtered difference signal could also be detected by a phase locked loop, which would lock in on the beat frequency of current from detector 3221.

Beamsplitter 3212 reflectivity is adjusted to obtain shot noise limited heterodyne detection, with excess laser noise removed by the difference circuit. This entire correction could be accomplished in the computer by using a separate A/D for each filtered signal and doing the difference by digital computation inside the computer. If both signals were digitized separately, other correlation techniques could be used to reduce the effects of source intensity noise. The advantage of this measurement is that the high frequency optical interference or heterodyne beat signal is produced for the duration of the particle's residence in the long flow tube. This tube could be meters in length. This could produce millions of beat cycles during the particle's transit, allowing phase sensitive detection in a very narrow bandwidth at megahertz frequencies, well above any 1/f noise sources. The power spectrum of a data set consisting of a large number of signal cycles will have a very narrow spectral width, which can be discriminated against broad band noise, by using the computed power spectrum of the signal and spectral discrimination algorithms. For example, a 1 meter long tube, with flow at 1 meter per second, will produce a heterodyne signal with a Fourier spectrum which consists of a narrow peak, with center in the megahertz range and a spectral width of a few Hertz. This signal can easily be retrieved from broadband noise by narrowband filtering or digital spectral analysis of the signal. If the flow variation (and Doppler frequency variation) is significant, a broader band analog filter could be used with spectral discrimination analysis of the digitized signal. For example, if the flow rate were 1 meter per second with a 1 meter flow tube, the heterodyne signal could be broken up and digitized in approximately 1 second data segments. Based upon the known variation in flow rate over long periods, the heterodyne signal would be filtered with a bandpass which covers the entire range of Doppler frequencies which span the entire flow rate variation. The Fourier transform or power spectrum of each 1 second data segment is then analyzed to find a narrow spectral peak located somewhere in the broader bandpass of this filter. While the center frequency of this peak may drift with flow rate over long periods, over any 1 second period the flow will be sufficiently constant to produce a narrow Doppler spectrum which can easily be discriminated against the broad band noise, because the spectral density of the narrow peak will be higher than that of the noise. This narrow spectrum can be insured by controlling the flow rate to be generally constant during each particle transit time through the flow tube. The pumping system could consist of a pressurized tank (with regulator), with a flow restriction (orifice) on the outlet. The flow through this orifice may vary slowly over long periods, but over 1 second periods, the flow will be very constant, without the short term variations introduced by pumps with mechanical frequencies greater than 1 hertz.

Figure 33:
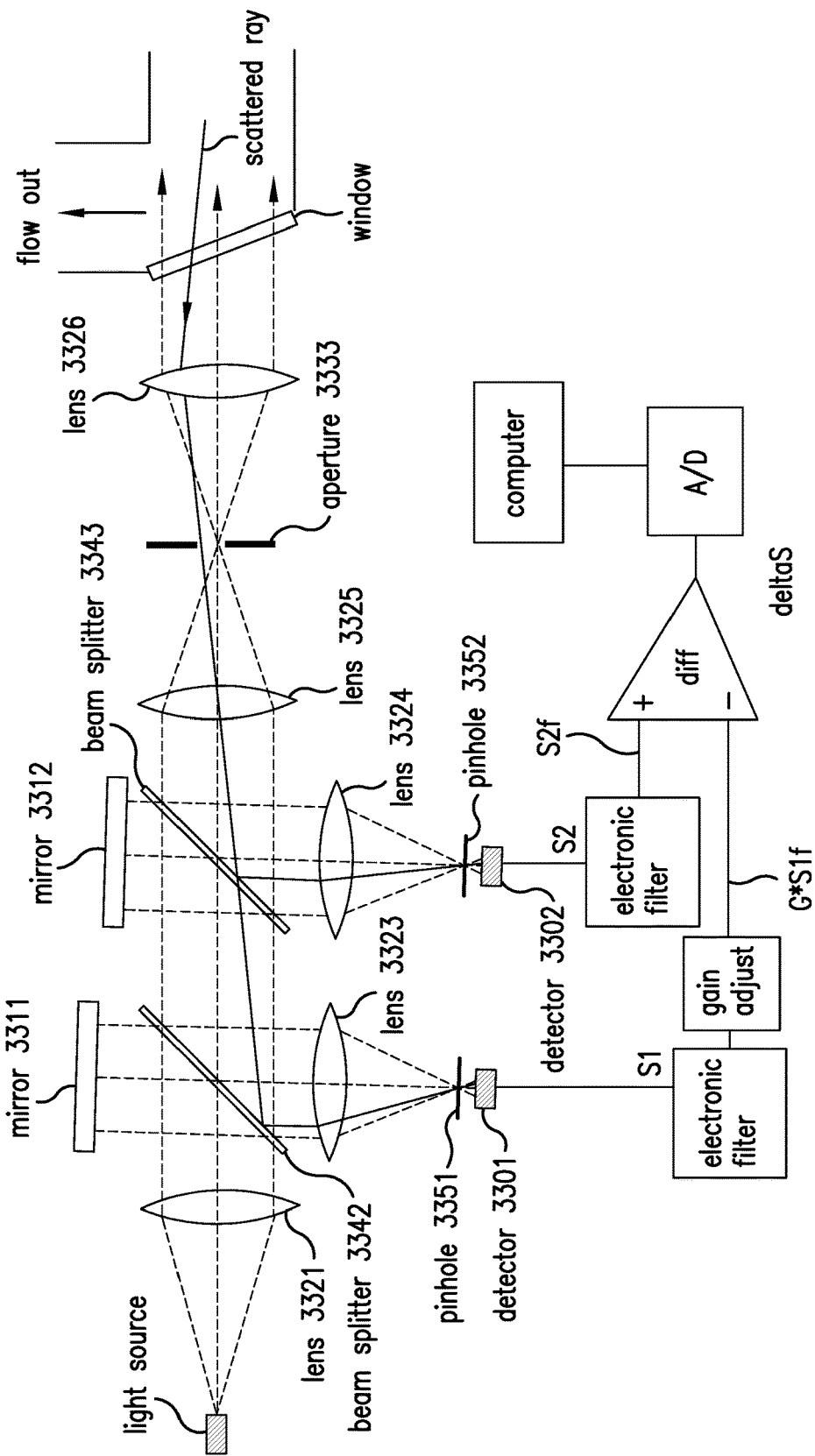
FIG. 33 provides a schematic diagram of an optical system for detecting particles at low particle concentration and utilizing a differential measurement, according to the present invention.

Another system for noise reduction is shown in FIG. 33, which shows only the detection portion of the system up to window 3231 of the flow tube shown in FIG. 32. In this case two interferometers, using detector 3301 and detector 3302, separately detect the oscillation of the interference signal at two different phases. The purpose is to eliminate the noise component of these signals by analysis of these phase shifted signals. For example, if the relative positions of mirror 3311 and mirror 3312 are adjusted to provide 180 degree optical phase shift between the two interferometers, then the two beat signals will be 180 degrees out of phase, however the common mode noise will still be in phase. Hence the difference of these signals (after the bandpass filtering) will eliminate the common mode noise but enhance the beat signals. The source light is generally collimated by lens 3321 and focused through aperture 3333 by lens 3325 and then generally collimated (or focused for a beam waist) by lens 3326 for projection down the flow tube which contains the flowing dispersion. Scattered light from any particles in the beam passes back through lens 3326, aperture 3333, and lens 3325 before being split off by two successive beamsplitters (beamsplitter 3342 and beamsplitter 3343) which use lens 3323 and lens 3324, respectively, to project the scattered light to detector 3301 or detector 3302, through pinholes. These pinholes define the range of scattering angles which are accepted by each detector and the number of coherence areas received by each detector. A portion of the source light is also split off by beamsplitter 3342 and beamsplitter 3343 and reflected by mirror 3311 and mirror 3312, respectively, to provide local oscillator for heterodyne interferometry by mixing with the scattered light on detector 3301 and detector 3302, respectively. Mirror 3311 and mirror 3312 are slightly tilted (exaggerated for illustration) so that the light reflected by each mirror does enter the source through the beamsplitters and lens 3321. Laser diode noise is sensitive to feedback in to the laser cavity. By tilting these mirrors, the pinhole 3351 and pinhole 3352 should be positioned to capture identical portions of the scattered wavefront which is parallel to the wavefront of each mirror reflection to provide generally a single interference fringe on each detector. Then usually the mean of the scattering angle range will be slightly less than 180 degrees. In this case aperture 3333 must be widened to allow passage of the source light and the scattered light, which do not pass through the same region at the plane of aperture 3333. However, if laser feedback noise is not a problem, then mirror 3311 and mirror 3312 can operate at 90 degree reflection (relative to the source beam) and aperture 3333 can be smaller to pass only the source light and scattered light over a small angular region around 180 degree scattering angle. In this case pinhole 3351 and pinhole 3352 could be eliminated if they do not offer any other light baffling advantages, because they will provide optical blocking over the same scattering angular range as aperture 3333. In general the sizes of these pinholes or apertures are chosen to only allow one fringe (or a minimum number of fringes) to be seen by each detector to maximize the beat signal amplitude on each detector. Also each detector must see the same fringe, or fringe set, so that the interferometric beat signals will be identical, but 180 degrees out of phase, on detector 3301 and detector 3302. The signals will have the same form as shown before:

$$S1 = \mathrm{sqrt}(S*T1)*(Ioc+n(t))*\mathrm{COS}(F*t+A1)+T1*(Ioc+n(t))$$

$$S2 = \mathrm{sqrt}(S*T2)*(Ioc+n(t))*\mathrm{COS}(F*t+^{\wedge}2)+T2*(Ioc+n(t))$$

Where T1 and T2 account for optical reflection and transmission differences between the two detector systems. After electronic filtering (either bandpass filtering at the beat frequency or high pass filtering, with cutoff below the beat frequency) we obtain the filtered version for each signal:

$$S1f = \mathrm{sqrt}(S*T1)*Ioc*\mathrm{COS}(F*t+A1)+T1*n(t)$$

$$S2f = \mathrm{sqrt}(S*T2)*Ioc*\mathrm{COS}(F*t+A2)+T2*n(t)$$

Then we use an adjustable gain, G, (and adjustable phase if needed) on one signal to balance these two detection channels. Here we have assumed that Ioc is much larger than n(t). The difference circuit, diff in FIG. 33, then produces the following difference signal at the input to the analog to digital converter (A/D):

$$\mathrm{delta}S = S2f - G*S1f$$

The gain G can be adjusted for minimum deltaS when no particles are in the flow tube (note: this same electronic design could be used to process the signals from detector 3221 and detector 3222 in FIG. 32). Then either mirror 3311 or mirror 3312 can be moved by micro-actuator to maximize the portion, of the deltaS signal, which is at the beat frequency while a low concentration sample of particles is flowing through the flow tube. The beat frequency component of deltaS is maximized when the mirror positions provide the following optical phase difference between the detection arms:

$A1-A2=m\pi$ where $m$ is an odd integer

When these two conditions are satisfied, the following equations will be satisfied:

$G=T2/T1$ $A1-A2=m\pi$ $deltaS=\text{sqrt}(S*T2)*Ioc*\text{COS}(F*t+A1)+T2*n(t)-(\text{sqrt}(S*T2)*Ioc*\text{COS}(F*t+A1-m\pi)+T2*n(t))$ and since $\text{COS}(x-m\pi)=-\text{COS}(x)$ for $m$ odd $deltaS=2*\text{sqrt}(S*T2)*Ioc*\text{COS}(F*t+A1)$ deltaS will be the pure beat signal from the moving particle without excess laser noise effects. However, residual noise sources which are not common to both channels may not be totally eliminated, such as shot noise of the individual detectors. But Ioc can be adjusted to a sufficiently high level to provide shot noise limited heterodyne detection for both detectors, with common mode noise eliminated by the differential measurement. The residual noise can be reduced by using power spectrum calculation, correlation, or matched filters for discriminated detection of the sinusoidal signal at the beat frequency, which can be calculated from the flow velocity.

Laser phase noise is another possible error source. However, for systems with flow tube lengths less than 1 meter (total maximum optical path differences below 2 meters), the phase noise, even from the worst sources (laser diodes), will be below 1 milliradian RMS. This noise will be much lower for gas lasers such as HeNe lasers. If laser phase noise (or short laser coherence length) is a problem, the optical paths for mirror 3311 and mirror 3312 can be extended to match the average optical path for the scattering particle during travel of the particle down the flow tube. For example, if a particle at the middle of the transit down the tube is approximately 0.5 meter from the midpoint between the beamsplitters, then the mirrors should be placed 0.5 meter away also. This could also be accomplished by using coiled single mode fiber optics, with coupling lens and reflecting end, to extend the optical path of the mirror arms in a compact space. Otherwise, the open air mirror arm paths could run parallel to the flow tube to minimize the total volume of the detection system. Also lasers must be chosen with coherence lengths longer than the optical pathlength difference of each interferometer arm. This pathlength difference is slightly longer than twice the length of the active flow tube section, if the mirror arms are not extended. Certain laser diodes and most gas lasers have coherence lengths greater than 2 meters so that each particle will produce more than a million beat frequency cycles during one passage through a 1 meter long flow tube. But shorter or longer tubes will also work well, as long as the source meets the coherence length requirements.

The signal to noise is maximized by using a narrow band filter, centered at the Doppler frequency of the moving particle. However, the flow velocity in the tube may not be constant with time and so the Doppler frequency may drift. Also laser phase noise may produce some variation of the frequency. The bandwidth of the analog narrow band filter must be sufficient to pass these frequency variations over the time scale of a complete analysis which may take hours. Therefore, the narrow band analog filter should cover the overall spectral width of long term Doppler frequency drift. The signal which passes through this filter will be digitized directly (with difference computed after digitization), or if the signal differences are done by analog electronics, then the difference signal will be digitized as shown in FIG. 33. The velocity and Doppler frequency drift over one transit time of the flow tube can be much smaller than over the entire measuring time. Therefore, the data should be processed to maximize the signal to noise given the very narrow bandwidth of the signal from one transit time. The power spectrum of each digitized data set, from each successive period of one particle transit time, will produce a narrow peak at the position of the Doppler frequency for that transit time period. For example, if the average flow velocity in the tube were 1 meter per second, and the light wavelength were such that the corresponding Doppler frequency were 1 Mhz, then a flow velocity variation of 2% about this average would produce a frequency variation of 20 Khz. So in this case the narrow band filter should be at least 20 Khz wide. However if, during any single transit, the velocity is constant to within 10 ppm, then the power spectrum of each transit would produce a 10 Hz wide peak at the Doppler frequency of that velocity. The power spectrum will provide excellent discrimination against signal noise outside of this 10 Hz frequency band. In this way, the best signal to noise is obtained due to the excellent frequency discrimination of the power spectrum; and the narrow band filter removes unwanted signal components which would tax the common mode rejection of the difference computation or analog difference circuit. To maximize the signal to noise, the power spectrum should be computed for each transit time data set and the peak of that spectrum should be found. If that peak is sufficiently narrow and greater than a certain threshold above the background spectrum, then a particle will be counted for that data set.

In some cases, the particle size of the detected particle may be important. A second optical system, which measures lower angle scattering, can be placed into the flow tube. This system can project a beam across the flow tube to detect and count larger particles which do not require the high sensitivity of the backscatter system shown in FIGS. 32 and 33. A laser beam is projected through two opposing windows in the sides of the flow tube. A lens collects scattered light at a low scattering angle. The beam can be shaped by anamorphic optics to produce a thin plane of light which passes through the flow stream. An additional lens can be added to collect scattered light at the angles of interest, as shown elsewhere by this inventor, but in this case the interaction volume will encompass generally the entire crossection of the flow tube.

This 180 degree optical phase technique can also be applied to conventional dynamic light scattering systems which measure heterodyned scattered light from multiple particles, moving due to Brownian motion. The interference of the local oscillator and the scattered light from each particle will produce a signal which consists of a group of sinusoids of random phase and frequency. Each of these sinusoids will be measured by both detectors with a 180 degree phase shift between them, so that when the two phase shifted signals are subtracted, the common mode excess laser noise cancels out leaving only the signal due to Brownian motion of the particles. The electrical bandwidth of the detection system must accomadate the bandwidth of the Brownian spectral broadening of the light which is scattered from the moving particles. This broadening is used to determine particle characteristics, including particle size.

Figure 34:
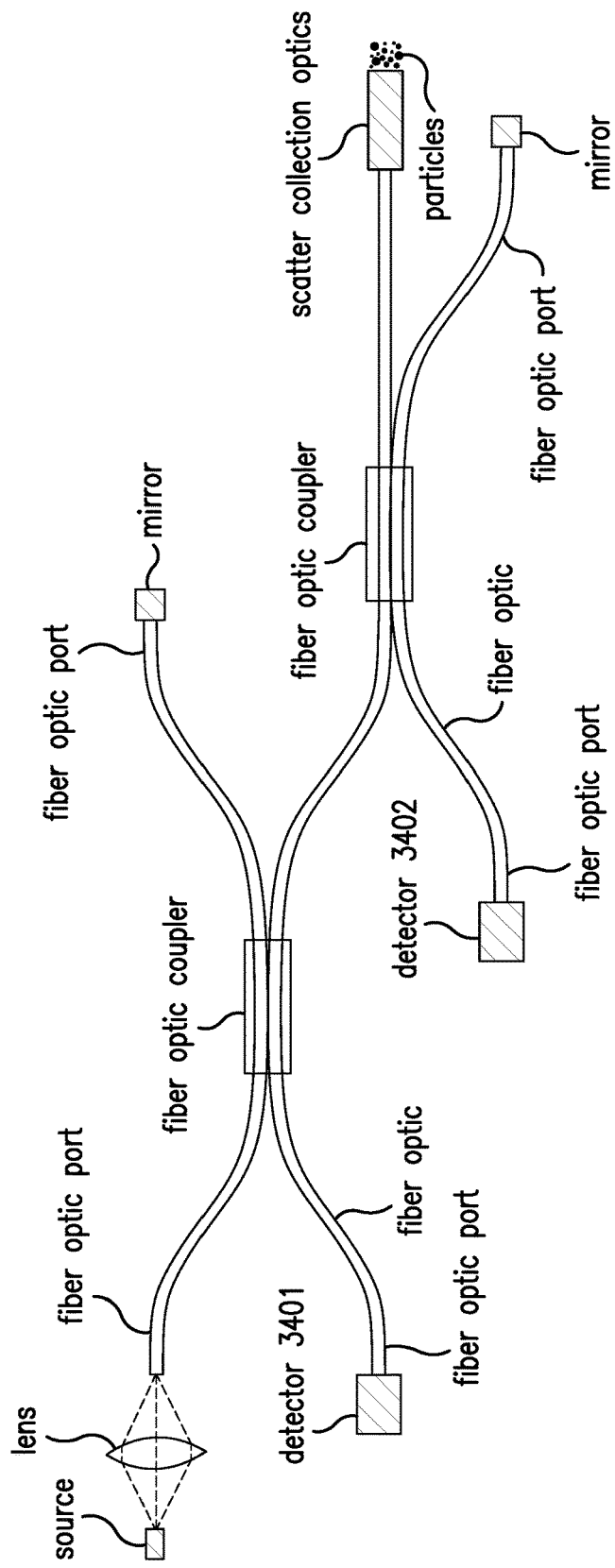
FIG. 34 provides a schematic diagram of a fiber optic system, performing the differential measurement of the optical system in FIG. 33 for detecting particles at low particle concentration and measuring particle motion and size distribution.

This double detector system can be designed as shown in FIG. 33, where the flow tube is replaced by a sample cell which holds a static, non-flowing, sample. The focal length of lens 3326 is chosen to provide the desired source beam shape in the particle dispersion. This double detector can also be used in a fiber optic system using fiber optic couplers, where the local oscillator is derived from a reflector on one of the output ports of each coupler, as shown in FIG. 34. Detector 3401 and detector 3402 have the same function as detector 3301 and detector 3302 in FIG. 33 and they would be connected to the same electronics and computer analysis as described before. The mirrors in FIG. 34 have function similar to mirrors 3311 and 3312 shown in FIG. 33, except that the optical paths are now fiber optic instead of air. As before, the optical path difference between the mirror reflected light and the scattered light must meet the following criteria for both detectors:

$A1-A2=m\pi$ where $m$ is an odd integer

If the optical path length of the fiber optic mirrored arms vary due to temperature or stress changes in the fiber optic, the phase of one arm could be controlled by an fiber optic phase modulator, and a feed back loop, to maintain the maximum heterodyne beat signal at the output of the difference circuit.

Figure 35:
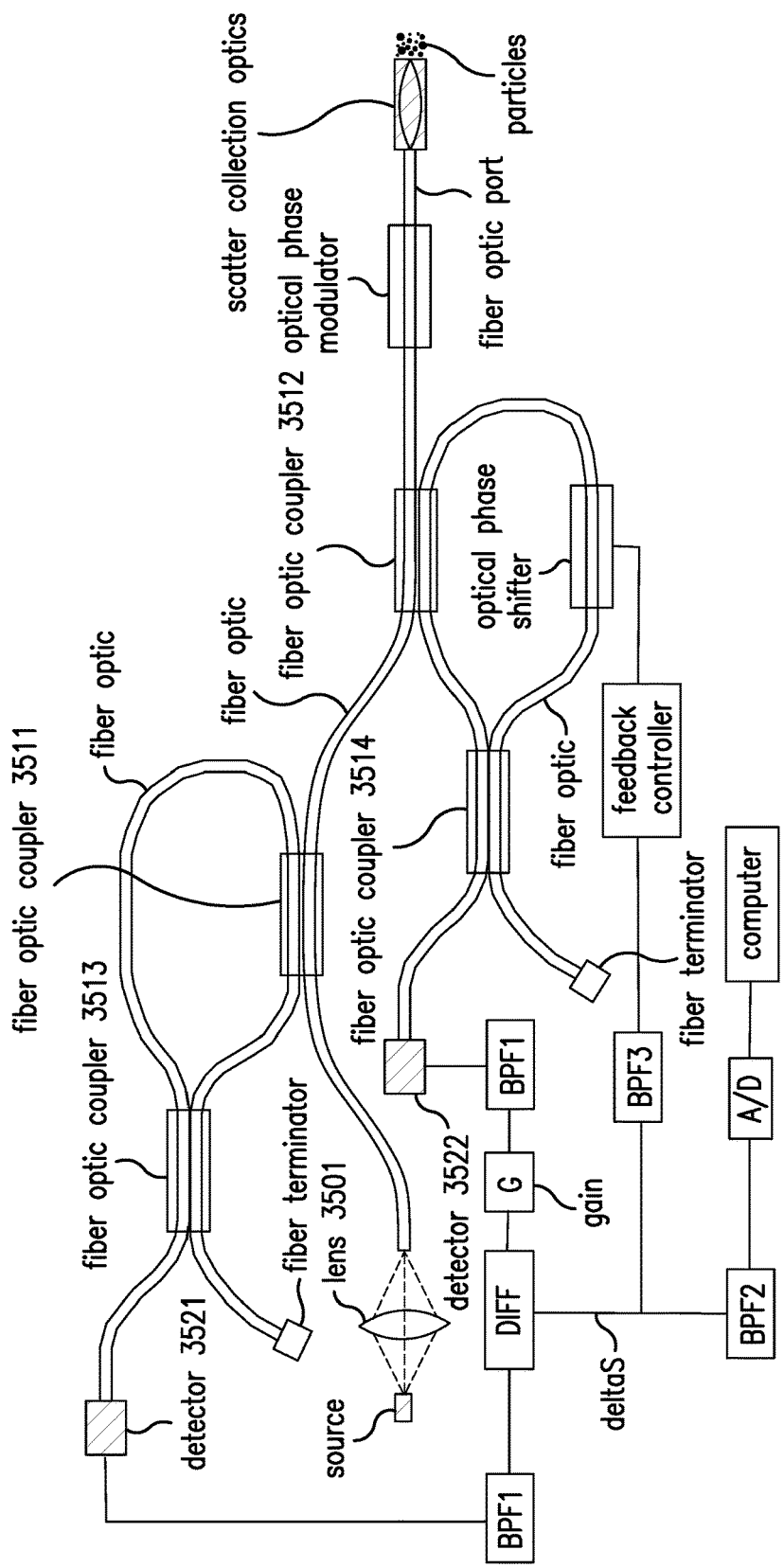
FIG. 35 shows a variation of the system in FIG. 34, with the advantages of low light reflection feedback into the laser source, low interferometric crosstalk between detectors, and active optical phase control.

FIG. 35 shows a system, which is similar to that shown in FIG. 34, with the advantages of low light reflection feedback into the laser source, low interferometric crosstalk between detectors, and active optical phase control. The light source is focused into a fiber optic by lens 3501. The source light travels through coupler 3511 and coupler 3512 to the scatter collection optics, which focus the light into the particle dispersion and collect light scattered from the particles as shown previously in this document. The scattered light, which travels back through the fiber optic, is split off by coupler 3512 to detector 3522, through coupler 3514, and by coupler 3511 to detector 3521 through coupler 3513. Source light is mixed with the scattered light through coupler 3511 and coupler 3513 for detector 3521 and through coupler 3512 and coupler 3514 for detector 3522. This source light provides the local oscillator for heterodyne detection on both detectors. An optical phase shifter (such as a piezo-electric fiber optic stretcher) is placed between coupler 3512 and coupler 3514 to control the optical phase of the local oscillator for detector 3522 through a feedback loop, which continually maintains the phase difference between detector 3521 and detector 3522 signals as shown previously:

$A1-A2=m\pi$ where $m$ is an odd integer

The heterodyne signals from the two detectors are bandpass filtered, by BPF1, to only pass the frequencies of interest and Fmod (see below). In addition, the signal from detector 3522 has adjustable gain G to balance the two signals as shown previously:

$G=T2/T1$

Both of the processed detector signals are subtracted by the DIFF difference circuit to produce the deltaS signal as described previously. The detection system may need to maintain the proper phase difference during periods when particles and scattered light are not present, to be ready for a particle transition. In this case, a phase modulator is placed between coupler 3512 and the scatter collection optics to modulate the optical phase of the scattered light with very small optical phase deviation. The frequency, Fmod, of this modulation is outside of the light scatter heterodyne frequencies of interest, to avoid contamination of the particle characterization signal. A feedback loop controls the phase shifter, between coupler 3512 and coupler 3514, to continually maximize the Fmod frequency component in the deltaS signal, accommodating thermal and stress induced optical phase drift in the fiber optics. The deltaS signal is filtered, by bandpass filter BPF3, to remove spurious signals and to pass only the Fmod frequency component to the feedback controller. The deltaS signal is filtered, by bandpass filter BPF2, to pass the scatter signals of interest and to remove the Fmod frequency component before being digitized for analysis by the computer. If particles are present continuously or for sufficient period to adjust the optical phase before data collection, then the feedback circuit could control by maximizing the scatter portion of the heterodyne signal, without the need for the optical phase modulator at Fmod. The same methods, as described previously using anti-reflection coatings and beam dumps, should be used to reduce the light reflection at all ends of fiber optics and surfaces of conventional optics to avoid laser feedback noise and interferometric noise. FIG. 36 shows details of the fiber terminator, in FIG. 35, which reduces light reflection back into the end of the fiber optic, due to Fresnel reflection at the fiber/air interface. A thick optical window, with refractive index which generally matches the index of the fiber optic core, is attached to the fiber end with adhesive or gel which also generally matches the fiber optic core refractive index. The back reflection is reduced substantially because the air/window reflecting surface is anti-reflection coated and that surface is moved far from the entrance to the fiber optic core. This anti-reflecting surface could also be tilted to direct the reflected beam away from the fiber optic core or said surface could be concave or convex to increase the divergence of the reflected light and reduce the light intensity at the fiber optic core. In either case, the back reflected diverging beam has extremely low intensity at the fiber optic core.

The system in FIG. 35 could be utilized in any dynamic scattering system by designing the BPF1 and BPF2 filters to pass the frequencies of interest for the particular application. This includes measurement of Brownian motion broadened scatter spectrum to determine particle size or the flow tube particle detector described previously. The system shown in FIG. 35 (and in FIG. 34) could replace the detection system in FIG. 33, by placing the end of the fiber optic, which interfaces with the scatter collection optics in FIG. 35, at the position of aperture 3333 in FIG. 33, to project a light beam down the tube and to collect scattered light from any particle in the tube, through lens 3326. The system in FIG. 35 could also be designed as an integrated optic chip to reduce production costs.

These techniques could be applied to remove excess laser noise from any heterodyne signals.

Zeta Potential

Figure 37:
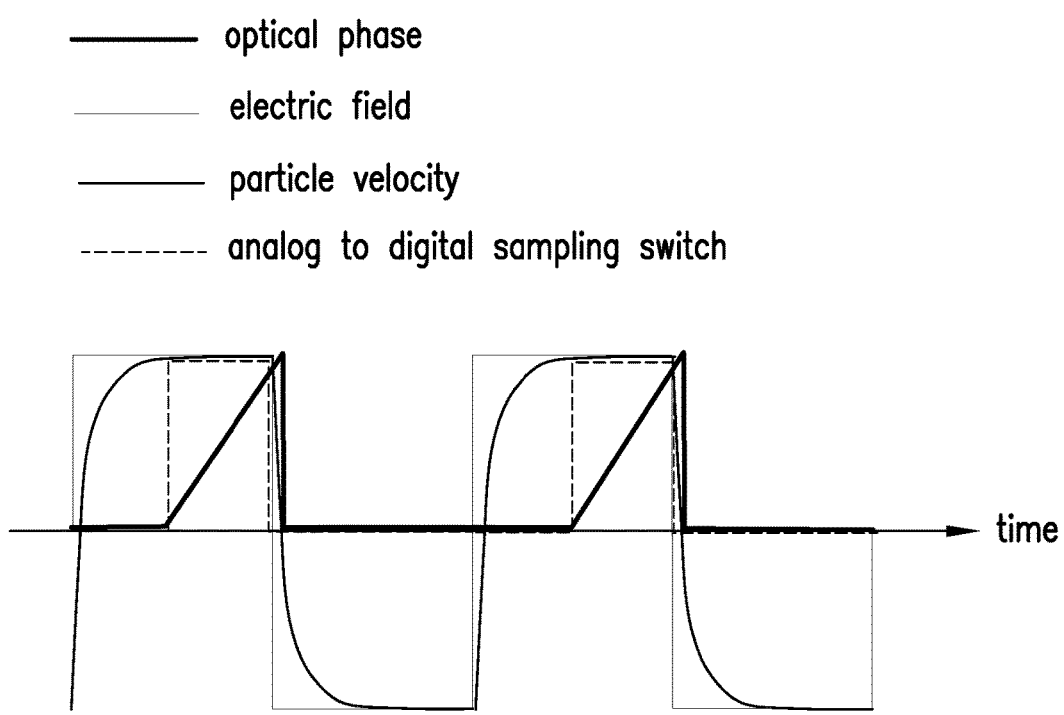
FIG. 37 shows plots of optical phase, electric field, particle velocity, and analog to digital sampling switch signal vs. time for charged particles in a modulated electric field.

The Zeta potential of particles can be determined from the electric mobility, of the particle, measured from the charged particle velocity in an electric field. However, motion of the dispersing fluid in the electric field can produce errors in the measurement of the particle motion. One way of reducing the fluid motion is to use an oscillating electric field, which rapidly oscillates positive and negative as shown in FIG. 37. Then the dispersing liquid cannot react as quickly as the particles, and the fluid motion is reduced significantly. FIG. 37 also shows the particle velocity due to this oscillating field. This motion can be measured by sensing the Doppler shift of light scattered by the moving particles. Since the particles cannot react immediately to the changes in the electric field, the particle velocity should be sensed over a reduced section of each cycle where the velocity has reached a stable value, as indicated by the analog to digital converter switch function shown in FIG. 37. When the switch is high the analog to digital converter (A/D) collects samples of the signal from the scattering detectors, shown in FIGS. 38 and 39. Likewise, the analog to digital converter (A/D) can also digitize signal during the corresponding segments of the negative electric field pulses and the same analysis applied to that data. The reduced A/D collection period is chosen to measure only while the particle velocity is generally constant. If the A/D period is longer, the spectrum of the signal can be corrected for the resulting spectral broadening by including the shape of the velocity function in calculation of W(f). (W(f) would be the power spectrum of the actual velocity vs. time function instead of the RECT function, see below).

Figure 38:
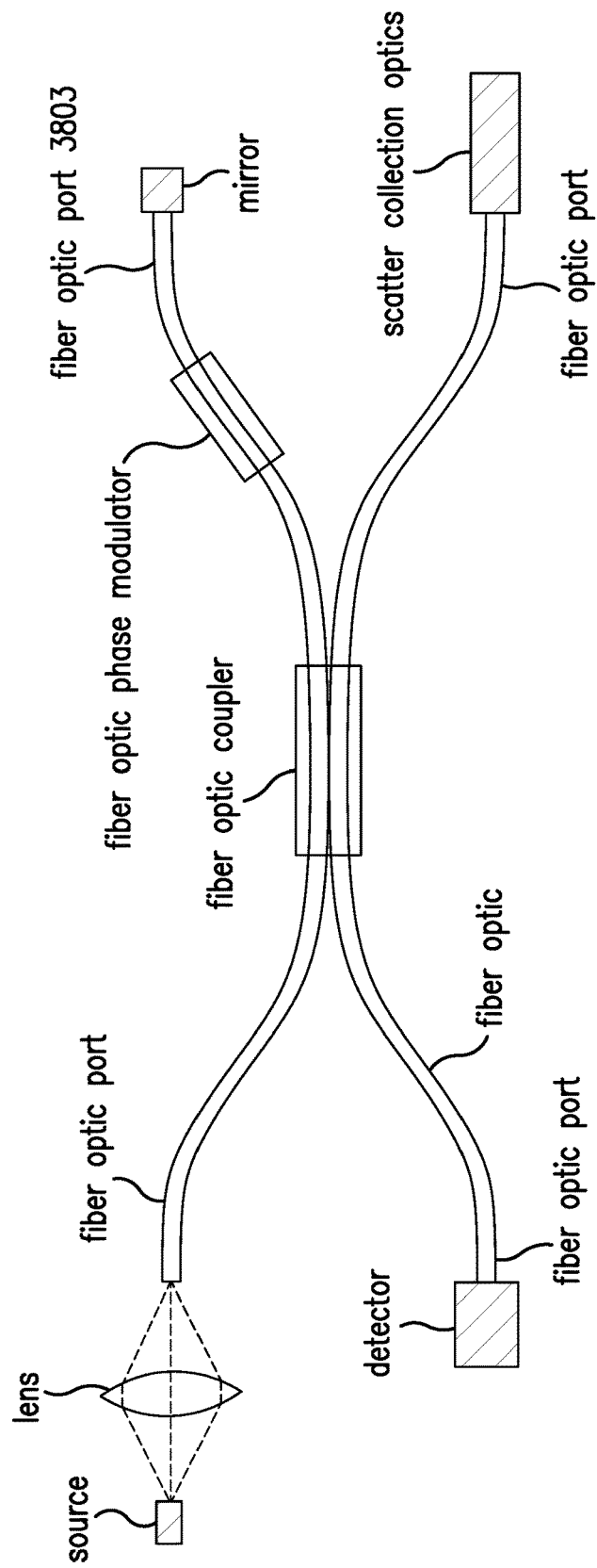
FIG. 38 provides a schematic diagram of a fiber optic system, according to the present invention, utilizing heterodyne detection to measure the spectrum of light scattered by moving particles, with the local oscillator provided by reflection from fiber optic port 3803 through a fiber optic coupler.
Figure 39:
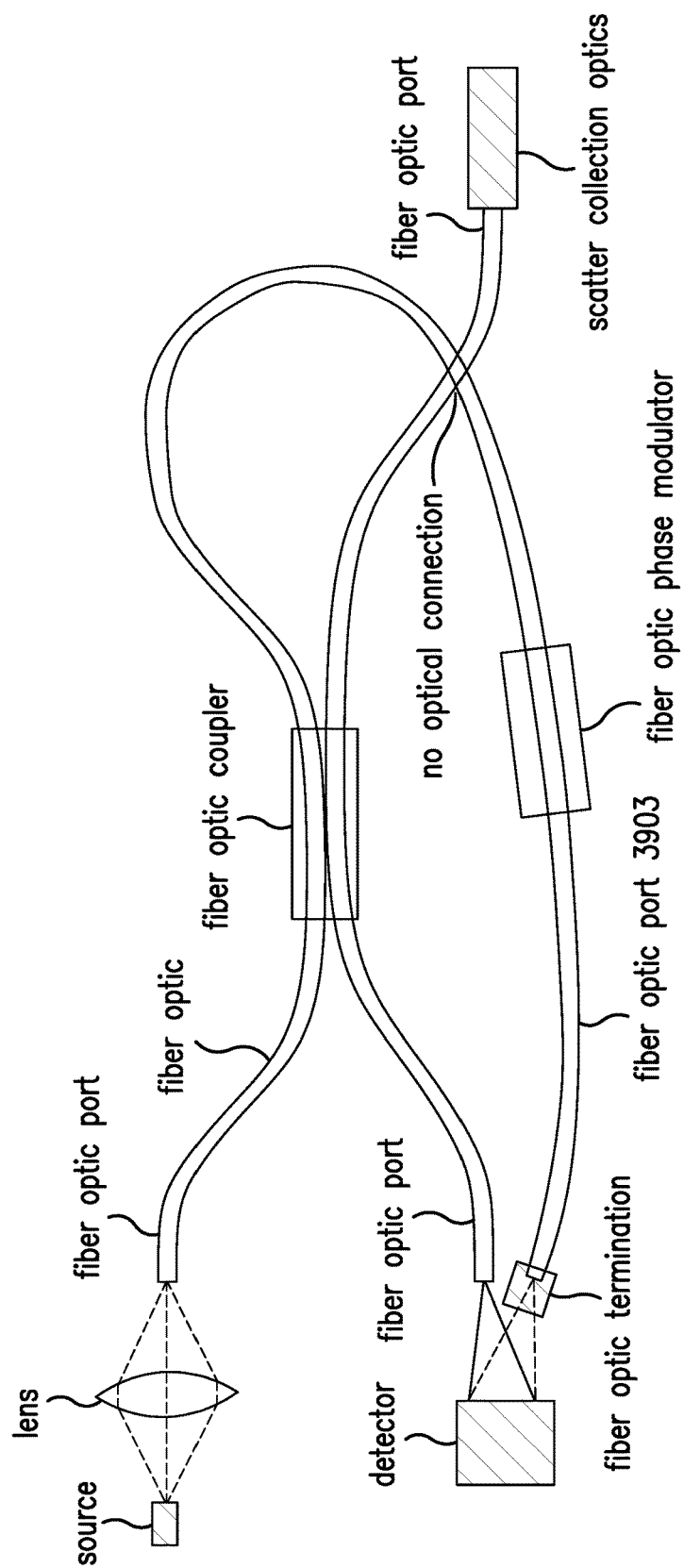
FIG. 39 provides a schematic diagram of a fiber optic system, according to the present invention, utilizing heterodyne detection to measure the spectrum of light scattered by moving particles, with the local oscillator provided directly from fiber optic port 3903.
Figure 68:
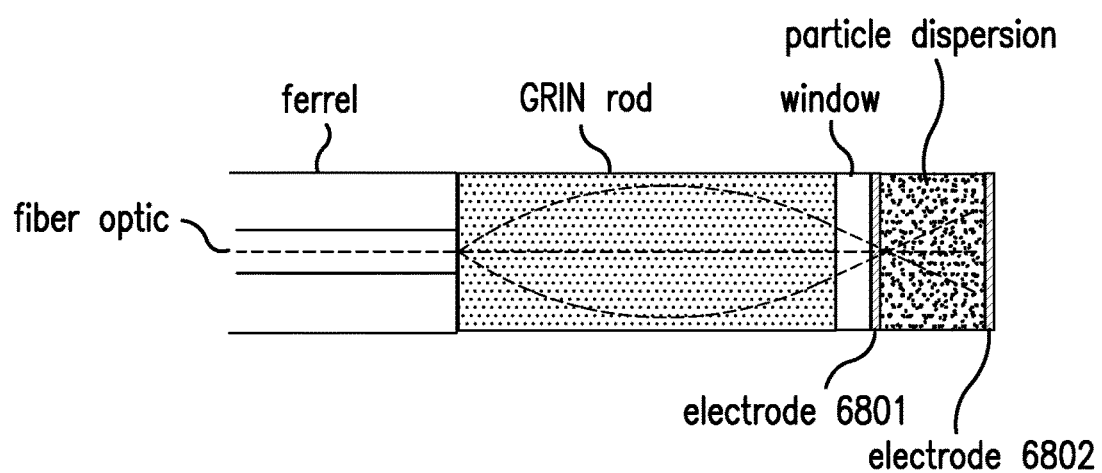
FIG. 68 provides a schematic diagram of scatter collection optics of a fiber optic system, measuring light scattered by particles and viewing particle dispersion between two electrodes, one electrode being transparent, according to the present invention.

FIGS. 38 and 39 show two configurations for a fiber optic system which uses heterodyne detection to measure the spectrum of light scattered by the moving particles. These designs can also be used for determining spectral broadening due to Brownian motion, for determining particle characteristics, including particle size. In FIG. 38 the local oscillator is provided by reflection from port 3803 (back through the fiber optic coupler to the detector); and in FIG. 39 the local oscillator is provided directly from port 3903 to the detector. In each case the scattered light is mixed with light from the optical light source to produce a beat frequency spectrum indicative of the particle motion due to the electric field and Brownian motion. The electric field should be generally parallel to the optical axis of the scatter collection optics to maximize the Doppler frequency. This can be accomplished by placing two electrodes in the particle dispersion, with a transparent electrode closest to the scatter optics. The scatter collection optics are detailed in FIG. 68. In FIG. 68, the source light is focused into the particle dispersion, through a GRIN rod (Gradient index lens) and a window. The focus spot is close to the interface between the window and the dispersion. This GRIN lens could also be replaced by a conventional lens. The local oscillator for heterodyne detection can also be provided by reflection of source light at either the interface between the fiber and GRIN rod, or at the interface between the window and the particle dispersion. The window is used to provide an appropriate surface for creating an electrode or for contacting the particle dispersion. In some cases, the window can be eliminated, with the source focus at the interface between the GRIN rod and the particle dispersion. Electrode 6801 is a planar electrode which covers the surface, which contacts the dispersion. A second planar electrode 6802 is placed in the dispersion at some distance from electrode 6801 to produce the electric field between the electrodes. Electrode 6801 must be electrically conductive and it must pass the source light and scattered light. These properties can be provided by three different designs for electrode 6801 in FIG. 68. Since the particle charge can be positive or negative, the particle velocity and Doppler shift can be positive or negative. Therefore, the spectrum of the heterodyne signal should be upshifted to be centered about some frequency which is greater than the largest negative Doppler frequency shift which is to be detected. This frequency upshift can be provided by optical phase modulation of the source light, just before the light is mixed with the scattered light, to provide a frequency shift to the entire spectrum. If the optical phase is ramped during the data collection, as shown in FIG. 37, the spectrum of the scatter detector current will be upshifted, so that both positive and negative sides of the spectrum can be seen. The optical phase shifter could also be replaced by an acousto-optic frequency shifter.

The power spectrum P(f) of the detector current, from data taken during the A/D sample period, in either configuration will consist of the Doppler spectrum, S(f), from the particle motion due to the electric field force on the particles, convolved with the convolution of Doppler spectrum, B(f), due to Brownian motion and the spectral broadening, and W(f), due to the finite width or shape of the velocity vs. time function.

$$P(f)=S(f)\Theta B(f)\Theta W(f)$$

Where $\Theta$ is the convolution operator

The goal is to determine S(f) which is indicative of the motion due to the electric field force. This can be solved for by inverting the P(f) equation using deconvolution algorithms where the impulse response for the deconvolution algorithm is:

$$H(f)=B(f)\Theta W(f)$$

For example, if the velocity is constant during the A/D sampling period, W(f) is the square of the SINC function (sin(x)/x) from the Fourier Transform of the RECT (rectangle) function representing the A/D sampling period. Use of this function is optional; W(f) could be eliminated from the above equations, but with additional spectral broadening in the result for S(f). B(f) is the Lorentzian function which describes the spectral broadening due to Brownian motion of the particles. So these two spectral broadening mechanisms can be removed from P(f) to produce the spectrum, S(f), due to only the particle motion caused by the electric field force on the particles, by using deconvolution algorithms such as iterative deconvolution. This deconvolution could be done multiple times over various frequency intervals for P(f), where each interval represents the region for a particular size of particles, because B(f) is particle size dependent. Therefore the various modes in the S(f) function should each be associated with a certain particle diameter, d, (or certain range of particle size centered about d) and a certain Brownian spectral broadening B(d,f). Each of these frequency intervals could be deconvolved individually, using the B(d,f) corresponding to the size of the particles in that interval. Otherwise, if this correspondence is not known, the entire spectrum could be deconvolved with the B(d,f) for either the average particle diameter d, or the largest particle diameter d of the particle sample. The solution, based upon the largest d, would provide the least amount of spectral sharpening and mobility resolution, but it would not produce artifacts from "over-sharpening" of the spectra, which would be caused by using the broader B(d,f) from a diameter d which is smaller than most of the particles in the sample. The size of the particles can be determined by turning off the electric field and measuring the Brownian broadened spectra alone and using known methods to determine the size distribution from the power spectrum. This measured Brownian spectrum (with electric field off) could also be used directly for B(f) in the deconvolution of the entire spectrum P(f); or individual modes of the Brownian spectrum, B(f), could be associated with certain modes of P(f) to break P(f) up into multiple frequency ranges (one for each mode) with a separate deconvolution and separate B(f) function for each deconvolution. The measured Brownian spectrum with zero electric field and no optical phase modulation is the positive frequency half of the full symmetrical Brownian spectrum, which is symmetrical about zero frequency. Therefore, B(f) is created by using the measured Brownian spectrum for positive frequencies only and using the mirror image of that spectrum for the negative frequency region, producing a full function B(f), which is symmetrical about zero frequency, from the positive frequency half spectrum provided by the measured Brownian spectrum at zero electric field, without optical phase modulation. If optical phase modulation is used during the measurement of B(f), with zero electric field, then that entire B(f) spectrum (centered about the optical shift frequency of the optical phase modulator) can be used directly to deconvolve P(f).

If P(f) were measured at various peak electric field values, the Brownian spectral broadening could be determined for each mode in S(f). As the electric field increases, the frequency scale of each mode in S(f) will expand proportionally, but B(f) is independent of electric field. At very high electric fields, the modes in S(f) will be well separated, but B(f) will be the same. Therefore, a set of simultaneous equations, for P(f), can be set up to solve for the S(f) portion of P(f):

$$P(f,E1)=S(f,E1)\otimes B(f)\otimes W(f)$$

$$P(f,E2)=S(f,E2)\otimes B(f)\otimes W(f)$$

$$P(f,E3)=S(f,E3)\otimes B(f)\otimes W(f)$$

This set is for 3 different values of electric field, E1, E2, and E3. But any number of equations can be formed by measuring at more values of electric field E. W(f) is known from the A/D switch function and velocity function. B(f) can be determined by deconvolving all simultaneous equations with one of many different trial functions of B(f). Only the true B(f) function will produce the same frequency scaled solution S(f, E) for each of the equations, where frequency scaled solution S(f, E) is given by:

$$S(f,E)=S(f\cdot E1/E,E1) \text{ for the } P(f,E1) \text{ equation}$$

$$S(f,E)=S(f\cdot E2/E,E2) \text{ for the } P(f,E2) \text{ equation}$$

$$S(f,E)=S(f\cdot E3/E,E3) \text{ for the } P(f,E3) \text{ equation}$$

The value of S(f) at each value of f is proportional to the scattered light of the particles with the velocity and corresponding Doppler shift equal to f. Therefore, the number or volume of particles at that velocity can be calculated by dividing S(f) by the appropriate scattering efficiency for the particles of corresponding size, which is calculated from the Brownian spectral broadening for that particular mode in S(f). In any case, once S(f) is determined, the particle number vs. particle velocity distribution, particle number vs. mobility distribution, and particle number vs. Zeta potential distribution can all be determined directly from S(f), because the particle velocity is proportional to frequency f with known constant of proportionality; and the mobility and Zeta potential can be calculated from the velocity using known relationships.

The above analysis can be applied to P(f) calculated from the data collected during each period of continuous A/D sampling in FIG. 37, or it can be applied to the power spectrum of the concatenation of the detector signal data sets from multiple said periods. Also, the detector current power spectra functions from multiple A/D periods can be averaged to produce a final averaged P(f) which becomes the input P(f) for the analysis described above.

Figure 40:
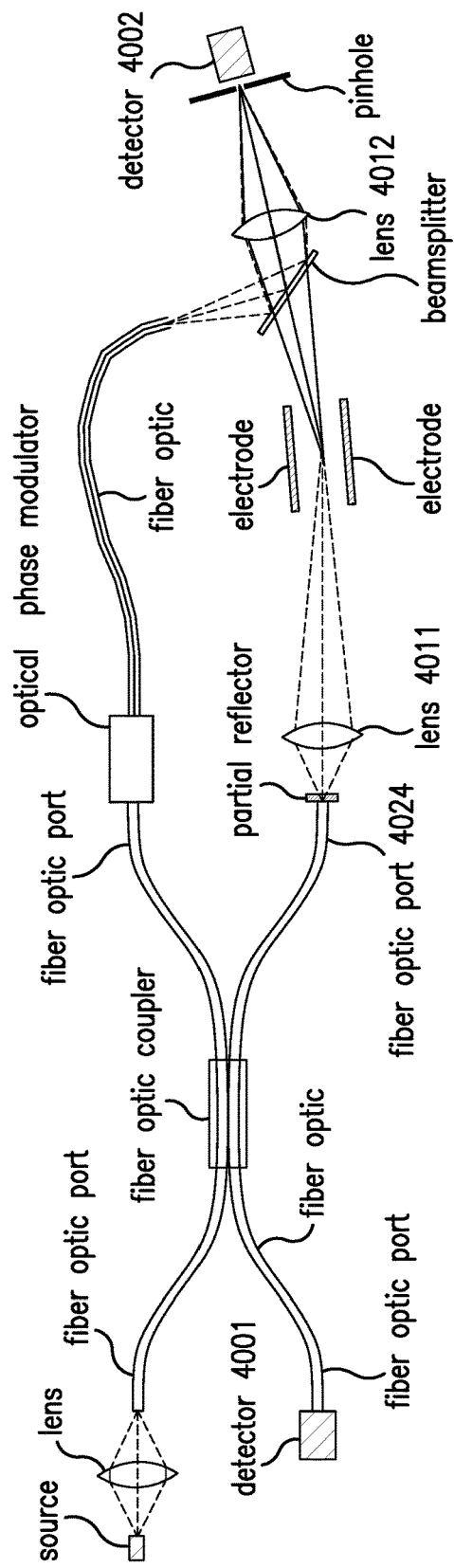
FIG. 40 provides a schematic diagram of a fiber optic system, according to the present invention, utilizing heterodyne detection to measure the spectrum of light scattered by moving particles and viewing a small volume of a particle dispersion between two electrodes.

Scatter signal measurement at low scattering angles is desirable for mobility measurement of particles to reduce the Doppler spectral broadening due to Brownian motion. However, large particles scatter much more light at small angles than small particles do; and so the scatter from any debris in the sample will overpower the Doppler signal from the electric field induced motion of the smaller charged particles in the electric field and cause errors in the Zeta potential measurement. FIG. 40 shows a method of measuring Dynamic light scattering from a small interaction volume created by restricting the size of the illuminating beam and the effective viewing volume. When only scattered light from a very small sample volume is measured, the scatter signal from large dust particles will be very intermittent, due to their small count per unit volume. The data sorting techniques, outlined by this inventor previously, can be used to eliminate the portions of the signal vs. time record which contain large signal bursts due to passage of a large particle. The system shown in FIG. 40 can also be used with those same data sorting techniques to sort and group data sets with different characteristics before final inversion to determine the particle size distribution, because the small viewing volume increases the signal change and discrimination during the passage of a large particle. And in the Zeta potential case, measurements can be made at low scattering angles without the scattering interference from dust contaminants, because the signal vs. time segments, which are contaminated by large particle signals, can be eliminated from the data set which is analyzed for mobility measurements.

The spectral power in certain frequency bands, as measured by fast Fourier transform of the data set or by analog electronic bandpass filters, could be used to categorize data sets. Also the ratio of scattering signals at two scattering angles would indicate the size of the particles. Consider a Zeta potential measuring dynamic scattering system (for example as shown in FIG. 40) where the scattering signal from the detector is digitized by an analog to digital converter for presentation to a computer algorithm. The entire data record is broken up into shorter data sets. In addition, the signal could be connected to analog filters and RMS (root mean squared) circuits, which are sequentially sampled by the analog to digital converter to append each digitized data set with values of total power in certain appropriate frequency bands and at certain scattering angles which provide optimal discrimination for larger particles. The use of analog filters may shorten the characterization process when compared to the computation of the Fourier transform. These frequency band power values are then used to sort the data sets into groups of similar characteristics. Since larger particles will usually produce a large signal pulse, both signal amplitude and frequency characteristics can be used to sort the data sets. A large peak signal value in any data set would also indicate the presence of a large particle in that set.

The use of analog filters is only critical when the computer speed is not sufficient to calculate the power spectrum of each data set. Otherwise the power spectra could be calculated from each data set first, and then the power values in appropriate frequency bands, as determined from the computed power spectrum, could be used to sort the spectra into groups before the data is processed to produce velocity and mobility distribution. Data sets, with very high signal levels at low scattering angles and low signal levels at high scattering angles, could also indicate the presence of large particles and debris. Or a simple signal level threshold could be used to reject data sets with large signal pulses due to debris. These large particle or debris data sets, as selected by the various criteria outlined above, are not included in the calculation of the final power spectrum which is used to calculate the particle velocity, mobility, and Zeta potential distributions.

The system in FIG. 40 shows two detectors: detector 4001 measures backscatter for size and mobility measurements (primarily for size due to large Brownian component) and detector 4002 measures forward scatter for size and mobility measurements (primarily for mobility due to small Brownian component). The fiber optic coupler provides the local oscillator for heterodyne detection, using a phase modulator as used in FIGS. 38 and 39. The beamsplitter mixes the phase modulated local oscillator light with the scattered light onto detector 4002. Lens 4012 and the pinhole at detector 4002 define a small viewing volume. The intersection of this restricted viewing volume with the focal spot of the source beam from lens 4011 defines a small scatter interaction volume, where the average count of larger debris particles is much less than one. The light rays, passing through lens 4011, represent light from the source and the rays, passing through the beamsplitter and lens 4012, represent scattered light. An electric potential is placed across the two plate electrodes, in FIG. 40, to produce the electric field to induce the charged particle motion. A partial reflector before lens 4011 provides the local oscillator for detector 4001. However, the Fresnel reflection at the fiber optic port 4024 should be sufficient to provide the local oscillator for detector 4001, without the partial reflector. The optical phase modulator can be a fiber optic phase modulator, which are inexpensive to manufacture. Other heterodyne system designs, with small interaction volumes, can be used to make this measurement as shown previously by the inventor. By replacing the flow cell with a non-flowing cell with electrodes, the same techniques can be employed using those designs. As shown previously, the particle size distribution is determined by turning off the electric field and optical phase modulator and measuring the Brownian induced spectral broadening, from which the size distribution can be determined using known methods. For determining B(f), to be used to deconvolve P(f), the electric field is turned off, but the optical phase modulator could be on to provide the positive and negative halves of the B(f) spectrum.

Note that any heterodyne system, described in this application, can be changed to a homodyne system by removing, tilting, or anti-reflection coating the surface or surfaces which create any significant reflection to the detector(s), of source light, which would create a local oscillator for heterodyne detection.

Methods and apparatus for determining particle size distribution by measuring scattered light and using centrifugation or settling Many particle size measuring systems measure the light scattered from an ensemble of particles. Unfortunately these systems cannot measure mixtures of large and small particles, because the scattering efficiency (the scattered intensity at a certain scattering angle per particle per incident intensity) of the smaller particles is much less than that of the larger particles. The contribution of scattered light from the smaller particles is lost in the more intense scattering distribution from the larger particles. These particle ensemble measuring systems also cannot resolve two closely spaced modes of a volume-vs.-size distribution or detect a size distribution tail of small particles in the presence of larger particles. This is true for both static (angular scattering) and dynamic (power spectrum or autocorrelation of the scattered light detector current) scattering distributions which must be inverted to determine the particle size distribution. This section describes methods and apparatus for centrifugal size separation and spatial separation of the particles, for subsequent spatial evaluation by either static or dynamic light scattering.

Particles in a centrifugal force field accelerate in the fluid until the viscous drag and centrifugal force is balanced. This velocity is the terminal velocity of the particle. To first order, this velocity is proportional to the product of the differential density of the particle to that of the surrounding liquid, the centrifugal acceleration, and the square of the particle diameter. If an ensemble of particles of various sizes is placed into a centrifugal force field, each size will reach a different terminal velocity and travel a different distance, in the direction of the centrifugal force, in a given time period. So the particles will spread out or become redistributed spatially according to size. This spatial distribution is then scanned by either a static or dynamic scattering system to accurately determine the particle size distribution. This idea could be implemented with dedicated optical scattering detection hardware or this concept could be added as a sample cell accessory to existing particle size instruments.

Figure 41:
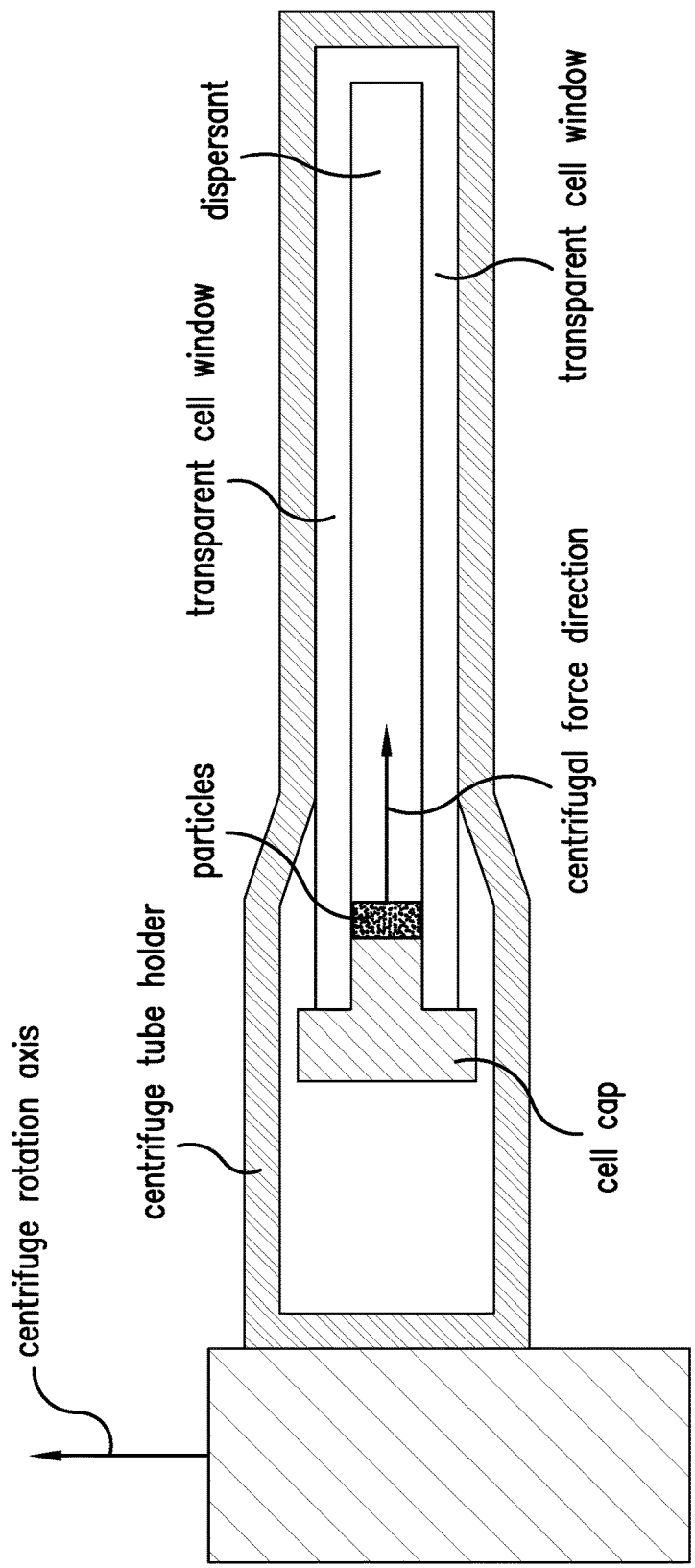
FIG. 41 provides a schematic diagram of a centrifuge cell holder and particle dispersion cell, before centrifugation, as used in the present invention.

The first step of the process is illustrated in FIG. 41. A sample cell, which has two optical windows, is filled with clean dispersant. The concentrated particle dispersion is introduced at the top of sample cell and capped. This cell is then placed into a standard centrifuge for centrifugation for a predetermined period of time. The sample cell may be designed to fit into a standard slot in a centrifuge rotor or a custom rotor may be designed to hold the sample cell (or cells). Many cells could be centrifuged at one time.

This technique will work with any starting distribution of the particles before centrifugation. Because size dependent separation will always occur, leaving smaller slower particles separated closer to their starting point, the smaller particle's size and concentration can be measured separately from the larger particles. This separation eliminates or greatly reduces the scattering cross-talk between particles of various sizes and prevents the smaller particles from getting lost in the scattering distributions of the larger particles.

Figure 42:
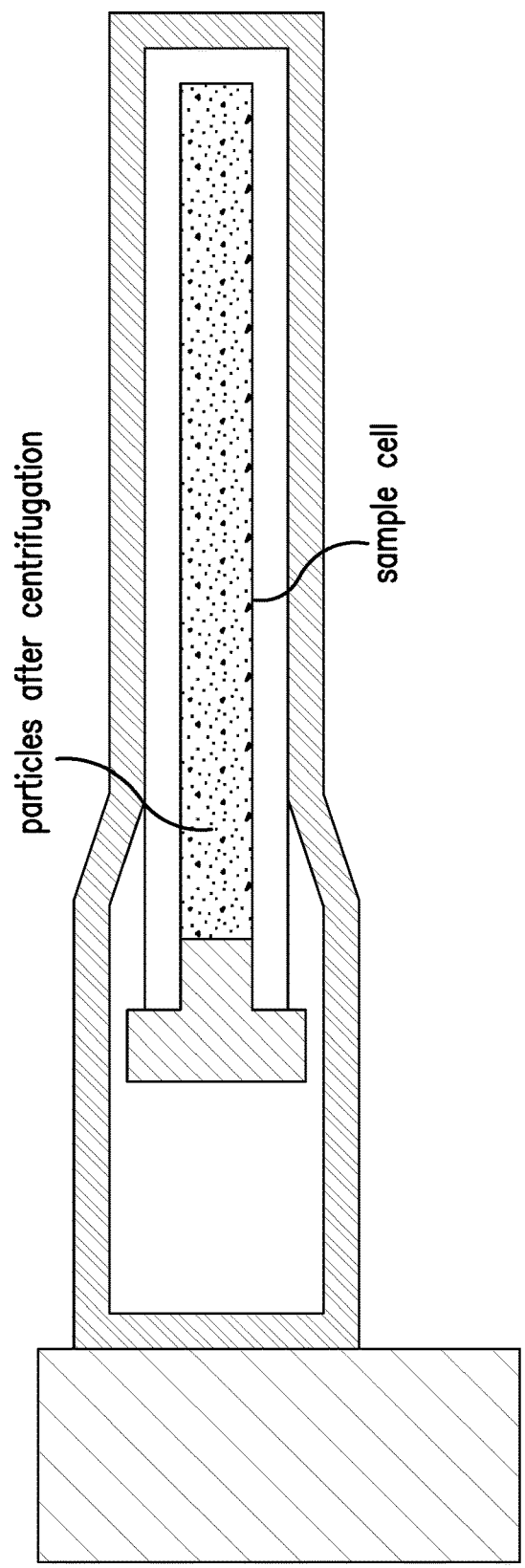
FIG. 42 provides a schematic diagram of a centrifuge cell holder and particle dispersion cell, after centrifugation, as used in the present invention.

The optimal starting particle concentration distribution is shown in FIG. 41 (see also FIG. 45), with all particles in a layer close to the axis of rotation for the centrifuge. In this case each particle size mode will separate out into an individual band of particles in the sample cell, during centrifugation. So a tri-modal size distribution (see FIG. 45) would produce three spatially separate bands along the direction X of the centrifugal force. In the case of a broad size distribution, the various size particles might be distributed along the X direction as shown in FIG. 42 (concentration distribution not shown).

Figure 43:
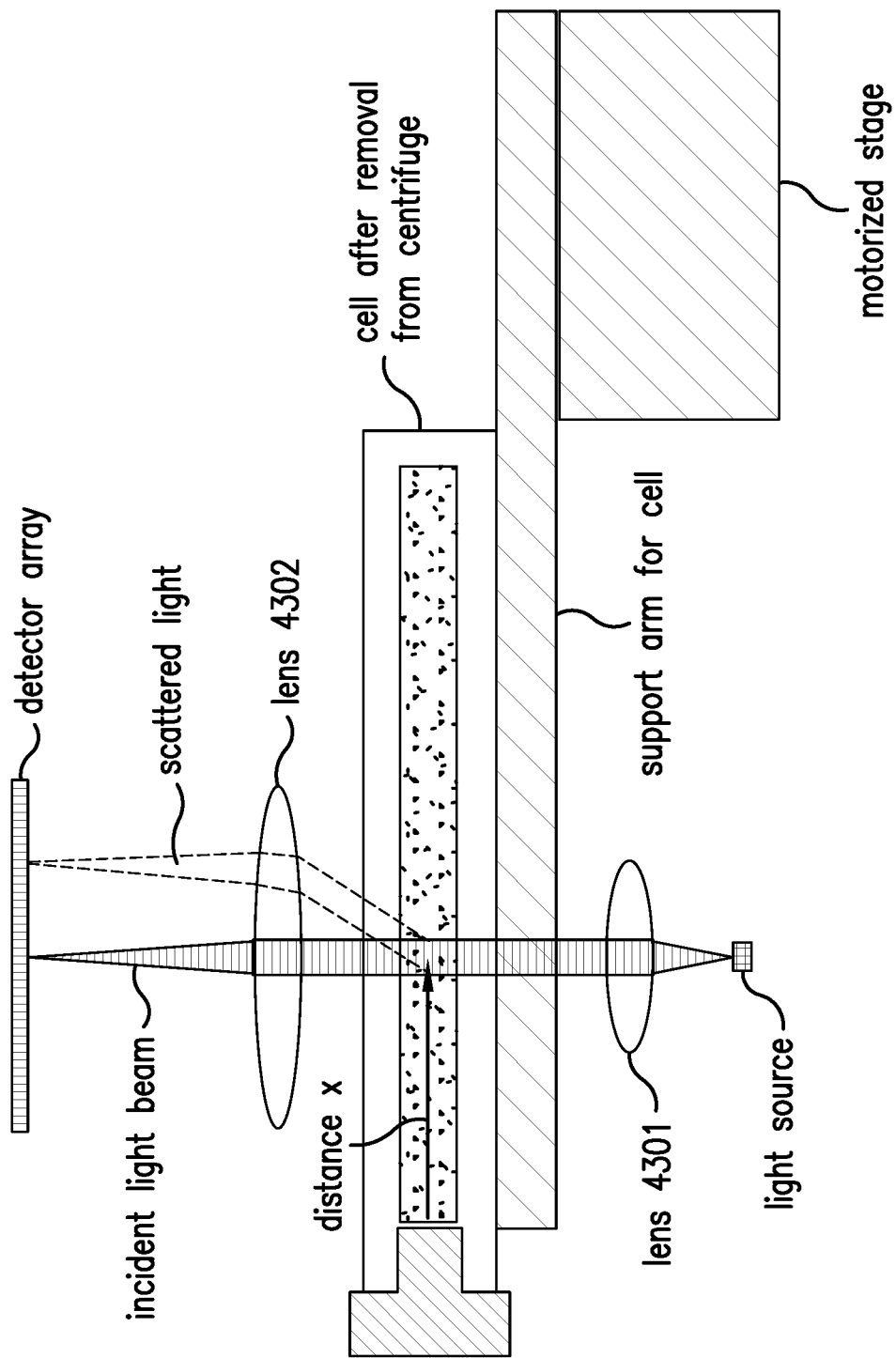
FIG. 43 provides a schematic diagram of optical and mechanical systems, used in the present invention, measuring the angular distribution of scattered light at various locations in a cell containing particle dispersion.

After centrifugation, the sample cell is removed from the centrifuge and inserted into a scattering instrument as shown in FIG. 43, for the case of static scattering. The static scattering optical system measures the light scattered at various angles. The light source is collimated or focused (to interrogate smaller portions of the sample cell for higher spatial resolution) by lens 4301. The resulting light beam passes through the sample cell and is scattered by the particles. The scattered light and the unscattered beam are focused onto an array of detectors in the back focal plane of lens 4302. A larger scattering angular range may be obtained by using multiple lens/array units or by using multiple light sources. The sample cell is scanned in the direction of the centrifugal force to measure the angular scattering distribution at various X positions. Many existing angular scattering methods can also be used to scan the cell and determine the particle size distribution at each X position. The cell and motorized stage could also be placed into commercially available dynamic or angular scattering instruments to scan the cell. Each detector element measures the light scattered over the angular range defined by that element. The scattering angle is the angle between the direction of the scattered light and the incident light beam. The resulting intensity-vs.-scattering angle distribution is inverted to obtain the particle size distribution. This is usually accomplished by iterative methods such as iterative deconvolution or regression. Also certain size parameters may be determined from intensity measurements at only a few scattering angles which would reduce the time per inversion and reduce the instrument cost. For example, consider the case where only 4 scattering angles are measured to determine the mean particle size at each position. The theoretical values for these 4 detectors vs. particle size may be placed in a lookup table. The 4 detector values from a measured unknown particle segment are compared against this table to find the two closest 4 detector signal groups, based upon least squares minimization. The true size is then determined by interpolation between these two best data sets based upon interpolation in 4 dimensional space. The theoretical values for these 4 detectors vs. particle size may be placed in a lookup table. The 4 detector values from a measured unknown particle are compared against this table to find the two closest 4 detector signal groups, based upon the least squares minimization of the functions such as:

$$(S1/S4-S1T/S4T)^2+(S2/S4-S2T/S4T)^2+(S3/S4-S3T/S4T)^2$$

or $$(S1/SS-S1T/SST)^2+(S2/SS-S2T/SST)^2+(S3/SS-S3T/SST)^2+(S4/SS-S4T/SST)^2$$

where $$SS=S1+S2+S3+S4$$

$$SST=S1T+S2T+S3T+S4T$$

where S1,S2,S3,S4 are signals from the 4 detectors, S1T, S2T,S3T,S4T are the theoretical values of the four signals for a particular particle size, and ^2 is the power of 2 or square of the quantity preceding the ^.

The true size is then determined by interpolation between these two best data sets based upon interpolation in 4 dimensional space. The look up table could also be replaced by an equation in all 4 detector signals, where particle size equals a function of the 4 detector signals. This disclosure claims the use of any number of detectors to determine the particle size, with the angles and parameterization functions chosen to maximize size sensitivity and minimize size sensitivity to particle composition.

In any case, these scattering measurements are made at various locations along the X direction (the direction of the centrifugal force) by moving the sample cell under computer control on a motorized stage. The intensity distribution is inverted at each location to calculate the size distribution of particles at that location. This computation is started by calculating the mean particle size at a few points (X values) along the cell. This size-vs.-X data provides an effective density for the particles, using the Stokes equation for centrifuge (equation 1a or equation 1) to solve for particle density viscosity ratio using the size vs. X values. This is accomplished by doing a regression analysis on either $X=V*t$ (using equation 1a) or $X=R2$ (using equation 1) vs. D to solve for (p1−p2)/q. The K value (including the effects of viscosity) in equation 2 could also be determined. Then using this effective density viscosity ratio or K value, the expected size range of particles at each X location is calculated based upon the theoretical motion of the particles in the centrifugal force field for the given period of time. The scattering distribution at each location (static or dynamic) is then inverted with a constrained inversion algorithm which limits the solution range of particle size at each location to cover a range which is similar to, but larger than, the range of sizes expected to be resident at that location, based upon equation 1a or equation 1. Equation 1 and 1a are first order equations; in certain cases the more exact expressions should be used. The constrained size range must be sufficiently large to accommodate the larger range of size allowed by errors in the knowledge of parameters, such as density and viscosity, in equation 1 or equation 1a. This prevents the particle size solutions in regions of larger particles from containing smaller particles which could not have been present at the location of the larger particles. These erroneous smaller particles might result from errors in the scattering model for high angle scattering from the larger particles. This high angle scattering tail for larger particles can change with particle refractive index and particle shape, and so it may not be known accurately. Therefore if small particles are allowed in a particle size solution for a region which should only have large particles, errors in the particle composition or high angle scattering measurements could cause the inversion algorithm to report small particles which are not real. These erroneous particles are eliminated by constraining the inversion algorithm to produce solutions with particles in only the appropriate size range for each value of X. The particle size distributions from these various locations are combined into one continuous distribution by adding them together as relative particle volume (relative among X locations) using the scattering efficiency (intensity per unit particle volume) of each particle size to calculate the particle volume at each location from the scatter intensity at that location. If the particle hydrodynamic properties (shape, density, etc.) are well known, measurement of particle concentration vs. X would provide the size distribution, without the need for size determination from the scattering distribution, because X and particle size would have a one to one correspondence based upon the Stokes equation, the centrifugal force and the length of time under that force. The particle concentration can be determined from the total scatter (extinction) or measurement of low angle scatter at each value of X. However, the direct measurement of the size distribution, using the angular scattering distribution, at each value of X is more accurate when particle separation is not perfect and when the hydrodynamic properties are not well known.

Figure 44:
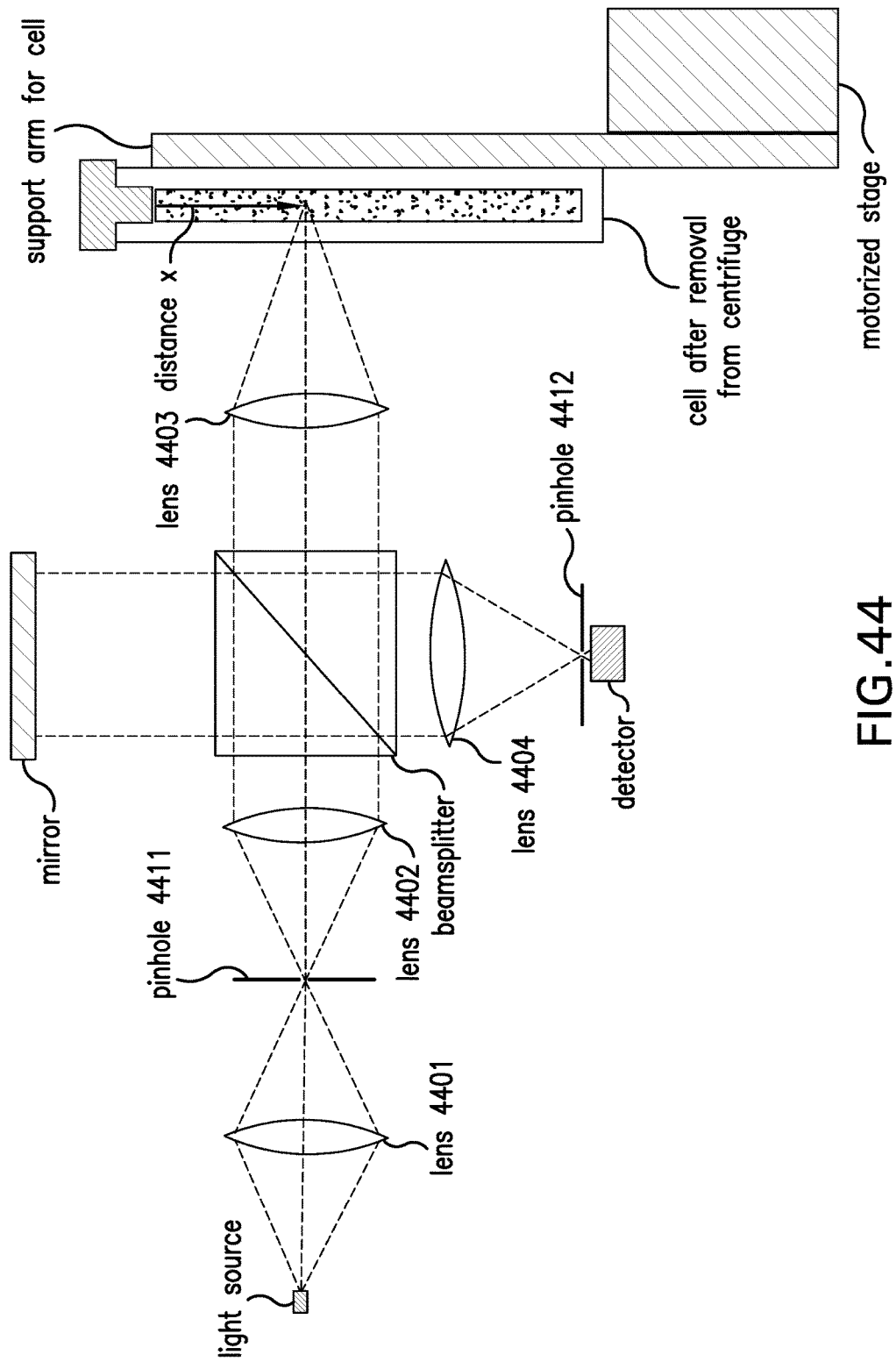
FIG. 44 provides a schematic diagram of optical and mechanical systems, used in the present invention, measuring dynamic light scattering at various locations in a cell containing particle dispersion.

The static scattering system could also be replaced by a dynamic scattering system as shown in FIG. 44. FIG. 44 shows one example of a dynamic scattering system, as shown in FIG. 1. Other dynamic light systems, which could also be used in this configuration, were described previously in this document. To use the systems in those figures, replace the cuvette, in those systems, with the centrifuge cell and motorized stage in FIG. 44. To determine the particle size distribution, either the autocorrelation function or power spectrum of the detector current is inverted to create the particle size distribution at each point in the cell. Dynamic light scattering has been used to measure particle size by sensing the Brownian motion of particles. Since the Brownian motion velocities are higher for smaller particles, the Doppler spectral broadening of the scattered light is size dependent. Both heterodyne and homodyne methods have been employed to create interference between light scattered from each particle, and either the incident light beam (heterodyne) or light scattered from the other particles (homodyne) of the particle ensemble. Heterodyne detection provides much higher signal to noise due to the mixing of the scattered light with the high intensity light from the source which illuminates the particles.

In FIG. 44 a light source is focused through a pinhole by lens 4401 to remove spatial defects in the source beam. The focused beam is recollimated by lens 4402 which projects the beam through an appropriate beamsplitter (plate, cube, etc.). The diverging light source, lens 4401, pinhole 4411, and lens 4402 could all be replaced by an approximately collimated beam, as produced by certain lasers. This generally collimated beam is focused by lens 4403 into the particle dispersion which is contained in the centrifuge cell or container with a window to pass the beam. The focused beam illuminates particles in the dispersion and light scattered by the particles passes back through the window and lens 4403 to be reflected by the beamsplitter though lens 4404 and pinhole 4412 to a detector. A portion of the incident collimated source beam is reflected from the beamsplitter towards a mirror, which reflects the source light back though the beamsplitter and through the same lens 4404 and pinhole 4412 to be mixed with the scattered light on the detector. This source light provides the local oscillator for heterodyne detection of the scattered light from the particles. The mirror position must be adjusted to match (to within the coherence length of the source) the optical pathlengths traveled by the source light and the scattered light. This is accomplished by approximately matching the optical path length from the beam splitter to the scattering particles and from the beam splitter to the mirror. The interference between scattered and source light indicates the velocity and size of the particles. The visibility of this interference is maintained by pinhole 4412 which improves the spatial coherence on the detector. Pinhole 4412 and the aperture of lens 4403 restrict the range of scattering angle (the angle between the incident beam and the scattered light direction) to an angular range approximately 180 degrees. Multiple scattering can be reduced by moving the focus of lens 4403 to be close to the inner surface (the interface of the dispersion and the window) of the sample cell window. Then each scattered ray will encounter very few other particles before reaching the inner window surface. Particles far from the window will show multiple scattering, but they will contribute less to the scattered light because pinhole 4412 restricts the acceptance aperture. Multiple scattering is reduced as long as the short distance of inner window surface to the focal point (in the dispersion) of lens 4403 is maintained by appropriate position registration of the cuvette.

This design can provide very high numerical aperture at the sample cell, which improves signal to noise, reduces multiple scattering, and reduces Mie resonances in the scattering function. Light polarization is also preserved, maximizing the interference visibility. But as described before, any dynamic light scattering system could be used in FIG. 44.

The sample cell (after centrifugation) is moved by a motorized stage so that the interaction volume of the scattering system is scanned along the length (x direction) of the cell. The stage stops at various positions to accumulate a digitized time record of the detector current. The time record at each position is analyzed to determine the particle size distribution at that position.

Usually either the power spectrum or autocorrelation function of the detector current vs. time record is inverted to produce the particle size distribution at each X position. This inversion may be constrained, as described above. These size distributions at various X positions are combined together to produce the complete distribution as described previously and in more detail later.

This process can be used with any starting concentration distribution. For example, if the starting distribution is homogeneous throughout the entire sample cell before centrifugation (see FIG. 46), then after centrifugation the low X region will only contain small particles because the faster larger particles have left that region. From the relative volume in each region (calculated from the theoretical scattering efficiency) and the theoretical concentration distribution vs. X for each particle size (calculated from the X position, the effective particle density, and theoretical terminal velocity for each size), the total particle volume in each particle size range can be calculated over the entire cell. These total particle volume values are then combined to generate the particle volume-vs.-size distribution for the entire sample.

The terminal velocity V in a gravitational field is given, to first order, by (see parameter definitions below):

$$V=2g(D^2)(p1-p2)/(9q) \text{ for gravitational acceleration } g \qquad (1a)$$

So the distance traveled by the particle in time t is simply V*t.

In order to understand the analysis of the resulting dispersion in a centrifuge, one must determine how the particles move within a centrifugal force field. A particle at radius R1 at time t=0 will move to radius R2 at time t, where R1 and R2 are radii measured from the center of rotation of the centrifuge. These parameters are determined by the modified Stokes equation (equation 1b) for particles in a centrifugal force field.

$$\ln(R2/R1)=2(w^2)(p1-p2)(D^2)t/(9q) \qquad (1b)$$

where w is the rotational speed of the centrifuge in radians per second p1 is the density of the particle p2 is the density of the dispersant q is the viscosity of the dispersant t is the duration of centrifugation D is the particle equivalent Stokes diameter (hydrodynamic diameter)

^ is the power operator ln is the natural logarithm operator

We may rewrite this equation in the following form:

$$\ln(R2/R1)=K(D^2) \qquad (2b)$$

where $K=2(w^2)(p1-p2)t/(9q)$

Particles at larger radii R1 will move farther due to the higher centrifugal acceleration at the larger radius. Therefore, the concentration of particles will decrease during the centrifugation process, because, for a given particle size, the particles at larger radii will travel faster. However, if the separation is accomplished by settling in a gravitational field, then the concentration is constant in the regions which still contain particles after settling. These regions would be particle size dependent because faster settling particles will reside closer to the bottom of the sample cell. Therefore, in any region where a certain size particle resides, the concentration of that particle size should be generally constant over that region for gravitational settling.

Equations 1, 1a, and 1b are only accurate under certain conditions, which include limits on particle velocity, particle concentration, etc. These equations should be replaced by the more accurate equations, if Equations 1, 1a, 1b do not accurately model the actual situation.

But first consider the centrifugal case. For any infinitesimal segment of the dispersion, the concentration will follow equation 3b.

$$C1*\Delta R1=C2*\Delta R2 \quad (3b)$$

where $\Delta R1$ is the length of the segment at t=0 and R=R1 and $\Delta R2$ is the length of the same segment at t=t and R=R2

If we let Z=ln(R), then $\Delta R=R\Delta Z$ and $$C1*R1*\Delta Z1=C2*R2*\Delta Z2 \quad (4b)$$

If the starting segment is between Z11 to Z12 at t=0; and the same segment fills the region between Z21 and Z22 at t=t. Then using equation 2b we obtain:

$$Z21-Z11=k(D^2) \quad (5b)$$

$$Z22-Z12=k(D^2) \quad (6b)$$

$$\Delta Z1=Z12-Z11 \quad (7b)$$

$$\Delta Z2=Z22-Z21 \quad (8b)$$

From equations 5b, 6b, 7b, and 8b we obtain:

$$\Delta Z1=\Delta Z2 \quad (9b)$$

$$C1*R1=C2*R2 \quad (10b)$$

$$C2=C1*EXP(-K(D^2)) \quad (11b)$$

where EXP is the exponential function.

Figure 45:
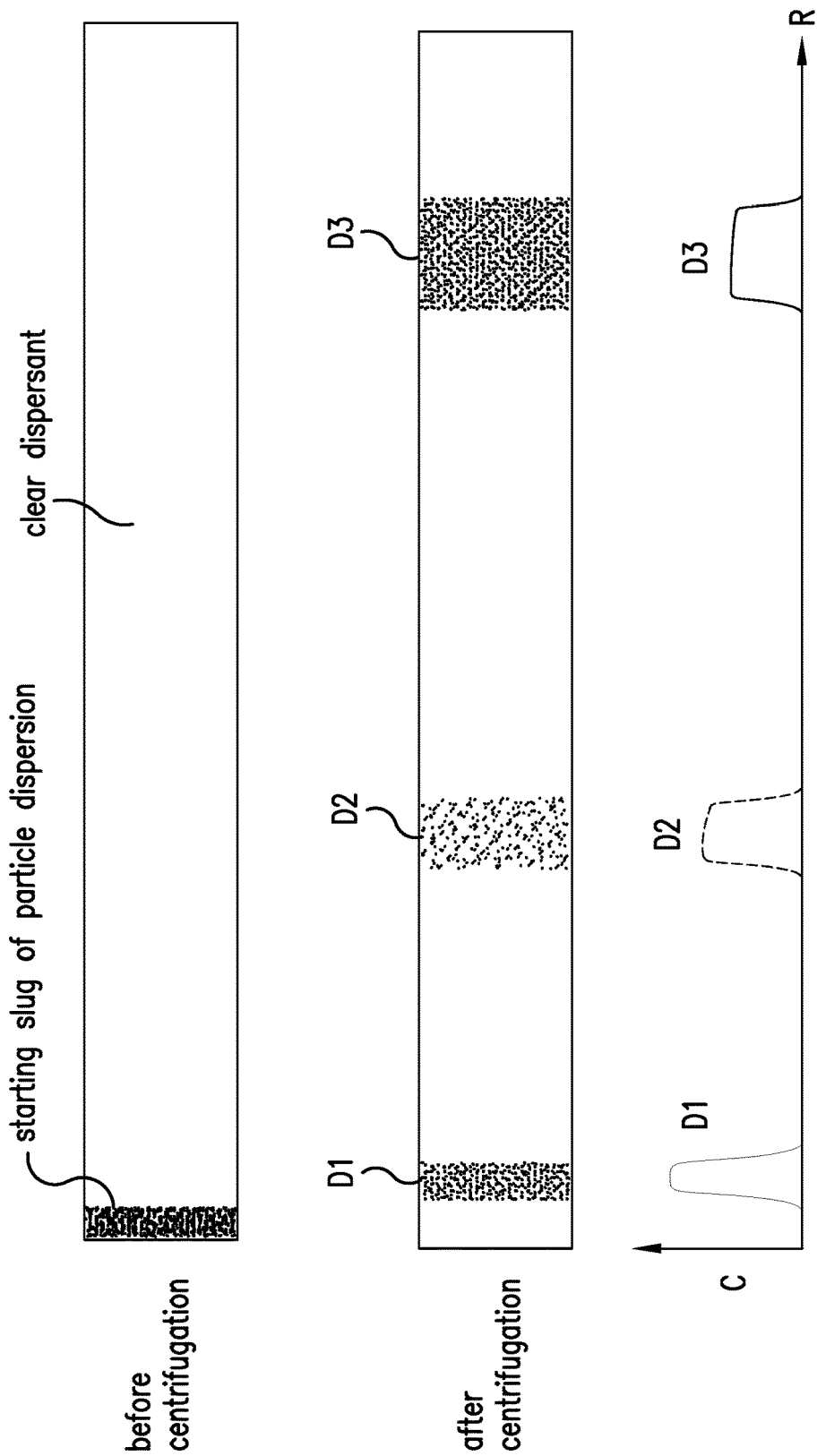
FIG. 45 shows the centrifugal separation of three different particle sizes, with all particles in a layer close to the centrifuge axis of rotation at the start of centrifugation, according to the present invention.

So any small segment of the dispersion at centrifugal radius R1 will move to radius R2 under the centrifugal force and change concentration from C1 to C2. Therefore, the particle concentrations measured at various R values must be corrected for the change in concentration from the original starting distribution. For the case where all of the particles start close to R1 as shown in FIG. 45, the measured concentration at R2 can be multiplied by R2/R1 to correct the concentration back to the starting concentration or the concentration can simply be multiplied by R2 before normalization for a concentration-vs.-size distribution (or volume percent vs. size). In the second case shown in FIG. 46, where the particles are uniformly dispersed throughout the sample cell at t=0, the concentration for each size is lowered by a factor of $EXP(-K(D^2))$ through out the cell volume where those particles reside. For the case of settling in a gravitational field (gravitational force along the R direction), which may be used for samples with high settling velocities, the concentrations remain the same during the settling process and no corrections are required in regions where all of the particles of each size are present. After a time, the larger particles will leave the region of lowest R value and the concentration of that largest size will drop in that region.

The detection process consists of measuring the angular light scattering data set for static scattering, or the power spectrum (or autocorrelation function) data set for dynamic scattering, at various values of R along the sample cell after centrifugation or settling. These data sets at each value of R will be described by $F_{jm}$ for the jth element of the mth data set at R=Rm.

Dataset element $F_{jm}$ is the jth element of the mth dataset collected at radius Rm. The index m increases with increasing centrifugal radius or increasing settling distance (in the gravitational case). Larger or denser particles will reside at larger values of m. The dataset can consist of any data collected to determine the particle size, such as scattered flux at the jth scattering angle, dynamic scattering detector power in the jth spectral band, or dynamic scattering autocorrelation function in the jth delay (tau). Any of these data values represent the net data values after background has been subtracted. The background is measured by collecting the data with no particles in the laser path at each value of R. Each data set is corrected for the incident intensity of the scattering source. Each static scattered data set is divided by the source intensity; and each power spectrum or autocorrelation function is divided by the square of the source intensity. So all values of $F_{jm}$ are normalized to the equivalent signal for unit incident intensity, for either static or dynamic light scattering.

$V_{ik}$ is the ith element of the kth particle volume-vs.-size distribution. $D_i$ is center diameter of the ith particle size channel of this volume-vs.-size distribution (the total particle volume in each particle diameter bin). This volume-vs.-size distribution can be converted to particle number-vs.-size or particle area-vs.-size by known techniques.

Definition: The sum of elements of vector Y, $Y_i$ from i=m to i=n is defined as:

$$SUM i{:}m{:}n(Yi)$$

Then let the function L=LX(n1,n2,n3,n4) be defined as:

$$S1j=SUM m{:}n1{:}n2(Fjm)$$

$$S2j=SUM m{:}n3{:}n4(Fjm)$$

$$L=SUM j{:}1{:}jmax((((S2j/(SUM j{:}1{:}jmax(S2j))-((S1j/(SUM j{:}1{:}jmax(S1j)))^2)$$

$j$max=max value of $j$ and $m$max=maximum value of $m$

The purpose of function LX is to compare the current data set (or sum of the last few data sets) to a prior (or sum of a few prior data sets) to determine if the size distribution has changed significantly, prompting the next calculation of $V_{ik}$. This will be described more clearly in the next section.

Starting with a Layer of Particles at Low R Value

The first method involves starting the centrifugation or gravitational settling process with all of the particles in a narrow R region at the low R end of the cell as shown in FIG. 45 (or at the top of the vertical oriented cell in the case of gravitational settling). This method will be described in more detail in FIGS. 48 and 49. After centrifugation or settling, particles with different terminal velocities will arrive at different centrifugal radii or X values (see FIGS. 43 and 45). The light beam in FIG. 43 should be shaped to provide a generally rectangular intensity profile (flat top profile) in the X direction. The motorized stage would then move in steps of distance equal to (or less than) the X width of this rectangular intensity profile so as to sample the entire cell with some minimal overlap between beam samplings of the particle dispersion. At each step, the scattering data is inverted to produce the size distribution (particle volume-vs.-particle diameter or size) for the particles in the beam at that step. The scattering system can usually be modeled as a linear system:

$$F=H*V$$

Where F is the vector of measured scatter values (angular scattering vs. angle, power spectrum vs. frequency, or autocorrelation function vs. delay). Element $F_j$ could be the scattered flux at the jth scattering angle, the dynamic scattering detector power in the jth spectral band, or the dynamic scattering autocorrelation function in the jth delay (tau). V is the particle volume-vs.-size distribution vector, the particle volume in each size bin. H is the theoretical model matrix for the particles. Each column in H is the F response for the corresponding size of the matrix multiplying element from the V vector. This model depends upon the refractive indices of the particles and the dispersant. This matrix equation can be solved for V at each R (or X) value; or certain parameters (such as mean diameter and standard deviation) of the size distribution could be determined using the search methods described above. In either case, the volume distribution at each X value must be scaled before being combined. Usually the volume, calculated by solving F=H*V for V or by using the lookup tables, is normalized to a sum of 1.0 (i.e. 100%). This normalized volume, Vn, must be scaled before being added to the volume distributions from other R values to produce the complete volume distribution, Vi. This is accomplished by first calculating the normalized Fn:

First calculate the vector $Fn=H*Vn$

Taking the measured data vector Fm, which produced Vn, calculate the value P by computing either:

$P=(SUM i:1:imax(Fmi/Fni))$ or $P=((SUM i:1:imax(Fmi))/(SUM i:1:imax(Fni)))$

Each size distribution is corrected for the scattering efficiency and theoretical centrifugal concentration change from the starting dispersion, $(EXP(-K(D^2)))$, to produce an absolute total particle volume measurement or at least one that is properly related to the other distributions measured at other values of R. The $EXP(-K(D^2))$ concentration correction is not required for the case of particle settling. The inversion at each value of Rk could be constrained to only solve for particle sizes that are expected to be in the range of R at that step, as determined from using equation 1 or 1a with the computed effective particle density viscosity ratio or K value. The solution could also be constrained to a certain size range centered on the peak of the full size distribution calculated from that data set. This peak size could also be estimated from the flux distribution with a polynomial equation of the scattering model, to save computation time. The final values of the constrained particle volume, Vik, calculated at the kth value of Rk for diameter Di, are summed together (over the various k values) to produce the final volume distribution, Vi:

$Vi=SUM k:1:kmax(Pk*Vik*EXP(K(Di^2)))$ for centrifugal force $Vi=SUM k:1:kmax(Pk*Vik)$ for settling (Note: k is an index and K is a constant, and Vi is the particle volume in the size bin whose center is at particle diameter Di)

Figure 46:
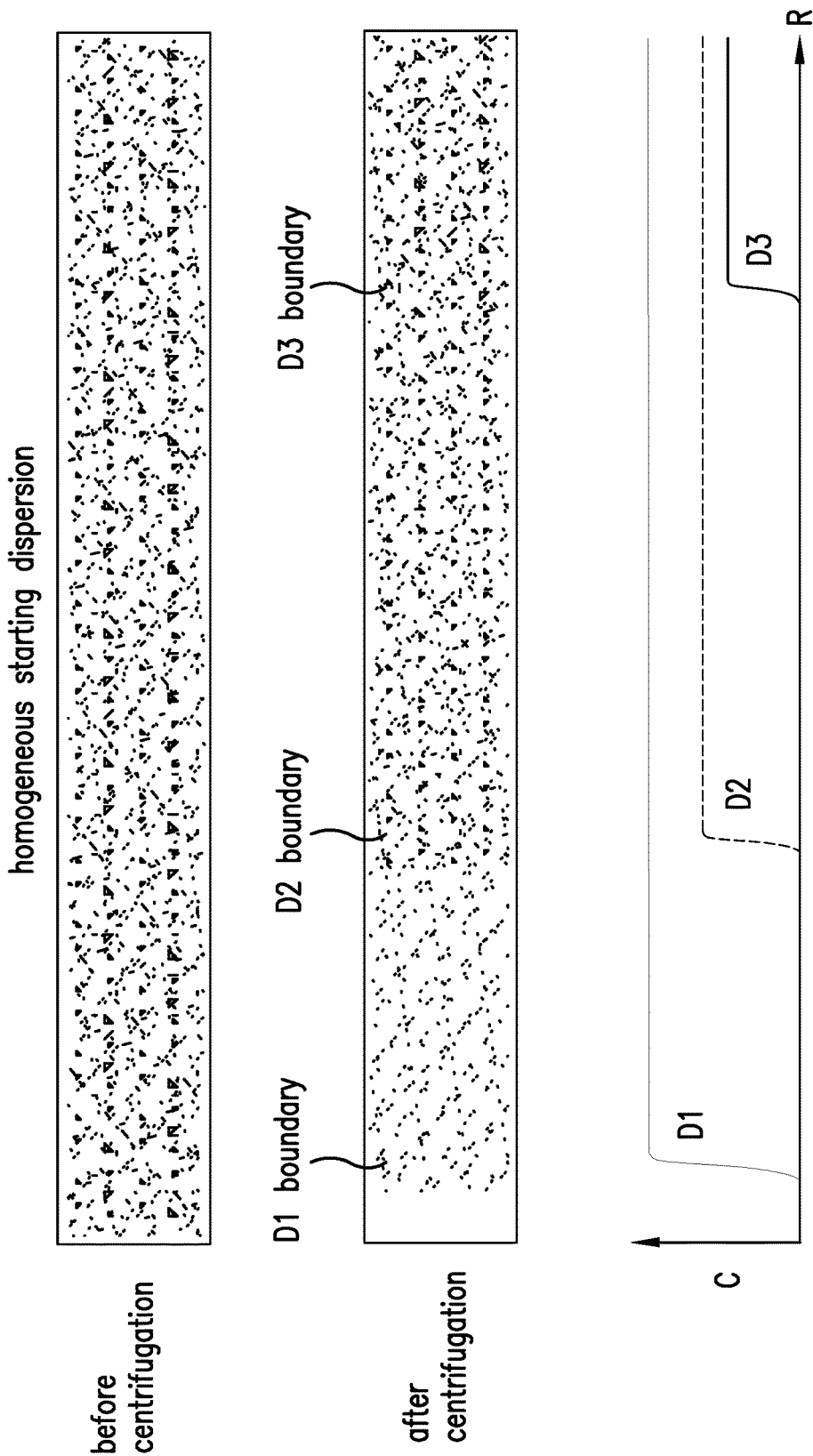
FIG. 46 shows the centrifugal separation of three different particle sizes, with a generally homogeneous dispersion at the start of centrifugation, according to the present invention.

Starting with a Generally Homogeneous Concentration Distribution of Particles Over the Entire Cell Another easier starting distribution is simply to fill the entire cell with the particle dispersion before centrifugation or settling. However, then the different particle sizes are not separated into bands for each size as shown in FIG. 45. The particle concentration distribution for the homogeneous start is shown in FIG. 46. All particles of a single terminal velocity (or hydrodynamic diameter) with the same starting point will move the same distance during centrifugation or settling. However, in the case of centrifugation, the force on each particle increases as the particle moves to larger centrifugal radius R, as shown by equation 1. So the starting concentration C1 (before centrifugation), for particles of hydrodynamic diameter D, will be lowered to concentration C2 after centrifugation as described by equation 11b. This effect is shown in FIG. 46. The starting dispersion is a homogeneous mixture of particles of three different diameters, D1, D2, and D3. Equation 11b shows that after centrifugation the concentration for each size will decrease by a factor of $EXP(-K(D^2))$. This is due to the fact that particles that leave a certain section of the cell will be replaced by other particles which move into it. However, at the low R end of the cell, no particles will replace the particles which move out of that region. Hence there will be boundaries, as shown in FIG. 46, below which no particles of a certain hydrodynamic size will reside, except by means of diffusion. Starting at the lowest Rk value, only the smallest particles in the original distribution will be measured. As the scattering detection beam moves to larger R values (by moving the cell along the X direction), more of the complete distribution will be measured but with lowered concentration as given by equation 11b. This process will easily measure smaller particles which will be separated out at the lower R values. This presents a problem for the simple inversion process as was described previously for use with the layer start (FIG. 45), because at larger R values multiple sizes will reside together. The poor resolution of a simple inversion process may cause some errors in the size of the larger particles which are mixed with the smaller particles. The following method reduces these errors:

1) starting at the lowest R value and progressing to larger R values, measure the first flux distribution with significant signal levels Fjn1 (at Rm with m=n1) and calculate the size distribution Vi1 from Fjn1. Each size distribution is corrected for the scattering efficiency, the scattered intensity, and $EXP(-K(D^2))$ to produce an absolute total particle volume measurement or one that is properly related to the other distributions measured at other values of R. The $EXP(-K(D^2))$ concentration correction is not required for the case of particle settling, which has uniform acceleration. Continue stepping to larger Rm values and measuring Fim, calculating the value L1 at each Rm until L1 becomes larger than some limit Lt at Rn2. At this point the scattered data has changed sufficiently to indicate that new particle sizes are present.

$Qj=((((Fjm/(SUM j:1:jmax(Fjm))-((Fjn1/(SUM j:1:jmax(Fjn1))^2)$ $L1=SUM j:1:jmax(Qj)$;

Invert the vector of flux or signal differences, Fj=Fjn2−Fjn1, to obtain the second volume distribution Vi2.

Starting at m=Rn2+1 calculate L2 at each Rm until L2 becomes greater than Lt (Fjn3 at Rn3) then invert the incremental signal values Fj=Fjn3-Fjn2 to obtain Vi3

$Qj=((((Fjm/(SUM j:1:jmax(Fjm))-((Fjn2/(SUM j:1:jmax(Fjn2))))^2)$ $L2=SUM j:1:jmax(Qj)$;

Starting at m=Rn3+1 calculate L3 at each Rm until L3 becomes greater than Lt (Fjn4 at Rn4) then invert the incremental signal values Fj=Fjn4-Fjn3 to obtain Vi4

$Qj=((((Fjm/(SUM j:1:jmax(Fjm))-((Fjn3/(SUM j:1:jmax(Fjn3))))^2)$ $L3=SUM j:1:jmax(Qj)$;

This cycle is continued until the end of the cell is reached at Rmmax. The volume-vs.-size distribution is calculated by summing all of the calculated Vik over k as described previously.

$$Vi = \text{SUM}k:1:k\max(Pk*Vik*\text{EXP}(K(Di^{\wedge}2))) \text{ for centrifugal}$$

$$Vi = \text{SUM}k:1:k\max(Pk*Vik) \text{ for settling}$$

This process provides two important advantages. The incremental flux, Fj, is inverted, by solving the F=H*V equation for V, at each inversion step to provide optimum accuracy and resolution. The jth value of vector F is Fj in equation F=H*V. The vector F contains the values of measured parameters, which includes scattered flux at each scattering angle or signal power from scattered signal fluctuations, as described previously. Inversions are only done when the incremental flux is significant, to save computer time. However, inversions can be done at more values of R, if computer time is not an issue.

The actual signals (for example Fjn3) could be inverted instead of inverting the incremental or differential (for example Fjn3−Fjn2) signals. Then the resulting Vik-1 would be subtracted from Vik to produce the Vik for the kth location. Essentially the differential operation is transferred from the measured parameter distribution to the particle size distribution. However, this differential method would not provide the full advantages of the signal separation described previously.

The strategies for both layer (slug) and homogeneous start are similar. The scattered signal (static or dynamic) is measured at the first radius where the signal to noise is satisfactory. The particle size distribution is calculated at this point from that data set (angular scattering distribution, or power spectrum or autocorrelation of the detector current). Then the scattering detection system scan continues to next radius where the signal characteristics have changed significantly to indicate the presence of particles of a new size. At this point the sum of all of the data sets since the last particle size calculation are added together (for example, the signal at each scattering angle is summed over the data sets from various R values) and inverted to calculate the second size distribution, in the case of the layer start. This summation is done for each scattering angle (or power spectrum frequency band or autocorrelation delay) by summing over the data sets. In the case of the homogeneous start, the difference between this latest data set and the data set at the last size distribution calculation could be inverted to calculate the second size distribution. Then the first data set is replaced by the latest data set and the cycle is repeated until the end of the cell is reached. Each size distribution calculation (inversion) can be constrained to the expected size region covered by the accumulated set of signals since the last size distribution calculation. However, complete unconstrained inversions can also be used. For the constrained inversion, the constrained size range may be based upon some region around the peak size of the data set (or accumulated data sets for layer start), or the expected hydrodynamic size over that region of centrifugal radii, using equation 1 or 1a. These constraints can be the same for both the layer and homogeneous start, because in the homogeneous start the differential signal is inverted and this signal covers the same size range as in the layer case if the two endpoints are at the same radii. Essentially, in the layer method, all of the data sets are summed by groups from certain regions where the particle size distribution does not change significantly. Each group sum is inverted to produce a size distribution. In the homogeneous method, the difference between the data sets, at the endpoints of each region of similar particle size, are inverted to produce a size distribution. Then the resulting size distributions are combined as shown before.

Computation time is saved by choosing groups of data, over which the size has changed less than a certain amount. If computation time is not a problem, the entire R range of the cell could be broken up into very small regions. The data sets in each region are summed to produce one data set which is analyzed to produce the particle size distribution in that region. Then the large number of size distributions from these regions are combined as described above in this disclosure. The most computationally intensive procedure is the inversion of the data to produce the size distribution. This procedure is usually an iterative algorithm or search algorithm to find the particle size distribution which produces a theoretical data set which has the best fit to the measured data set. So the number of regions should be minimized to save computation time. However, if the computer is very fast, the entire cell can be broken up into small segments of R and the particle size distribution can be generated for each of these small segments and then added together as described before without determining where the signal shape has changed significantly to indicate the presence of particles of a new size.

Figure 47:
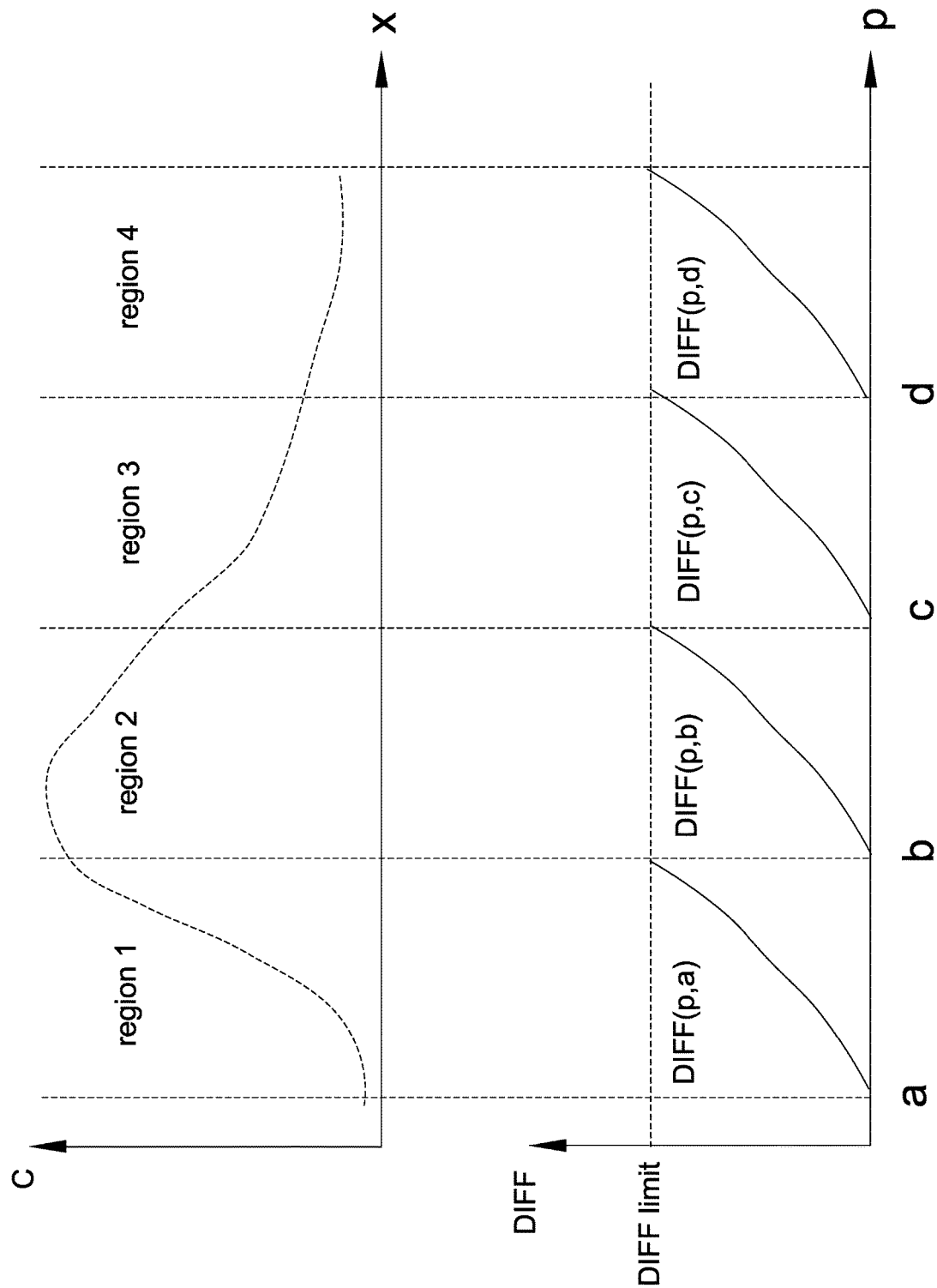
FIG. 47 shows a plot of particle concentration vs. x and DIFF function vs. p, according to the present invention.

The following equations and FIG. 47 provide another description of a data analysis process. Each signal is the sum of multiple data acquisitions at various values of X (different m indices). These values of m are spread over a narrow range of X (or R). Over this narrow X range, the particle size does not change significantly. The sum of these data acquisitions lowers the noise and averages out the local particle concentration variations. These data sums, Sjp, are compared to determine where the signal shape has changed significantly to indicate the presence of particles of a new size. This comparison is accomplished by comparing the difference of squares, DIFF, against a DIFF limit. When DIFF exceeds DIFF limit, the sum of all of the signal sets since the last particle size calculation are added together (the signal at each scattering angle is summed over the data sets from various R values) and inverted to calculate the next size distribution in the case of the layer start.

$$Sjp = \text{SUM}m:np1:np2(Fjm)$$

Where np1 and np2 are the m values at the endpoints of the pth set of datasets which are summed over m to produce the jth signal value Sjp $$\text{DIFF}(p2,p1) = \text{SUM}j:1:j\max((Sjp1/(\text{SUM}j:1:j\max (Sjp1)) - Sjp2/(\text{SUM}j:1:j\max(Sjp2)))^{\wedge}2)$$

FIG. 47 shows how different X (or R) regions are defined. The particle concentration, C, is plotted vs. X and DIFF is plotted vs. the dataset index p. At points b, c, and d, DIFF has exceeded the limit and all of the prior data sets in that region are summed to produce a single dataset which is inverted to create the particle size distribution in that region. In FIG. 47, the sum of datasets between points a and b produce the dataset for determining the particle size distribution in region 1, for the layer start. In the case of homogeneous start, the Sjp dataset at point a is subtracted from the Sjp dataset at the end point b to produce the data to be inverted for the particles of region 1. If the concentration distribution is smooth, np2−np1 can be small. For np2=np1, Sjp=Fjp.

When the system starts in the homogeneous case before centrifugation, the techniques are briefly listed below. These techniques assume that the first data set is collected at the minimum centrifugal radius and successive data sets are collected in sequence progressing towards larger centrifugal radii.

1) Subtract the prior data from the present data and invert the difference to obtain the particle size distribution for that region. Then combine regions scaled by the absolute particle volume represented by each differential data set.

2) Constrain the size distribution from the present inversion to match the size distribution results of the inversion of data, from the prior measured region, in the primary size region of the prior measured region.

3) Invert all of the data sets from different regions, individually, and then combine the resulting particle size distributions by concatenating the group of size distributions, which individually consist of the size distribution in the primary size region of each data set, and scaling them to each other in overlapping size regions.

Figure 48:
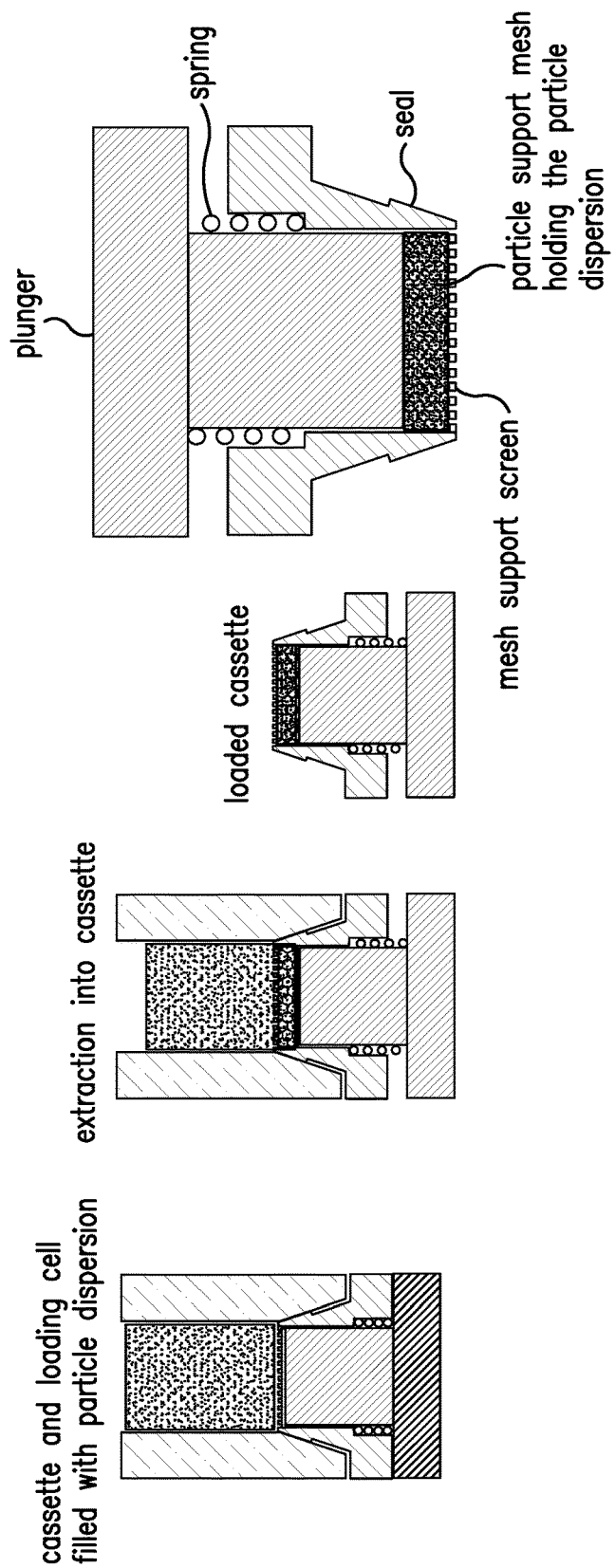
FIG. 48 shows a particle dispersion cassette loading procedure, as used in the present invention.
Figure 49:
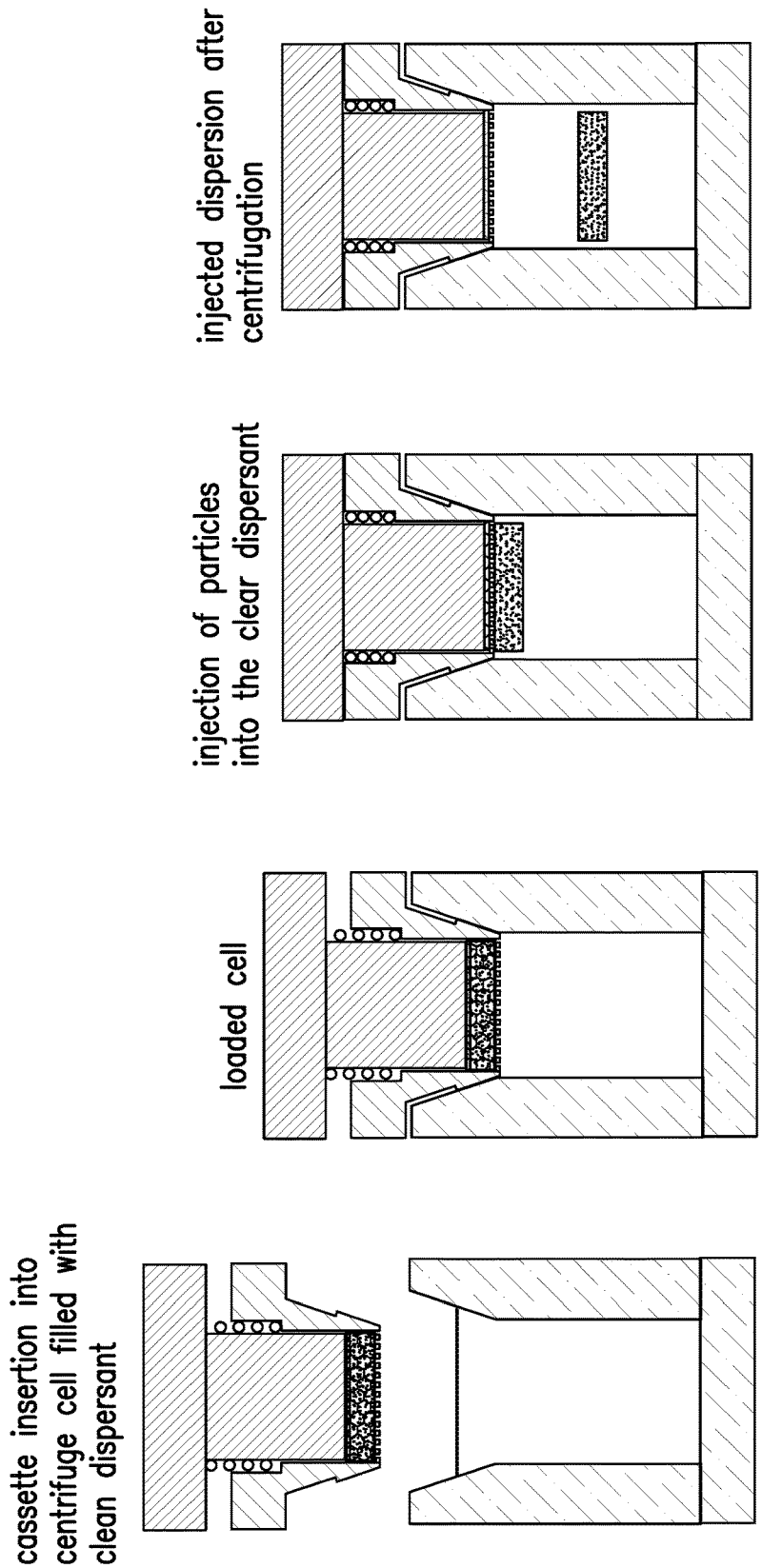
FIG. 49 shows a procedure for injecting particles, from a loaded particle dispersion cassette, into a centrifuge cell, as used in the present invention.

As you can see, the homogeneous method is the more difficult method for signal inversion because of the inaccuracies in the signal differences. However this method is the easiest to implement because you simply fill the cell with a homogeneous dispersion. In the case of the layer method, a thin layer of dispersion must be placed at the top of a cell filled with clear dispersant. A method for accomplishing this is shown in FIGS. 48 and 49.

A cassette for dispensing a layer of dispersion at the top of the cell is built into the cell cap. The cassette consists of a mesh, for holding the dispersion, which is sandwiched between a plunger and a support screen. The surface tension of the dispersion and the mesh/screen retain a thin layer of dispersion after it is extracted by a spring loaded plunger. This cassette is loaded by a process shown in FIG. 48. With plunger compressed, the cassette is inserted into the loading cell which is then filled with the particle dispersion. The plunger is then released slowly to allow a spring to withdraw the plunger and a thin layer of dispersion into the cassette to the retracted position. The spring could be replaced by threads on the cap which would allow the cap to be threaded in and out to extract or inject sample. Now when the loaded cassette is turned upright, the dispersion layer is held in the cassette by surface tension of the liquid and the mesh/grid structure, as shown in FIG. 49. The openings in the mesh are sufficiently small, that the surface tension of the dispersant will prevent the dispersion from passing through the mesh, except under force. The loaded cassette with retracted plunger is inserted into a centrifuge (or settling) cell, which is filled with clean dispersant. The cassette seal fits the cell opening, allowing air bubbles to pass around the seal as the cassette is inserted. This creates a sealed cell, without air bubbles, filled with clean dispersant. The plunger is then slowly compressed (or threaded in) to push the particle dispersion layer into the top of the clean dispersant. This layer is so small, that the additional volume of the layer is accommodated by slight distortion of the cassette seal or slight leakage past the seal. The plunger is then locked into the compressed position with a clip or other means. The loaded cell is placed into a centrifuge for centrifugation or simply set vertically to allow gravitational settling of larger or denser particles. The user could also wait until after the cell is placed into the centrifuge or settling stand, to compress the plunger, to avoid any distortion of the particle layer due to cell movement while being placed into the centrifuge or settling stand. After centrifugation or settling, the cell is scanned by either a static or dynamic scattering system to determine the size distribution as described previously. During transfer to the scattering instrument, agitation of the cell must be avoided to prevent movement of the particles from their separated bands. But if some mixing does occur, the scanning analysis will detect it and correct the size distribution, because the entire particle size distribution is measured over each R region.

This process could also be accomplished with a cell cap which has only the mesh and/or screen, without the plunger and spring. If the thin mesh and/or screen is immersed into the particle dispersion and agitated, the dispersion will fill the mesh and/or screen and be held by surface tension for transfer to the cell. Then when the cap is placed onto a cell with clean dispersant, the clean dispersant will wet the air/particle dispersion interface of the cap, reducing the surface tension forces. During the centrifugation process, the particles will be pulled out of the mesh and/or screen into the clear dispersant by the centrifugal force.

In both the layer and homogeneous start cases, the duration and centrifugal acceleration (determined from centrifuge rotation speed) of the centrifugation must be controlled so that the particle sizes of interest remain in suspension and that sufficient separation of the sizes occurs. If the duration is too short, you will have poor separation. If the duration is too long, some of the larger particles may all be impacted on the bottom surface of cell (or the large R end of the cell), where they cannot be detected by the scattering system. The duration could be optimized by scanning the cell after a short duration to determine the distance which the largest particles have moved. Then the computer could calculate the additional duration and rotation speed required to spread the particles, in the size region of interest, across the cell for maximum separation and size resolution.

Another advantage of this method is the reduced sensitivity to particle composition. In other ensemble particle size methods, such as dynamic and static light scattering, the major need for an accurate scattering model (particle and dispersant refractive indices, and particle sphericity) is to account for light scattering from particles of one size interfering with light scattered by particles of another size. This usually causes the incorrect presence or absence of addition modes or tails in the particle size distribution. However, since the particles are spatially separated by size before scanning, there is very little scattering crosstalk between different sizes. This is true for both the layer and homogeneous start cases because both of them separate the scattered signals to be representative of certain size bands. The layer start case does it directly and the homogeneous start case uses subtraction of a prior signal to create a differential signal input from a cumulative spatial distribution. In fact, if the spatial separation is clean, the scattering model (the theoretical functional description of the scattering distribution vs. size) can be determined from the scattering data sets collected over the cell scan by either using equation 1 or equation 1a to determine the hydrodynamic size, or by using the maximum calculated optical size (from scattered light measurements) for that region.

Figure 50:
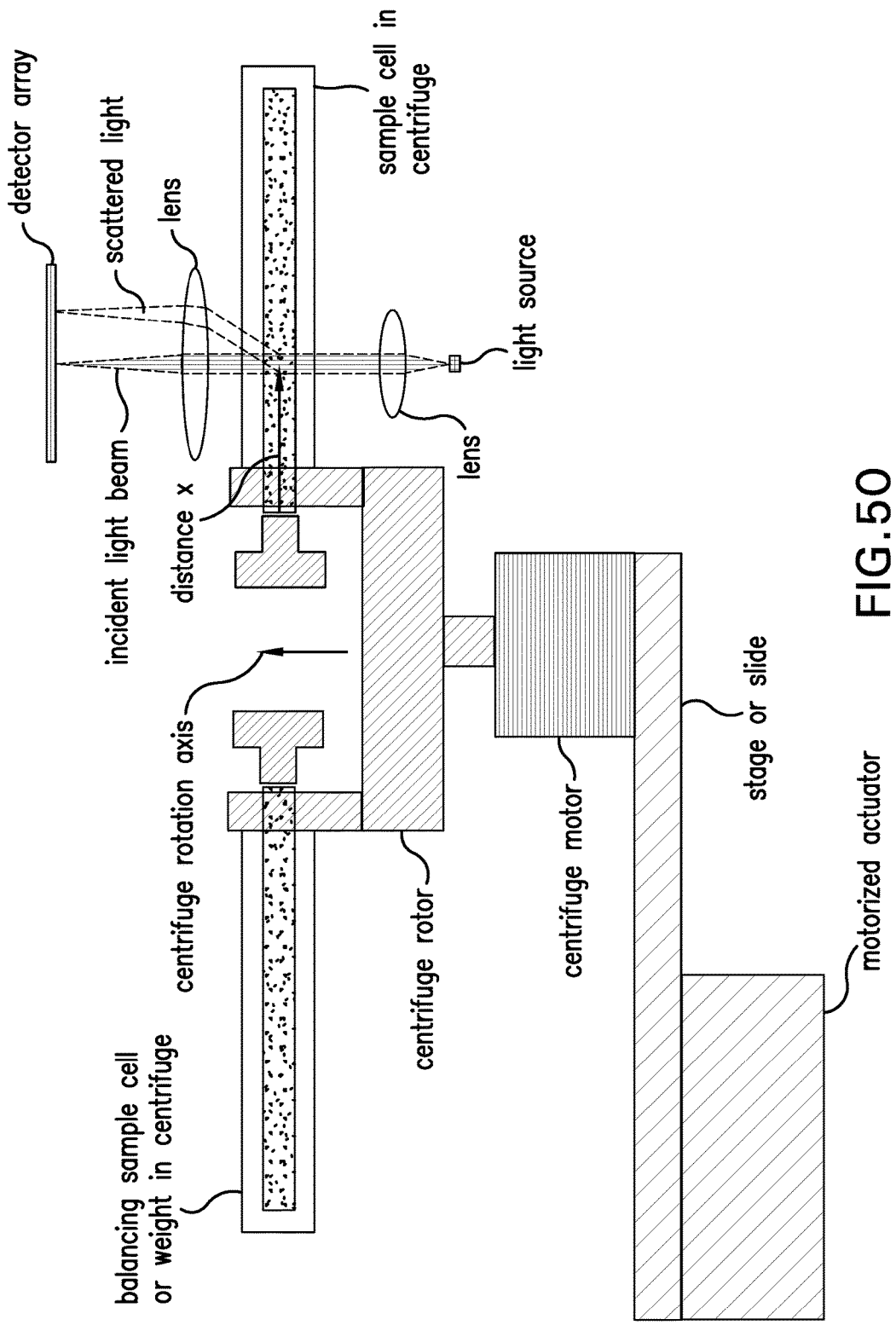
FIG. 50 provides a schematic diagram of optical and mechanical systems, measuring the angular distribution of scattered light at various locations along a cell in a centrifuge, according to the present invention.

For very broad particle size distributions, the largest particles may reach the end of the centrifuge cell before the smallest particles have moved a sufficient distance to provide good size separation. In this case the total size distribution may be created from a group of scans of the centrifuge cell at various centrifugation periods. To accomplish this, the first scan will determine the largest particle size in the sample. Then the computer will determine the added centrifugation period required to drive the largest particles to the end of the cell. After this period, the cell is scanned again to produce the first particle size distribution. The next centrifugation period is calculated to drive the smallest well detected size, of this latest scan, to the end of the cell. This sequence of scanning the cell, size measurement, and calculating the period for the next centrifugation cycle is repeated until the smallest particles have moved sufficiently to be clearly resolved in size. Since the sample cell must be removed from the centrifuge and placed into the scanning scattering system during each cycle, this process can be labor intensive. FIG. 50 shows a method for automating this process. The centrifuge rotor and motor are mounted to a scanning stage which allows the optical system to scan the cell during centrifugation. Then the process described above could be accomplished completely under computer control without intervention. The light source is pulsed to illuminate the sample when it is aligned with the light beam during each rotation of the centrifuge. The angular distribution of scattered light at each position along the X direction is constructed from integration of the scattered light from many source pulses at each X position. The system in FIG. 50 is somewhat complicated to manufacture. Another possibility is to place sources and detectors in a conventional centrifuge to determine when the particles have reached the end of the sample cell or when the particles have left the inner radius of the cell. A scatter detection system (detector, source, and optics) is placed on each end of the sample cell to detect when the particle concentration increases above some limit at the far end (large X or R) and when the particle concentration drops below some limit at the near end (small X or R). When either of these events occur, an audible alarm or light indicator is set to tell the operator to turn off the centrifuge and remove the cell for scanning by a scatter instrument. The detectors and sources, which travel with the rotating centrifuge, are powered by batteries in the centrifuge rotor. The particle concentration vs. R distribution or particle size distribution determined from this first measurement can determine the centrifuge settings (rotation rate and period) for any additional centrifugations or settlings. The repeated sequence of scanning the cell, size measurement, and calculating the period for the next centrifugation cycle can also be accomplished with the systems shown in FIGS. 66 and 67, which are described later.

Once the effective particle density viscosity ratio or K value is determined from the first particle size scan or from the known value for the material, the hydrodynamic diameter which corresponds to each value of X could be determined from Stokes equations (equation 1a or 1). Then the particle size distribution could be determined by measuring the particle concentration vs. X. The particle concentration can be determined from the scattering extinction or total scattered light at each X position over a limited size range. This process will produce a particle size distribution based upon hydrodynamic diameter of the particles, while the scattering techniques, described above, produce an optical size. Below approximately 5 micron particle diameter, the scattering crossection becomes particle size dependent and the particle volume must be corrected for changing scattering crossection.

In some cases, the direction of centrifugal force should be parallel to the gravitational force to avoid settling of the particles on to the cell window. However this is usually not required in the centrifuge because the centrifugal acceleration is usually over 1000 times the gravitational acceleration and the length to thickness ratio of the cell might be only 20:1. In this case, only a small fraction of the largest particles will settle and contact the window. But if this settled fraction becomes significant, then the direction of centrifugal force should be made parallel to the plane of the gravitational force vector to eliminate this problem.

In the case of particle separation by gravitational settling, the cell could be scanned by the scattering system during the settling process. If the sample were settled outside of the scattering instrument, mixing of the separated particles could occur during insertion of the cell into the scattering instrument. By starting the particle settling in the scattering instrument, the cell never has to be moved during the entire process and the cell scan can be performed at various times during the settling process to improve size resolution.

The angular scattering measurements may contain speckle noise if a laser source is used. The speckle noise will cause errors in the scattered light measured by each detector. If the particles move a small amount during the signal collection, the speckle noise will average out and the errors will be reduced. This averaging process can also be accomplished by averaging the scattered signals from groups of angular scattering signal captures which are individually taken from slightly different X positions. In other words, each scattering data set, used in the analysis, is the average of many angular signal set captures, each one from a slightly different X (or R) value. The distance of each step (perhaps a few microns) between each of these signal captures is much less than the step (greater than 50 microns) between each analyzed data set. So the X (or R) value for each data set would be the average X (or R) value over the group of captures for that data set. This process will reduce the amount of speckle noise in the scattering pattern and improve the accuracy of the measured scattering signals. An ultrasonic probe could also be placed into the dispersion during data collection to induce small amounts of particle motion during a single data collection (signal integration) period to average out the speckle, however this may distort the layered structure of the particle dispersion. This ultrasonic method of reducing speckle could also be applied to any angular scattering measurement including existing methods used for ensemble particle scattering which do not use centrifugal or settling methods.

The homogeneous particle sample could also be placed into the scattering instrument before centrifugation to determine the approximate particle size distribution by angular scattering from the particle ensemble. With knowledge of the dispersant viscosity and density, and the particle density, the proper centrifuge settings of centrifugal acceleration (rotation speed) and centrifugation duration are calculated by a computer algorithm using equation 1 above to insure that the largest particles just reach the large R value end of the sample cell by the end of the centrifugation. In this way the maximum size separation and particle size distribution accuracy is obtained. If the user requests analysis of a certain size range, the computer can use equation 1 to determine the centrifuge settings which will spread the particles in that range across the full length of the cell. Of course, a reasonable estimate of the particle density is needed to compute these settings. This pre-centrifugation/settling measurement of a homogeneous sample could be used to calculate the above parameters for both the homogeneous and layer start cases.

For large dense particles, the settling or centrifugal induced terminal velocities may be too large to obtain a controlled spread across the sample cell. Also, particles may settle to the bottom of the cell while the cell is being inserted into the scattering instrument. In this case, dispersants with higher viscosity could be used to allow spatial/size separation of large dense particles in the centrifuge. Then after centrifugation, the particles are held in place by the high viscosity. For example, glycerin could be added to water dispersant to adjust the viscosity to reduce the terminal velocities of the largest particles so that centrifugation can easily distribute the particles across the cell and that distribution is held in place during transfer of the cell to the scattering instrument.

Figure 51:
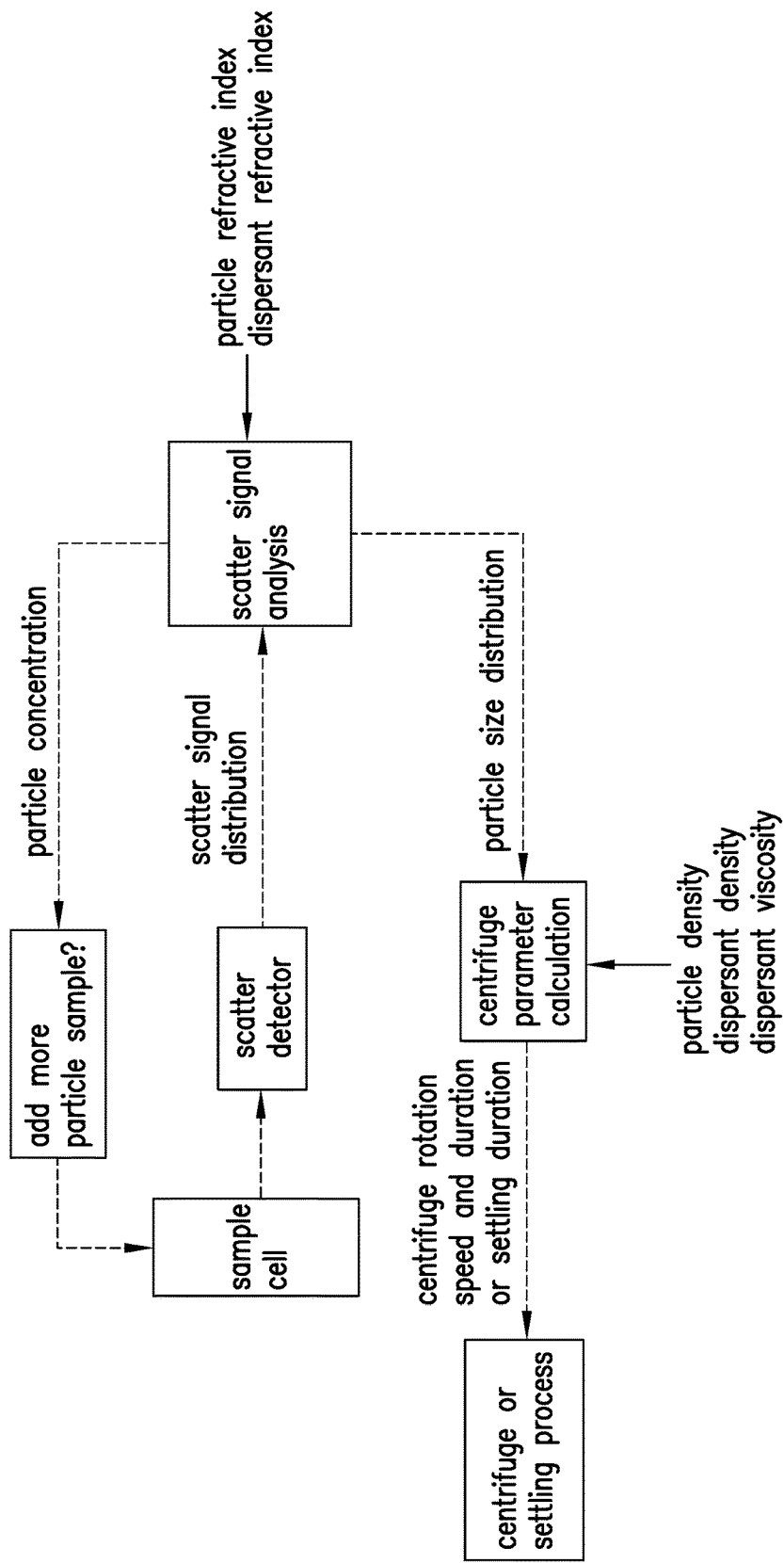
FIG. 51 provides a block diagram of the process which adjusts the particle concentration and centrifuge parameters to the optimum values, according to the present invention.

The scattering efficiency problems described at the beginning of this disclosure are worst for particles of diameter below approximately 5 microns. These methods can be used for any particle size range, but they probably will provide most advantage for small particles. Therefore, these techniques are usually applied below 100 microns where the scattering angles are larger and angular alignment tolerances are relaxed. With these relaxed alignment conditions, the sample cell, filled with clear dispersant, could be inserted into a holder, in the instrument, which registers the cell into a corner under spring load. The source beam is then aligned to the appropriate point, on the detector array, which defines the zero scattering angle. The cell is then scanned to obtain the scattering background at various R values along the cell. A known small amount of concentrated particle dispersion is injected into the cell. This cell is agitated to provide a homogenous concentration and then the cell inserted back into the holder. The instrument collects one set of scattering data. Based upon the scattered signal intensities, the instrument calculates the amount of additional concentrated particle dispersion which should be added to the cell to provide optimal scattering signal levels, as illustrated in FIG. 51. The instrument also estimates the particle size distribution to determine the optimal settings for the centrifuge, using the particle density, and the density and viscosity of the dispersant, in equation 1 or 1a. The cell is removed from the instrument and centrifuged, using these optimal settings. After centrifugation, the cell is inserted back into the position registration holder in the instrument and the cell is scanned by measuring scattering data at various R values as described above. This pre-centrifugation/settling measurement of a homogeneous sample could be used to calculate the above parameters for both the homogeneous and layer start cases.

Figure 66:
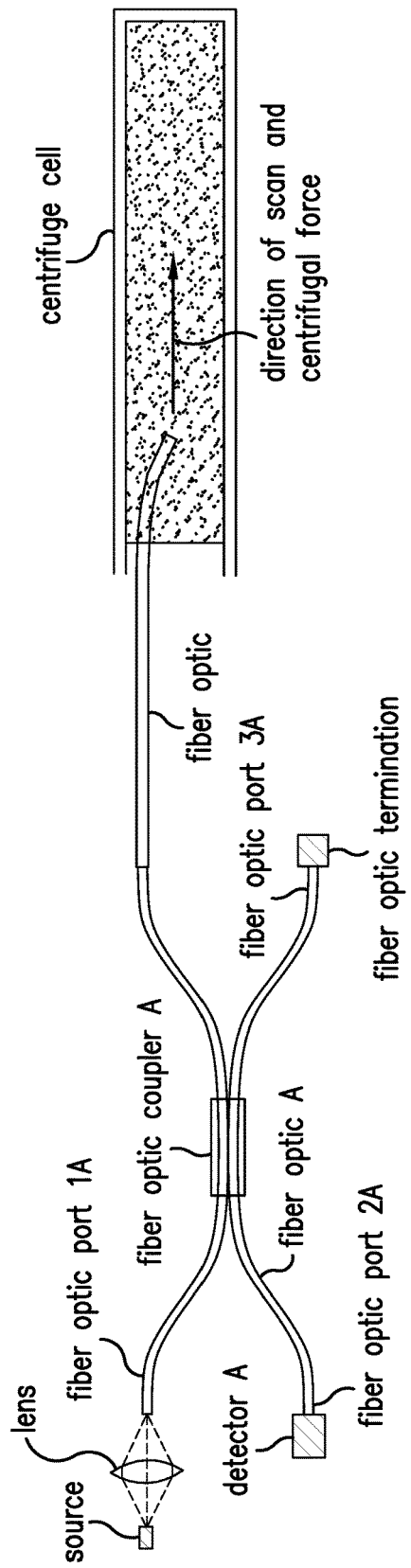
FIG. 66 provides a schematic diagram of a fiber optic system, which mixes source and scattered light to measure the motion and size distribution of particles, measuring scattered light at multiple positions in a centrifuge sample cell, according to the present invention.

FIG. 44 shows a method for scanning the centrifuge cell with an external dynamic light scattering system. This procedure requires that the centrifuge cell be removed from the centrifuge, unless the optical system is built into the centrifuge system. Both of these modes are claimed by this disclosure. However, use of a commercial centrifuge and an attached optical system may be more practical. This also avoids any potential distortion of the spatial particle distribution inside of the cell as it is moved from the centrifuge to an external optical system and this concept provides for automated multiple scans at various times during the centrifugation process, by stopping the centrifuge, scanning, and restarting the centrifuge, under computer control, as described previously. A stationary optical system could be mounted on top of a commercial centrifuge to scan the centrifuge cell in the centrifuge after spinning has stopped. Many systems could be designed to fit into the centrifuge, using the ideas already proposed in this disclosure, using either angular scattering (static scattering FIG. 43) or dynamic scattering to scan the cell while it is in the centrifuge. The centrifuge rotor could have slots, in the cell holder, through which the optical system could scan the sample cell after the centrifuge has stopped and returned to a scanning position. However, another approach is to scan the dispersion in the cell with a small probe, which can be moved throughout the cell with a computer controlled actuator, as shown in FIG. 66. This configuration uses a fiber optic dynamic light scattering system as described previously. The fiber optic port in the dispersion can be simply the bare fiber end, which will produce sufficient reflection for heterodyne mode and could also work in homodyne mode by eliminating that reflection. The fiber optic, which may be less than 200 microns in diameter, could be supported inside of stainless steel tubing such as that used for hypodermic needles. Hence a needle like probe could be inserted into the dispersion. Scattering signals would be collected at various locations along the direction of the centrifugal force in the cell to measure particles which have been separated in size by the centrifugal force or gravity, as described previously. However, in this case the scan is completed while the cell is still in the centrifuge. The scanning motion actuator and fiber system are mounted above the centrifuge. The cell is centrifuged without a cell cap so that the actuator can insert the fiber into the top of the cell, after the centrifuge has stopped and moved to the nominal position for insertion, as shown in FIG. 66. The optical system (or fiber optic tip) is then moved by the actuator to move the probe to various positions in the cell and digitize the detector signal for a sufficiently long time to accurately produce the power spectrum or autocorrelation function of the detector signal at each location. Then these data sets are used to determine the particle size distribution as described previously. The entire process of completing these multiple measurements is called a scan. Since the fiber optic probe is so small, it does not effect the spatial particle concentration distribution in the cell, because it displaces a minimal volume of dispersion as it moves through the cell. And data is collected from the cell opening to the cell bottom to measure undisturbed dispersion at each step. The probe would also be stepped sideways between each scan so that it would avoid scanning through dispersion which had been disturbed by a previous scan.

Therefore, the cell could be scanned at multiple times during the total sample centrifugation to measure different particle size ranges, all under computer control without user intervention. By sensing the particle concentration and size at shortest and longest centrifuge radius, the computer could determine when the centrifugation should stop. Using particle density and size, the computer could calculate the time required to separate the next particle size group from the shortest radius region. When this time becomes too long, the centrifuge could warn the operator and/or stop. When particles at the smallest size end of the range of interest are absent from the region of shortest centrifuge radius in the cell, the centrifugation can be stopped. It could also be stopped when only the smallest particles of interest remain at the shortest centrifuge radius.

The tip of the fiber in the dispersion could be bent at various angles to provide the least disturbance to the dispersion or it could be bent at right angle to avoid Doppler shifts from settling particles by bending the tip so that the optical axis of the fiber is perpendicular to the settling direction. But normally settling will not be a problem, if centrifugation is required to obtain particle motion. Most angles will work well, but a straight fiber probe would provide the least disturbance to the dispersion so that multiple scans can be made in different portions of the cell without affecting each other.

Figure 67:
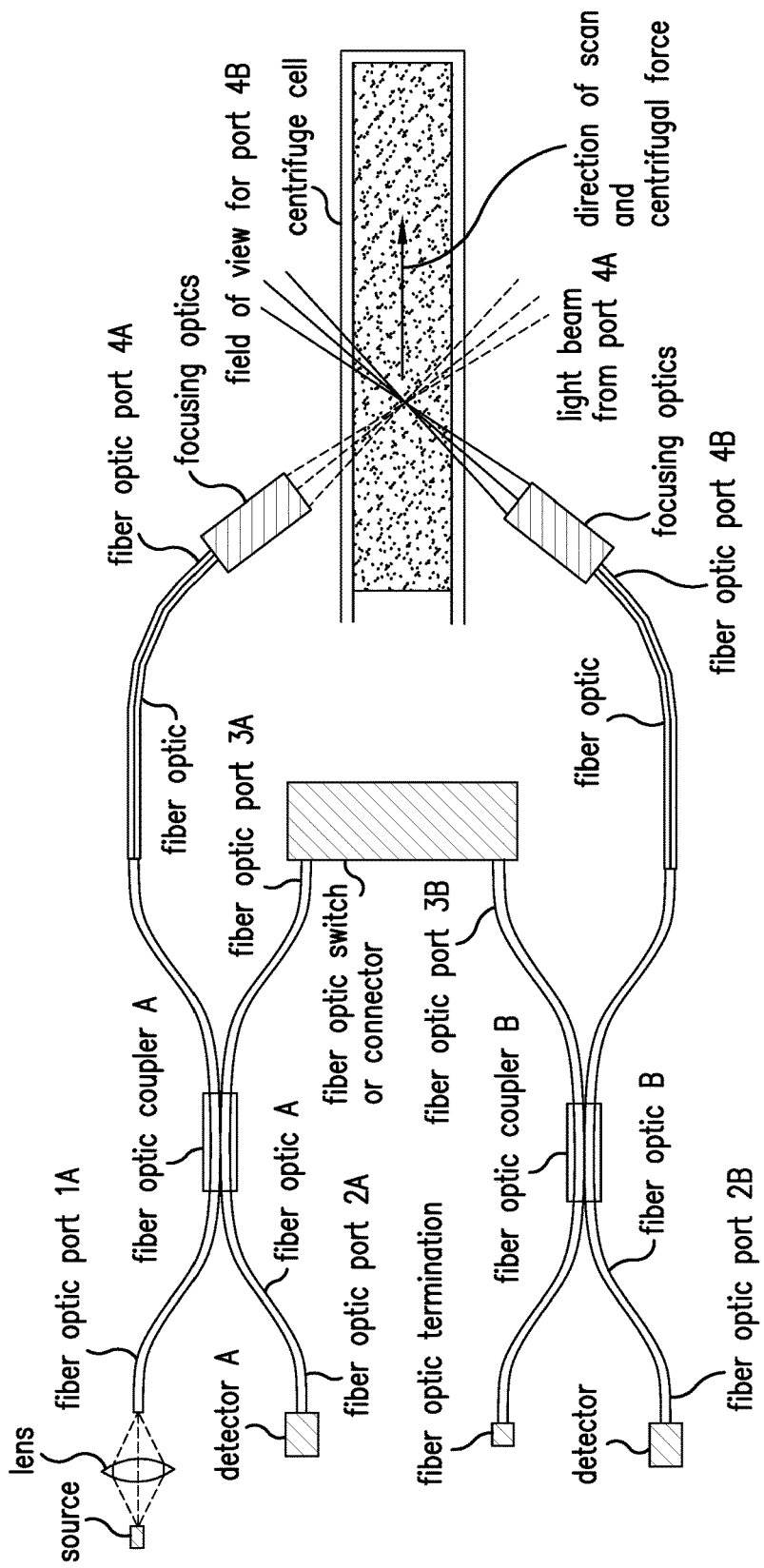
FIG. 67 provides a schematic diagram of a fiber optic system, which mixes source and scattered light to measure the motion and size distribution of particles, measuring scattered light at multiple positions in a centrifuge sample cell, at multiple scattering angles and in both homodyne and heterodyne detection modes, according to the present invention.

The disturbance to the particle concentration distribution can be avoided completely by using a scanning system which does not contact the dispersion as shown before in FIG. 43. The sample cell would be scanned by moving the optical system, shown in FIG. 43, along the sample cell, while the sample cell resides in the stopped centrifuge, after centrifugation is complete. Another concept, which could replace that design, is shown in FIG. 67. This system measures dynamic light scattering signals at two scattering angles, 180 degree scatter back through fiber optic coupler A (detector A) and lower angle scatter through fiber optic coupler B (detector B), which operate in heterodyne or homodyne mode through selection of the fiber optic switch between port 3A and 3B. This system has the flexibility of operating at multiple scattering angles and switching to homodyne mode, when excess laser noise causes high error in the heterodyne mode. As before, the interaction volume of the optical system, which is the intersection between the light beam from port 4A and the field of view of port 4B, is scanned along the direction of the centrifugal force in the cell. The optical system projects light and receives scattered light through windows in the sides of the cell. Fiber optic coupler A directs light into the cell and collects scattered light back through port 4A. Fiber optic coupler B receives scattered light through port 4B. This scattered light can be detected directly in homodyne mode by opening the fiber optic switch between ports 3A and 3B; or it can mix the scattered light with source light by closing the fiber optic switch, to operate in heterodyne mode. In homodyne mode, detector B may need to be a photon multiplier or avalanche photodiode for sufficient sensitivity. Photon counting may also be employed to provide sufficient sensitivity for the very small homodyne signals. This design (FIG. 67) is also claimed for application in conventional dynamic light scattering applications where centrifugation is not used (for example, where Brownian motion of the particles is measured to determine particle size).

The configurations shown in FIGS. 53, 54, 55, 56, and 67 could be used to measure static angular scatter at appropriate scattering angles for the particle size range of interest. The time average of the scatter signal from the dynamic scattering system will provide the static angular scattered intensity, by removing the local oscillator. By removing the fiber optic couplers, while preserving continuous fiber optic paths between the collection optics and the detectors and between the beam forming optics and the source, the detectors can measure the scattered intensity level at each angle to determine the particle size distribution at each position in the cell.

Some advantages of these methods are listed below:

1) Samples with very low density differences between the dispersant and the particle are difficult to measure due to the high sensitivity of size to small errors in density. The methods described above can provide accurate size measurements even for samples with low density differences between the dispersant and the particle, because the size can be measured from optical scattering, which has low sensitivity to density.

2) When the density difference between the dispersant and the particle is small, particle diffusion can become significant as compared to the terminal velocity. The methods described above will provide accurate size distribution for these cases, even when diffusion has distorted the spatial distribution of particles (also see the analysis below).

3) The size accuracy is not sensitive to particle composition because the effects of large angle scattering tails, from larger particles, on the scattering of smaller particles is reduced by the spatial separation of particles based upon size.

4) The best information can be used to determine the particle size distribution. If the spatial distribution of the particles provides better particle size accuracy (using scattering measurements to determine the particle concentration distribution vs. R and equations 1 or 1a to determine the hydrodynamic size at each value of R), then it will be used instead of the size distribution calculated from the static or dynamic scattering distribution alone.

5) The scattering efficiency function could be produced empirically from the spatially separated modes of samples with known mixture ratios because each mode is measured individually in the same sample. There would be no need for absolute scattering measurements of individual samples to determine the dependence of scattering efficiency on particle size.

6) Knowledge of the dispersant viscosity and density, and particle density, are not required to obtain accurate particle size distribution measurement when using the scattering distribution to determine size at each value of R.

Real Time Measurement of Terminal Velocity

High resolution particle size measurement has not been demonstrated for particle ensembles. High size resolution can only be obtained through sample dilution and individual particle counting. However, the count accuracy of particle counters is limited by Poisson statistics of the counting process. This is particularly problematic for broad distributions commonly seen in industrial processes. The following describes a methodology for measuring particle size distributions of particle ensembles, with high size resolution and volumetric accuracy. This is accomplished by measuring the terminal velocities of particles in a centrifugal force field, produced in a rotating centrifuge and/or a gravitational field.

Figure 52:
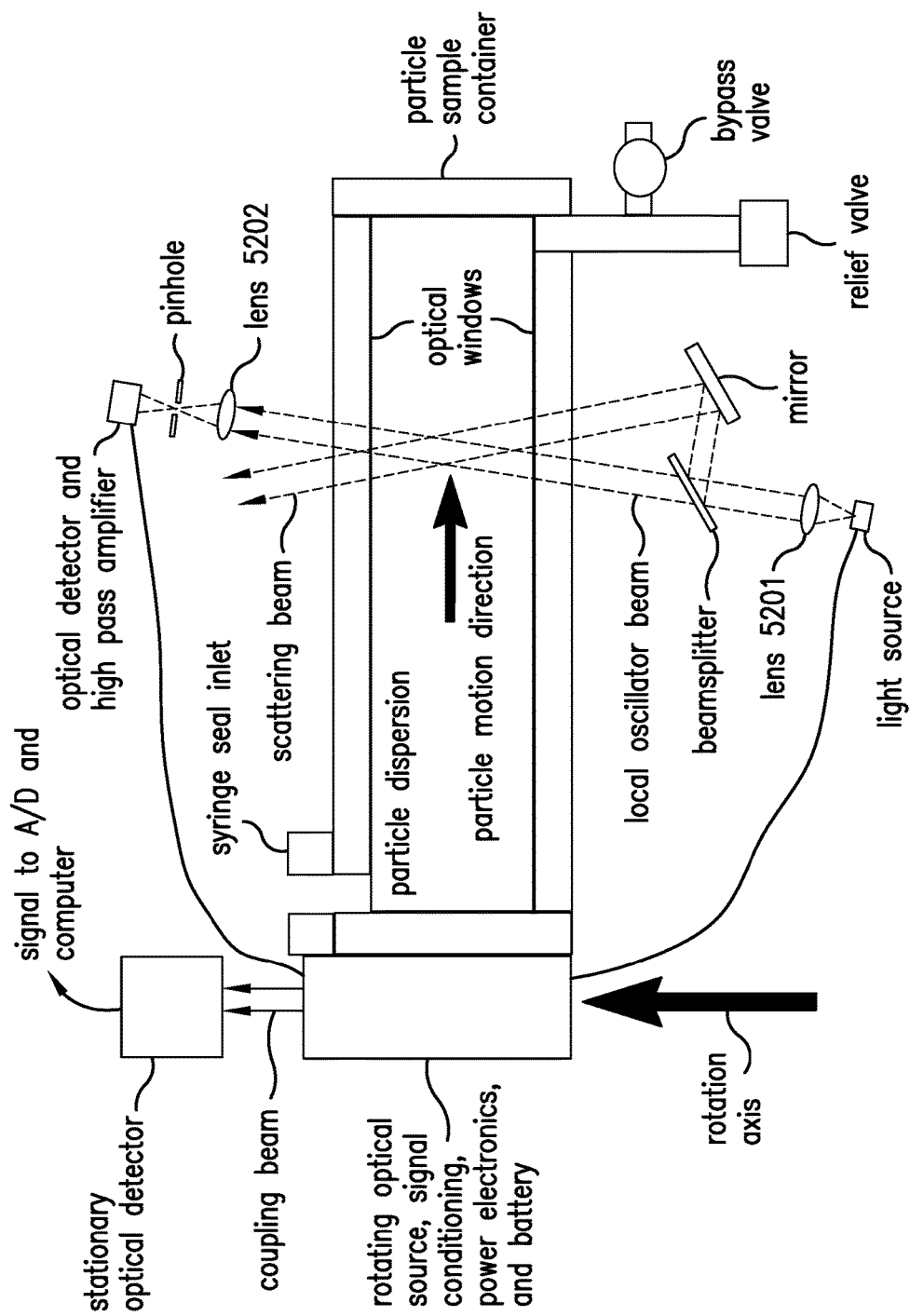
FIG. 52 provides a schematic diagram of optical and mechanical systems, measuring particle motion and size distribution during centrifugation, according to the present invention.

FIG. 52 shows the concept of this invention. The particle dispersion is injected into a sample container or cell, which has two optical windows. Two beams of light, originating from the same light source, intersect within the dispersion between the windows. An optical source, such as a laser diode, is generally collimated by lens 5201. This beam is split by a beam splitter to produce two mutually coherent beams of light, the first of which passes through the particle dispersion and is focused by lens 5202 through a pinhole onto an optical detector. The second beam is reflected by a mirror to intersect the said first beam within the particle dispersion. The scattered light from said second beam is also focused through the same pinhole to produce a heterodyne optical signal on the detector, whose frequency is indicative of the velocity of the particles. In this heterodyne configuration, said first beam is the local oscillator and the angle between said first and second beams defines the measured scattering angle for light scattered from said second beam by the particles. This angle could be sufficiently small to avoid MIE scattering efficiency resonances and Brownian motion spectral broadening; but the angle must be sufficiently large to produce large Doppler shifts. For particles below approximately 200 nanometers diameter, the Brownian spectral broadening may be used to determine size. The detector signal is amplified and high pass filtered to separate the beat frequency portion of the heterodyne signal from the large generally zero frequency component, which is generally due to the local oscillator.

The entire sample, container, and optical system are contained in an arm of a rotating centrifuge. Near to the center of rotation is a battery and electronics for powering the detector and light sources. The high pass filtered signal is transferred from the rotating system to the A/D converter (analog to digital converter) of a stationary computer through an optical rotary connection consisting of an optical source, such as an LED, which rotates with the centrifuge, and a stationary optical detector. The LED intensity is modulated by the high pass filtered signal and read by the stationary detector to transfer the signal to the A/D. This rotary connection could also be accomplished by wireless slip-rings, brush slip-rings, radio transmitter/receiver, digital storage devices, and electronic rotary connectors, some of which use mercury for conduction of the signal. The use of the high pass filter, to remove the large zero frequency component, will improve signal integrity through this rotary connection. The enormous zero frequency component of the heterodyne signal could produce spurious signals in the rotary connection, in the spectral region of interest. The signal could be transmitted between the rotating centrifuge and stationary computer as either an analog or digital signal. For digital transmission, the A/D converter would be in (and move with) the centrifuge and for analog transmission, the A/D converter would be in the stationary receiver or computer. Digital transmission may provide higher signal to noise in the transmission process. The signal could also be digitized and stored in a storage device (such as flash memory), which moves with the centrifuge and which is read by the stationary computer after the centrifuge stops.

If the A/D converter were placed in the rotating electronics, then digital light (or electrical) signals could be transmitted through the rotary connection (or by other means mentioned previously). The analog to digital converter would digitize the detector signal and this digital signal would be transmitted from the rotating electronics to the stationary electronics. This system would be relatively immune to noise in this connection and would provide easy access to scattering signals from multiple detectors by time multiplexing. The advantages of measuring scattering signals at various scattering angles are discussed later in this disclosure.

The velocity of the particles being pulled by the centrifugal force depends upon particle size and density. Larger or denser particles can attain larger velocities and produce higher heterodyne beat frequencies. The local velocity over a small region about centrifugal radius R is given by Vo below:

$$\ln(R2/R1)=2(w^2)(p1-p2)(D^2)t/(9q) \text{ (from previous description)} \quad (1)$$

$$Vo=k1*R$$

Where $k1=2(w^2)(p1-p2)(D^2)/(9q)$

Any particle of a certain size and density will produce a narrow heterodyne spectrum (power spectrum of the heterodyne detector signal), which can easily be separated from the narrow spectra of other particles of slightly different size, resulting in high size (and density) resolution and accuracy. The spectrum of a particle ensemble, with a multimodal size distribution, will consist of a group of line spectra which only need correction for scattering efficiency to produce accurate particle size distribution. Ideally a group of particles of identical diameter and density would all move at the same velocity, producing a narrow peak in the power spectrum of the heterodyne signal. However, other spectral broadening mechanisms must also be considered. For example, since the centrifugal force varies with radius from the centrifuge center of rotation, the centrifugal force on the particles will vary across an interaction volume of finite size. This spectral broadening can be removed by deconvolution or by solving simultaneous equations, which model the broadening process, as described previously by this inventor. Equations 1, 1a, and 1b are only accurate under certain conditions, which include limits on particle velocity, particle concentration, etc. These equations should be replaced by the more accurate equations, if Equations 1, 1a, 1b do not accurately model the actual situation.

The distance (or scattering pathlength) between the windows may be shortened to lower multiple scattering when measuring high concentration particle dispersions. Also the optical system could be folded to create a compact system which could be inserted into a commercial laboratory centrifuge. Also the beamsplitter could be replaced by a fiber optic coupler. Other configurations of heterodyne systems for measuring particle velocity are also possible and are claimed for use in this invention. Other heterodyning configurations, including those shown in this application, can also be used in the system shown in FIG. 52 to measure the Doppler spectrum of the light scattered from the particles. The scatter optics of fiber optic systems (for example FIGS. 19 and 66) can be placed into the dispersion to measure the Doppler spectrum. Non-fiber systems (for example FIGS. 1 and 4) and fiber systems (for example FIG. 67) can illuminate and receive scattered light through the windows. In all cases, the illumination beam orientation and scattering angles should be chosen to provide sufficient Doppler shift from the particle motion induced by the centrifuge or settling. The inventor has described many optical systems, which can measure the velocity of moving particles, by detecting scattered light. Any of these systems can be utilized in this concept for determining the velocity distribution, from which the particle size distribution is calculated.

The interaction volume of the scatter detection system should view a region close to the large R (radius) end of the centrifuge or the bottom of a gravitational settling sample cell, to maximize the total data collection time. After a certain time, the largest particles will start to leave the interaction volume, without replacement from particles at smaller R values, as shown in FIG. 46. This certain time is maximized by placing the interaction volume close to large R radius of the centrifuge or close to the bottom of a gravitational settling cell.

Usually centrifuges have long speed ramp up and slow down periods. Also different centrifuge speeds may be used to cover different particle size ranges. Therefore, the heterodyne spectrum should be corrected for the actual centrifugal force by monitoring the rotational velocity of the centrifuge and shifting the relationship between size and heterodyne spectral frequency accordingly, in real time.

Another aspect of this invention is the method of introducing the particle dispersion into the sample container. For low concentration samples, a scattering background signal should be measured with clear dispersant and then the particle dispersion should be measured separately; and these two spectra are then subtracted from each other to eliminate the effect of system background scatter and noise. This is easily accomplished by employing a compression seal at the inlet and a low pressure relief valve at the outlet of the container, as shown in FIG. 52. The compression seal could match the tapered end of a syringe body and plunger (without syringe needle) so the sample or dispersant could be forced into the container under pressure, forcing the prior sample out through the relief valve. Then a user could repeatedly introduce various particle samples (or dispersants for background) without turning any valves between each sample change. The syringe body tip is pressed into the inlet seal and the plunger is then used to force the prior sample out through the relief valve. Then clear fluid can be introduced through the same inlet to flush and then fill the cell for background signal measurement. After the background measurement, the particle dispersion is introduced through the same inlet to fill the cell volume with particle sample for size measurement. The contents of the sample container can also be blown out by using an empty syringe (or compressed gas)

to force air or gas through the container. A bypass valve may also used for flushing the sample container, without the need the pressure from a syringe.

Larger or denser particles will have high velocities, due to the centrifugal force, and these particles may all move through the sensing region too quickly to obtain a heterodyne spectrum. In these cases, the sample cell and optical system can be oriented to allow gravity to provide a much lower force on the particles, with the gravitational force generally along the same direction as the centrifugal force, as indicated in FIG. 52. By using gravity as the lowest force and varying the centrifuge rotational speed, a large range of particle size and density can be accommodated, by varying the force on the particle ensemble and measuring heterodyne spectra at various values of acceleration. The sequence of acceleration values should be from low acceleration to high acceleration to avoid missing any large particles.

The sample could also be placed between two flat transparent windows, which could be disc shaped. The outer edges of these discs are sealed to provide a thin disc shaped sample cell. The particle dispersion is then injected to fill the cavity between the disc windows. The disc sample cell is spun about its axis of symmetry perpendicular to the disc plane. The particles will accelerate along the tangential direction of rotation and reach generally the same rotational speed of the discs. The centrifugal force will pull the particles out radially. A heterodyning optical system, including the system shown in FIG. 52, would view through the rotating disc window to measure the radial particle velocities and particle size distribution. In the case of FIG. 52, the optical system, consisting of the light source, lens 5201, beamsplitter, mirror, lens 5202, pinhole, detector, and all electronics would be stationary. Only the disc sample cell and particle dispersion would rotate. Most of FIG. 52 would still apply except that the particle sample container crossection would be the crossection of the disc sample cell, without need for a rotating signal coupling because the optical system would not be part of the rotating assembly.

The radial component of the particle motion provides the terminal velocity and particle size. Theoretically, the tangential velocity component of the particles would be perpendicular to the scattering plane and hence it would produce zero Doppler frequency shift in the scattered light spectrum. However, a beam of finite size would view some particles with velocities which are not perpendicular to the scattering plane and would produce a scattering spectrum which interfered with that due to the radial centrifugal component. Therefore the scattering plane should be adjusted to be parallel to the radial direction. Alternatively, the angle between the scattering plane and radial direction could be adjusted so that the narrow Doppler shifted spectrum, due to the tangential velocity component, would be shifted to frequencies well above that of the radial velocity distribution to avoid interference between the two spectra. The anti-aliasing filter must remove frequencies from this tangential velocity spectrum, which alias into the spectrum from the radial velocity component. Likewise, the tangential velocity of dust and other scatterers on the disc surfaces will also produce spectra, which are shifted to higher frequencies and further removed by background subtraction (by measuring the spectra without particles present in the cell).

Another advantage of these ideas is the ability to electronically change the particle size range and size resolution by adjusting the ADC sampling rate and anti-aliasing filter. Once the particles reach terminal radial velocity due to the centrifugal force, a broadband spectra could be measured to determine the frequency region of the Doppler spectrum. Then the sampling rate would be adjusted to optimize resolution in that frequency region. The user could also adjust the sampling rate to look at fine details of the particle size distribution in certain size ranges. After entering a size range of interest, the computer would calculate the proper sampling rate and anti-aliasing filter parameters to optimize size resolution.

This rotating disk cell could also be scanned along the radial direction by an angular or dynamic scattering system, during or after centrifugal rotation of the cell. The methods described previously for FIGS. 43, 44, 45, 46, and 47 could be used to measure and analyze the scattering data.

The power spectrum of the optical detector current contains a constant local oscillator and a frequency dependent component. The frequency dependent component is described by the following equations:

$$P(f)=(Io*S(d,a,nm,np))*(E*G^2)/(4pi^2*(f-G*v)^2+(EG^2)^2)$$

where $G=2*nm*\sin(a/2)/w1$
$E=kT/(3*pi*eta*d)$
$v=c*(pp-pm)*(d^2)*a$
P=power spectrum of the detector current
S=scattering efficiency per unit particle volume
d=particle diameter
pp=particle density
pm=dispersant density
eta=dispersant viscosity
f=frequency
np=refractive index of particle
nm=refractive index of dispersant
a=scattering angle
v=terminal particle velocity
c=constant which depends on dispersant viscosity and particle shape for spherical particles c=2/(9*eta)
^2=square of quantity
g=acceleration due to centrifugation or gravitational settling
k=Boltzman's constant
T=dispersant temperature
w1=wavelength of the source light
Io=the incident light irradiance
This equation can be reduced to the form:

$$P(f)=c*((\sin(a/2)/w1)^2)*(Io*S(d,a,nm,np)/((f-fs)^2+fb^2)$$

where
fs=B*d^2*sin(a/2)*g*(pp-pm)/w1 Doppler frequency shift due to terminal velocity
B=2*nm*c
fb=c*(sin(a/2)/w1)^2/d spectral broadening due to Brownian motion This equation is accurate in most cases, but in some cases (high particle concentration or high terminal velocities for example) the more complete equation must be used to maintain accuracy. The scattered light intensity S(d,a,nm,np) per unit particle volume and per unit incident light irradiance depends upon the scattering angle (a), particle diameter (d) and refractive indices of the particle (np) and dispersant (nm). This scattering efficiency is small for small particles and generally grows with increasing particle diameter up until approximately 1 micron. Above 1 micron, the scattering efficiency oscillates versus particle diameter. This behavior depends upon the scattering angle and refractive indices, but the behavior is similar for most types of spherical particles. The oscillations are caused by optical interference between the light diffracted by the particle and transmitted by the particle. For non-spherical particles these oscillations are dampened by the random orientation of the scatters. So in general, the amplitude of these oscillations may be difficult to predict. The best strategy is to choose optimal scattering angles where oscillations are small but will still give sufficient Doppler shift to avoid low frequency noise in the detector electronics, through filtering.

This equation for P(f) is for particles of a single diameter d. Most particle dispersions consist of particles of many diameters, which can be described by a particle size distribution, the particle volume per unit particle diameter interval. Then the total power spectrum is the sum of the power spectra from each of the particles. As shown by the equation for P(f), the spectrum for any particles consists of a zero-centered symmetrical Brownian broadened spectrum, which is shifted in frequency by the Doppler frequency of the terminal velocity (terminal Doppler shift), due to the centrifugal force or gravitational force on the particle. For large particles the Brownian spectrum is narrow and the terminal Doppler shift is large due to the large terminal velocity. Large particles of identical size will each produce a narrow spectral peak at the same frequency. Therefore the amplitude of that peak will describe how many particles of that size are present in the interaction volume. A narrow spectral peak will exist at a different frequency for each monosized particle group. Hence, after correction for scattering efficiency S(d,a,nm,np), the power spectrum of an arbitrary particle size distribution of large particles will be generally equivalent to the particle size distribution, because there is generally a one to one correspondence between particle size and frequency. As the particles become smaller, the Brownian spectrum is broader and the terminal Doppler shift is smaller due to the smaller terminal velocity. Then other techniques, such as shown in Table 1, must be employed. For the case of centrifugation, the particle size distribution must be also corrected for the concentration effects described in equation 11b. Each value of the particle size distribution, V(d), must be divided by $EXP(-K(d^2))$ from equation 11b to produce a corrected particle size distribution Vc(d) at each diameter d=di. This correction is not required for gravitational settling, as described previously.

$$Vc(di)=V(di)/EXP(-K(di^2))$$

The larger scattering angles provide larger Doppler frequency shifts for a given particle velocity. Hence, larger scattering angles are sometimes needed for smaller particles which have lower velocities in the centrifugal force field. Also, small particles produce less scattered light per unit particle volume. Therefore the optical detector may need to subtend a larger angular width to generate sufficient signal level, for smaller particles. The Doppler shift is proportional to the sine of half of the scattering angle. The angular subtense of the detector must be small for two reasons: to include only a few coherence areas on the detector and to reduce the spectral spread due to the variation of Doppler frequency with scattering angle.

As shown above, the Doppler shift is proportional to sin(a/2). For small, low density particles such as 0.1 micron polystyrene spheres, centrifugal accelerations of 100,000 G's (one G=acceleration of gravity) will produce an approximately 10 Hertz Doppler frequency at 10 degrees scattering angle. And this frequency increases proportional to the square of the particle diameter. At a 10 degree scattering angle, the scattering efficiency is a well behaved function of particle diameter below 1 micron particle diameter. Above 1 micron, the 10 degree scattering efficiency shows many large oscillations as a function of particle diameter, while the scattering efficiency at 1 degree is smooth and well behaved. The Doppler shift for 0.1 and 1 micron particles are approximately 1 Hertz and 100 Hertz, respectively at 1 degree, and approximately 10 and 1000 Hertz, respectively at 10 degrees. Therefore, to cover an extended size range, the scattered light must be measured at multiple angles to provide sufficient Doppler shift for small particles (using large angles) and to avoid scattering resonances for larger particles (using small angles). Larger angles are also needed at lower acceleration levels, to maintain sufficient Doppler shifts. By measuring multiple scattering angles, the size regions, where scattering efficiency oscillations occur, may be avoided by solving the problem in regions of well behaved scattering efficiency.

This invention will greatly improve both the accuracy and resolution of particle size measurement over a large particle size range, because each particle will create a narrow detector current power spectral line whose position is size dependent. The spectrum consists of a symmetrical Lorentzian Brownian broadened spectrum which is shifted by the Doppler frequency of the terminal velocity, due to the centrifugal force or gravitational force on the particle. As the scattering angle decreases, the Brownian spectral width decreases relative to the Doppler shift and the size resolution increases. Smaller particles have a broader Brownian spectrum and smaller acceleration induced Doppler shift. The scattering angle should be large enough to push the Doppler spectrum above the low frequency noise of the system, but very large angles will degrade size resolution, because the Brownian spectral width will become comparable to the Doppler shift. In general this tradeoff cannot reduce the spectral line broadening to negligible levels. One solution is to measure the Brownian spectrum, when the Brownian spectral width is much larger than the Doppler frequency shift spectrum of the particle terminal velocity, due to the centrifugal force or gravitational force on the particle. For small particles the power spectrum consists of a wide Brownian broadened spectrum, shifted by a small Doppler shift, because the Brownian motion velocities are high (high diffusion coefficient) and the velocity, due to the centrifugal force or gravitational force on the particle, is small. Then measurement of the Doppler shift is difficult. As shown previously, the Brownian portion of the detector power spectrum is also particle size dependent. After the larger particles have moved out of the interaction volume, the size distribution of the remaining smaller particles could be determined by deconvolving the power spectrum, which consists of primarily Brownian motion spectral broadening. This smaller particle size distribution is then combined with the larger particle size distribution, which was determined from the Doppler frequency shift spectrum of the particle terminal velocity, due to the centrifugal force or gravitational force on the particle.

This broadening could also be accounted for in the theoretical model for the dynamic properties of scattered light. This Brownian spectral broadening could be reduced by using the same deconvolution techniques as described by this inventor for measurements of Zeta potential. However the effects of broadening can also be resolved by measuring the power spectra (or autocorrelation functions) of the optical scattering light detector at various scattering angles and various accelerations. The particle volume distribution (the particle volume per unit particle diameter interval) can be determined from these multiple spectra, by solving a single set of linear equations as shown in the matrix equation, Pt=P*V, shown in Table 1.

TABLE 1

| column vector Pt | matrix P | | column vector V |
|---|---|---|---|
| Pt(f1, a1, g1) | P(f1, a1, g1, d1) ...... | P(f1, a1, g1, dn) | |
| Pt(f2, a1, g1) | P(f2, a1, g1, d1) ...... | P(f2, a1, g1, dn) | |
| . | . | . | V(d1) |
| . | . | . | V(d2) |
| Pt(fm, a1, g1) | P(fm, a1, g1, d1) ...... | P(fm, a1, g1, dn) | . |
| ............ | ............ | ............ | . |
| Pt(f1, a2, g1) | P(f1, a2, g1, d1) ...... | P(f1, a2, g1, dn) | . |
| Pt(f2, a2, g1) | P(f2, a2, g1, d1) ...... | P(f2, a2, g1, dn) | . |
| . = | . | . | . |
| . | . | . | . |
| Pt(fn, a2, g1) | P(fn, a2, g1, d1) ...... | P(fn, a2, g1, dn) | . |
| ............ | ............ | ............ | . |
| Pt(f1, a2, g2) | P(f1, a2, g2, d1) ...... | P(f1, a2, g2, dn) | V(dn) |
| Pt(f2, a2, g2) | P(f2, a2, g2, d1) ...... | P(f2, a2, g2, dn) | |
| . | . | . | |
| . | . | . | |
| Pt(fn, a2, g2) | P(fn, a2, g2, d1) ...... | P(fn, a2, g2, dn) | |

V(d) is the volume distribution versus the particle diameter (d). If V(d) is the particle number distribution, S(d,a, nm,np) is the scattered light intensity per particle per unit incident light irradiance. Each total power spectrum, Pt, is the addition of all the power spectra, P, from each particle in the scattering volume or interaction volume. Table 1 shows a matrix equation where Pt is the vector of total measured power spectra (from all of the particles) under various conditions of frequency f, scattering angle a, and acceleration g. The matrix consists of values of the power spectrum for various combinations of f, a, g, and particle diameter d. Each row in the matrix has the same f, a, and g, which all correspond to the Pt vector element for that row. And each column in the matrix has the d value, which corresponds to the V(d) vector element multiplying that column. The P values in the matrix are calculated from the complete theory, including motion due to the acceleration force and Brownian motion, as shown previously. Table 1 shows one example, where the power spectral density is measured at various frequencies (f1, f2, . . . fn), scattering angles (a1,a2) and acceleration levels (g1,g2). These spectra create a set of linear equations, which are usually overdetermined and solved by least squares or other iterative techniques to obtain the volume distribution V(d). The most straight forward method is to simply invert the matrix equation in Table 1. However, the use of constraints (particle count or total volume positivity and size range, for example) on the values of V(d) is most effective in obtaining accurate results. These constraints may require the use of iterative techniques (for example, penalty functions in Newton's method, Marquardt Levenburg, etc.) or constrained optimization algorithms. The equation (or a more complete equivalent equation) for P(f) given above is used to calculate the elements of the matrix in Table 1. All of the examples given so far are only for describing the method and apparatus, this invention assumes that any number of accelerations, scattering angles, and detection frequencies may be needed to optimize the condition of this system of equations. Also power spectra may be replaced by their inverse Fourier Transform (the autocorrelation function of the scattered detector) to form a similar set of equations in time instead of frequency space. However, the best performance will be seen by using the power spectrum, because the spectrum of each particle is clearly separated in frequency space.

Also these different spectra may be solved as separate linear systems (separated by scattering angle or acceleration for example) if this is advantageous. Notice that the Doppler frequency shift (fs) is proportional to the difference (pp–pm) between the particle and dispersant densities and the acceleration (g). However the Brownian width does not depend on the density difference.

Therefore, this density difference can be determined by solving for the density difference as a parameter in the equation set, by using non-linear techniques.

For the case of centrifugation, the particle size distribution must be also corrected for the concentration effects described in equation 11b. Each value of the particle size distribution, V(d), must be divided by $EXP(-K(d^2))$ from equation 11b to produce a corrected particle size distribution Vc(d) at each diameter d=di. This correction is not required for gravitational settling, as described previously.

$Vc(di) = V(di)/EXP(-K(di^2))$

Techniques for reducing the effects of spectral broadening due to Brownian motion are the same for Zeta potential and centrifugal systems. In both cases, the particle velocity distribution due to the preferred force (electric field for Zeta potential and centrifugal or gravitational force for particle size) is broadened by Brownian motion. Therefore any broadening reduction method, used in one measurement type, can also be used in the other. For example, the matrix equation in Table 1 could be used with Zeta potential by replacing the theoretical model for centrifugation with the model for electric mobility. Then the accelerations (g1, g2, etc.) would be replaced by various electric field levels and the form of equations in Table 1 could be used to improve resolution in Zeta potential measurements.

Crosscorrelation could also be used to reduce the effect of Brownian motion spectral broadening on the calculation of the velocity distribution. Multiple heterodyne detectors, each measure scattered light from a different interaction volume in the particle dispersion. Two examples of such systems are shown in FIGS. 72 and 73. The multiple interaction volumes are chosen to be in regions with generally the same acceleration, such that identical particles would have generally the same velocity in each interaction volume. The heterodyne detector signals from any two detectors would contain a generally uncorrelated (uncorrelated between said detector signals) portion due to Brownian motion and a correlated portion due to the Doppler shift caused by acceleration induced motion. The Fourier transform of the crosscorrelation function (the cross-spectrum) of these two detector signals would produce a spectrum which ideally contains only the contribution from the correlated portion. In this way, the uncorrelated Brownian contribution is reduced to produce a cross-spectra with minimal Brownian spectral broadening, because the Brownian motion of two different groups of particles are generally uncorrelated. This cross-spectrum would be analyzed as described previously for the power spectrum.

This crosscorrelation technique can also be applied to Zeta potential measurement. The heterodyne detector signals from any two detectors would contain an uncorrelated (uncorrelated between said detector signals) portion due to Brownian motion and a correlated portion due to the Doppler shift caused by electric field induced motion. The Fourier transform of the crosscorrelation (the cross-spectrum) of these two detector signals would produce a spectrum which ideally contains only the contribution from correlated portion.

In both cases, centrifuge/settling induced motion and electric field induced motion, the crosscorrelated signal sets could also be measured sequentially on one detector. The scatter detector signal is measured over two different time periods, with sufficient time delay between the periods such that the Brownian portion of the data set from first period is generally uncorrelated with the Brownian portion of the data set from the second period. The Fourier transform of this crosscorrelation function will have reduced spectral broadening due to Brownian motion. This can be repeated for many sequential data set pairs, to create a set of cross-spectra. The resulting cross-spectra can be averaged, over all spectra at each frequency, to produce an accurate estimate of the acceleration induced portion of the detector current power spectrum. A similar reduction of Brownian broadening is obtained by taking the Fourier transform of the large delay (large values of tau) portion of the autocorrelation function of the scatter detector current. Calculate the Fourier transform of only the region of the autocorrelation function where correlation of the Brownian component (exponential) is smaller, relative to the correlation component (sinusoidal) from centrifuge/settling induced motion or electric field induced motion. This method can also be applied to the scatter detector signals from fringe pattern systems (FIGS. 57 and 58) and line ruling systems (FIGS. 59, 60, 61, and 62).

This method can also be applied to any case where deterministic motion must be separated from random motion.

The following describes various optical configurations for measuring the spectral characteristics of scattered light at multiple angles.

All optical configurations in this disclosure assume the following:

The designs can be extended to any number of scattering angles.

The sample cell or sample container may refer to either the disc shaped cell (which rotates without optics or electronics) or the small cell (which rotates with the optics and electronics).

Fiber Optic Configuration 1

Figure 53:
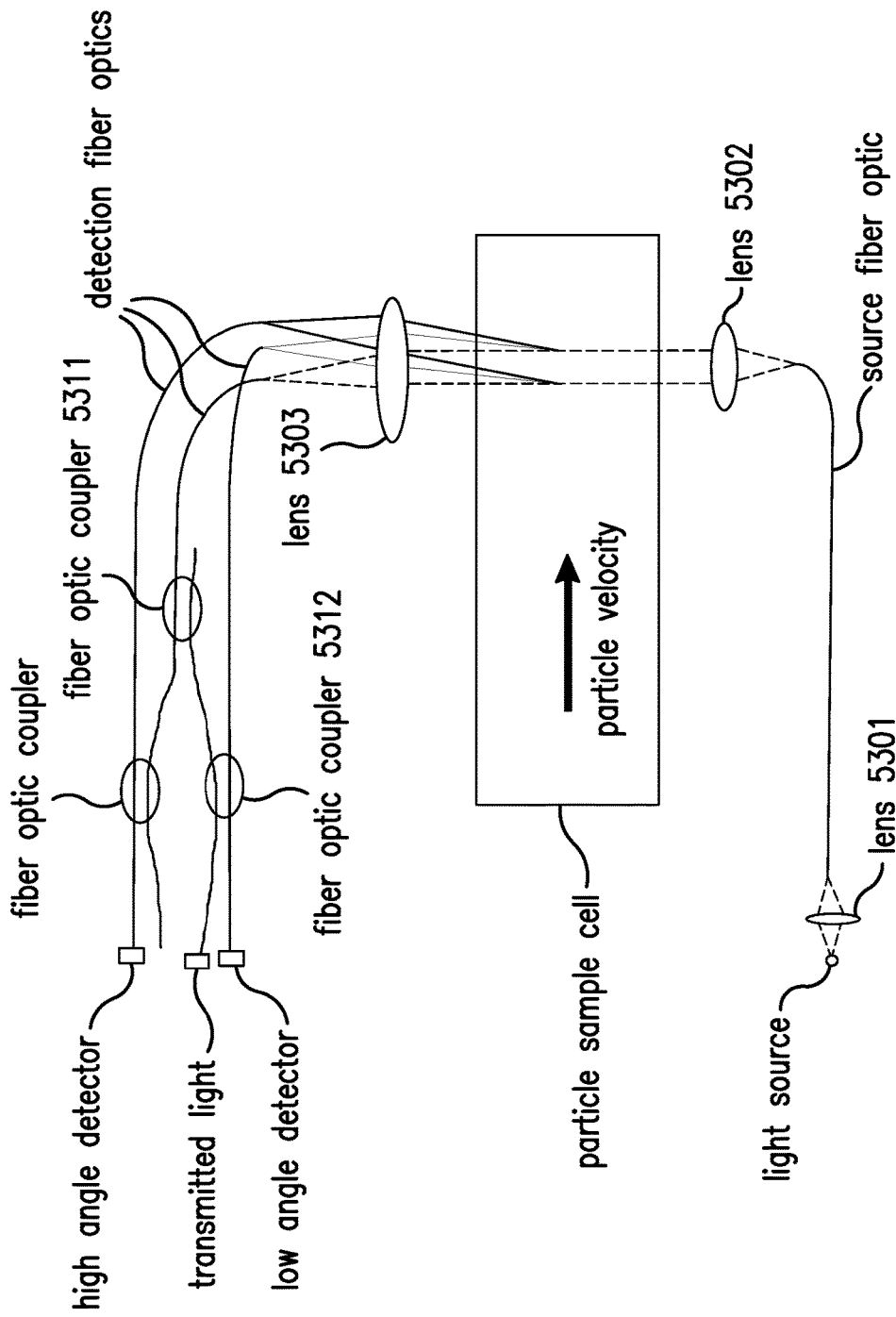
FIG. 53 provides a schematic diagram of a fiber optic system, measuring particle motion and size distribution during centrifugation, according to the present invention.

This configuration uses fiber optics to carry light to and from the particle sample (see FIG. 53). The fibers also collect light from separate scattering angles and mixes that light with light from the source, using fiber optic couplers. The light source, which may be a laser, is focused, by lens 5301, into the source fiber optic. The beam exiting this fiber is generally collimated by lens 5302 to produce the incident beam for the particles. Lens 5303 focuses the scattered light into multiple fibers. Each fiber intercepts a different range of scattering angles. The incident beam is also collected by a fiber optic to provide the local oscillator which is mixed with these separate scattering beams by using fiber optic couplers. Fiber optic coupler 5311 splits the source light into two or more fibers to be further mixed with scattered light in the other fiber optics, using fiber optic coupler and fiber optic coupler 5312. The power spectrum of detector current for the low angle and high angle detector will follow the theory described above. The amount of light transmitted by the sample may also be measured to help in optimizing particle concentration to avoid multiple scattering. The angle, between the optical axis of the beam passing through the sample cell and the particle velocity direction, should be adjusted to provide sufficient Doppler shift of the scattered light for the given scattering angle, using known relationships for Doppler systems. This angle is shown schematically in FIGS. 53, 54, and 55, and does not show the actual angle, which will be smaller than 90 degrees in most cases.

Fiber Optic Configuration 2

Figure 54:
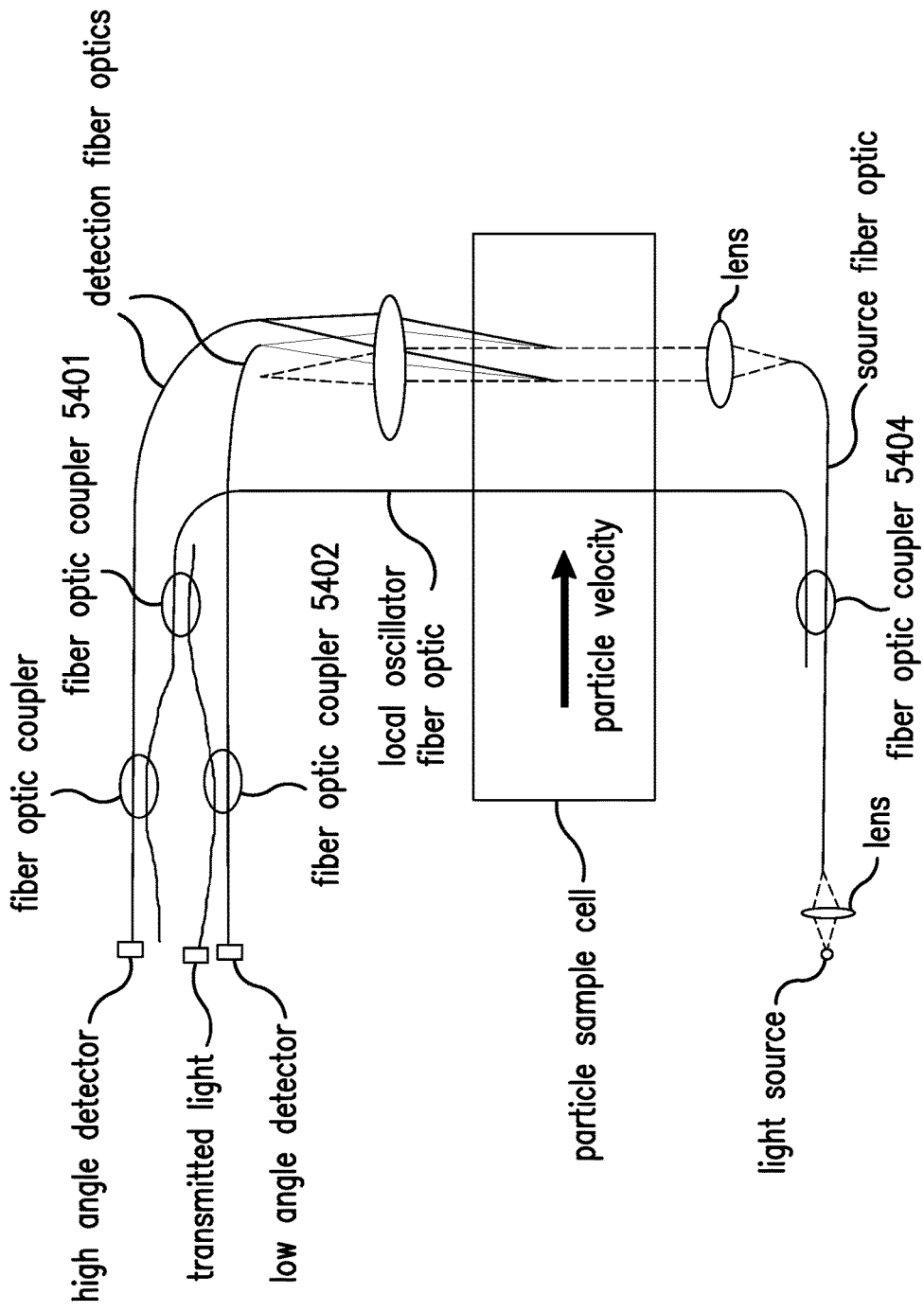
FIG. 54 shows a variation of FIG. 53, utilizing a fiber optic coupler to obtain the local oscillator light directly from the light source fiber optic.

The second fiber optic configuration, shown in FIG. 54, is similar to the first one shown in FIG. 53, except that the source light is split off from the source fiber, by fiber coupler 5404, and mixed directly with the scattered light using fiber optic coupler (of FIG. 54) and fiber optic couplers 5401 and 5402, as shown in FIG. 54. This configuration uses fiber optics to carry light to and from the particle sample (see FIG. 54). The fibers also collect scattered light from separate scattering angles and mixes that light with light from the source, using fiber optic couplers. The light source, which may be a laser, is focused, by a lens, into the source fiber optic. The beam exiting this fiber is generally collimated by the lens between the source fiber optic and the sample cell to produce the incident beam for the particles. The lens, between the sample cell and the detection fiber optics, focuses the scattered light into multiple fibers. Each fiber intercepts a different range of scattering angles. The source light is split off from the source fiber, by fiber coupler 5404, which distributes the source light to the low and high angle detectors through fiber optic coupler 5401. Fiber optic coupler 5401 splits the source light into two or more fibers to be further mixed with scattered light in the other fiber optics, using fiber optic coupler and fiber optic coupler 5402. The local oscillator fiber optic passes around the particle sample cell.

The source light beams can also be focused to a beam waist inside of the particle sample cell. Then lens 5303 would image each beam waist on to the tip of the corresponding detection fiber optic.

Beamsplitter Configuration 1

Figure 55:
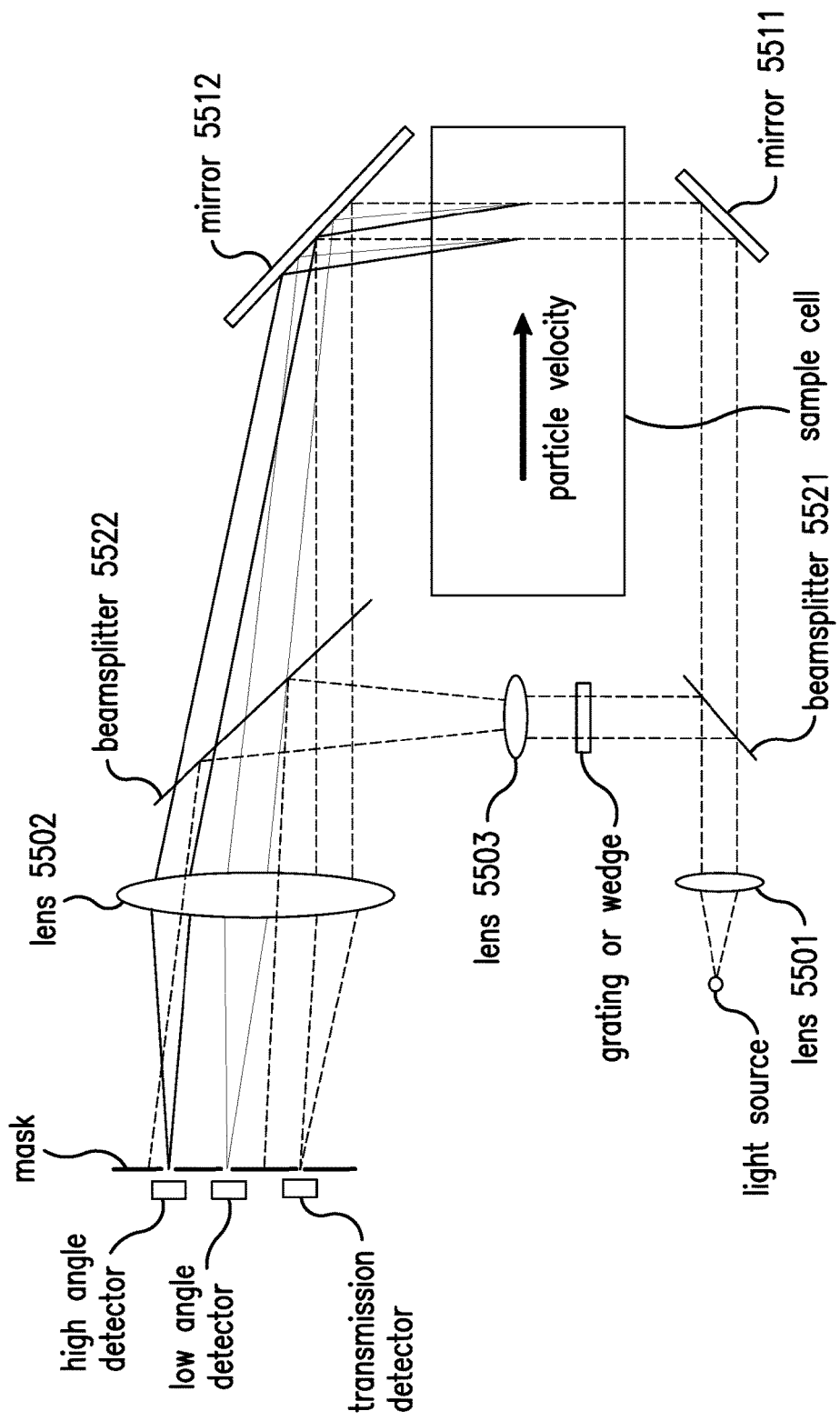
FIG. 55 provides a schematic diagram of optical and mechanical systems, measuring particle motion and size distribution during centrifugation and utilizing beamsplitters to provide the local oscillator light, according to the present invention.

This configuration uses beamsplitters to provide the local oscillator (see FIG. 55). Again the source beam is generally collimated by lens 5501 and folded through the sample cell by mirror 5511. Mirror 5512 folds the incident beam and scattered beams through lens 5502, which focuses these beams onto an array of mask apertured detectors. A small portion of the source beam is split off by beamsplitter 5521 to provide the local oscillator to be mixed with the scattered light on the detector. An optional grating or optical wedge (only partially placed in the beam) could provide multiple local oscillator beams which would line up with each of the scattering detector apertures. And lens 5503 may be used to expand the local oscillator beams to lower alignment problems at the mask. Beamsplitter 5522 folds these local oscillator beams through lens 5502 to be mixed with scattered light on each detector.

Beamsplitter Configuration 2

Figure 56:
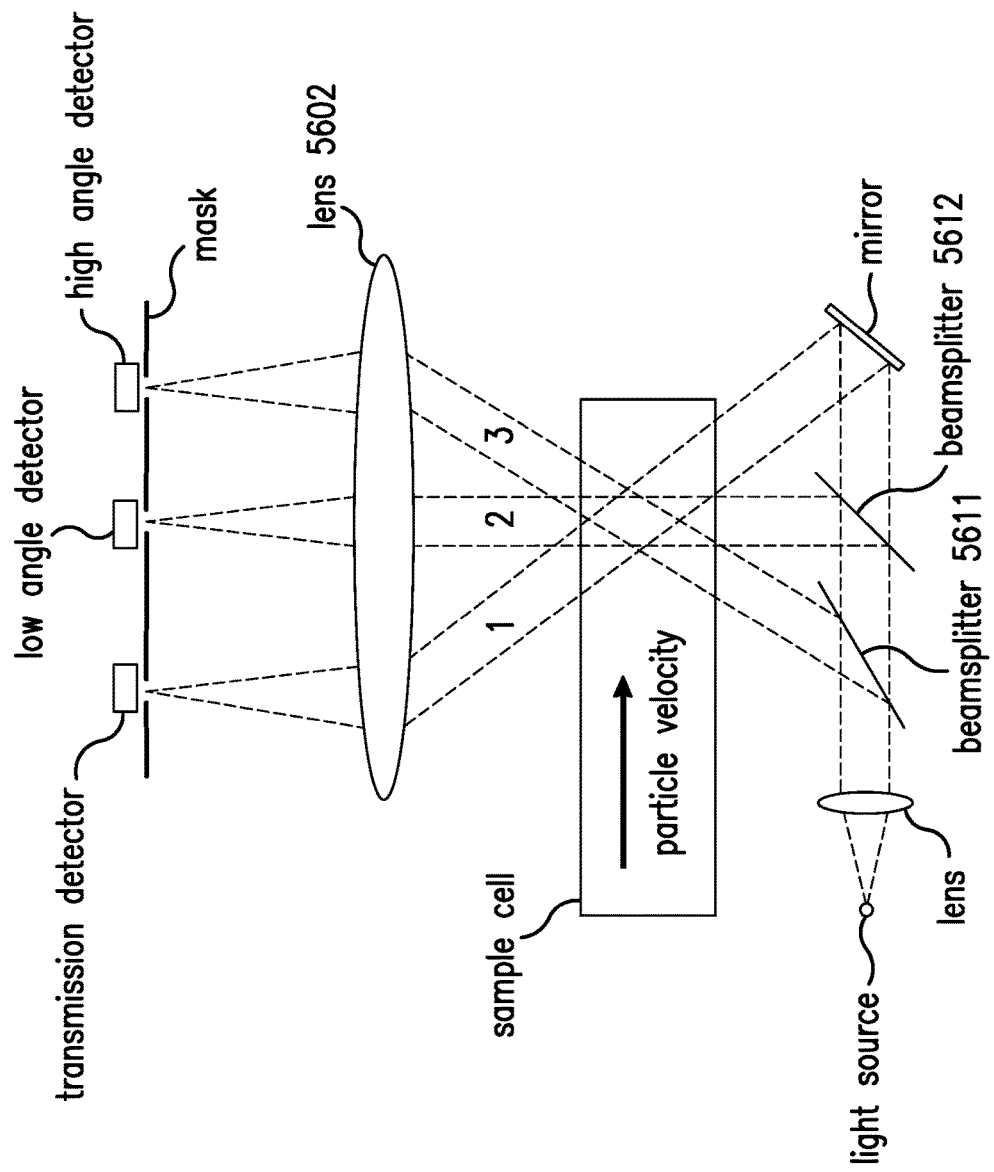
FIG. 56 provides a schematic diagram of optical and mechanical systems, measuring particle motion and size distribution during centrifugation, by projecting the local oscillator light through the scattering volume, according to the present invention.

In this configuration, the local oscillator is provided through the scattering volume, as shown in FIG. 56. Notice that the 3 beams passing through the sample cell are numbered 1, 2, and 3. Beam 1 is the incident beam, which creates the scattered light. Beams 2 and 3 are local oscillator beams which mix with the scattered light at various angles. Again these mixed beams are focused by lens 5602 onto an array of mask apertured detectors. Beamsplitter 5611 and 5612 provide the local oscillators at the various scattering angles. The reflectivity of these beamsplitters should be optimized to produce generally the largest heterodyning signal on the detectors.

Figure 57:
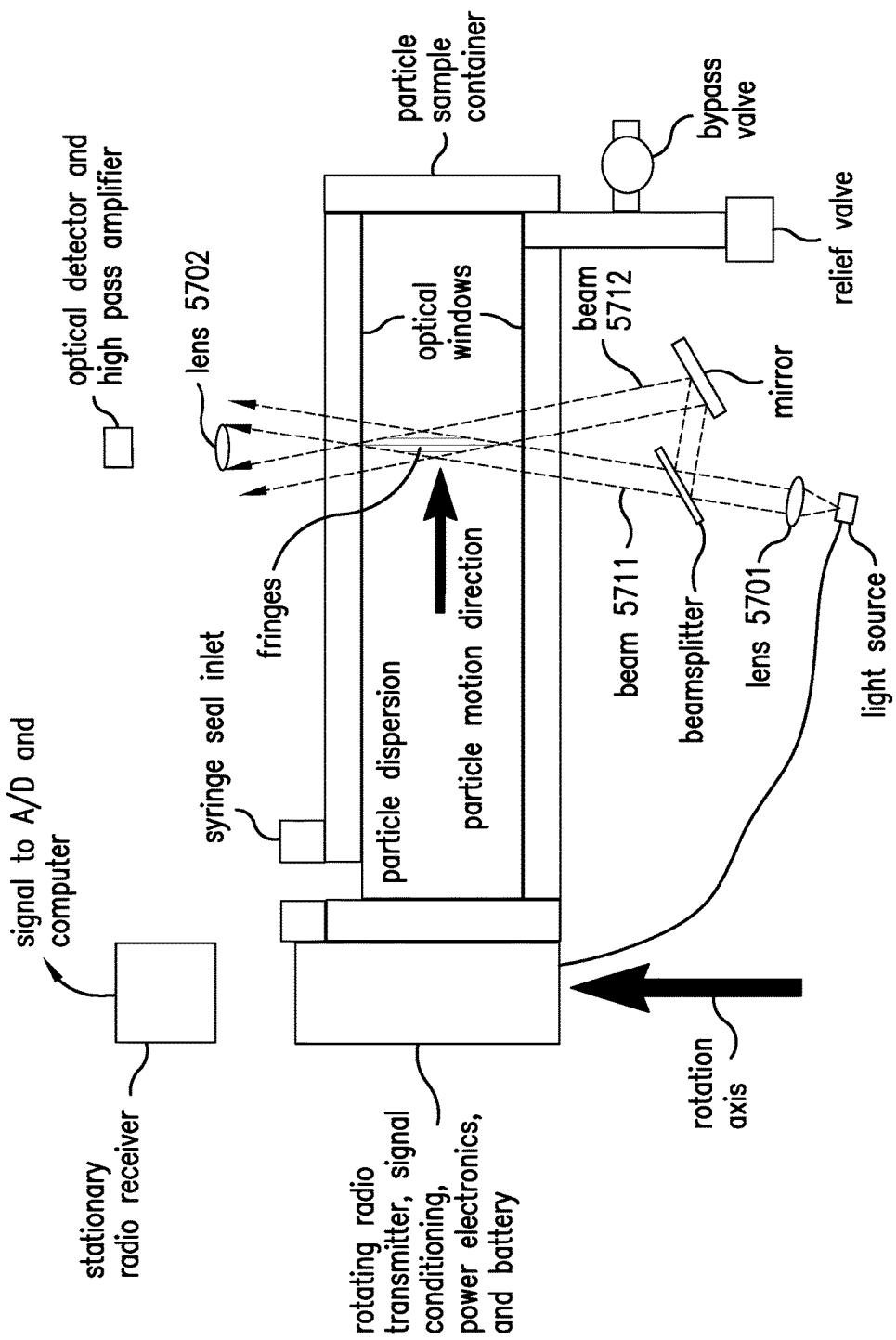
FIG. 57 provides a schematic diagram of optical and mechanical systems, measuring particle motion and size distribution during centrifugation, utilizing a radio transmitter or digital storage to transfer data to a stationary computer, according to the present invention.

The Doppler frequency shift changes with scattering angle. Therefore, collection of scattering over wide range of scattering angles will create significant spectral broadening of the shifted spectrum, requiring deconvolution to retrieve size resolution. However, collection over a narrow angular range will maximize the errors caused by Mie resonances. By measuring over a wide range of scattering angles, the Mie resonances are washed out. This is accomplished by measuring the scattered light from particles flowing through a modulated light pattern, such as a group of interference fringes. As the particles flow through the fringe pattern, the scattered light from each particle is modulated with a frequency indicative of particle velocity and size. The spectral width of the scattered light is not broadened significantly by collecting scattered light over a wide range of angles in this fringe field, which may be produced through interference between two light beams as shown in FIG. 57 and FIG. 58.

A coherent light source, such as a laser diode, is focused or collimated into the sample container by lens 5701. A beamsplitter produces a second beam 5712 which creates interference fringes with beam 5711 in the sample container. Light scattered by particles in the fringe region is collected by lens 5702, which focuses this light onto a detector. As the moving particles pass through the interference fringes, the scattered light from each particle oscillates due to the oscillating intensity of the illumination interference pattern. The modulation frequency of the scattered light signal from the detector will be proportional to the particle velocity. The signal from the detector may (or may not) be electronically filtered before being transmitted to the stationary A/D (analog to digital converter). In this case, a radio transmitter is used in the rotating system to transmit the scattering signal to a stationary radio receiver at the input to the A/D. The A/D may also be placed between the detector and the transmitter so that digitized detector signals would be transmitted to the stationary receiver.

In general for these centrifuge systems, commercially available wireless FM, Blue Tooth, or wireless digital microphone technology could be used to transmit the digital or analog data from the rotating centrifuge to the stationary computer. These devices have sufficient signal to noise and bandwidth. The detector signal could also be stored in digital storage (flash memory chip, for example) in the rotating system and then read out by connection to the computer after the centrifuge has stopped. A quick connect structure could be used to automatically connect the digital storage to the stationary computer after stopping. The use of rotational coupling may be preferred to allow computer control of centrifuge parameters during the centrifugation process. The scatter data (for example, the power spectrum of the detector current) can be analyzed periodically during the centrifuge process to optimize the centrifuge rotation velocity schedule for the remaining data sets. The optical rotational coupling, radio transmitter, and digital storage are three means of transferring the scattered light signal from the rotating system to the stationary computer. Any transmission techniques, including all three of these techniques, are claimed for all configurations associated with this disclosure.

Figure 58:
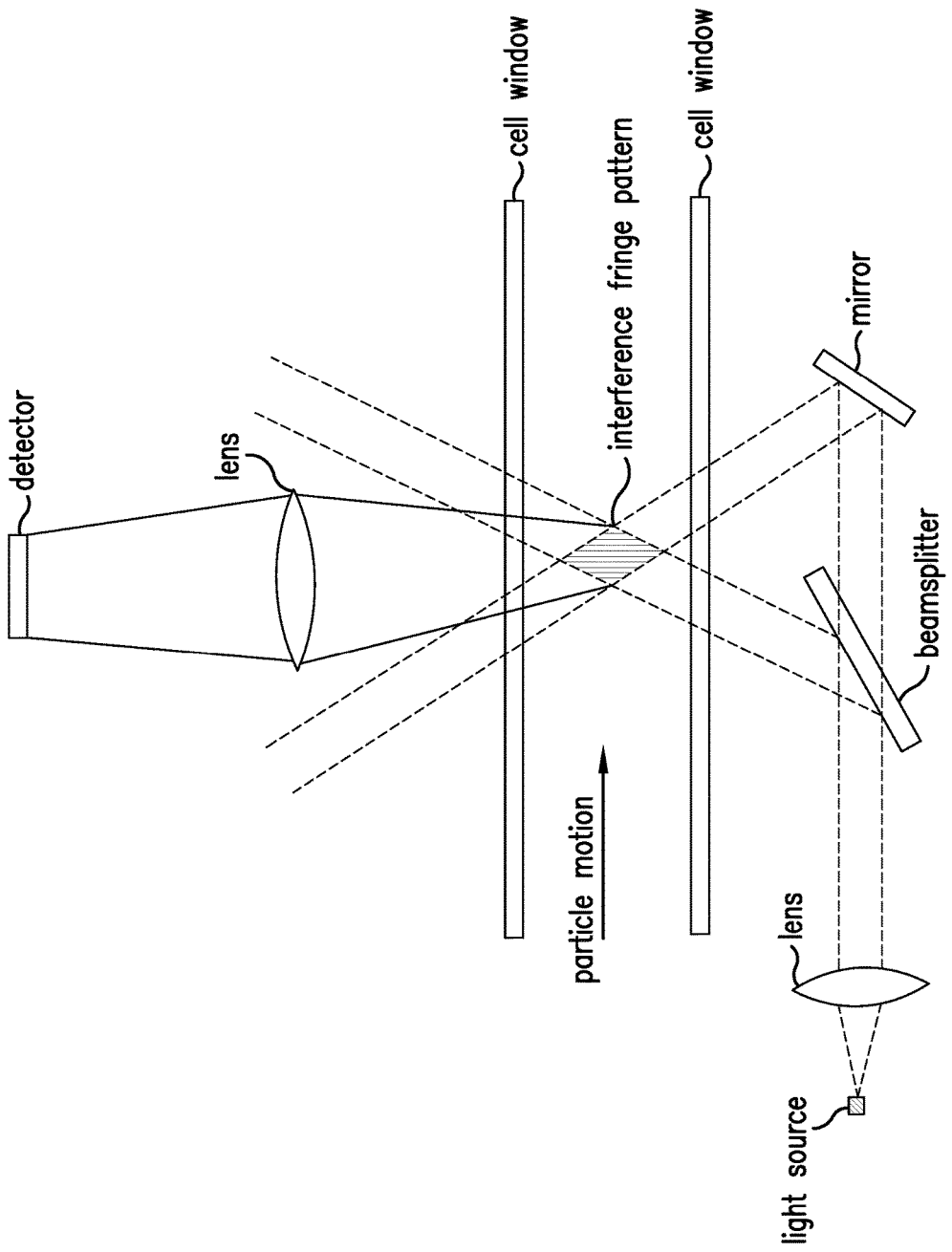
FIG. 58 provides a schematic diagram of an optical system, utilizing an interference fringe pattern to measure the motion and size distribution of particles, according to the present invention.

FIG. 58 shows another variation of this fringe system, with more detail of the collection optics. Usually the fringe field will be imaged onto the detector to provide discrimination against other light sources. And the angular acceptance may be large with minimal effect on the scattered signal spectrum, because the same fringe field modulates the scattering signals at all scattering angles.

Since the fringe field (FIGS. 57 and 58) or the image of the target (FIGS. 59, 60, 61) has limited depth of focus in the sample container, some particles will pass through regions where the fringes are out of focus. This will cause spectral broadening of the modulation spectrum and the impulse response of the linear system which describes the scattered signals. By reducing the pathlength through the sample container, the particles may be restricted to the region of best focus for the target or fringe field. In addition, the resulting scattering signal spectrum may be deconvolved by including the spectral broadening in the scattering model and inverting that model by use of iterative optimization techniques or deconvolution. The spectral broadening due to variation of the target image or fringe field throughout the interaction volume, can be used as the impulse response for a convolution relationship:

$$Pbr = Hb \Theta P$$

$\Theta$ is the convolution operator. P is the power spectrum without broadening and Pbr is the measured power spectrum with broadening. Hb is the impulse response which describes the broadening. Hb is calculated from theoretical model of the fringe or target image structure, using the Fourier transform of the intensity profile. Also Hb can be measured directly from the spectral distribution Pbr from a large group of particles with a narrow size distribution. In either case, the convolution equation is solved for P, given Pbr and Hb, using known deconvolution techniques.

Even with wide angular collection, Mie resonances may still be a problem for narrow wavelength bandwidth sources. Another problem is size dynamic range. A single fringe spatial frequency can only handle particles with diameters smaller than the inter-fringe spacing, but with sufficient size (and velocity) to cause high modulation frequency. A particle, which is much smaller than the fringe inter-fringe spacing, may travel too slowly to produce a scatter signal modulation frequency above the 1/f noise of the detection system. Fringe patterns with smaller inter-fringe spacing are needed for small, low velocity particles. The best solution is multiple fringe spacings. By using multiple beamsplitters and detectors, multiple fringe fields may be created with different inter-fringe spacings. Each fringe field is imaged onto a separate detector to separate the modulated scatter signals for each fringe field.

Figure 59:
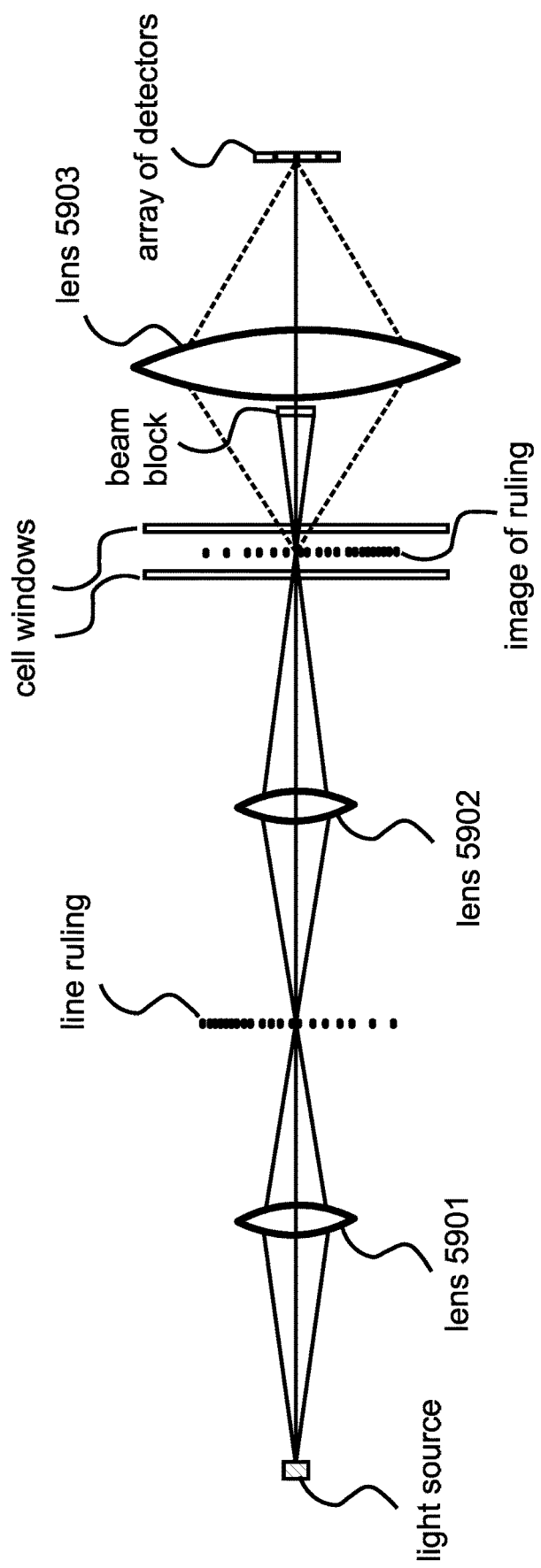
FIG. 59 provides a schematic diagram of an optical system, utilizing a line ruling to measure the motion and size distribution of particles, as used in the present invention.
Figure 60:
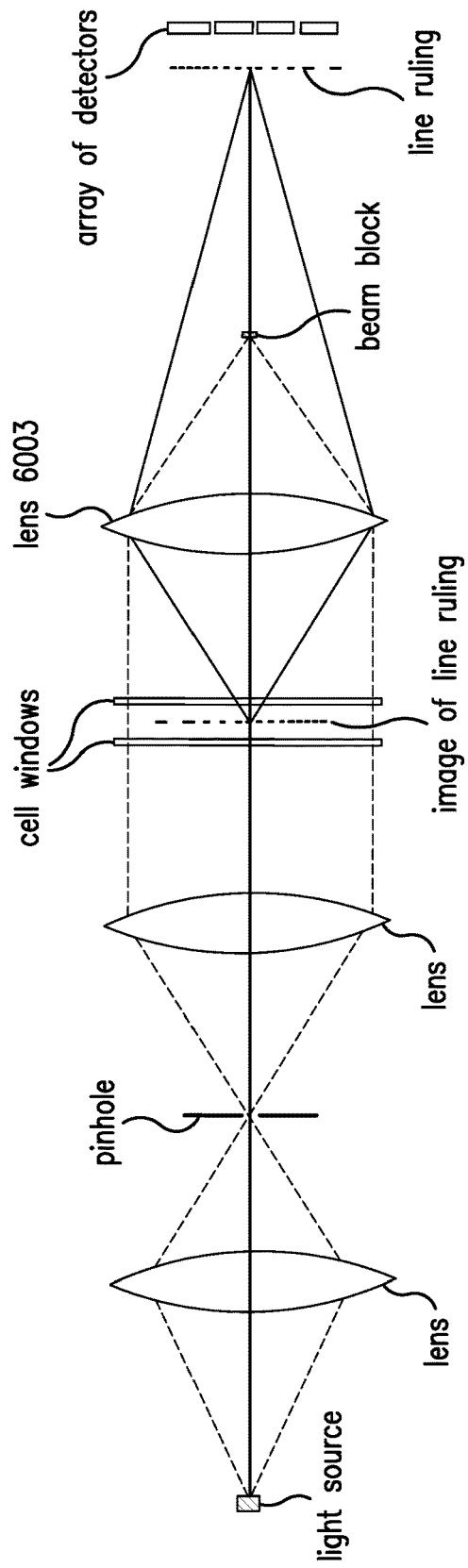
FIG. 60 provides a schematic diagram of an optical system, utilizing a line ruling, on front of an array of detectors, to measure the motion and size distribution of particles, according to the present invention.
Figure 61:
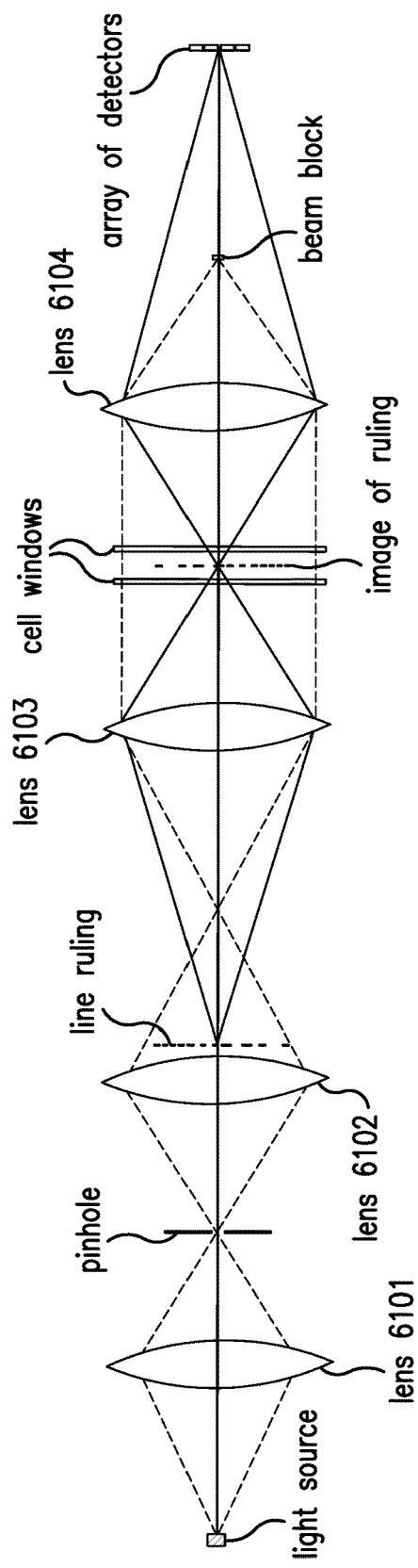
FIG. 61 provides a schematic diagram of an optical system, utilizing a line ruling to measure the motion and size distribution of particles, with generally collimated light in a sample cell, according to the present invention.
Figure 62:
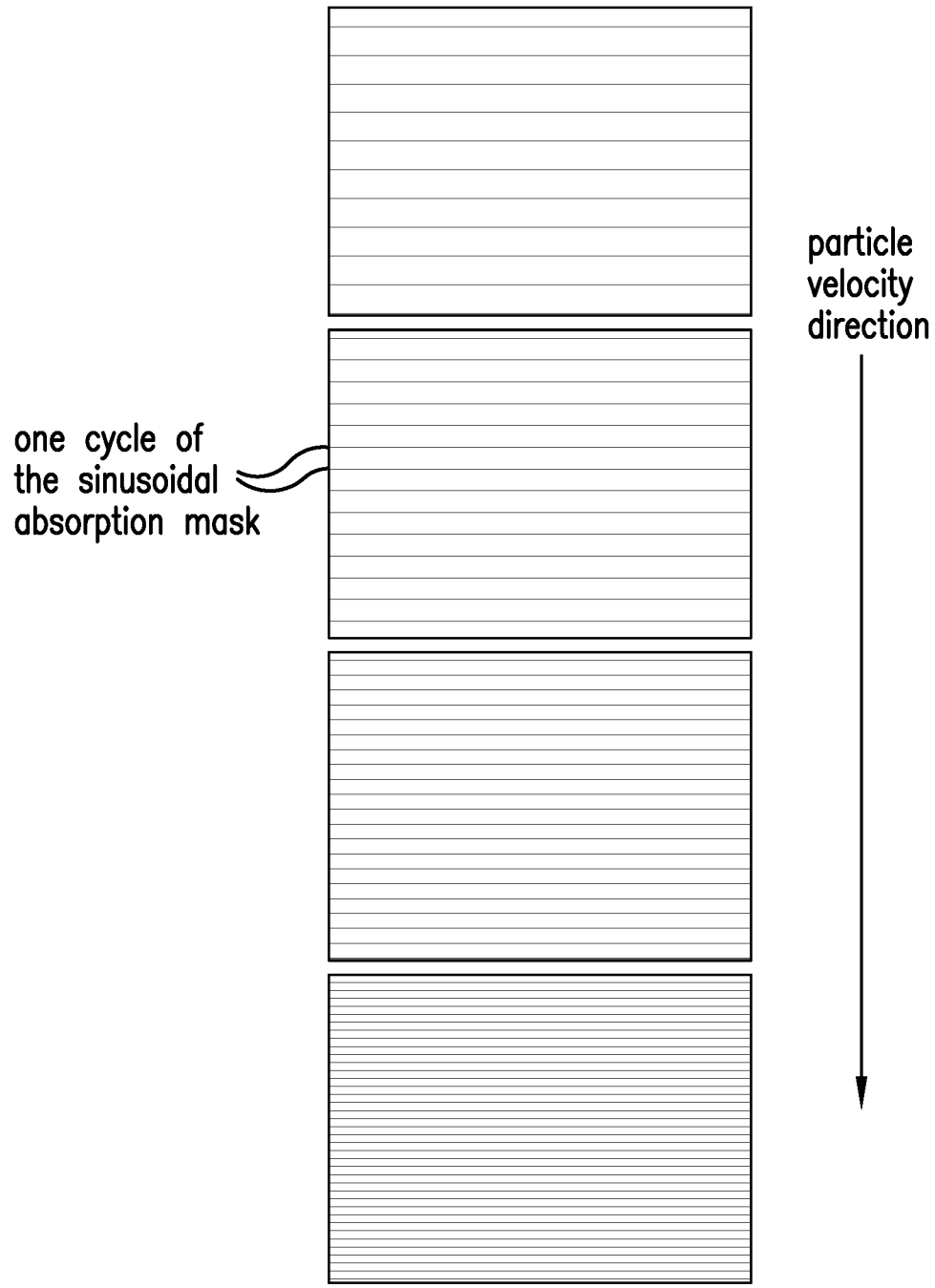
FIG. 62 shows an example of a line ruling with regions of various frequencies, as used in the present invention.

Since this multiple beam splitter concept may be expensive to manufacture, a better alternative is to image a sinusoidal absorption (or reflection) grating, with various fringe spacings, into the particle dispersion. As each particle passes through the grating image, the scattered light from that particle is modulated by the periodic intensity profile of the image. A standard optical absorption resolution target could be used to produce an image with multiple regions, each region with a different sinusoidal spatial wavelength as shown in FIG. 62, which shows a mask (or image of a mask) with four regions. The spatial frequency of each region is only for illustrative purposes. Optical systems incorporating this type of sinusoidal absorption grating (also called a line ruling) are shown in FIGS. 59, 60, and 61. Each region of the target image is imaged onto a separate detector. By using a white light source, Mie resonances are greatly reduced; but a laser source or LED may be preferred if chromatic aberration is a problem. In FIG. 59, a light source (a white light source, LED, or laser for example) is focused by lens 5901 onto a line ruling or sinusoidal target with multiple regions, each with a different fringe spacing or sinusoidal wavelength. The line ruling size is exaggerated for illustrative purposes; the light source illuminates the entire line ruling. The light rays from the source only indicate the image planes of the source and not the beam diameters at any plane. Lens 5902 images this target into the particle sample container. Lens 5903 images this target image onto a set of detectors, which are positioned to capture the image of each target region onto a separate detector. The direct light from the source is blocked by a beam block which is placed on front of lens 5903 to block the passage of source beam illumination to the detectors, while passing generally only the scattered light, to the detectors. Only the light scattered from particles passing through the fringe image reaches the detectors.

FIG. 61 shows another variation of this idea. The light source is spatially filtered through a pinhole by lenses 6101 and 6102, and generally collimated through the sample container region by lens 6103. Lens 6103 also images the multi-region line ruling or sinusoidal grating into the sample container, which contains the particle dispersion between two cell windows. Each separate region of the line or fringe pattern image has a different spatial frequency and is imaged onto a separate detector, by lens 6104. The source light is blocked in the back focal plane of lens 6104. Only the modulated scattered light reaches the detectors. Each detector sees the scattered light from only one spatial frequency region in the fringe pattern image, in order to separate the modulated signals.

FIG. 60 shows a more compact version of this design. As in prior designs, the particles are moving through a sample cell, between two optical cell windows. And as each particle moves through the image of a line pattern, the scattered light from that particle is modulated by the periodic intensity distribution. The line ruling or pattern is placed in a plane which is conjugate to the region containing the particles. However, in this case the detector array is directly behind the ruling with each detector element aligned behind a different spatial frequency segment of the ruling. This configuration eliminates one lens and allows for greater demagnification of the ruling image. If lens 6003 were a microscope type objective with high magnification, then the ruling and detector array could be larger, lowering the alignment tolerances of the ruling and detector array elements. At very large magnification, separate detectors could be used instead of a detector array. The beam block could also be replaced by a pinhole, in FIGS. 60 and 61, to measure the modulation caused by total light lost by scattering and absorption. The light passing through the pinhole is generally the unscattered light. The amount of light removed by particle scatter, will be removed from this unscattered light. So as a moving particle passes into a region of a bright fringe, the amount of removed light will increase, creating a modulation in the unscattered light signal. In both cases, pinhole or beam block, the higher frequency components of the signal will be similar. However in the case of the pinhole, the modulated scatter signal will be riding on top of a large unscattered light offset, which must be removed by analog or electronic filtering. In size regions where Mie resonances are a problem, the pinhole may be preferred because total light lost may be less sensitive to Mie resonances.

FIGS. 58, 60, and 61 show a light source followed by two lenses and a pinhole to remove unwanted portions of the source light. This subsystem could be replaced by a laser or other collimated source for illuminating the particles in the sample cell.

In FIGS. 59, 60, 61, and 62, and the description above, the terms, line ruling, ruling, sinusoidal grating, sinusoidal absorption grating, and resolution target, refer to the same general object, which is a mask with periodic absorption (or reflection), with periodicity in the direction of the particle motion. The use of any one of these five terms in this document is assumed to include the other four terms. The best type of mask is one with a sinusoidal absorption pattern (see FIG. 62) which will produce single frequency modulation of the scattered light from particles of a single velocity. While other periodic absorption profiles (other than sinusoidal) can be used, they will produce harmonics in the scattering signal, which must be removed from the power spectrum by deconvolution, as described previously, with equation $Pbr=Hb\Theta P$. The impulse response, Hb, would be determined from the Fourier transform of the periodic profile. Alternatively, Hb can be measured directly from the spectral distribution Pbr measured from a large group of particles with a narrow size distribution.

Each of these detector signals can be transmitted separately to the computer through multiple transmission channels. Also the signals could be sent sequentially because the spectral properties of each detector signal are stationary over short periods of time. The signal properties only change when the largest particle fraction passes through the interaction region. So a short signal segment can be sent from each detector sequentially on a single transmission channel. Also a fast A/D and multiplexer could do sequential multi-channel sampling where each successive sample point is from the next detector. This A/D signal is then transmitted to the computer receiver and disassembled and recombined into separate detector data streams in the computer.

For very small particles, which need short inter-fringe spacing, either the crossed laser beam (FIG. 58) or heterodyne system (FIGS. 52, 53, 54, 55, 56) should be used to obtain optimal accuracy, because the image resolution of the white light system may not produce sufficient resolution of fringe spacings below 1 micron. Either the crossed beam system, using high resolution fringe patterns, or the heterodyne system can measure Doppler shifts at smaller particle velocities. By using the white light/sinusoidal target system for particles above approximately 1 micron and crossed-beam or heterodyne below approximately 1 micron, particles over a wide size range from 0.1 micron to greater than 1000 microns could be measured.

As mentioned before, Mie resonances may present a problem for ensemble scattering measurements because the scattering amplitude will be a multi-valued function of particle size. However in the size region between 2 and 10 microns where these resonances occur, the particle concentration could be lowered to insure that only a few particles are in the beam at any time. Low numbers of particles will produce a discrete set of line spectra in the power spectrum instead of a broad continuum, one line for each particle. These line spectra can be separated for individual counting and sizing of particles based upon their Doppler frequency. Then the variation of the amplitude of each spectral line due to Mie resonances or scattering efficiency variations will not affect the size determination. In most applications, the particle volume vs. size distribution is relatively uniform; and the particle count vs. size distribution is proportional to the volume distribution divided by the particle diameter cubed. So larger particles will have much lower particle number concentrations and the line spectra/counting method could be employed without coincidence problems in the line spectra. This method can count and size individual particles, with many particles in the beam at one time, provided that no two particles have the same size. Even if two particles did have the same size, the amplitude of that spectral line would be double the expected amplitude and that line could be identified and counted as two particles. This technique is very powerful in that it allows counting and sizing of individual particles in the beam even when large numbers of particles are in the beam at one time. This method is described in more detail in another filed application, "Methods and Apparatus for Determining the Size and Shape of Particles", filed by this inventor.

Also many of the heterodyne and fringe systems, described by this inventor in "Methods and Apparatus for Determining the Size and Shape of Particles", can be placed into a centrifuge to produce the same data as described in this document.

Figure 63:
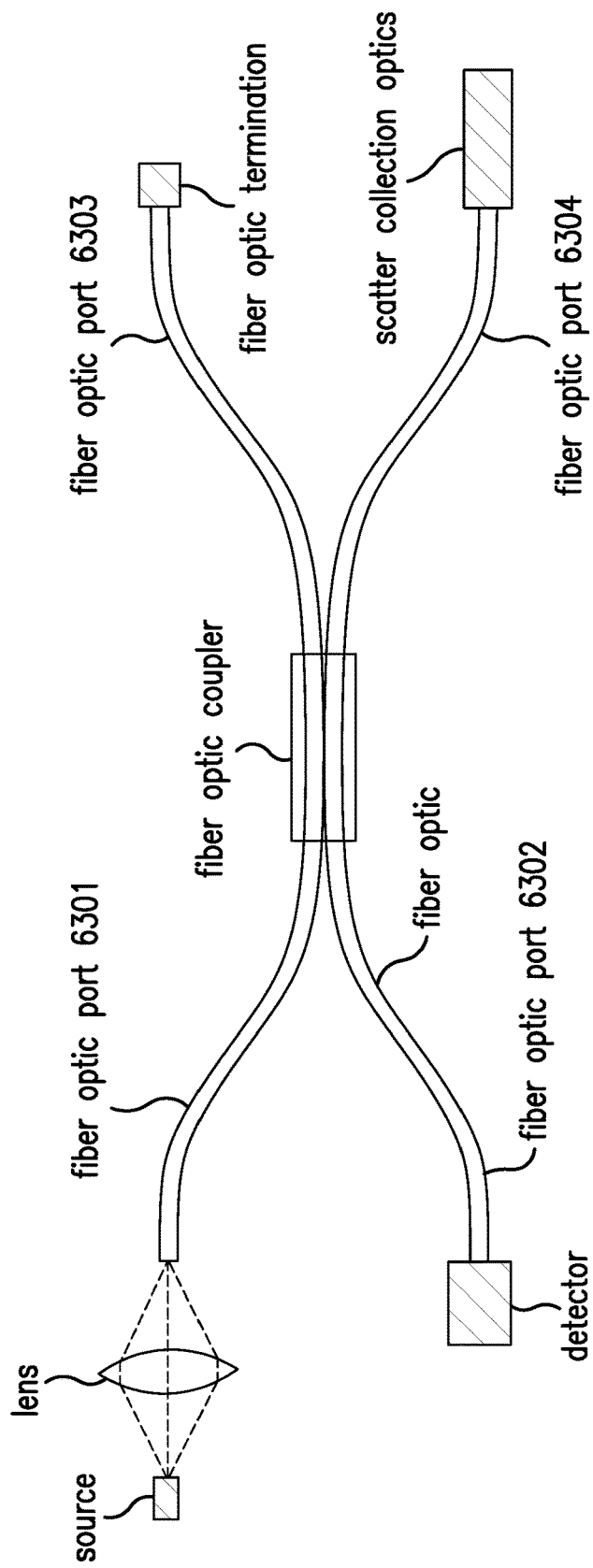
FIG. 63 provides a schematic diagram of a fiber optic system, which mixes source and scattered light to measure the motion and size distribution of particles, according to the present invention.
Figure 64:
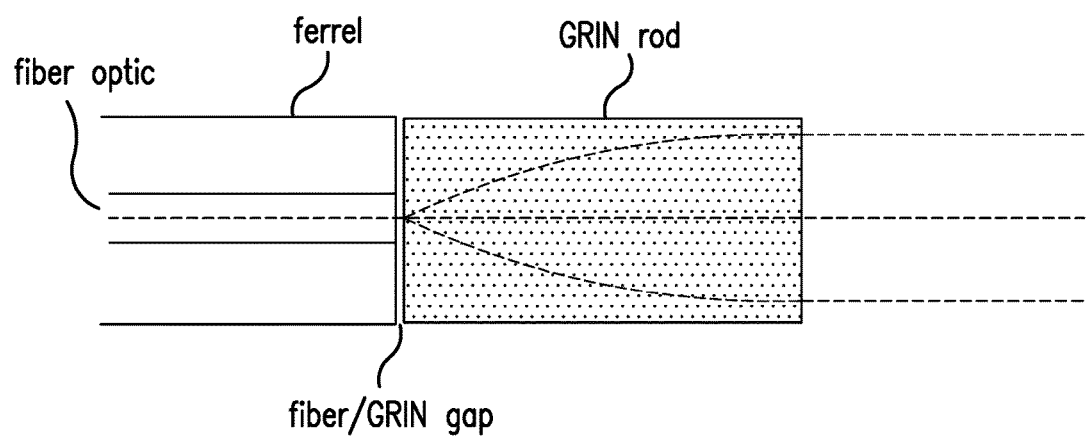
FIG. 64 shows a configuration, for port 6304 of FIG. 63, providing a generally collimated light beam.

The particle velocity detection systems in FIG. 52 and FIG. 57 can be replaced with the fiber optic system shown in FIGS. 63 and 64, using the same analysis of the power spectrum of the scatter detector current. The tip of the scatter collection optics would be immersed into the dispersion inside the particle sample container at the end closest to the rotation axis. The light beam from the scatter collection optics would be projected into the particle sample container, in a direction generally parallel to the particle motion direction. For larger or denser particles, this system could also be used in settling mode by aligning the particle velocity axis of the sample chamber with the direction of gravitational force. The basic fiber optic interferometer is illustrated in FIG. 63. A light source is focused into port 6301 of a fiber optic coupler. This source light is transferred to port 6304 and port 6304 light scattering optics which project the light into the particle dispersion and collect light scattered from the particles. This scattered light is transferred back through the fiber optic and coupler to the detector on port 6302. If the coupler has a third port, a portion of the source light also continues on to port 6303 which may provide a local oscillator with a reflective layer. If the local oscillator is not provided at port 6303, a beam dump or anti-reflective layer may be placed onto port 6303 to eliminate the reflection which may produce interferometric noise in the fiber optic interferometer. The beam dump could consist of a thick window which is attached to the tip of the fiber with transparent adhesive whose refractive index generally matches that of the fiber and the window. This will reduce the amount of light which is Fresnel reflected back into the fiber at the fiber tip. The other surface of the window can be anti-reflection coated, and/or be sufficiently far (thick window) from the fiber tip, so that no light, which is reflected from that surface, can enter the fiber. The details of the scatter collection optics are shown in FIG. 64. A GRIN rod or conventional lens is used to project the source light into the dispersion. The projected beam can be weakly focused, or generally collimated, to provide generally equal contribution of scatter from particles throughout an extended region of the sample container, as shown by scatter collection optics A in FIG. 65. The local oscillator light can be produced by reflection at the fiber/GRIN gap or at the other surface, of the GRIN rod, which contacts the particle dispersion. In this way, the heterodyne signals from a large group of scatters could be measured for a long period, which ends when the highest velocity particles leave any portion of the region where scatter can be detected. After the larger particles have left that region, the centrifuge can be stopped (or the sample cell could be turned to be perpendicular to the settling direction) and then the Brownian motion of the remaining smaller particles could be measured, with the same heterodyne system, to determine the size distribution of particles which are too small to have sufficient terminal velocity to be measured under the centrifugal force or settling. The beam could also be strongly focused, as long as the larger particles remain in the smaller scatter interaction volume for sufficient time to gather the Doppler shifted signals. As before, after the larger particles leave the interaction volume via settling or centrifugal force, the remaining smaller particles can be measured by measuring the dynamic light scattering due to Brownian motion of the remaining particles.

In the case, shown in FIGS. 63 and 64, the optical axis of the scatter collection optics is generally parallel to the direction of particle motion. And heterodyne detection is used to measure the Doppler broadened power spectrum of the detector current to determine the velocity distribution of the particles under a centrifugal or gravitational force. Many other heterodyning systems can also be used in this configuration, including those shown in FIGS. 1, 2, 3, 4, 5, 6, 10, 11A, 11B, 12, 13, 14, 19, 25, 26, 27, 29, and 31. The sample cell, in those Figures, is replaced by the centrifugal cell, where the scatter collection optic system is immersed into the dispersion, with optical axis generally parallel to the particle motion direction.

The fiber optic system and electronics would be mounted into the center portion of the rotor to minimize the centrifugal force on the fiber components. And the scatter signals would be transmitted to the stationary computer by any of the methods described above, including optical coupling and radio transmission.

Figure 65:
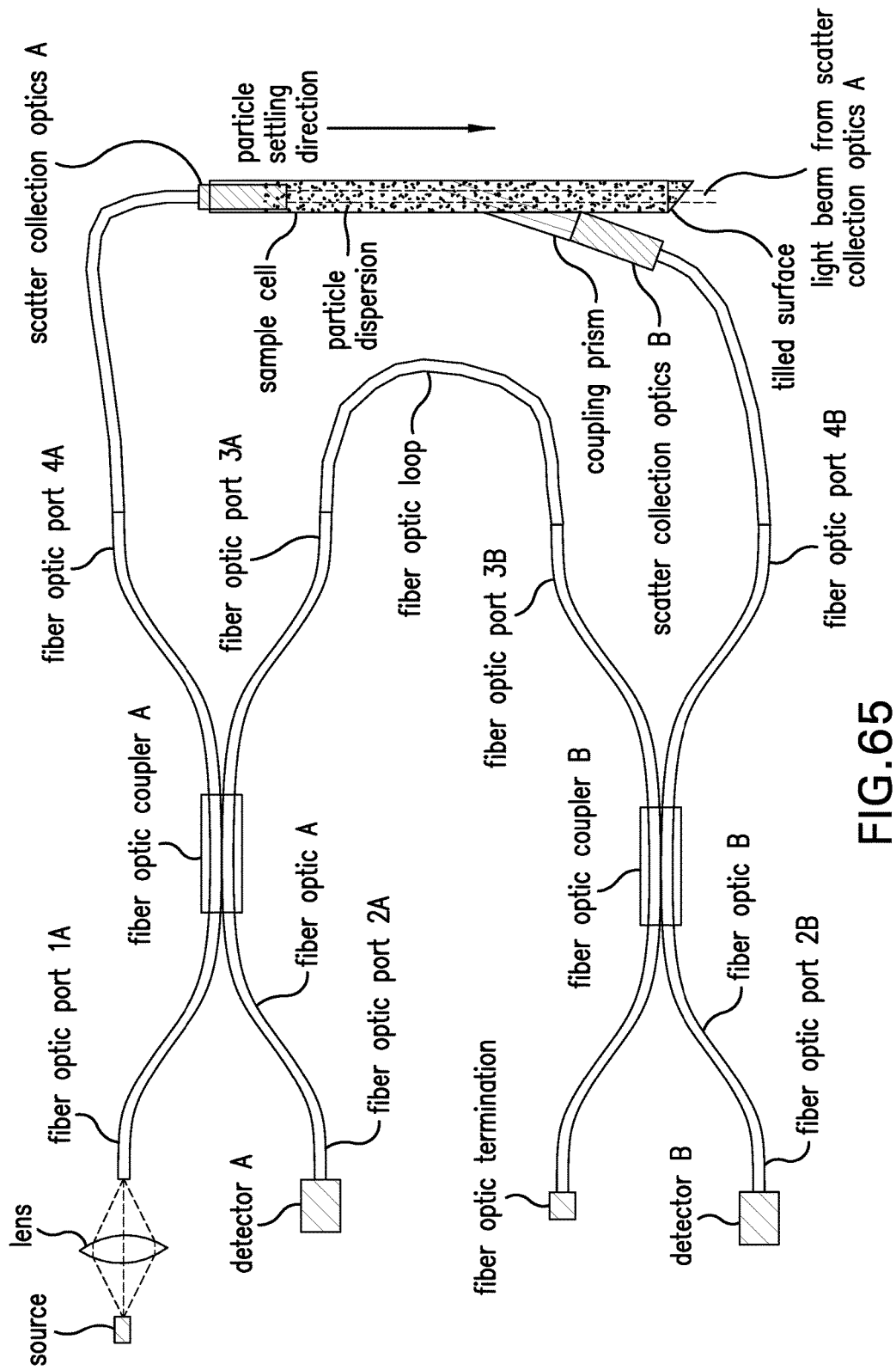
FIG. 65 provides a schematic diagram of a fiber optic system, which mixes source and scattered light to measure the motion and size distribution of particles, utilizing scatter measurements at multiple scatter angles, according to the present invention.

The scattering efficiency (the scattered intensity per unit particle volume and per unit incident intensity) for large particles is much higher and less multi-valued at lower scattering angles. Therefore, to detect the larger particles in settling and centrifugal mode, or Brownian motion mode, additional detectors are required to measure scattered light at lower scattering angles as shown in FIG. 65. FIG. 65 shows system A, which projects light into the sample cell and collects scattered light at approximately 180 degrees along with the local oscillator which is Fresnel reflected from the exit surface of the scatter collection optics A, as described previously. A second optical system B is connected to port 3A of system A to provide local oscillator to be mixed with scattered light from scatter collection optics B, which collect scattered light at lower scattering angles. The length of the fiber optic loop is chosen to match the total optical pathlength from the source through port 3B to detector B with the total optical path through port 4A and port 4B to detector B. In this way Detector A collects high angle scatter and Detector B collects low angle scatter. Both detectors operate in heterodyne mode using the light from a single source. Scatter collection optics B collects scattered light through a coupling prism which is attached to the window of the sample cell with index matching adhesive to reduce Fresnel reflections at that interface. Both detectors will see dynamic scattering which includes both a Brownian motion component and centrifugal or settling component in the power spectrum of the detector current. Essentially, the power spectrum is a symmetrical function, whose spectral width is determined by spectral broadening caused by Brownian motion. The center of this symmetrical function is shifted to the Doppler frequency due to settling or centrifugal induced motion of the particles. So for very small particles, the spectrum will be very broad, with the center of the function close to zero frequency. For large particles, the spectrum will be narrow with a large shift from zero frequency. These two effects are included in the matrix equation which is used to model this power spectrum, as shown previously in Table 1. This model is then inverted to determine the particle size distribution from the measured power spectrum, as described previously. Better size distribution accuracy is obtained by measuring the power spectrum under two different conditions, using the appropriate model for each condition, and then combining particle size results from inverting these two models separately or by combining the matrices, of both models, into one single matrix and solving that larger linear system. The first condition is with particles under centrifugal or gravitational force along the direction, which provides maximum Doppler shift for the low angle scattering detector, generally parallel to the angular bisector between the forward scatter direction and the light beam in the sample cell. The second condition is in the absence of the centrifugal force or with the gravitational force generally perpendicular to the angular bisector between the forward scatter direction and the light beam in the sample cell. At this angle the Doppler shift due to gravitation will be minimized. If the most important size information is contained in the backscatter direction, then the two cases should be with alignment of the gravitational or centrifugal force in directions parallel to, and then perpendicular to the light beam (instead of the bisector mentioned previously). Another useful data separation is to measure the Brownian motion of the smaller particles after the larger particles have been removed from the dispersant due to settling or centrifugal force, so as to remove the background signal fluctuations caused by the larger particles. Also power spectrum measurements can be made at various times during the settling or centrifugation process to measure different size fractions of the sample as described previously in this document. In this case a focused light beam may be more appropriate to provide a smaller interaction volume, which larger particles can leave more quickly, providing faster separation of different size fractions.

The inventor has described many optical systems, which can measure the velocity of moving particles, by detecting scattered light from the particles during motion. Any of these systems can be used with these centrifuge/settling concepts by positioning the particle dispersion sample cell such that the interaction volume of the optical system generally coincides with the appropriate region in the sample cell. The orientation, relative to the particle motion direction, of the optical system is chosen to provide sufficient Doppler spectral shift to determine the particle characteristics. Any of these systems can be placed into an acceleration field created by centrifugation or gravity (for example) to measure the velocity distribution of particles in the acceleration field. The signal information is transferred from the moving system to the stationary computer by any the means described previously. The particle size distribution is determined from the velocity distribution, the particle size and density, and dispersant properties. The inventor also claims the use of any systems which can measure velocity distributions.

Many of the scattering detection systems, described in the application "Methods and Apparatus for Determining the Size and Shape of Particles" by this inventor, can also be employed as the detection means in the systems described in this document.

Many figures in this document contain optical rays which are drawn only to define object planes, image planes, and focal planes. The numerical apertures, scattered ray angles, beam diameters, and lens diameters are not necessarily drawn to scale.

A version of the scatter collection optics, for zeta potential measurement, is detailed in FIG. 68. In FIG. 68, the source light is focused into the particle dispersion, through a GRIN rod (Gradient index lens) and a window. The focus spot is close to the interface between the window and the dispersion. This GRIN lens could also be replaced by a conventional lens, which places the focus at the same plane. The local oscillator for heterodyne detection can also be provided by reflection of source light at either the interface between the fiber and GRIN rod, or at the interface between the window and the particle dispersion. The window is used to provide an appropriate surface for creating an electrode or for contacting the particle dispersion. In some cases, the window can be eliminated, with the source focus at the interface between the GRIN rod and the particle dispersion. Electrode 6801 is a planar electrode which covers the surface, which contacts the dispersion. Electrode 6801 could be a coating on the window surface, as shown in FIG. 68. A second planar electrode 6802 is placed in the dispersion at some distance from electrode 6801 to produce the electric field between the electrodes. Electrode 6801 must be electrically conductive and it must pass the source light and scattered light. These properties can be provided by two different designs for electrode 6801 in FIG. 68:

1) a partially reflecting/absorbing conducting layer
2) an electrode made from materials which transmit light and are electrically conductive For measurement of zeta potential or electrophoretic mobility, the function B(f) is produced from the spectrum which is measured with the electric field off. The measured Brownian spectrum, with zero electric field and no optical phase modulation, is the positive frequency half of the full theoretical Brownian spectrum, plus the negative frequency portion of the spectrum, which is folded into the positive frequency region. The full theoretical Brownian spectrum is symmetrical about zero frequency, with no optical phase modulation. Therefore, the positive frequency half of B(f) is created by subtracting the contribution of the folded negative spectrum from the measured Brownian spectrum to produce a true, or actual, positive frequency spectrum due to the Brownian motion. Combining the mirror image of this true positive frequency spectrum, for the negative frequency region, with the true positive frequency spectrum in the positive frequency region, produces a full function B(f), which is symmetrical about zero frequency. This measured Brownian spectrum is obtained from the positive frequency half spectrum provided by measuring the power spectrum at zero electric field, without optical phase modulation. If optical phase modulation is used during the measurement of B(f), with zero electric field, then that entire B(f) spectrum will be centered about the optical frequency shift of the optical phase modulator. This shifted spectrum also needs to be corrected for the portion of the spectrum which is folded from negative frequencies. If the optical frequency shift of the optical phase modulator is large, the folded spectrum contribution is negligible and the measured spectrum can be used directly, as B(f), to solve for S(f), without correction for folding. The spectral folding correction is outlined below.

Heterodyne detection cannot determine the direction of particle motion, unless the local oscillator is frequency shifted (frequency shift fo) by optical phase modulation or optical frequency shifting. But in all cases, the negative frequencies of the measured power spectra (Pm(f) and Pom(f)) are folded into the positive frequencies:

$Pm(f)=P(f+)+P(|f-|)$ Pm is the measured power spectrum with electric field on $Pom(f)=Po(f+)+Po(|f-|)$ Pom is the measured power spectrum with electric field off P is the actual power spectrum, without folded contribution, with electric field on Po is the actual power spectrum, without folded contribution, with electric field off Where |x|=absolute value of x f+=f>0 and f-=f<0

If Pm and Pom are used in place of P and Po, respectively, in the prior equations, the theory of those equations must include the addition of the portion, of the spectra, which is folded from negative frequencies into positive frequencies, to preserve accuracy in the determination of Zeta potential or electrophoretic mobility. Otherwise, the true spectra, without folded contribution, P and Po, can be derived from Pm and Pom, respectively. Po(f), in positive f space, is obtained from the measured spectrum by subtraction of the negative portion of the spectrum which is folded into the positive frequency space. For the case where fo=0, the negative f portion of Po(f) can be obtained by assuming that Po(f) is symmetrical about f=0. Since the portion of the spectrum due to Brownian motion is symmetrical about frequency fo for Po(f), and symmetrical about frequency fo−fv for P(f), the folded part of the spectrum Pm and Pom can be determined and subtracted from these measured spectra to produce the spectra P and Po, without the folded contribution. B(f) is derived from Po(f). When fo or fo+fv are large, the subtracted portion is determined from the symmetrical portion in the f>0 space which is the mirror image of the f<0 portion. The following equations describe the removal of the folded contribution, from the measured power spectrum (Pm or Pom), to produce P(f) or Po(f):

$P(f)=Pm(f)-Pm(f-2*(fo+fv))$ where fv=frequency shift due to electric field induced motion of the particles fo=the optical frequency shift introduced by the optical frequency shifter $Po(f)=Pom(f)-Pom(f-2*fo)$ In some cases, very large particles can contribute scatter signals which will distort the signals from smaller particles. Particle settling could be used to remove larger particles from the interaction volume, as shown in FIG. 28 which shows a variation on the concept in FIG. 9. The sample chamber has an extension above the interaction volume, providing a generally horizontal surface so that particles cannot settle into the interaction volume from above that generally horizontal surface. Hence, the interaction volume will gradually be depleted of larger particles, which settle out of the volume. Scatter data can be collected at various times during this settling process to measure different size ranges of the distribution separately, because each particle size, in the particle dispersion size distribution, will be depleted from the interaction volume at a different time, when the particles cannot be replaced by settling particles above the generally horizontal surface. The bottom portion of the sample cell enclosure is shortened or removed completely to allow the particle dispersion to flow down and out of the interaction volume when the sample cell is emptied and rinsed in preparation for the next sample. The sample chamber could also have an inlet for direct insertion of sample dispersion for small samples which cannot fill an entire flow loop. The interaction volume is the volume of dispersion from which the scatter detector can receive scattered light.

Since the larger particles will have higher settling velocities, they will settle out of the interaction volume first in the scattering chamber. Hence the particle size distribution in the interaction volume will change with time. After a long period of time, only the smaller particles will remain. In the case where the settling velocity of larger particles is low, the interaction volume could be reduced to shorten the time required for larger particles to settle out of that volume. When this concept is used to measure different size ranges of the distribution, separately in time, the interaction volume could also be reduced for particles with low settling velocities. Any system (for example systems in FIGS. 1, 2, 3, 4, 5, 6, 7, 8, 10, 11A, 11B, 19, and 27), which measures scattered light, could interact with the particle dispersion directly or through a window. The window could have a generally horizontal orientation, with a generally vertical orientation (parallel to the gravitational acceleration) of the optical axis of the scattering optics. The beam would be focused, with high numerical aperture, close to the optical surface which interfaces with the particle dispersion. Then only particles close to the focus will contribute to the scattered light signal. The interaction volume can be reduced to less than 100 microns in length, so that slowly settling particles, moving parallel to the optical axis, will quickly settle out of the interaction volume and the generally horizontal window surface would act as the generally horizontal surface, which is described above for FIG. 28. Another case is shown in FIG. 28, where the optical axis is generally horizontal, and the particles settle in a direction which is generally perpendicular to the optical axis. This orientation can also use any particle size sensor system sensor (for example systems in FIGS. 1, 2, 3, 4, 5, 6, 7, 8, 10, 11A, 11B, 19, and 27) with a generally horizontal optical axis orientation. In both cases, generally horizontal or vertical optical axis, the particle size distribution will change in the interaction volume as particles, which pass through the interaction volume, are not replaced by particles of the same size, from above. The motion of these particles can be caused by forces created by gravitational or centrifugal acceleration. And the function of the generally horizontal surface can be provided by a surface which prevents particles from moving into the interaction volume from locations beyond a certain distance from the interaction volume. Those locations are on the side of the interaction volume, from where the particles are moving towards the interaction volume.

The chamber in FIG. 28 is designed to block particles from settling into the interaction volume from above. This could also be accomplished by a generally horizontal plate which resides above the interaction volume, as described previously. This plate could be turned out of position while the chamber is filled to avoid trapping air bubbles. Then the plate could be turned into position above the interaction volume when large particle removal, by settling, is required. The plate should be shaped appropriately to follow the shape of the interaction volume, so large particles settle out of all portions of the interaction volume in approximately the same time period.

The homogeneous start method may be applied to the particle settling method, described above and exemplified in FIG. 28, using gravitational or centrifugal acceleration. The chamber should surround the interaction volume on the maximum number of sides, while still allowing for exchange of particle dispersion in and out of the chamber. The surrounding chamber wall will reduce convection currents and other dispersion flows close to the interaction volume, to remove the effects of these currents on the particle settling process.

The generally horizontal surface, in FIG. 28, can also be replaced by the air/liquid interface at the top of a sample cell. One requirement is that the thickness of particle dispersion above the interaction volume must be short to allow the particles to settle through and out of the interaction volume without being replaced by particles of the same size from above, in a reasonable time. In this case the detector is stationary. However, the particles of different sizes settling out of the interaction volume at various times provides the same information as that obtained by scanning a sample cell after settling particles are redistributed within the cell. For homogeneous samples, the analysis methods and equations, described previously for the homogeneous start, may be applied to the sequential stationary scatter detector measurements of dynamic or static scattering (scattered light or attenuation) measured in a configuration where particle settling is blocked from above the interaction volume, as exemplified in FIG. 28, for example. The only difference is that the data corresponding to various R values, in the scanning methods described previously, will be measured at different times by a stationary detector, which measures either dynamic scattered or static scattered light to calculate a particle size distribution at each time. The data set which is equivalent to the small R data in the scanning method will be the last data set measured in the set of sequential measurements of the stationary detector. The interaction volume in FIG. 28 can be the interaction volume of either a dynamic scattering system or static angular scattering system, using the methods described previously, to analyze the sequential data sets collected as the particles move out of the interaction volume, due to gravitational or centrifugal forces. In the centrifuge case, the scatter detector signals could be transmitted from the moving centrifuge to the stationary computer, using methods described previously for real time measurement of terminal velocity.

This inventor has described many dynamic scattering and angular scattering systems, which have very small interaction volumes. A solid/liquid (for example the generally horizontal plate) or gas/liquid interface (for example the air/dispersant interface at the top of a sample cell) is placed close to that interaction volume. The position of the interface is chosen to block moving particles, beyond a certain distance from the interaction volume, so that these particles cannot pass through the interaction volume. The particle motion can be created by forces including gravity and centrifugal force. For example, if the force is gravity parallel to the vertical, then a solid plate could be placed, in generally horizontal plane, generally above the interaction volume to block particles from above. Particles of different effective sizes will move together in groups as illustrated in FIG. 46. The effective size of the particle depends upon the physical particle size and particle density. However, the actual physical particle size is determined by the scattering measurement. The distance between the interface and the interaction volume determines the time when fastest moving particles will first pass through the interaction volume, causing the DIFF function to increase beyond the DIFF limit. The equations described previously for the homogeneous start case, can be applied to this case:

$Sjp = \text{SUM} m{:}np1{:}np2 (Fjm)$ $\text{DIFF}(p2,p1) = \text{SUM} j{:}1{:}j\max((Sjp1/(\text{SUM} j{:}1{:}j\max (Sjp1)) - Sjp2/(\text{SUM} j{:}1{:}j\max(Sjp2))^{\wedge}2)$ In this stationary detector case, m corresponds to the time of each data set instead of the position along the cell, which is scanned by a detector system.

This method can also be used when centrifugal force is used to move the particles through the interaction volume and the small R end of the sample cell defines a limit to the dispersion (acting like the generally horizontal surface in the settling case). In this case, particles of different sizes, will be depleted from the interaction volume at different times, just as in the settling case. One requirement is that the thickness of particle dispersion between the small radius end of the sample cell and the interaction volume must be short to allow the particles to move through and out of the interaction volume without being replaced by particles of the same size, in a reasonable time. The particles moving out of the interaction volume provides the same information as that obtained by scanning a sample cell after centrifugation. For a homogeneous sample, the methods described for the homogeneous start, may be applied to the sequential measurements of dynamic or static scattering (scattered light or attenuation) measured in a this configuration. The only difference is that the data corresponding to various R values, in the scanning methods described previously, will be measured at different times by the stationary detector system in the sequential case. The data set which is equivalent to the small R data in the scanning method will be the last data set measured in the set of sequential measurements of the stationary detector. The interaction volume can be the interaction volume of either a dynamic scattering system or static angular scattering system, using the analysis methods described previously, to analyze the sequential data sets collected as the particles settle out of the interaction volume.

In general, the analysis methods described previously for the layer start (FIG. 45) and homogeneous start (FIG. 46) can be applied to the case where the stationary scatter detection system records scatter data sets at one location in the sample cell sequentially in time, during the settling or centrifugation process. As described above for the homogeneous case, as the particles pass, with centrifugal or gravitational force, through the interaction volume, scatter measurements at various times (sequential case), during the settling or centrifugation process, will provide the same data sets as would be collected by scanning the cell (scanning case) with a moving optical system, after the centrifugal or settling process is completed. For both layer start and homogeneous start, the data set, measured at the largest R value in the scanning case, will correspond to the first data set (shortest time delay from the start) of the sequential case; and the data set, measured at the smallest R value in the scanning case, will correspond to the last data set of the sequential case (longest time delay from the start). The same equations and data analysis can be used in both the scanning and sequential cases, as described previously. In both the homogeneous and layer start cases, the absolute volume distribution (particle volume concentration vs. particle size) is calculated for each data set at each R position (scanning case) or at each time (sequential case). A data set is the group of scatter measurements (inducting power spectrum, autocorrelation function, or angular scattering distribution). In the layer start, the values of the absolute volume distributions (each absolute volume distribution is calculated from a separate data set) are added together at each value of particle size to produce the final volume distribution. In the homogenous start case, the absolute volume distributions are calculated from the differences between successive data sets or between chosen data sets. These volume distributions are added together to produce the final volume distribution. The sequential chosen data sets may be limited to data sets with sufficient differences (DIFF for example), which indicate that the particle size distribution has changed in the interaction volume, between adjacent sequential chosen data sets, as described previously for the scanning case. These analysis methods and data set choosing methods are described in the previously filed application. The difference between the scatter measurements at times TIME1 and TIME2 represents the scatter signals from the particles which left the interaction volume, between times TIME1 and TIME2, and were not replaced by the same size particles from smaller R values (centrifugation) or higher levels in the dispersion (vertical settling). For the homogeneous start case, these scatter measurement differences are analyzed using the same procedure as described previously for the differences between scatter measurements at two different R positions when a sample cell is scanned after centrifugation, using the equations shown previously. For example, the second volume distribution, Vi2, would be calculated as described previously for the homogeneous case:

Continue measuring to larger TIMEm values and measuring Fim, calculating the value L1 at each TIMEm until L1 becomes larger than some limit Lt at TIMEn2.

$$Qj=((((Fjm/(SUMj:1:jmax(Fjm))-((Fjn1/(SUMj:1: jmax(Fjn1))^2)$$

$$L1=SUMj:1:jmax(Qj);$$

Invert the vector of flux or signal differences, Fj=Fjn2−Fjn1, to obtain the second volume distribution Vi2.

In this stationary detector case, m corresponds to time instead of position R along the cell. The parameter R is changed to TIME for the stationary detector case.

The inner surface of the sample cell at minimum R value prevents the replacement of particles in the interaction volume, in the centrifuge case. The air/liquid interface at the top of the sample cell or the generally horizontal surface (as exemplified in FIG. 28, for example) prevents the replacement of particles in the interaction volume, in the settling case. The advantage of this method is that each data set (or differential data set for the homogeneous start case) produces a volume distribution from particles in a narrow size range, without crosstalk between size ranges. In this way each size range is measured separately reducing the need to remove the cross scatter sensitivity between size ranges and reducing the deconvolution errors due to broadening of the scattering functions.

The distance of the interaction volume from the end of the sample cell, the air/liquid interface at the top of the sample cell, or the generally horizontal surface is determined by the terminal velocities of the particles. Large or dense particles may require a longer distance to insure that no particle size is depleted from the interaction volume before the detector is activated. This method can be used in settling or centrifugal modes. In the case of settling, the scatter detection system views a stationary interaction volume in a stationary sample cell containing the particle dispersion. For smaller particles, the higher acceleration of a centrifuge may be required to provide higher particle velocities, shorter measurement time, and less error due to particle diffusion. In the centrifuge case, the scatter detection system could view a stationary point in space through which the sample cell and particle dispersion pass during each rotation of the centrifuge. The centrifuge rotor is slotted to allow optical access to the windows of the centrifuge cell. FIG. 50 shows an example of a centrifuge system, which could be used for this purpose. While the dispersion, in the centrifuge cell, is passing across the interaction volume of the scatter measuring system in each rotation, the scatter signals are collected. In the case of angular scatter, all scatter detectors or detector array elements are integrated during this pas s age. The integrators can be started and stopped by a threshold detector which monitors the scatter signals or the unscattered light from the light source beam (the region around, and including, the zero scattering angle in the plane of the detector array for example). These integrated values are sampled by a multiplexer and an analog to digital converter. Each sequential data set can be the sum of integrations made over many rotations of the centrifuge.

Many optical systems, which measure scattered light, can perform the following measurements. These systems include the dynamic scattering and angular scattering systems described by this inventor. These measurements include the following:

(1) to scan a sample cell after removal from the centrifuge, measuring the scattered signals at various locations in the sample cell (2) to scan a sample cell in a centrifuge after the centrifuge has stopped by providing optical access through the sample cell in the centrifuge, measuring the scattered signals at various locations in the sample cell (3) to scan the sample cell, in the centrifuge, during rotation of the centrifuge by providing optical access through the sample cell in the centrifuge, measuring the scattered signals at various locations in the sample cell and/or various times during the centrifugation (4) to view a single point in the sample cell during rotation of the centrifuge by providing optical access through the sample cell in the centrifuge, measuring the scattered signals at various times during the centrifugation. (sequential case)

(5) any of cases (1), (2), (3), or (4) where the particle motion is provided by gravitational acceleration FIG. 50 is an example of a system which can accomplish methods (2), (3), or (4).

In each of these apparatus cases, the scatter data can be analyzed using the methods described previously for the appropriate starting case, homogeneous or layer start. For the scanning cases, the data is collected at various values of R with an optical system, which scans the sample cell along the direction of particle motion, by moving the cell or the optical system. For the sequential case, the data is collected at various times with an optical system, which is stationary relative to the particle motion direction during the settling or centrifugation process. The data analysis for the sequential case is the same as the analysis for scanning case, by replacing scatter data measured at various distances, R, with scatter data measured at different times. The methods for choosing which data sets to analyze (which locations in the scanning case and which times in the sequential case) use the same criteria for selection as described for the appropriate case, homogeneous start or layer start. These analysis methods and data set choosing methods are described previously.

Also in this document, any use of the term "scattering angle" will refer to a range of scattering angles about some mean scattering angle. The angular range is chosen to optimize the performance of the measurement in each case. For example the use of the terms "low scattering angle" or "high scattering angle" refer to two different ranges of scattering angles, because each detector measures scattered light over a certain range of scattering angles FIG. 75 describes a system for control of the particle concentration by injection of measured amounts of particle dispersion into the flow system, which contains the sample cell, to increase the concentration to appropriate levels for measurement. This adjustment could also be accomplished by starting at high concentration and adding controlled amounts of clear dispersant to decrease the concentration of particles, in the flow loop and sample cell, to the level appropriate for scatter measurement. These concentration adjustments are needed in all types of scattering systems, to avoid multiple scattering in ensemble scattering systems and to avoid coincidence counting in particle counters. Both of these concentration control methods are claimed for all applications, including those which are not described in this application.

In this application, any heterodyne systems can be converted to a homodyne system by removal of the local oscillator source light on the scatter detector. Removal of local oscillator associated optics may reduce homodyne system cost. Also, all lenses are represented by simple single element lenses to simplify the drawings. Actual lenses may include multi-element lenses, gradient index lenses, and diffractive optics, which are optimized for the design conjugates and fields of each optical system.

Any system, described in a figure which shows a sample cell, can be used without the sample cell and/or with a window (or windows) in place of the sample cell window (or windows). For example, some applications require on-line measurements in a process stream, where the interaction volume of the optical system is placed into the particle dispersion in the process stream. The optical system illuminates the process stream particle dispersion and receives scattered light from the particles through at least one window. Two windows would be used for optical systems where the light source and detector(s) are on opposite sides of the interaction volume.

In this application, the algorithms, which are used to determine the particle size distribution from either the dynamic scattering data or static angular scattering data, can also include algorithms presently available for this purpose.

Some equations, which are written in this application and which exist in the literature, may contain errors as written in this application. While the inventor has attempted to avoid such errors, some may still exist. In any of these cases, the correct equation is assumed. These equation errors do not detract from the functionality of the method or apparatus which use them, because that same functionality is maintained when using the correct equation.

The invention may be modified in ways which will be apparent to the reader skilled in the art. Such modifications should be considered within the spirit and scope of the following claims.

Figure 77:
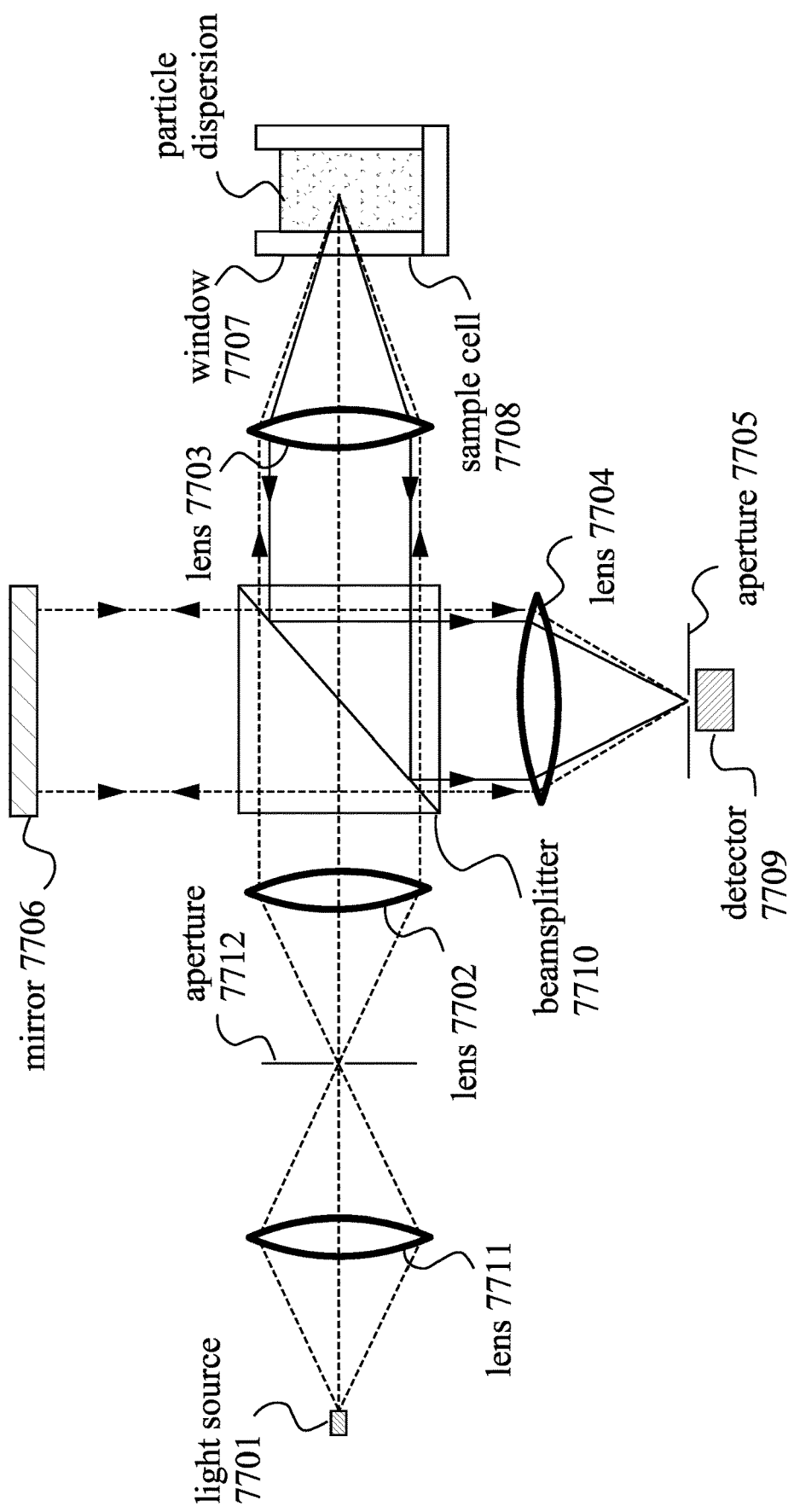
FIG. 77 provides a variation of FIG. 1 showing illumination and scattered rays.

In some figures in this disclosure, the light rays for scattered light and source light are not shown separately in the figure. Source light refers to light, from the light source, which has generally not been scattered from particles. FIG. 77 shows a version, of FIG. 1, where the source light rays and scattered light rays are shown separately. The rays from the light source are indicated by dashed lines in FIG. 77. Light from light source 7701 is focused, by lens 7711, through aperture 7712 to remove artifacts from the source intensity profile or to limit the extent of the source illumination. When the function of aperture 7712 is not required, lens 7711 and aperture 7712 can be eliminated and light source 7701 can be placed at the position of the opening of aperture 7712 in FIG. 77. Lens 7702 creates a generally collimated beam of source light which is reflected by beamsplitter 7710 and mirror 7706 to produce the local oscillator light for heterodyne detection on detector 7709. This reflected source light is focused by lens 7704 to form a focused spot generally in the opening of aperture 7705.

The source light is reflected by beamsplitter 7710 to mirror 7706, which reflects the source light back through beamsplitter 7710 to be focused through aperture 7705 by lens 7704. The light, which is transmitted by beamsplitter 7710, is focused by lens 7703 into the particle dispersion through window 7707. The solid light rays represent rays scattered by at least one particle in the particle dispersion. This scattered light is generally collimated by lens 7703, before reflection by the beamsplitter 7710 to lens 7704 which focuses the scattered light to a spot generally in the opening of aperture 7705. The source light and scattered light are combined generally coherently to produce a heterodyne signal on detector 7709. The position of the source light spot can be aligned to the opening of aperture 7705 by tilting mirror 7706 about at least one axis. Scattered light, which does not overlap with the source light intensity profile on the detector, will not produce high interferometric visibility in the heterodyne signal. In general, aperture 7705 removes scattered light which is not strongly contributing to the heterodyne signal and improves alignment of the scattered light and source light on the detector. Aperture 7705 also defines a small dispersion scatter volume or interaction volume, which can reduce multiple scattering as described in FIG. 78. And aperture 7705 can also provide a mechanism for aligning the source and scatter light spots by individually maximizing the passage of light from each spot through the aperture. One method of alignment is to align the aperture 7705 to maximize the passage of only the scattered light (by blocking the reflection from mirror 7706), which places aperture 7705 in a position which is generally optically conjugate to the focused spot of the source in the particle dispersion. Then mirror 7706 is tilted, about at least one axis to maximize the passage of only the source light by blocking the scattered light from reaching the detector. In some cases, the mirror tilt could also be fine adjusted to maximize the heterodyne signal. When the coherently mixed region of the source and scattered light is larger than desired, the aperture can also limit the portion of the light distribution which is received by the detector. The desired size of the light distribution will be discussed below. When the function of aperture 7705 is not required, aperture 7705 may be eliminated. The distance between mirror 7706 and beamsplitter 7710 can be adjusted to match optical path lengths for the source and scattered light at the detector for low coherence length light sources, or to focus the source light through aperture 7705, when the light beam is poorly collimated in the beamsplitter.

Figure 78:
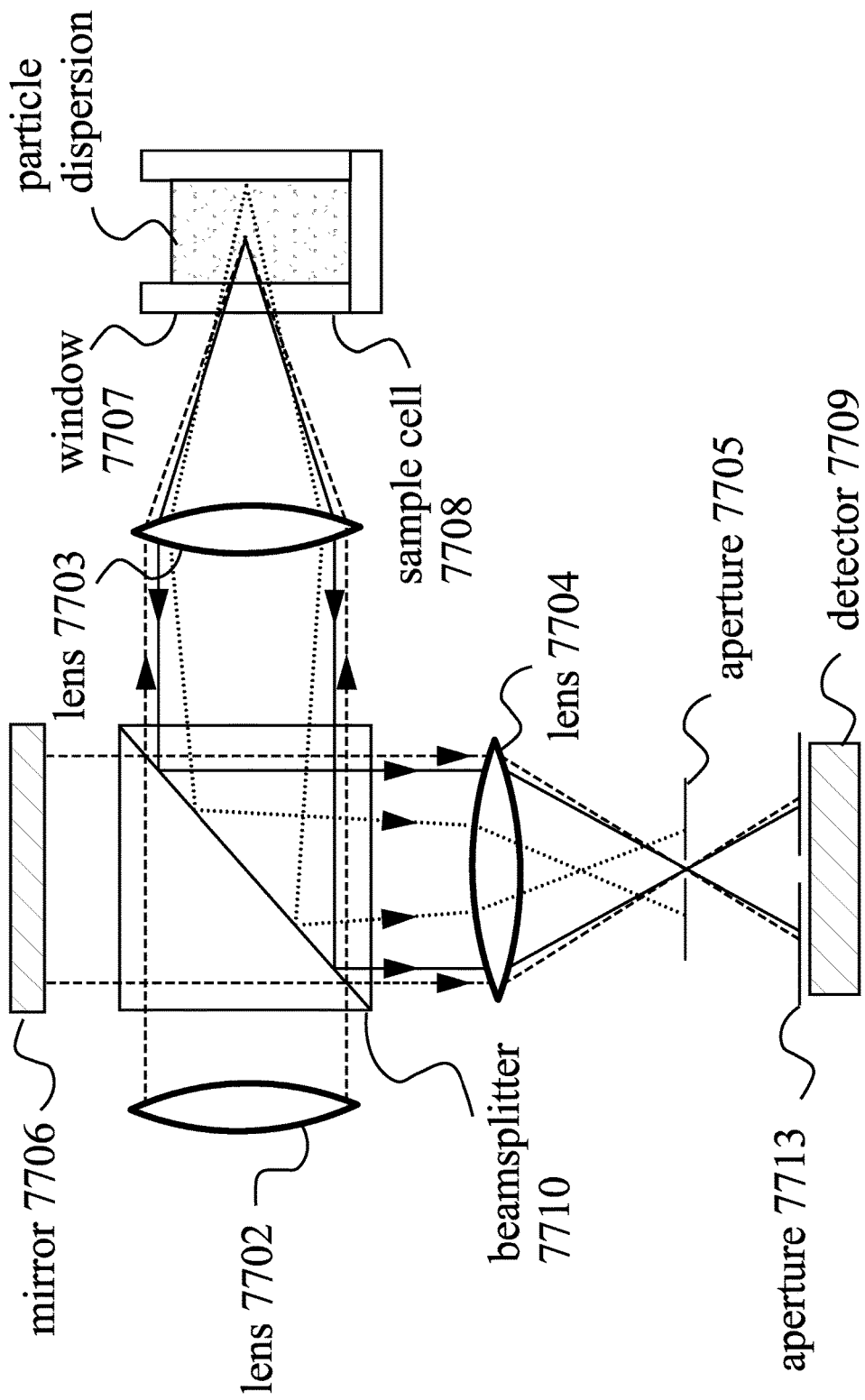
FIG. 78 provides a variation of FIG. 77 with more detail of scattered rays.

FIG. 78 shows a portion of FIG. 77, with more detail of the scattered rays. The solid lines show scattered rays from a particle in the focused spot of source light in the dispersion. As described previously, this scattered light is generally collimated by lens 7703, reflected by beamsplitter 7710, and focused by lens 7704 through the opening of aperture 7705 for coherent optical mixing on detector 7709. FIG. 78 also shows light scattered by a particle which is not in the source focused spot in the particle dispersion, as represented by the dotted lines. The scattered light of this particle is focused between lens 7704 and aperture 7705. The heterodyne signal is lower for this particle because the scattered light overfills the opening of aperture 7705, such that the amount of scattered light passed by aperture 7705 and coherently mixed with the source light on detector 7709 is reduced. Therefore, the size and position of the opening of aperture 7705 controls the region in the dispersion where particles can contribute significantly to the heterodyne signal. This region control is similar to the function of aperture 7705 in FIG. 77. The size of the opening of aperture 7705 determines the size of the region in the particle dispersion which provides significant contribution to the heterodyne signal. Particles which are not close to the image, in the dispersion, of the opening of aperture 7705 will not contribute significant scattered light to detector 7709. This image is conjugate to the opening of aperture 7705 through the optical properties of lens 7703, lens 7704, and beamsplitter 7710. Therefore, to maximize heterodyne signal, the source spot, which is focused by lens 7703, should be aligned generally into the image of the opening of aperture 7705 in the particle dispersion. This first alignment step can be accomplished by moving at least one of the group comprising the light source, lens 7702, lens 7704, and aperture 7705 in at least one direction until a scatter light signal from particles is maximized on detector 7709. After this first alignment step, mirror 7706 is tilted about at least one axis to align the source light spot to pass through the opening of aperture 7705. This optical design generally only detects light scattered by particles in a limited interaction volume of the particle dispersion. The distance of this limited interaction volume from window 7707 determines the path for scattered rays from particles, which travel back through the particle dispersion to detector 7709. If the light source focused spot and the image of the opening of aperture 7705 are aligned at, or close to, the interface between the particle dispersion and window 7707, the paths for detected scattered rays through the particle dispersion are minimized. This path reduction reduces multiple scattering, where a scattered ray is scattered again by another particle before reaching the detector. This multiple scattering causes errors in the spectral broadening of the scattered light due to Brownian motion and causes errors in the particle information derived from that spectral broadening. Therefore, alignment of the limited interaction volume close to this interface can improve particle information accuracy, especially at high particle concentration where multiple scattering is a particular problem. When the source focused spot is at, or close to, the interface between the particle dispersion and window 7707, the partial Fresnel reflection of light from that interface through aperture 7705 will become significant, when the interface is generally perpendicular to the optical axis. In this case, mirror 7706 may be eliminated to allow the partial reflection from that interface to provide the reflected source light for the heterodyne detection. The source light, which is partially transmitted by the interface, illuminates the particles to produce scattered light. The mixture of the scattered light and the source light, partially reflected from the interface, provides the heterodyne signal on detector 7709. The window surface at that interface can also be coated to increase reflectivity and increase the heterodyne signal amplitude. When the source focused spot is at, or close to, that interface, the partial Fresnel reflection from that interface will be focused generally into the opening of aperture 7705 to be passed with the scattered light to detector 7709. This partial reflection at the interface between the window and the particle dispersion can be utilized for optical mixing in any of the optical systems, described in this application, which focus the source light into the sample cell. When the focused spot of the source light is at, or close to, the interface between the particle dispersion and the sample cell window, a mirror, with the function similar to the function of mirror 7706, can be removed to allow mixing of the scattered light with the source light reflected from the interface between the dispersion and the sample cell window. Examples of these systems are shown in FIGS. 1, 2, 3, 5, 6, 7, 70, 72, 73, 77 and 78. This concept can also be utilized in systems with partially reflecting mirrors, which provide the source light for heterodyne detection, when the focused spot of the source light is at, or close to, the interface between the particle dispersion and the sample cell window. In FIGS. 8 and 30, the source focus is not at the interface. In FIGS. 8 and 30 the partially reflecting mirror would be removed to allow mixing of scattered light with source light reflected from the interface between the dispersion and the sample cell window, when the focused spot of the source light is at, or close to, the interface. And in FIGS. 4, 29 and 69, the convex partial reflector would be removed to allow this mixing. The convex particle reflector is lens 405, the lens between lens 2903 and the sample cell, and 6905 in FIGS. 4, 29 and 69 respectively. In all of these cases, the size of the interaction volume in the dispersion is controlled by the aperture close to the detector and multiple scattering is reduced by placing the interaction volume close to the interface between the particle dispersion and the window surface.

FIG. 78 also shows a second aperture 7713, which selects a portion of the overlapping intensity distributions from the scattered light and source light. A larger distance between aperture 7705 and aperture 7713 (or detector 7709) may reduce required light spot alignment precision by providing a large area of overlap between the optical wavefronts of the source light and scattered light on aperture 7713 or detector 7709. Aperture 7713 chooses a portion of the optical interference pattern to isolate generally a portion of a single fringe or speckle in the interference pattern to improve interferometric visibility and increase heterodyne signal amplitude. Aperture 7713 is not required when detector 7709 is properly sized and aligned to accept generally the same portion of the optical interference pattern as aperture 7713.

Figure 79:
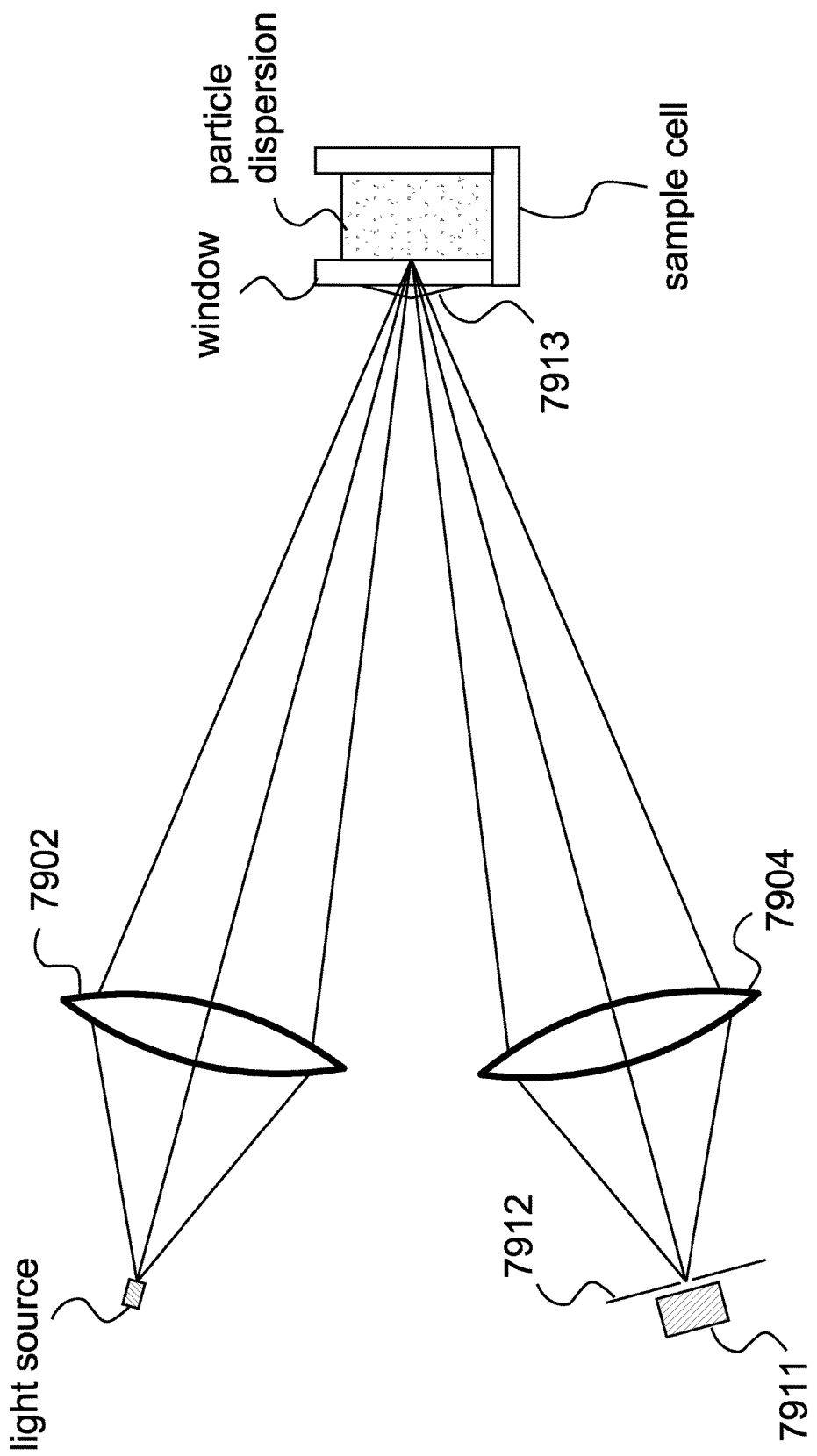
FIG. 79 provides a schematic diagram of an optical system without a beamsplitter.

These concepts of source light and scatter light alignment, use of an aperture to define a small interaction volume, and placement of the interaction volume close to the window/dispersion interface can be applied to any optical system utilizing a reflector (or partial reflector) and a beamsplitter, where the source light is focused into the particle dispersion. Some examples of these optical systems are described in FIGS. 1, 2, 3, 4, 5, 6, 7, 8, 22, 29, 30, 69, 70, 71, 72, 73, and 74. These concepts can also be applied to systems without a beamsplitter, as described for a variation of FIG. 2 and as described in FIG. 79.

FIG. 69 and FIG. 70 show other variations of FIG. 4 and FIG. 1, respectively. Lens 403 (or 103) is eliminated and lens 6902 (or lens 7002) directly focuses the laser light into the particle dispersion. Lens 6904 (or lens 7004) images the source focus spot in the dispersion to aperture 6912 (or 7012), which passes light to detector 6911 (or detector 7011). The local oscillator is provided by source light reflected by either the partially reflecting convex surface, 6905 in FIG. 69, or by the optional folding mirror 7021 and mirror 7022, which is placed at the focus of the source beam in FIG. 70. An optional optical isolator, 7030, may be used to reduce reflected light, which could enter the laser and cause laser noise. When the focus of the source light is positioned generally at the interface of the particle dispersion and the window, the light, which is partially reflected by that interface, will pass through aperture 6912 (or 7012) along with the scattered light from particles in the interaction volume. Then both the scattered light and source light, reflected by the interface, are focused through aperture 6912 (or 7012) to be optically mixed on the detector for heterodyne detection, eliminating partial reflector 6905 (or mirrors 7021 and 7022). The interface partially reflects the incident source light back though aperture 6912 (or 7012). The source light, transmitted by the interface, illuminates the particles to create scattered light.

The accuracy of dynamic light scattering systems is limited by the total time required to collect the data needed to accurately determine the stochastic properties, such as the power spectrum or autocorrelation function, of the stochastic process of particle Brownian motion. This data collection time can be reduced by the apparatus and method of FIGS. 71, 72, 73, 74, and 76. FIG. 71 shows a particle dispersion which is illuminated by a broad beam of source light from lens 7102, after passing through beamsplitter 7106. FIG. 71 also shows a detector array (7105), which is in the image plane of a plane in the particle dispersion, via lens 7104 and beamsplitter 7106. The dotted lines, in FIG. 71, show the imaging of a single point in the particle dispersion to a region on detector array 7105. These dotted lines represent some of the light ray paths for light scattered from a point in the particle dispersion to the detector. Detector array 7105 is also illuminated by unscattered source light via the beamsplitter (7106), mirror (7107) and lens (7103). The coherent mixing of unscattered light, from the light source of FIG. 71, and scattered light from the particles creates a heterodyne signal, on each detector element, indicative of the Brownian motion and particle size of the particles viewed by that detector element. The combination of lens 7103 and mirror 7107 are designed to create a source light beam which covers the detector array 7105, after passing through lens 7104. This combination of lens 7103 and mirror 7107 could also be replaced by a convex or concave mirror, depending upon the positions of the optics and the focal length of lens 7104. Lens 7103 could also have either negative or positive optical power depending upon the positions of the optics and the focal length of lens 7104. FIG. 71 shows a case where the combination of lens 7103 and mirror 7107 creates a focused spot generally in the focal plane of lens 7104, producing a generally collimated beam of source light which covers the detector array 7105. The detector array can also include a group of arbitrarily positioned detectors, without an array structure. This optical system creates a plurality of heterodyne detectors, wherein each detector views scattered light from a generally different portion of the particle dispersion, because each detector is generally optically conjugate to a generally different region in the particle dispersion through lens 7104. Hence the heterodyne signal on each detector element is generally not correlated with heterodyne signals from other detector elements. The information contained in N concurrently recorded data sets, from N generally different groups of particles, will provide similar information to N sequentially recorded data sets from one group of particles. Therefore, the average of the power spectra of the detector element signals from this detector array will have better reproducibility than a power spectrum from a digitized data record from a single detector, recorded over the same elapsed time. Likewise, the average of the autocorrelation functions of the detector element signals from this detector array will have better reproducibility than an autocorrelation function from a single detector. The autocorrelation function or power spectrum can be inverted to produce a particle size distribution. An individual power spectrum is calculated from each digitized signal vs. time of each detector element; then these individual power spectra are summed (or averaged) at each frequency, in the spectra, to create an average power spectrum for the entire set of detectors. This average power spectrum will have better reproducibility than a single detector spectrum. The standard deviation of the averaged power spectrum values will decrease generally as one divided by the square root of the number of power spectra in the average. For example, the averaged power spectrum from averaging of spectra from 9 detector elements would reduce the standard deviation of power spectrum values by a factor of 3 relative to a single detector. The same benefit is obtained for the autocorrelation function of the detector signal. Likewise, an individual autocorrelation function is calculated from each digitized signal vs. time of each detector element; then these individual autocorrelation functions are summed (or averaged) at each delay, in the autocorrelation function, to create an average autocorrelation function for the entire set of detectors. This summation (or average), Fs, for N detectors, is described by the following equation:

$$Fs(Xj) = SUM i:1:N(Fi(Xj))$$

Where SUM i:a:b(Fi) is the summation of Fi over index i for i=a to i=b. Fs is the final summed function and Fi are the individual functions being summed. Fi(Xj) is the function measured from the ith detector at the jth abscissa value for the function Fi. For the power spectrum, Fi(Xj) is the power spectrum value from the ith detector at the jth frequency. For the autocorrelation function, Fi(Xj) is the autocorrelation function value from the ith detector at the jth delay or tau value. In either case, the total time of the measurement is reduced by a factor of 1/N. Therefore, the equivalent function value variance of an 800 second measurement with a single detector is obtained by a 16 detector system with only a 50 second measurement time. For example, a 16 detector system could comprise a 4×4 detector array with two 1 Mhz analog to digital convertors, each with an 8 channel multiplexer using commercially available components.

FIG. 72 shows a similar concept where lens 7203 and a 2-dimensional diffracting/refracting structure 7208 create a set of illumination spots in the particle dispersion. Only one of the illumination focal spots is shown by the solid lines focused by lens 7203 into the sample cell. The 2-dimensional diffracting/refracting structure comprises an array of holes, an optical phase array, lens array, prism array, or a binary optic. This structure can create a group beamlets of different angles, which are focused to different points in the particle dispersion by lens 7203. Likewise, lens 7204 and structure 7208 also create a matching set of local oscillator spots (only one of the local oscillator focal spots is shown by the solid lines focused by lens 7204 onto detector array 7205) through the beamsplitter 7206 and mirror 7207, one light spot for each element in the 2-dimensional detector array (7205). Lenses 7203 and 7204 image the scattered light from the illumination spots onto the array of detectors, such that scattered light from each spot is generally individually detected by one of the detectors (one to one correspondence between illumination spots and detectors). Therefore, in FIG. 72 each illumination spot/detector element pair provides illumination and scatter beams similar to the beams in the single system of FIG. 77. However in FIG. 72 the function of aperture 7705 is provided by the size of each detector element (or an aperture on each detector element) in the 7205 array of detector elements. The system in FIG. 72 could be more efficient, than the system in FIG. 71, because each detector receives source light and scattered light from an individual focused laser spot of potentially higher intensity. This technique will also work for any set of detectors such as a linear 1-Dimensional array, using a 1-dimensional diffracting/refracting structure (such as a diffraction grating of parallel lines) for 7208. Custom binary optics, lens arrays, or other custom diffracting/refracting optics can produce the array of laser spots in the dispersion, directly, eliminating lens 7203 and requiring lens 7204 to directly image the illumination spots onto the detectors. Then the position (or curvature) of mirror 7207 is designed to focus the source light spots (reflected by beamsplitter 7206) onto array 7205, through lens 7204. Optical structure 7208 could also be replaced by an array of lenses which produce an array of illumination spots in the particle dispersion and on detector array 7205 through beamsplitter 7206, mirror 7207, and lens 7204 thereby eliminating lens 7203. With the array of lenses, the distance between the lens array 7208 and the interaction volumes in the sample cell of FIG. 72 would be adjusted to provide generally equal optical pathlengths for the scattered and unscattered source light between the lens array optic 7208 and detector array 7205. These optical pathlengths could also be generally matched by moving mirror 7207. Mirror 7207 could also be positioned in the beams, which are reflected by beamsplitter 7206, in a plane which is conjugate to the array of illumination spots. Then each reflected illumination spot will be focused onto a detector through lens 7204. Then each lens array element, corresponding illumination spot, and corresponding detector would have an optical path similar to the path shown in FIG. 70. In either case, with or without lens 7203, mirror 7207 can be eliminated by positioning the interaction volumes at, or close to, the interface between the particle dispersion and the window. Then the partially reflected light, of each illumination spot, from that interface will provide the local oscillator light for the corresponding detector element, as described previously. The size of each detector element should be designed to only include a partial speckle (or a few speckles) of the spatial optical interference pattern to maximize interferometric visibility and heterodyne signal amplitude. An array of apertures could also be utilized, wherein each aperture is configured, as shown by aperture 7705 in FIG. 78, with a distance between each aperture and the corresponding detector element to reduce alignment sensitivity of the source light spot and scatter light spot at each aperture opening. Then the aperture openings, detector elements, and light spots must have sufficient separation to avoid significant mixture of light from adjacent light spots on adjacent detector elements. In FIGS. 71 and 72 the pinhole (7111 and 7211) and the first lens (7101 and 7201), remove spatial defects in the light source, if required. If the source is sufficiently free of spatial defects, the pinhole and first lens can be eliminated by replacing the pinhole with the light source. This concept, of making multiple concurrent measurements from different portions of the particle dispersion and averaging the resulting power spectra, can also be applied to measurements from multiple separate optical systems, at additional system cost. This idea of using generally concurrent power spectral measurements from multiple scatter signals, each originating from a generally different portion of the particle dispersion, and averaging the resulting power spectra is also claimed for cases where multiple optical systems are used to measure the multiple scattering signals from different portions of the particle dispersion. The concepts described in FIG. 71 and FIG. 72 are the most economical designs for implementing this concept, because all of the scattered light and illumination light for a plurality of detectors pass though one beamsplitter. And the use of array optic and array detector structures can provide alignment of all detectors with only one alignment procedure. The signal from each detector element could be digitized by a separate analog to digital convertor. In order to lower cost, the signal from each detector element can be addressed by a multiplexer, which multiplexes signals to an analog to digital convertor. For example, an 8 channel multiplexed 1 megahertz analog to digital convertor could continually cycle through signals from 8 detector elements in each multiplexing cycle, with a sampling rate of 125 kilohertz per detector element. If the multiplexer is slower, each detector element could be sampled at multiple sample times for each of the 8 multiplexing positions in a multiplexing cycle. In this way, each detector element digitized sampled signal would consist of concatenated sampled signal segments, which are not contiguous segments of the signal. The power spectrum could be calculated from these concatenated segments by using known data windowing methods.

The diffracting/refracting structure, optic 7208, can be added to many designs, including those in FIG. 3 and FIG. 22, to measure scattered light from multiple portions of the particle dispersion, concurrently. In FIG. 3, a 7208 optic could be placed in this sequence: light source, lens, pinhole, lens, 7208 optic, beamsplitter. In FIG. 22, a 7208 optic could be placed in this sequence: light source, lens, 7208 optic, beamsplitter 2201. In both cases, the 7208 optic would produce multiple illumination spots in the particle dispersion and a matching set of local oscillator spots on the detector through beamsplitters. In both cases, the scatter detector and pinhole would be replaced by an array of detectors, whose positions match the image of the multiple illumination spots and local oscillator spots on the detector array.

Multiple systems, each system as shown in FIG. 69, could also be projected through a single beamsplitter by replacing lens 6902 and lens 6904 each with an array of lenses, lens array 6902 and lens array 6904. Also partial reflector 6905 would be replaced by an array of partial reflectors, reflector array 6905; and detector 6911 and aperture 6912 would be replaced by an array of detectors, detector array 6911. Lens array 6902 produces an array of light spots in the particle dispersion, and lens array 6904 images each one of those spots onto an individual detector in detector array 6911. Therefore, each detector element in array 6911 receives scattered light from a different illumination spot in the particle dispersion and the beam which produces that spot is also reflected by a reflector in array 6905 to provide the source light for optical mixing on that detector element. In this way, a plurality of detection systems, each as shown in FIG. 69, utilize the same beamsplitter. In this case, a lens array of 6902 lenses would produce an array of focused beams which pass through the beamsplitter and are focused into the sample cell. If these focused spots are at, or close to, the interface between the particle dispersion and the sample cell window, the partial reflection of each focused light beam by that interface could provide the source light for optical mixing, as described previously; and partially reflecting array 6905 could be eliminated. This dispersion/window interface reflecting configuration reduces multiple scattering to provide measurement at high particle concentration, as described previously in FIG. 78. Each reflected beam and scattered light from each corresponding region of the dispersion would be individually intercepted by each lens in an array of 6904 lenses. Each reflected beam and corresponding scattered light are individually focused and mixed onto a separate detector element of an array of detectors which replace 6911 and 6912. If the illumination focused spots are far from the interface, such that the interface reflected light on the detectors is of low intensity, an array of 6905 reflectors could be utilized as convex partial reflectors to provide the reflected light for mixing, where each of the 6905 reflectors would reflect a separate focused beam to a separate detector element. And each detector element would receive scattered light from generally a different region in the particle dispersion, so that each detector signal has low correlation with any other detector signal for the averaging method described previously. In the case of an array of 6905 reflectors or a single reflector 6905 in FIG. 69, the convex surface can be coated to increase the reflectivity and local oscillator intensity. The other generally flat side of 6905 can be anti-reflection coated to reduce the local oscillator contribution from that surface.

FIG. 73 shows a combination of the concepts in FIG. 3 and FIG. 72. Scattered light is detected individually from each of a plurality of regions in the particle dispersion. The scattered light from each region produces a current, or signal, in a separate detector, in one-to-one correspondence. Each detector signal can be digitized to produce a separate power spectrum or autocorrelation function of each detector current as described previously. These functions are then averaged over the group of detectors to produce a final averaged function of higher accuracy and repeatability. The averaging process comprises averaging the values at each point (frequency in the power spectrum or delay time in the autocorrelation function) in the function, over all of the detector signals. This process produces an averaged function of higher accuracy because the scattered light from each region in the particle dispersion is generally uncorrelated with scattered light from other regions when those regions do not have significant overlap. A light source 7319 is focused through a pinhole 7311 by lens 7301. This pinhole 7311 removes long tails and artifacts in the intensity distribution of the light source. As described previously, pinhole 7311 and lens 7301 may not be required. 7311 and 7301 can be removed and 7319 can be placed at the opening of 7311. Lens 7302 produces a light beam which is generally collimated. This beam passes through a diffractive/refractive optic, 7308, which produces multiple illumination beams 7323 from the light beam exiting lens 7302. The optic 7308 can be constructed from optical structures, including diffractive arrays, refractive arrays (including groups of prisms), and binary optics, which serve a similar function as 7208 in FIG. 72. These multiple beams, which each have a different angular direction, are focused through optical window 7320 into the particle dispersion 7321 by lens 7303, after passing through optional aperture 7315. Each of these beams creates a separate focused illumination spot in the particle dispersion. Only one of these focused beams is shown in FIG. 73. Scattered light from each focused spot passes back through lens 7303, which produces a scattered beam which is generally collimated for each illumination spot. These scattered beams 7322 pass through optional aperture 7314 and are partially reflected by beamsplitter 7305 to detector array 7316, through lens 7304, which produces a focused spot of scattered light on the detector array for each of the 7322 beams. Apertures 7314 and 7315 act as light baffles to control stray light, if required. Aperture 7314 also defines the scattering angle range for detection. Beamsplitter 7305 also partially reflects the illumination beams 7323 to partially reflecting mirror beamsplitter 7324 and mirror 7325, which directs the illumination beams to detector array 7316 through beamsplitter 7305 and lens 7304, which produces a focused spot of source light on the detector array for each of the 7323 illumination beams. This partially reflected source light provides the source light (local oscillator) for heterodyne detection on each detector element of the array. The detector array 7316 is aligned with the focused spots from lens 7304, such that each focused spot of scattered light falls on a separate detector. The tilt of mirror 7325 is adjusted, such that each focused spot of illumination light also falls on a separate detector. Each detector receives an individual illumination light spot and scattered light spot, which interfere optically to create a heterodyne signal on that detector. Each detector size must be limited to only a portion of one, or at most a few, interference speckles, or coherence areas, to maximize the interferometric visibility and heterodyne signal. If detectors are large, each detector should have an aperture to limit the effective size of the detector. This concept holds for any number of detectors, including one detector, as shown in FIG. 3 without optic 7308. The partially reflecting mirror beamsplitter 7324 passes illumination light onto detector 7317, which, as described for detector 502, measures noise in the light source to provide a source light signal for the light source noise correction techniques described in this application, if required. Beams 7322 and 7323 can be separated so that source light (local oscillator) does not pass back though lens 7302 to the light source, preventing light source noise through coherent feedback coupling to the source.

Beamsplitter 7305 could also be split into two beamsplitters: one beamsplitter for beam 7323 and the other beamsplitter for beam 7322. Lens 7303 could also be split into two lenses, one lens for beam 7323 and the other lens for beam 7322. Then the angle between beams 7323 and 7322 could be increased so that beams could pass generally through the centers of each lens and still intersect in the particle dispersion. This configuration could produce lower optical aberrations than the single lens 7303 by limiting the number of off axis rays. This concept, shown in FIG. 73, can be applied for any number of detector arrays with any number of individual detectors, including the case of one illumination spot and one single detector, without optic 7308.

FIG. 74 shows a combination of the concepts in FIG. 22 and FIG. 72. Scattered light is detected individually from each of a plurality of regions in the particle dispersion. FIG. 74 shows a probe version of this concept, where the end, of the probe with the concave optic, is immersed into the particle dispersion. The scattered light, from each region, produces a current or signal in a separate detector, in one-to-one correspondence to each region. Each detector signal can be digitized to produce a separate power spectrum or autocorrelation function of each detector signal. These functions are then averaged over the group of detectors to produce a final averaged function of higher accuracy and repeatability. The averaging process comprises averaging the values at each point (frequency in the power spectrum or delay time in the autocorrelation function) in the function, over all of the detector signals, as described previously. This process produces an averaged function of higher accuracy because the scattered light from each region in the particle dispersion is generally weakly correlated with scattered light from other regions when those regions do not have significant overlap. The detector element spacing is chosen to separate adjacent regions. A light source 7413 is focused into the particle dispersion, through the diffractive/refractive optic 7408, beamsplitter 7401, and mirror 7405, by lens 7402. Diffractive/refractive optic 7408 produces multiple illumination beams from the light beam exiting lens 7402. The optic 7408 can be constructed from optical structures, including diffractive arrays, refractive arrays (including groups of prisms), and binary optics, which serve the same function as 7208 in FIG. 72. These multiple beams, which each have a different angular direction, are focused through concave optic 7409 into the particle dispersion, creating multiple illumination spots and interaction volumes in the particle dispersion. The concave optic has a least one concave surface, with a center of curvature generally coincident with the center of the interaction volumes to reduce focal shifts due to changes in dispersant refractive index. At least one concave surface should be in contact with the particle dispersion, which contains the interaction volume, as shown in FIGS. 74 and 76. In both FIGS. 74 and 76, the particle dispersion generally fills the cavity formed by the concave surface, of the concave optic, closest to the interaction volume. If only one dispersant is used, this concave optic could also be replaced by a flat window on the probe or the flat window of a sample cell. Each of these beams, from 7408, creates a separate focused illumination spot and interaction volume in the particle dispersion. Only one of these focused spots and interaction volumes (7410) is shown in FIG. 74. Scattered light from each focused spot passes through lenses 7403 and 7404, which focus the scattered light onto detector arrays 7412 and 7411, respectively. Each detector array, 7412 and 7411, is generally in the image plane of the illumination spots in the particle dispersion, through lenses 7403 and 7404, respectively. Each detector element of arrays, 7412 and 7411, is also generally in the image plane of a corresponding illumination focus spot from the light source 7413, through beamsplitters 7405 and 7407, respectively. The focus of a source illumination beam and the image of a corresponding detector element (or detector aperture) in the particle dispersion will generally not shift when the scattered light and source light pass through the concave surface of 7409 with center of curvature at the illumination focus. If the other interaction volumes of other detector elements are close to the center of curvature, their position will be also generally independent of dispersant refractive index. Lenses 7403 and 7404 define a different range of scattering angle for each of the two detector arrays, so that each detector array measures scattered light over a different range of scattering angle. Information from multiple scattering angles can be utilized to improve the determination of particle size. Beamsplitter 7401 also partially reflects the illumination beams from optic 7408 to partially reflecting mirrors (beamsplitters) 7405 and 7407, which direct the illumination beams to detector array 7412 and detector array 7411, respectively to provide the source light to be mixed with scattered light for heterodyne detection on each detector in the arrays. For a single detector array system, the tilt of beamsplitter 7401 could be changed to direct source light directly to the detector array 7412, allowing removal of beamsplitter 7405, as shown in FIG. 76. This may require that detector array 7412 be moved towards the position of detector array 7411, so that the source beam, reflected by beamsplitter 7401, will not contact the 7408 optic. This would also require change in position of lens 7403 to reposition the scattered light onto detector 7412. This beamsplitter tilt and beamsplitter removal modification is also applicable to single detector systems, including the system shown in FIG. 22. Each detector array is aligned with the focused spots from lens 7402 and optic 7408, such that each focused spot of scattered light falls on a separate detector. The tilts of beamsplitters 7405 and 7407 are adjusted, such that each focused spot of illumination light also falls on a separate detector, in each detector array. Each detector receives an individual illumination light spot and scattered light spot, which interfere to create the heterodyne signal. Each detector size should be limited to only allow a portion of one, or at most a few, interference speckles, or coherence areas, to maximize the interferometric visibility and heterodyne signal. If detectors are large, each detector should have an aperture to limit the effective size of the detector. This concept holds for any number of detectors per detector array, including one detector, as shown in FIG. 22. The designs in FIGS. 73 and 74 are converted to single detector systems by removing the diffractive/refractive optic and replacing each detector array by a single detector and pinhole, as shown in FIG. 22, for example. Also, the characteristics of the interaction volume may be chosen to simplify alignment by choosing the magnification of lens 7402 and the magnifications of lenses 7403 and 7404, such that each illumination spot is either larger or smaller than the volume viewed by each detector. Then the alignment tolerance between the illumination spot and detector view, for each detector, is relaxed. This design choice is also applicable to single detector systems, as shown in FIG. 22, for example. This concept can be applied for any number of detector arrays with any number of individual detectors, including the case of one illumination spot and one single detector, without optic 7408.

Scatter measurements at multiple scattering angles can improve the accuracy of particle size measurement. The design in FIG. 74 is expanded to more than 2 detector arrays by adding more lenses with the function of 7403 and 7404 and by adding more beamsplitters with the function of 7405 and 7407.

FIG. 76 shows a modification of FIG. 74, where the source light is reflected directly onto the detector array by beamsplitter 7601, without the need for beamsplitter 7405. All of the components of similar function with those in FIG. 74 are given the same number, by replacing the 74 prefix with 76. So the description for FIG. 74 can be applied to FIG. 76, except for the function of beamsplitter 7601, which now directs source light directly onto detector array 7612. This concept can also be applied to FIG. 22, for a single detector. Multiple detector arrays and multiple scattering angles could also be employed by adding more lenses with similar function to 7603 and a beamsplitter, for each detector array, between beamsplitter 7601 and mirror 7605. Each beamsplitter would reflect source light to a different detector array. And as before, this concept can be applied for any number of detector arrays with any number of individual detectors, including the case of one illumination spot and one single detector, without optic 7608.

The equivalent of diffractive/refractive optic 7408 (optics 7208, 7308, 7408, and 7608 for example), can be removed from any multiple detector system, including systems shown in FIGS. 72, 73, 74, and 76. This optic can be replaced by another lens or the lens ahead of the diffractive/refractive optic can be changed to provide a broad region of illumination in the particle dispersion and on the detector array. Then a portion of the particle dispersion will be illuminated by a beam of generally uniform intensity, without the multiple focused source spot structure. Each detector will still receive scattered light from a generally separate portion of the particle dispersion, because each detector, in the detector array, is still conjugate to a generally different region in the particle dispersion through at least one lens. And the reflected source light beam, of generally uniform intensity, will irradiate the detectors for heterodyne detection. Heterodyne detection will occur at each detector element, as shown in FIG. 71, for example. This design, without illumination spots, may provide for easier alignment and lower cost.

The multiple detector ideas can be applied to many systems described previously, including FIGS. 1, 2, 3, 4, 5, 6, 7, 8, 20, and 22. The configuration of FIG. 71 can be used in these systems, without the diffractive/refractive optic, 7208. And the configuration of FIG. 72 can be used in these systems, with the diffractive/refractive optic, 7208. In each Figure, the diffractive/refractive optic, 7208, is placed between the optics of equivalent function to lens 7202 and beamsplitter 7206. The multiple detector concept can also be utilized with the optical systems of FIGS. 32 and 33. The detector 3221 in FIG. 32 could be replaced by a group of detectors or a detector array. When the pinhole (or aperture) of FIG. 32 is generally in the focal plane of lens 3203, the pinhole selects a range of scattering angles which is generally the same for each detector. The position and size of each detector selects generally a different collimated sub-volume (or interaction volume for that detector) in the particle dispersion, within the collimated light source beam. And the partial reflection, of source illumination light by beamsplitter 3212 for each collimated sub-volume, is passed by the pinhole to be mixed with the scattered light from generally the corresponding collimated sub-volume in the particle dispersion to produce the heterodyne signal on each detector. The selection of a narrow scattering angle range by the pinhole and a generally different interaction volume for each detector reduces the crosstalk between interaction volumes, wherein each detector does not receive scattered light from the same group of particles. The pinhole reduces scatter transfer between adjacent columnar interaction volumes by reducing scattering at lower scattering angles for each detector. The distance between detector 3221 and the pinhole may be adjusted to scale the size of the scattered light beam to the overall size of the detector group or detector array. This method and apparatus could be applied to the application of FIG. 32 or any other dynamic light scattering application, including the measurement of Brownian motion and particle size as described for FIGS. 71, 72, 73, 74, and 76. The window 3231 and sample flow tube of FIG. 32 could be replaced by the cell of FIG. 71, wherein the interaction volumes would comprise columnar volumes in the particle dispersion. This design is useful for measuring scattered light from larger volumes of particle dispersion per detector to improve representation of a larger homogeneous particle dispersion. And as described previously, detector 3222 and lens 3202 are optional. Likewise, this concept can be utilized in FIG. 33, where both detector 3301 and detector 3302 can be replaced by a group of detectors, detector group 3301 and detector group 3302. However in this case, the function of beamsplitter 3212, in FIG. 32, is replaced by the function of mirror 3311 or mirror 3312. If the 180 degree difference method is not required, one of the two detector/lens/beamsplitter/mirror systems can be eliminated in FIG. 33. If the difference method is utilized, then corresponding detectors of group 3301 and group 3302 should be aligned to see generally the same interaction columnar sub-volume. The signals from the multiple detectors of a detector group in FIGS. 32 and 33 are averaged to improve repeatability, as described previously for FIGS. 71, 72, 73, 74, and 76.

Also any of these multiple detector systems can be used in homodyne (self-beating) mode by removal of the local oscillator reflection by removing the reflector or partial reflector. The method of averaging multiple power spectra or multiple autocorrelation functions, as described previously, can be applied to scatter signals from multiple homodyne detectors, where the dynamic scattering signal is generated by optical interference (mixing) between the light scattered from each particle and the light scattered from a large group of the rest of the particles. Averaging of power spectra or autocorrelation functions of self-beating scatter signals, which originate from particles in generally different interaction volumes in the particle dispersion, will also benefit by the 1/N factor described previously.

The concepts of FIG. 1 and FIG. 33 can be combined to provide the laser amplitude and phase noise corrections of FIG. 33 for a dynamic light scattering measurement by eliminating aperture 3333, lens 3326, the window, and sample flow tube in FIG. 33. Then the sample cell of FIG. 1 is positioned such that the focus, of the source light in the opening of aperture 3333, is located in the particle dispersion of FIG. 1. In this new configuration each detection assembly, the assembly of mirror 3311/beam splitter 3342/detector 3301 and the assembly of mirror 3312/beam splitter 3343/detector 3302, provides the function of the detection assembly of mirror/beamsplitter/detector in FIG. 1 or the detection assembly of mirror 7706/beamsplitter 7710/detector 7709 in FIG. 77. The mirrors 3311 and 3312 could also be tilted, relative to the optical axis, to the orientation of the mirror in FIG. 1 or FIG. 77. Then detectors 3301 and 3302 measure heterodyne signals, which are generally some odd multiple of 180 degrees out of optical phase, from light scattered by particles in the sample cell with the focused light source spot in the particle dispersion. The electronic filters of FIG. 33 could be high pass filters or wide band pass filters designed to transmit the heterodyne frequencies required to describe the broadening of the scattered light spectrum due to Brownian motion of the particles in the sample cell. The same difference methods (difference S2f−G*S1f for example) are utilized, as described for FIG. 33, to remove the effects of laser amplitude and phase noise from the heterodyne signal of light scattered from particles moving with Brownian motion to determine the size distribution of the particles. The major difference is that the electronic filters must pass the much wider frequency spectrum of the broadening of the scattered light spectrum due to Brownian motion of the particles. The laser noise correction method and apparatus concept of FIG. 33 can be utilized in the configuration of FIG. 1 and any other configurations which include a beamsplitter and a mirror. And the power spectrum or autocorrelation function of the corrected signal (deltaS) is analyzed to determine particle characteristics, such as particle size distribution.

In general, all particle dispersions may be analyzed with these methods, including particles dispersed in liquid or gas. In particular, the methods and apparatus described in FIGS. 32 and 33 could be utilized to detect particles dispersed in a gas which flows through the sample flow tube. Also, any beamsplitter in any Figure comprises all types of partial reflectors which transmit and reflect portions of light passing through the partial reflector, including partially reflecting windows, pellicle beamsplitters, cube beamsplitters, and plate beamsplitters. Also any method or apparatus in this disclosure can be adapted to measure scattered light from aerosols. In some cases, where a sample cell window only provides a sample confining function, the window and sample cell could be eliminated for measuring aerosols, by placing the interaction volume(s) of the optical system in the aerosol. The interaction volume is the volume in space from which scattered light can be received by the detector. This interaction volume is usually the intersecting volume of the illumination beam and the detector field of view. FIG. 2 shows another version of these concepts where mean scattering angles, lower than 180 degrees, are measured by separating the incident and scattered beams. Mie resonances are reduced at lower scattering angles. Also multiple scattering is reduced by eliminating the scattering contribution of particles far from the focus of lens 203 in the particle dispersion. Only particles in the interaction volume of the intersection of the incident light cone of source light and scattered light cone, derived from the image of the pinhole 212 in the sample cell and aperture opening, contribute to scattering passing through pinhole 212. If this interaction volume is close to the inner wall of the sample cell window, all scattered rays will have a very short transit through the particle dispersion, with minimal multiple scattering. The sample cell window could be tilted slightly so that the reflection of the incident beam from a window surface does not enter pinhole 212 through the aperture or through the opening of lens 204. However if the partial light reflection from the interface of the particle dispersion and the window is sufficiently large for heterodyne detection, the light partially reflected by that interface could provide the source light for mixing with scattered light for heterodyne detection, without the need for the mirror, of FIG. 2, by providing the proper window tilt to pass the interface reflection through the lens 203 aperture and pinhole 212. Pinhole 212 is generally optically conjugate to the focus of the source light in the particle dispersion. When the focus of the source light is positioned generally at the interface of the particle dispersion and the window, the light, which is partially reflected by that interface, will pass through pinhole 212 along with the scattered light when the light reflected by that interface is generally collimated by lens 203. Then both the scattered light and source light, reflected by the interface, are focused through pinhole 212 to be optically mixed on the detector for heterodyne detection; and the mean scattering angle is generally equal to 180 degrees minus the angle of reflection at the interface. In this case, the beamsplitter only serves to redirect the light to lens 204 because the source light for heterodyne detection is reflected by the interface, not reflected by the beamsplitter. Therefore the beamsplitter could be eliminated by rotating the optical axis of the assembly of lens 204, pinhole 212, and the detector to be generally parallel to, and generally centered on, the collimated beam of scattered and reflected light from lens 203. This interface reflection concept could be combined with the concepts of FIG. 69 and FIG. 70 to produce an optical system with only two lenses, as described in FIG. 79. The components of FIG. 79 have similar functionality to the corresponding numbered components in FIGS. 69 and 70. The light source is focused generally at, or close to, the interface between the window of the sample cell and the particle dispersion by lens 7902. The interface reflects a portion of the source light to lens 7904, which focuses that light through aperture 7912. The light transmitted by the interface passes into the particle dispersion to be scattered by particles. Therefore aperture 7912 is generally optically conjugate to the focused spot of the light source. The image of the aperture at the source spot could be slightly larger than the source light spot to allow for easy alignment of aperture 7912 to capture the source light, reflected from the interface, and the scattered light from the particles. The intersection of the detector viewing volume (as defined by lens 7904 and aperture 7912) and the source focused spot should be slightly inside of the dispersion, so that aperture 7912 will also pass light which is scattered from particles in the intersection volume of the detection viewing volume, of lens 7904 and aperture 7912, and the illuminated volume in the particle dispersion. This intersection volume is similar to the interaction volume described previously. The scattered light from this interaction volume and the source light reflected from the interface, are focused through aperture 7912 by lens 7904. This scattered light and source light are optically mixed on the detector to produce a heterodyne signal indicative of the motion of the particles which scatter the detected light. This optical system is inexpensive and easy to align. Also since the interaction volume is at, or close to, the window surface, scattered light passes through the particle dispersion within a short path, providing low multiple scattering and providing accurate scattering measurements at high particle concentration. Many systems have been described previously in this application where the source light for heterodyne detection is derived from source light which is partially reflected by the interface between a window and the particle dispersion. In these cases, the interface acts as a partial reflector to pass a portion of the source light into the particle dispersion to produce scattered light from particles, and to reflect another portion of the source light to the detector for heterodyne detection. Usually the difference in refractive index of the particle dispersion and the window will create sufficient reflectivity of source light for heterodyne detection. In cases where this reflection is not sufficient, appropriate optical coatings on the window interface surface may be utilized to increase the reflectivity. The method and apparatus of the coupling prism in FIG. 65 can also be utilized in the design of FIG. 79. A prism can be attached (with refractive index matching adhesive to lower Fresnel reflection) to the air/window interface to pass the incident beam, from lens 7902, with a prism surface generally perpendicular to the optical axis of 7902. A second prism can be attached (with refractive index matching adhesive) to the air/window interface to pass the scatter/illumination beam to lens 7904, with a prism surface generally perpendicular to the optical axis of 7904. These prisms reduce Fresnel reflections and the surfaces of these prisms can be anti-reflection coated to further reduce reflected light. This concept can also be combined with the prism design of FIG. 20. Both of these prisms can be combined into one prism, where two surfaces provide the reflection reduction for light entering and exiting from the sample cell, and the third surface is attached with refractive index matching adhesive to the window, as shown by prism 7913 in FIG. 79. If the light source is a laser, the light from lens 7902 should have a small nonzero incidence angle on the prism surface to avoid light reflection back into the laser cavity. Reflected light in a laser cavity (of a laser diode for example) can cause instability and laser noise. This prism allows measurement of scattered light at lower scattering angles, where Mie resonances are reduced.

In cases where an aperture is conjugate to a plane in a region and the aperture defines the size of that region, the size of that region is a function of the size of the aperture opening and the magnification of the optical system which creates the conjugate relationship.

Particles of interest are particles with characteristics which are in the measurement range of the optical and detection systems.

The methods described for detecting particles in the flow tube in FIGS. 32 and 33 can also be enhanced by selecting only signals with both the expected frequency characteristics and expected duration of those frequency characteristics in the detector signal, where the expected characteristics comprise a particle residence time, which is derived from the particle dispersion flow velocity and the length of particle dispersion flow in the illuminated volume of the sample flow tube. And the expected frequency is derived from the flow velocity and the wavelength of light from the source.

Many methods for correcting the power spectrum of the scatter signal for background drift or laser power drift have been described previously. These methods can also be applied to the autocorrelation function of the scatter signal by replacing the power spectrum with the autocorrelation function and replacing frequency with the time delay or time lag in the power spectrum equations and methods described previously.

Various apparatus, for measuring the velocity of particles, have been described in this disclosure. Many of these optical systems measure the particle motion by detecting the scatter signal from particles moving in a spatially modulated source light intensity distribution. Since the scattered light is proportional to the incident light intensity, the scattered light is modulated as the particle moves in the spatially modulated intensity distribution. This spatially modulated intensity distribution can be created by optical interference between light beams or by imaging of a structure, with a spatially periodic light transmission, into the particle dispersion, for example. Examples of these apparatus are shown in FIGS. 52, 56, 57, 58, 59, 60, 61, and 62. As indicated previously, the scatter signal characteristics are indicative of motion of any particle which scatters light to a detector. This motion includes motion induced by gravitational, centrifugal, electric forces, and Brownian motion of the particles. These modulated intensity methods do not require heterodyne coherent mixing of source and scattered light to produce a modulated signal on the detector. Therefore, any light, which is emitted or scattered by the particle, which is dependent upon the incident light intensity on the moving particle, will be modulated by the spatially modulated source incident light intensity distribution as the particle moves. And the detector signal, of this light, can be analyzed to utilize the power spectrum or autocorrelation function of a characteristic of the detector signal to determine the Brownian motion of the particles, without the coherence requirements of heterodyne detection of scattered light. Therefore, any modulated light from the moving particle, including light which is not scattered, can be utilized to determine the Brownian motion and particle size by utilizing a spatially modulated source intensity distribution. This apparatus and method of spatial intensity modulation provides a dynamic detector signal with characteristics of Brownian motion, but without the large local oscillator offset of a heterodyne detector, which imposes source laser noise onto the detector signal. Also the dynamic properties of many types of light emission from the particles can be analyzed, in addition to scattered light. And the characteristics of particle Brownian motion and size can be determined from analysis of this light emission, using analysis, of the detector signal power spectrum or autocorrelation function, which is similar to the analysis employed in dynamic light scattering. For example, particle Brownian motion and size could be determined from the dynamic properties of fluorescence detected from particles moving within a spatially modulated light intensity distribution. In this case, the light source wavelength is chosen to be in the fluorescence excitation wavelength band of the particles and an optical filter is placed before the detector to pass the wavelength range of the fluorescence emission, while suppressing the light at the source wavelength. This adaptation could be utilized in FIGS. 52, 56, 57, 58, 59, 60, 61, and 62, for example. Using this method and apparatus, certain particle size information can be associated with certain particle composition characteristics.

The terms, beamsplitter and beam splitter, have the same meaning in this specification and claims. Also the terms, beamsplitting and beam splitting, have the same meaning in this specification and claims.

Some equations, which are written in this application and which exist in the literature, may contain errors as written in this application. While the inventor has attempted to avoid such errors, some may still exist. In any of these cases, the correct equation is assumed. These equation errors do not detract from the functionality of the method or apparatus which use them, because that same functionality is maintained when using the correct equation. This invention may be modified in ways which will be apparent to the reader skilled in the art. Such modifications should be considered within the spirit and scope of the following claims.

For very small particles, the heterodyne signals may be buried in laser source noise. FIG. 5, FIG. 6, and FIG. 7 show detectors 501, 601, 701, which measure the heterodyne signal from the particles. In FIG. 19, detector 1902 is also the heterodyne detector. FIG. 5, FIG. 6, and FIG. 7 show additional detectors 502, 602, 702, which measure the intensity of the local oscillator laser noise, by measuring a signal which is proportional to the light source intensity. FIG. 19 also shows additional detectors, detector 1901 (the detector on the light source) and detector 1913 (a laser power monitor on port 1903 of the fiber coupler). Both of these detectors in FIG. 19, measure signals which are proportional to the intensity of the light source. Any of these additional detectors, or any detector which monitors the laser power or a signal proportional to the laser power or laser intensity, can be used to monitor the laser noise. Another possibility is to monitor the light which has passed through the particle dispersion by placing a detector in the sample cell area. In any of these cases, if we define a heterodyne detector current as I1 and the laser monitor detector current as I2 we obtain the following equations which hold for each of the heterodyne detectors.

$$I1 = \text{sqrt}(R*R*T*Rm*Io(t)*Is(t))*\text{COS}(F*t+A) + R*T*Rm*Io$$

$$I1 = \text{sqrt}(R*R*T*Rm*Io(t)*S*R*T*Io)*\text{COS}(F*t+A) + R*T*Rm*Io$$

$$I2 = K*R*Tm*Io(t)$$

where:
I1 and I2 are normalized (detector responsivity=1).
COS(x)=cosine of x
The symbol * indicates multiply
K is a constant which describes the ratio of other efficiencies (optical and electrical), between the I1 and I2 channels, which are not due to the beamsplitter and partial reflecting mirror. I2 is the signal which is proportional to the laser power or laser intensity, which includes the fluctuations of that laser intensity.
R and T are the reflectivity and transmission of the beamsplitter, respectively.
Rm and Tm are the reflectivity and transmission of the partially reflecting mirror, respectively.
sqrt(x)=square root of x
Io(t) is the source beam intensity as function of time t
F is the heterodyne beat frequency at a heterodyne detector due to the motion of a particle which produces scattered light Is(t). And A is an arbitrary phase angle of the heterodyne signal for the particular particle. In an actual particle dispersion, I1 will comprise numerous sinusoidal terms, each term representing the motion of a different particle. And in the case of Brownian motion, the frequency and phase of these sinusoids change with time. However, these correction equations still apply to any number of particles by replacing COS(F*t+A) with the appropriate heterodyne term for the particle dispersion.

Is(t) is the scattered light intensity from the particle:

Is(t)=S*R*T*Io(t) where S is the scattering efficiency for the particle. S includes the product of the scattered intensity per incident intensity and optical scatter collection efficiency.

The light source intensity will consist of a constant portion Ioc and noise n(t):

$$Io(t)=Ioc+n(t)$$

By substitution, we may then rewrite equations for I1 and I2:

$$I1=R*T*sqrt(S*R*Rm*(Ioc+n(t)))*COS(F*t+A)+R*T*Rm*(Ioc+n(t))$$

$$I2=K*R*Tm*(Ioc+n(t))$$

If we use high pass or bandpass filters to accept only the higher frequencies, which contain the particle size information, we obtain high pass signals, I1hp and I2hp for I1 and I2, respectively:

$$I1hp=R*T*sqrt(S*R*Rm)*Ioc*COS(F*t+A)+R*T*Rm*n(t)$$

$$I2hp=K*R*Tm*n(t)$$

Where we have assumed that n(t) is much smaller than Ioc. And also n(t) is the portion of the laser noise that is passed by the high pass filter bandwidth (see below). In certain situations, these high pass filters are replaced by band pass filters which only pass frequencies carrying particle information.

The laser noise can be removed to produce the pure heterodyne signal (in this case a signal proportional to COS(F*t+A)), by calculating Idiff through the following relationship:

$$Idiff=I1hp-(T*Rm)/(K*Tm)*I2hp=R*T*Sqrt(S*R*Rm)*Ioc*COS(F*t+A)$$

This relationship is realized by high pass or bandpass filtering each of the I1 and I2 detector currents. One or both of these filtered signals are amplified by programmable amplifiers, whose gains and phase shifts are adjustable. The difference of the two outputs of these amplifiers is generated by a difference circuit or differential amplifier. With no particles in the beam, the gain and phase shift of at least one of the programmable amplifiers is adjusted, under computer control or manual control, to minimize the output of the difference circuit. At this minimum, the theoretical gain ratio the relationship, (gain of I2)/(gain of I1)=T*Rm/(K*Tm), should be obtained. At this gain, the source intensity noise component in the heterodyne detector beat signal, with particles present, is removed in the difference signal, which digitized by an analog to digital converter (A/D), for inversion to particle size. This adjustment, to minimize the difference circuit output when particle scatter is negligible, can be applied to heterodyne systems of any configuration, where I1 is the heterodyne signal and I2 is a signal proportional to the light source intensity. In the general case, the equations take the following form, where B1 and C are constants and het(t) is the heterodyne term due to scatter from at least one moving particle:

$$I1hp(t)-B1*I2hp(t)=C*het(t)$$

When no particles are present, het(t)=0 and B1 is determined by:

$$B1=I1hp(t)/I2hp(t) \text{ when } het(t)=0$$

B1 is a general constant which corresponds to the gain ratio (gain of I2)/(gain of I1)=T*Rm/(K*Tm) in the previous example. B1 is determined by measuring I1hp and I2hp when het(t) is negligible (very low particle concentration) and calculating B1=μhp(t)/I2hp(t). Then for any het(t)>0:

$$Idiff=C*het(t)=I1hp(t)-B1*I2hp(t) \text{ where } B1=T*Rm/(K*Tm) \text{ for the previous example}$$

$$het(t)=(I1hp(t)-B1*I2hp(t))/C \text{ for the general case}$$

where C is a constant determined by methods comprising calibration measurement or theoretical model of the optical system.

This entire correction could be accomplished in the computer by using a separate A/D for each filtered signal and determining the difference by digital computation of the computer. The phase and gain adjustments mentioned above, without particles in the beam, could be accomplished digitally. The gain adjustment is accomplished digitally by a digital multiply by constant B1.

The coefficient ratio R/K can also be calculated to be used in the equation for Idiff, using the following equations:

$$T*Rm/(K*Tm)=I1dc/I2dc \text{ (for the example above)}$$

$$B1=I1dc/I2dc=\text{mean}(I1(t))/\text{mean}(I2(t)) \text{ (for the general case)}$$

In general, the mean signal level (Idc or Ioc) has a generally constant relationship with n(t) at any stage in the optical system. Therefore, after correcting for frequency response at each stage, the relationship between Idc and n(t) is generally constant if n(t) originates at the optical source and then the following holds:

$$I1dc/I2dc=n1(t)/n2(t)$$

If both signals were digitized separately, other correlation techniques could be used to reduce the effects of source intensity noise. In any case, the beamsplitter reflection may be adjusted to obtain shot noise limited heterodyne detection, with excess laser noise removed by the difference circuit or difference calculation described above.

These noise correction techniques can be applied to any heterodyning system by simply adjusting the filtering of currents I1 and I2 to pass the signal of interest, while blocking the generally zero frequency component (Ioc) of Io(t). Excess laser noise and other noise components, which are present in both the heterodyne signal and the light source, can be removed from the signal of interest through this procedure. One application is dynamic light scattering, where the heterodyne signal is contaminated by laser source noise in the optical mixing process. The filters on I1 and I2 would be designed to pass the important portion of the Doppler broadened spectrum and to remove the large signal offset due to the local oscillator. Then by using the subtraction equation for Idiff or het(t), described previously, the effects of laser noise can be removed from the Doppler spectrum, improving the particle size accuracy. In the case of fiber optic heterodyning systems, the laser monitor current, I2, could be obtained at the exit of the unused output port (port 1903 in FIG. 19) of the fiber optic coupler which is used to transport the light to and from the particle sample, because this port carries light only from the optical source, without any scattered light. I2 could also be obtained from the laser detector (for example the detector on a light source as shown by detector 1901 in FIG. 19).

Also the signals at port 1903 in FIG. 19 could be replaced by the signals at detectors 501, 601, 701 (1912) and detectors 502, 602, 702 (1903) respectively, in FIGS. 5, 6, and 7, for example. This subtraction for Idiff or het(t) could be accomplished by the analog difference circuit or by digital subtraction after digitization of both the filtered laser noise contaminated heterodyne signal and the filtered source monitor as outlined previously. This procedure could also be accomplished using the unfiltered signals, but with much poorer accuracy due to the large signal offsets.

Using FIG. 19 we can describe another version of this correction which simply measures the power spectrum at port 1912 (detector 1902) and port 1903 (detector 1913) in FIG. 19. The signal at port 1911 (detector 1901) could also be used in place of the detector 1913 signal. Also the signals at port 1912 and port 1903 in FIG. 19 could be replaced by the signals at detectors 501, 601, 701 (1912) and detectors 502, 602, 702 (1903) respectively, in FIGS. 5, 6, and 7, for example. The following equalities define the power spectrum measurements, which are all functions of frequency:

P2bkg=power spectrum measured at port 1912 with clean dispersant (without particles) in the sample region P3bkg=power spectrum measured at port 1903, while P2bkg is being measured on port 1912

P2meas=power spectrum measured at port 1912 from the particle dispersion (with particles) in the sample region P3meas=power spectrum measured at port 1903, while P2meas is being measured on port 1912

I3dc=DC offset, constant portion, or mean of signal producing P3meas

I2dc=DC offset, constant portion, or mean of signal producing P2meas

Then the measured power spectrum, P2meas, can be corrected for the background power spectrum and the drift in the background power spectrum by using the following equations, where P(f~0) is the power spectral density at frequencies close and equal to zero:

$$Pcorrected=P2meas-P2bkg-((I2dc/I3dc)^2)*(P3meas-P3bkg)$$

or $$Pcorrected=P2meas-P2bkg-(P2meas(f\sim 0)/P3meas(f\sim 0))*(P3meas-P3bkg)$$

All of the power spectra are functions of frequency, so these mathematical operations are performed at each frequency. The background corrected power spectrum, Pcorrected, would then be inverted to obtain the particle size distribution.

The use of this method can be illustrated in the following example where detector 2 is the scattered light heterodyne detector (detectors 501, 601, 701, port 1912 for example) and detector 3 is the light source detector (detectors 502, 602, 702, port 1903 for example). The following definitions are:

Pp=a component of the power spectrum of detector 2 power spectrum due to light scattered from particles.

P2b=power spectrum of detector 2 measured without particles (P2bkg)

P2m=power spectrum of detector 2 measured with particles (P2meas)

P3b=power spectrum of detector 3 measured without particles (P3bkg), measured generally concurrently with the measurement of P2b P3m=power spectrum of detector 3 measured with particles (P3meas), measured generally concurrently with the measurement of P2m Pnb=a component of the power spectrum of a detector power spectrum due to laser noise while measurements are made without particles Pnm=a component of the power spectrum of a detector power spectrum due to laser noise while measurements are made with particles P2e=a stable component of the power spectrum of detector 2 power spectrum which is multiplied by a power gain constant.

P2s=a stable component of the power spectrum of detector 2 power spectrum which is not multiplied by a power gain constant.

P3e=a stable component of the power spectrum of detector 3 power spectrum which is multiplied by a power gain constant.

P3s=a stable component of the power spectrum of detector 3 power spectrum which is not multiplied by a power gain constant.

Where each of the functions starting with P are a power spectrum of a detector signal as a function of frequency. Then the following equations are defined for P2m, P2b, P3m, and P3b:

$$P2m=g2*(Pp+P2e+Pnm)+P2s$$

$$P2b=g2*(P2e+Pnb)+P2s$$

$$P3m=g3*(P3e+Pnm)+P3s$$

$$P3m=g3*(P3e+Pnb)+P3s$$

where g2 and g3 are power gain constants relating components of the power spectrum to the total calculated power spectrum, for detectors 2 and 3 respectively. These power gain constants are functions of parameters comprising electronic and optical parameters such as electronic power gain, optical reflectivity, optical transmission, and detector responsivity.

A corrected power spectrum, Pcorr, is calculated to obtain a power spectrum, Pp, which is derived only from scatter signal component of particles using the following equation:

$$Pcorr=P2m-P2b-(g2/g3)*(P3m-P3b)$$

Substituting the equations from above we obtain:

$$Pp=Pcorr/g2$$

This equation for Pcon is the generalized equivalent to the prior equation:

$$Pcorrected=P2meas-P2bkg-((I2dc/I3dc)^2)*(P3meas-P3bkg)$$

where $((I2dc/I3dc)^2)=g2/g3$=power gain ratio

Since the Ioc component passes through the same optical and electronic paths as Pnm or Pnb, in most cases, $g2/g3=((I2dc/I3dc)^2)$. In cases where this relationship is not true, g2/g3 can be calculated from a theoretical model of the electronic and optical system, utilizing methods similar to the calculation of I1hp and I2hp, described previously for detector signals. The ratio g2/g3 can also be determined by calculating the following ratio of measurements performed at very low particle concentration (Pp=0):

$$g2/g3=(P2m-P2b)/(P3m-P3b) \text{ when } Pp=0 \text{(when } Pp \text{ is negligible)}$$

If P2e=P3e and P2s=P3s, then P2b is equal to (g2/g3)*P3b, and the measurements of signal power spectrum without particles (P2b and P3b) are not necessary and the power spectrum correction equation becomes:

$$Pcorr=P2m-(g2/g3)*P3m$$

$$Pp=Pcorr/g2$$

In any case, Pp=Pcorr/g2 even when the laser noise power spectrum, Pn, has changed between the power spectrum measurements with and without particles, which are Pnm and Pnb respectively.

In this document, the terms power spectrum and autocorrelation function refer to all variants of these functions, unless indicated otherwise. For example, each value in a power spectrum function can refer to a value of power per frequency interval or a value of total power within a specified frequency interval, where the abscissa value corresponding to the value of total power is usually the frequency of the center of that frequency interval, for example. The frequency intervals can also have arbitrary spacing such as linear or logarithmic (such as in octave analysis for example). In some cases, the function type and abscissa type are determined by the equation which utilizes the function, as found in some convolution equations, where the power spectrum is defined on logarithmic abscissa scale.

For example, the summation (or average), Fs, for N detectors in the description for FIG. 71 (and also related to multiple detectors of FIGS. 72, 73, 74, and 76) is given by:

$$Fs(Xj) = SUM i:1:N(Fi(Xj))$$

Where SUM i:a:b(Fi) is the summation of Fi over index i for i=a to i=b. Fs is the final summed function and Fi are the individual functions being summed. Fi(Xj) is the function measured from the ith detector at the jth abscissa value for the function Fi. For the power spectrum, Fi(Xj) is the power spectrum value from the ith detector at the jth frequency. The average is Fs(Xj)/N.

For the case where F is a power spectrum, each value of function F can represent the value of power per frequency interval at abscissa value Xj or a value of total (integrated) power within a specified frequency interval centered at abscissa value Xj.

The homogeneous start method, described previously, comprises the case where the particle size distribution and/or particle concentration is generally the same throughout the dispersion in the sample cell before gravitational or centrifugal forces are applied to move particles. In the layer start method, the particle size distribution and/or particle concentration is not the same throughout the dispersion in the sample cell before gravitational or centrifugal forces are applied to move particles, because the particles are concentrated at one end of the sample cell. Also any references to gravitational acceleration or centrifugal acceleration comprise the cases where gravitational or centrifugal force, respectively, is applied to a particle, including the case where that particle has reached terminal velocity and has zero acceleration.

The term sample cell comprises a container which contains a particle dispersion or a container through which a particle dispersion flows. A sample cell comprises a design with appropriate transparent surfaces to allow light to illuminate particles in the cell and to allow particle scattered light to exit from the cell. These transparent surfaces may comprise optical windows in the cell walls. The sample cell may also comprise an inlet and outlet to allow fluids to flow through the sample cell.

Some equations, which are written in this application and which exist in the literature, may contain errors as written in this application. While the inventor has attempted to avoid such errors, some may still exist. In any of these cases, the correct equation is assumed. These equation errors do not detract from the functionality of the method or apparatus which use them, because that same functionality is maintained when using the correct equation. This invention may be modified in ways which will be apparent to the reader skilled in the art. Such modifications should be considered within the spirit and scope of the following claims.

What is claimed is:

1. An apparatus for determining characteristics of particles as determined from measurements of scattered light from particles, comprising:
   a) illumination means which illuminates particles wherein said illumination means comprises a light source,
   b) a sample cell which contains a particle dispersion and which provides optical access for said illumination means to illuminate at least one particle in said sample cell, wherein a portion of light from said illumination means is scattered by particles,
   c) at least one detection means which measures at least one parameter derived from light scattered from at least one particle in said sample cell, wherein said detection means comprises at least one light detector,
   d) force means which produces forces on said particles to cause particle motion, wherein said measurements of said detection means provide information derived from at least one motion characteristic of said particle motion, wherein at least one particle group is not totally physically separated from another particle group by said forces, wherein particles of each particle group are different from another particle group in at least one particle characteristic, and
   e) calculation means which determines at least one characteristic of said particles by utilizing said measurements of said detection means.

2. The apparatus of claim 1, wherein said forces comprise gravitational forces.

3. The apparatus of claim 1, wherein said forces comprise centrifugal forces.

4. The apparatus of claim 1, wherein said motion characteristic of particle motion comprises particle velocity which is derived from light scattering measurements.

5. The apparatus of claim 1, wherein said motion characteristic of particle motion comprises a change in particle position.

6. The apparatus of claim 1, further comprising:
   a) an optical system which measures scattered light from a volume of particle dispersion, wherein said optical system comprises said illumination means and said detection means,
   b) a surface which is close to said volume, wherein particles do not move through said surface into said volume, wherein said surface comprises a solid surface or a gas to liquid interface, wherein said particle dispersion is homogeneous in said volume before application of said forces, and
   c) detection control means which utilizes said detection means to measure scattered light at various times as particles of different velocities move out of said volume at different times.

7. The apparatus of claim 1, further comprising:
   a) beam splitting means for combining light, from said illumination means, with said scattered light on at least one detector in said detection means to measure detector signals with characteristics derived from frequency characteristics of said scattered light due to said particle motion, wherein said detector signals are derived from optical interference between light from said illumination means and said scattered light, and
   b) means which calculates at least one particle characteristic utilizing at least one signal characteristic derived from said detector signals.

8. The apparatus of claim 1, further comprising:
a) a periodic spatial mask, positioned at a location which is optically conjugate to a plane in said particle dispersion through an optical means, to create a spatial modulation of a light intensity distribution or a spatial modulation of a light detection response distribution, wherein particle motion creates modulation of the light scattered from said particles, wherein said modulated scattered light is detected by said detection means, and
b) means which calculates at least one particle characteristic utilizing at least one signal characteristic derived from said detection means.

9. The apparatus of claim 1, further comprising:
a) an optical system comprising said detection means and said illumination means, wherein said detection means detects scattered light primarily from particles in a region of said sample cell,
b) translation means which creates translational motion between said sample cell and the said optical system, and
c) detection control means which utilizes said detection means to measure scattered light characteristics from particles in each of a set of regions, wherein the center of each region is located at a different position in said sample cell and wherein said translational motion provides motion between regions.

10. The apparatus of claim 1, further comprising detection control means which measures said scattered light characteristics at different times, wherein motions of particles occur between each said time.

11. The apparatus of claim 9, further comprising:
a) detection means, wherein said detection means measures scattered light characteristics at a set of scattering angle ranges in each of said regions, and
b) calculation means which determines at least one particle characteristic from said scattered light characteristics, which are measured at said scattering angle ranges in said regions.

12. The apparatus of claim 9, further comprising:
a) detection means, wherein said detection means measures dynamic light scattering characteristics in each of said regions, and
b) calculation means which determines at least one particle characteristic from said dynamic light scattering light characteristics, which are measured in each of said regions.

13. The apparatus of claim 1, wherein said force means comprises a centrifuge, and wherein said sample cell, said illumination means, and said detection means move together in said centrifuge.

14. The apparatus of claim 1, wherein said force means comprises a centrifuge, wherein said sample cell is attached to a rotating portion of said centrifuge, and wherein said illumination means and said detection means are detached from the rotating portion of said centrifuge.

15. The apparatus of claim 1, wherein said force comprises centrifugal force, further comprising:
a) a centrifuge which holds said sample cell in a rotating portion of said centrifuge, wherein said sample cell can be detached from said centrifuge after application of centrifugal force on said particles in said sample cell,
b) an optical system comprising said illumination means and said detection means, wherein said optical system is not an integral part of said centrifuge,
c) means which attaches said sample cell, after detachment from said centrifuge, to a sample cell holder after application of centrifugal force to the particles in said sample cell, wherein said holder is not an integral part of said centrifuge,
d) translation means which creates translational motion between said sample cell and said optical system, wherein a preferred direction of said translational motion is generally along a direction of said particle motion, and
e) detection control means which utilizes said detection means to measure scattered light characteristics from particles in each of a set of regions, wherein a center of each region is located at a different position in said sample cell and wherein said translational motion provides motion between regions.

16. The apparatus of claim 1, further comprising:
a) means which determines a group of scatter characteristics for each of various measurement conditions of particles in said dispersion,
b) means which calculates a difference between groups of scatter characteristics with different measurement conditions to produce a set of differential scatter characteristics,
c) means which calculates a particle characteristic distribution from each member of said set of differential scatter characteristics, to produce an individual particle characteristic distribution for each member of said set of differential scatter characteristics, and
d) means which combines said individual particle characteristic distributions into one particle characteristic distribution.

17. A method for determining characteristics of particles as determined from measurements of scattered light from particles, comprising:
a) providing a sample cell which contains a particle dispersion and which provides optical access for an illumination means to illuminate at least one particle in said sample cell, wherein a portion of light from said illumination means is scattered by particles and wherein said illumination means comprises a light source,
b) producing forces on said particles by utilizing a force means to cause particle motion,
c) illuminating particles with an illumination means,
d) measuring at least one parameter derived from light scattered from particles, utilizing at least one detection means, wherein said detection means comprises at least one light detector, wherein said measurements of said detection means provide information derived from at least one motion characteristic of said particle motion, wherein at least one particle group is not totally physically separated from another particle group by said forces, wherein particles of each particle group are different from another particle group in at least one particle characteristic, and
e) determining at least one characteristic of said particles by utilizing said measurements of said detection means.

18. The method of claim 17, wherein said forces comprise gravitational forces on particles.

19. The method of claim 17, wherein said forces comprise centrifugal forces on particles.

20. The method of claim 17, wherein said motion characteristic of particle motion comprises particle velocity which is derived from light scattering measurements.

21. The method of claim 17, wherein said motion characteristic of particle motion comprises a change in particle position.

22. The method of claim 17, further comprising:
a) utilizing a centrifuge to produce centrifugal forces on particles in a sample cell while said sample cell is attached to said centrifuge, wherein said sample cell can be detached from said centrifuge,
b) detaching said sample cell from said centrifuge after centrifugal forces are applied to said particles in said sample cell,
c) attaching said sample cell to a cell holder which is not an integral part of said centrifuge,
d) performing translational motion between said sample cell and an optical system, wherein a preferred direction of said translational motion is generally along a direction of said particle motion, wherein said optical system comprises said detection means and said illumination means and wherein said optical system is not an integral part of said centrifuge,
e) measuring scattered light characteristics from particles in each of a set of regions, wherein a center of each region is located at a different position in said sample cell, and wherein said translational motion provides motion between regions, and
f) determining characteristics of particles from said scattered light characteristics.

23. The method of claim 17, further comprising:
a) determining a group of scatter characteristics for each of various measurement conditions of particles in said dispersion,
b) calculating a difference between groups of scatter characteristics with different conditions to produce a set of differential scatter characteristics,
c) calculating a particle characteristic distribution from each member of said set of differential scatter characteristics, to produce an individual particle characteristic distribution for each member of said set of differential scatter characteristics, and
d) combining said individual particle characteristic distributions into one particle characteristic distribution.

24. The method of claim 23, wherein said measurement condition is selected to be a location of a region, wherein said detection means detects scattered light from said region, wherein said detection means measures scattered light characteristics from particles in each of a set of regions, wherein a center of each region is at a different location.

25. The method of claim 24, wherein said regions are selected to be adjacent regions.

26. The method of claim 23, wherein said condition is selected to be time of measurement.

27. The method of claim 23, wherein said different condition is chosen based upon change in scatter characteristics between chosen conditions.

28. The method of claim 17, further comprising:
a) measuring a scattering signal which contains frequency dependent information related to motion of particles,
b) calculating at least one power spectrum of a signal derived from said scattering signal,
c) determining characteristics of particles from said at least one power spectrum.

29. The method of claim 17, further comprising:
a) performing translational motion between said sample cell and an optical system, wherein said optical system comprises said detection means and said illumination means,
b) utilizing said detection means to measure scattered light characteristics from particles in each of a set of regions, wherein a center of each region is located at a different position in said sample cell, and wherein said translational motion provides motion between regions, and
c) calculating at least one characteristic of said particles by utilizing said measurements of said detection means, wherein said measurements are affected by at least one motion characteristic of said particle motion.

30. The method of claim 17, further comprising
a) measuring a power spectrum of said scattering signal for each of various values of force and/or scattering angle,
b) creating a set of simultaneous equations which relate said measured power spectra to theoretical power spectra and particle characteristics, wherein said measured power spectra are functions of frequency, scattering angle, and force, wherein said theoretical power spectra are functions of frequency, scattering angle, force, and particle characteristics, and wherein said theoretical power spectra include effects of Brownian motion of particles,
c) utilizing said simultaneous equations to determine particle characteristics from said measured power spectra.

31. A method for determining characteristics of particles as determined from measurements of scattered light from particles, comprising:
a) containing a particle dispersion in a sample cell which provides optical access for a illumination means to illuminate at least one particle in said sample cell, wherein a portion of light from said illumination means is scattered by particles and wherein said illumination means comprises a light source,
b) attaching said sample cell to a rotating portion of a centrifuge,
c) producing forces on said particles to cause particle motion, wherein said force comprises centrifugal force produced by said centrifuge, wherein said sample cell is attached to said rotating portion of said centrifuge during application of said centrifugal force on said particles,
d) detaching said sample cell from said centrifuge after said application of centrifugal force on said particles in said sample cell,
e) attaching said sample cell to a cell holder which is not an integral part of said centrifuge,
f) illuminating particles with said illumination means,
g) detecting scattered light utilizing said detection means which measures at least one parameter derived from light scattered from particles, wherein said detection means comprises at least one light detector,
h) performing translational motion between said sample cell and an optical system, wherein a preferred direction of said translational motion is generally along a direction of said particle motion, wherein said optical system comprises said detection means and said illumination means and wherein said optical system is not an integral part of said centrifuge,
i) measuring scattered light characteristics from particles in each of a set of regions wherein a center of each region is located at a different position in said sample cell, wherein said translational motion of step (h) provides motion between regions, said measuring comprising performing step (f) and step (g), and
j) calculating at least one characteristic of said particles by utilizing said measurements of said detection means, wherein said measurements are affected by at least one motion characteristic of said particle motion.

32. The apparatus of claim 1, wherein said measurements comprise at least one of the group consisting of measuring light scattering over various ranges of scattering angles and dynamic light scattering measurements.

33. The apparatus of claim 1, wherein said calculation comprises at least one of the group consisting of calculating differences between angular scattering information, calculating differences between dynamic scattering information, and analysis of dynamic light scattering information by analysis of frequency components of a scatter signal power spectrum.

34. The method of claim 17, wherein said measuring comprises at least one of the group consisting of measuring light scattering over various ranges of scattering angles and measuring dynamic light scattering.

35. The method of claim 17, wherein said determining comprises at least one of the group consisting of calculating differences between angular scattering information, calculating differences between dynamic scattering information, and analysis of dynamic light scattering information by analysis of frequency components of a scatter signal power spectrum.

36. The method of claim 17, utilizing particle characteristics of a homogeneous particle dispersion to improve the function of steps (b), (d) and (e), comprising:
- f) measuring scattering characteristics of a generally homogeneous particle dispersion before application of said forces,
- g) determining particle characteristics of said homogeneous particle dispersion by inverting scattering characteristics from step (f), and
- h) utilizing said particle characteristics of said homogeneous dispersion to determine operational parameters for said forces of step (b) to improve the function of steps (b), (d) and (e).

* * * * *